(12) United States Patent
Gray et al.

(10) Patent No.: US 12,365,696 B2
(45) Date of Patent: Jul. 22, 2025

(54) SMALL-MOLECULE FOCAL ADHESION KINASE (FAK) INHIBITORS

(71) Applicant: DANA-FARBER CANCER INSTITUTE, INC., Boston, MA (US)

(72) Inventors: Nathanael Gray, Stanford, CA (US); David Scott, Newton, MA (US); Brian Groendyke, Chestnut Hill, MA (US); Behnam Nabet, Boston, MA (US); Mikaela Mohardt, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 907 days.

(21) Appl. No.: 17/606,543

(22) PCT Filed: May 7, 2020

(86) PCT No.: PCT/US2020/031791
§ 371 (c)(1),
(2) Date: Oct. 26, 2021

(87) PCT Pub. No.: WO2020/231726
PCT Pub. Date: Nov. 19, 2020

(65) Prior Publication Data
US 2022/0242882 A1 Aug. 4, 2022

Related U.S. Application Data

(60) Provisional application No. 63/007,542, filed on Apr. 9, 2020, provisional application No. 62/845,998, filed on May 10, 2019.

(51) Int. Cl.
*C07D 513/14* (2006.01)
*A61K 31/551* (2006.01)
(Continued)

(52) U.S. Cl.
CPC .......... *C07D 513/14* (2013.01); *A61K 31/551* (2013.01); *A61K 31/5517* (2013.01); *A61K 45/06* (2013.01); *A61P 35/00* (2018.01)

(58) Field of Classification Search
None
See application file for complete search history.

(56) References Cited

U.S. PATENT DOCUMENTS

| 6,271,225 B1 | 8/2001 | Seio et al. |
| 2012/0040961 A1 | 2/2012 | Gray et al. |

FOREIGN PATENT DOCUMENTS

| CN | 1268949 A | 10/2000 |
| CN | 107151250 A | 9/2017 |

(Continued)

OTHER PUBLICATIONS

Zhou et al., "Research progress in focal adhesion kinase inhibitors", Central South Pharmacy, 2017, vol. 15, No. 11, pp. 1555-1562.
(Continued)

*Primary Examiner* — Randall L Beane
*Assistant Examiner* — Sophia Reilly
(74) *Attorney, Agent, or Firm* — ArentFox Schiff LLP; Daniel W. Clarke; Shawn P. Foley

(57) ABSTRACT

Disclosed are compounds that possess inhibitory activity against FAK. Also disclosed are pharmaceutical compositions containing the compounds and methods of using the compounds to treat cancer mediated by aberrant FAK activity.

26 Claims, 2 Drawing Sheets

(51) Int. Cl.
*A61K 31/5517* (2006.01)
*A61K 45/06* (2006.01)
*A61P 35/00* (2006.01)

(56) References Cited

FOREIGN PATENT DOCUMENTS

| WO | 1999011647 A1 | 3/1999 |
| WO | 2010080712 A2 | 7/2010 |
| WO | 2012045194 A1 | 4/2012 |
| WO | 2014145909 A2 | 9/2014 |
| WO | 2017148406 A1 | 9/2017 |
| WO | 2019243550 A1 | 12/2019 |

OTHER PUBLICATIONS

Kalogirou, et al., "Reaction of 3,4,4,5-tetrachloro-4H-1,2,6-thiadiazine with benzyltriethylammonium chloride," Tetrahedron Letters, Aug. 4, 2018, vol. 59, pp. 3589-3593.

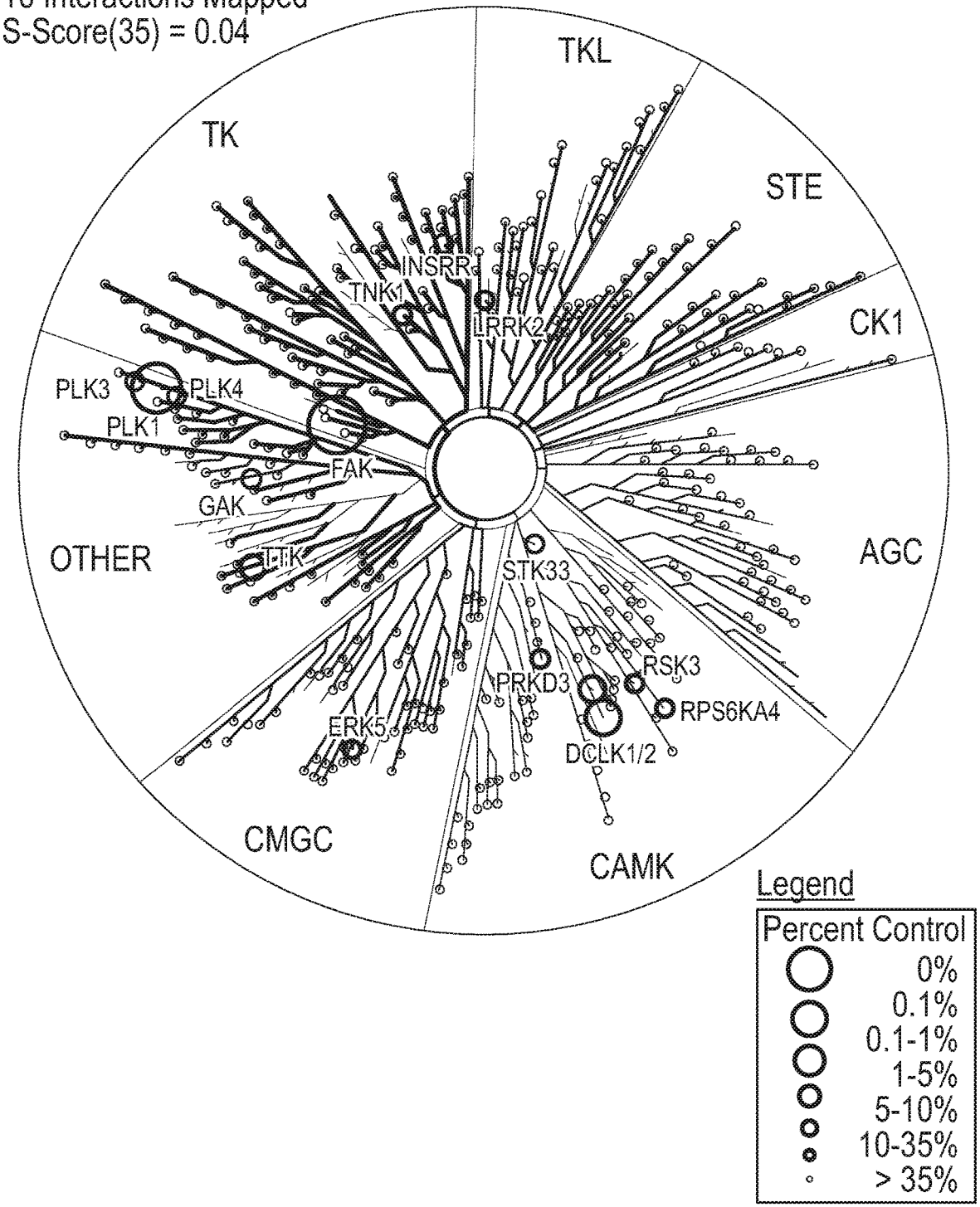

SMALL-MOLECULE FOCAL ADHESION KINASE (FAK) INHIBITORS

RELATED APPLICATIONS

This application is a national stage application, filed under 35 U.S.C. § 371, of International Application No. PCT/US2020/031791, filed May 7, 2020, which claims the benefit of priority under 35 U.S.C. § 119 (e) to U.S. Provisional Application No. 62/845,998, filed May 10, 2019 and U.S. Provisional Application No. 63/007,542, filed Apr. 9, 2020, each of which is incorporated herein by reference in its entirety.

BACKGROUND OF THE INVENTION

Focal adhesion kinase (FAK) is a non-receptor tyrosine kinase that localizes at sites of cell adhesion to the extracellular matrix (ECM) and mediates signaling events downstream of integrin engagement of the ECM (van Nimwegen et al., Biochem. Pharmacol. 73:597-609 (2007)). FAK expression is required for many normal cellular functions (Parsons et al., Clin. Cancer Res. 14:627-632 (2008)). FAK is often unregulated in many cancer types and control a variety of functions that are important for malignant phenotype, such as adhesion, movement, invasion, proliferation, and survival (Symeonides et al., J. Immunother. Cancer 5:17 (2017)).

PTK2, the gene that encodes FAK, is commonly amplified in many cancers including ovarian cancer, breast cancer, and pancreatic adenocarcinoma (Sulzmaier et al., Nat. Rev. Cancer 14:598-610 (2014)). FAK has been identified as a genetic dependency in global cancer screening efforts (Tsherniak et al., Cell 170:564-576 (2017)) and regimens combining FAK inhibitors and immunotherapy have also shown significant responses in preclinical cancer models (Jiang et al., Nat. Med. 22:851-860 (2016)). Therefore, targeted inhibition of FAK may be an attractive therapeutic strategy across many cancers.

SUMMARY OF THE INVENTION

A first aspect of the present invention is directed to a compound represented by a structure of formula (I):

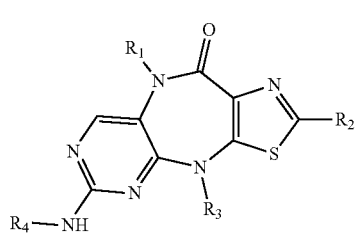

(I)

wherein:

$R_1$ is hydrogen, optionally substituted alkyl, optionally substituted carbocyclyl, or optionally substituted heterocyclyl;

$R_2$ is hydrogen, optionally substituted alkyl, optionally substituted carbocyclyl, or optionally substituted heterocyclyl;

$R_3$ is hydrogen, optionally substituted alkyl, optionally substituted carbocyclyl, or optionally substituted heterocyclyl;

$R_4$ is optionally substituted pyrazolyl, optionally substituted pyridinyl, optionally substituted benzopiperidinyl,

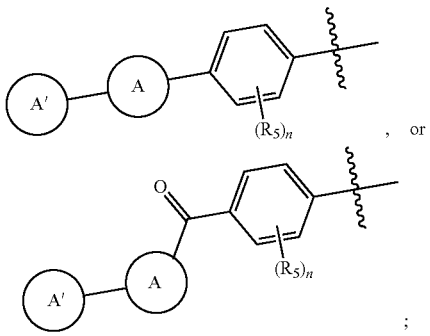

, or

;

each $R_5$ is independently H, OH, CN, alkyl, alkoxy, halo, haloalkyl, haloalkoxy, amino, acyl, or amide;

n is 0, 1, or 2;

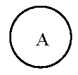

is an optionally substituted amide or an optionally substituted heterocycle;

is absent if

is an optionally substituted amide, and if

is optionally substituted heterocycle,

is absent, optionally substituted piperidinyl, or optionally substituted piperazinyl;

or a pharmaceutically acceptable salt or stereoisomer thereof.

A second aspect of the present invention is directed to a pharmaceutical composition containing a therapeutically effective amount of a compound of formula I, or a pharmaceutically acceptable salt or stereoisomer thereof, and pharmaceutically acceptable carrier.

A further aspect of the invention is directed to a method of treating a cancer mediated by aberrant (e.g., dysregulated)

FAK activity, comprising administering to a subject in need thereof a therapeutically effective amount of a compound of formula (I) or a pharmaceutically acceptable salt or stereoisomer thereof. In some embodiments, the disease is pancreatic cancer, ovarian cancer or lung cancer.

Further aspects of the present invention are directed to methods of making the compounds.

In contrast to known FAK inhibitors, compounds of the present invention are potent against FAK and have fewer off-targets. As described in the working examples, in a panel of 403 kinases, inventive compound 3 (FAK $IC_{50}$ 62 nM) engages only 4 other kinases with greater than 65% inhibition at 10 µM concentration.

BRIEF DESCRIPTION OF THE DRAWINGS

FIG. 2 is a TREEspot plot showing the high degree of selectivity of inventive compound 5 across a panel of >400 kinases

DETAILED DESCRIPTION OF THE INVENTION

Figure 1:
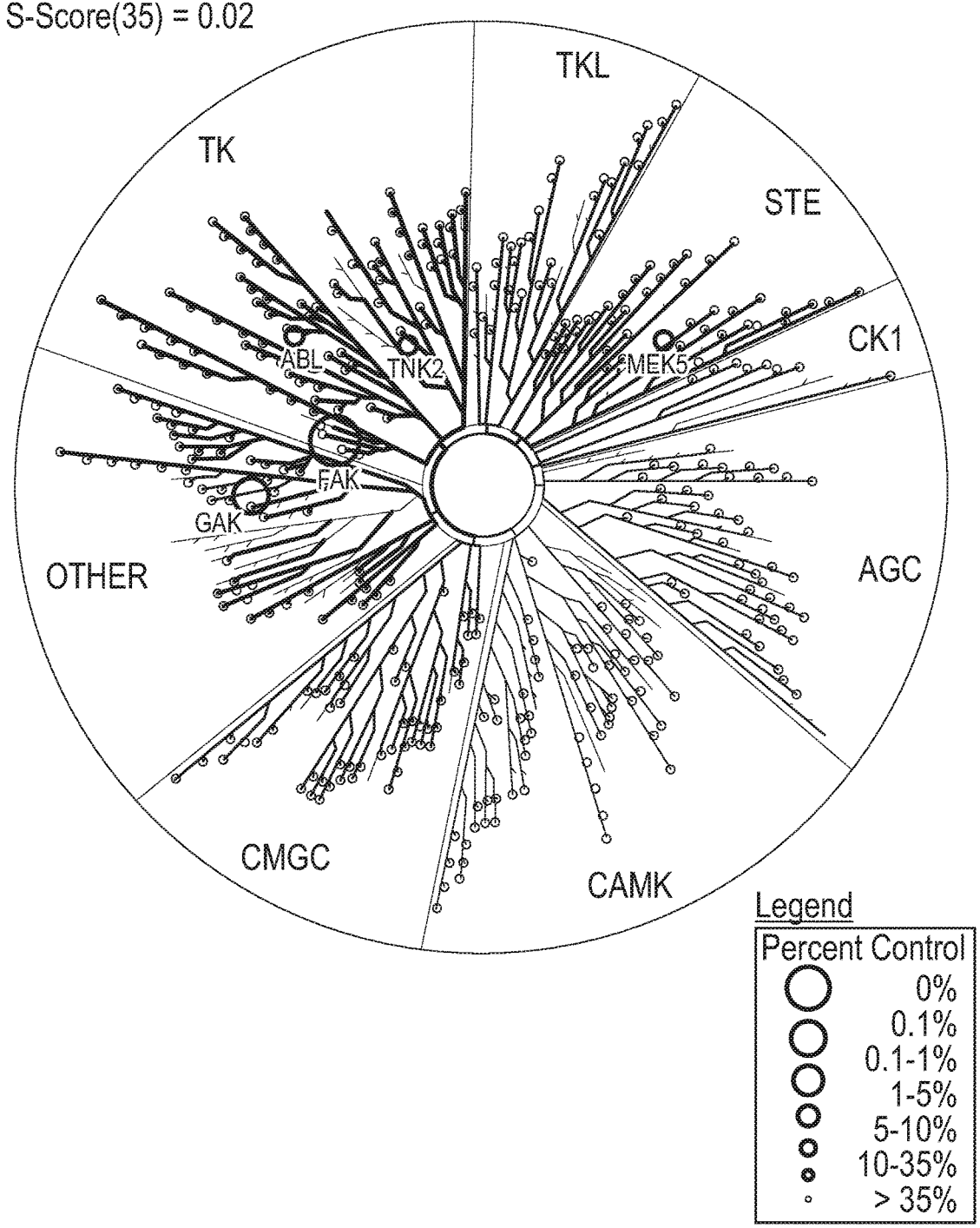
FIG. 1 is a TREEspot plot showing the high degree of selectivity of inventive compound 3 across a panel of >400 kinases.

Unless defined otherwise, all technical and scientific terms used herein have the same meaning as is commonly understood by one of skill in the art to which the subject matter herein belongs. As used in the specification and the appended claims, unless specified to the contrary, the following terms have the meaning indicated in order to facilitate the understanding of the present invention.

As used in the description and the appended claims, the singular forms "a", "an", and "the" include plural referents unless the context clearly dictates otherwise. Thus, for example, reference to "a composition" includes mixtures of two or more such compositions, reference to "an inhibitor" includes mixtures of two or more such inhibitors, and the like.

Unless stated otherwise, the term "about" means within 10% (e.g., within 5%, 2% or 1%) of the particular value modified by the term "about."

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

With respect to compounds of the present invention, and to the extent the following terms are used herein to further describe them, the following definitions apply.

As used herein, the term "alkyl" refers to a saturated linear or branched-chain monovalent hydrocarbon radical. In one embodiment, the alkyl radical is a $C_1$-$C_{18}$ group. In other embodiments, the alkyl radical is a $C_0$-$C_6$, $C_0$-$C_5$, $C_0$-$C_3$, $C_1$-$C_{12}$, $C_1$-$C_8$, $C_1$-$C_6$, $C_1$-$C_5$, $C_1$-$C_4$ or $C_1$-$C_3$ group (wherein $C_0$ alkyl refers to a bond). Examples of alkyl groups include methyl, ethyl, 1-propyl, 2-propyl, i-propyl, 1-butyl, 2-methyl-1-propyl, 2-butyl, 2-methyl-2-propyl, 1-pentyl, n-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, heptyl, octyl, nonyl, decyl, undecyl and dodecyl. In some embodiments, an alkyl group is a $C_1$-$C_3$ alkyl group.

As used herein, the term "alkylene" refers to a straight or branched divalent hydrocarbon chain linking the rest of the molecule to a radical group, consisting solely of carbon and hydrogen, containing no unsaturation and having from one to 12 carbon atoms, for example, methylene, ethylene, propylene, n-butylene, and the like. The alkylene chain may be attached to the rest of the molecule through a single bond and to the radical group through a single bond. In some embodiments, the alkylene group contains one to 8 carbon atoms ($C_1$-$C_8$ alkylene). In other embodiments, an alkylene group contains one to 5 carbon atoms ($C_1$-$C_5$ alkylene). In other embodiments, an alkylene group contains one to 4 carbon atoms ($C_1$-$C_4$ alkylene). In other embodiments, an alkylene contains one to three carbon atoms ($C_1$-$C_3$ alkylene). In other embodiments, an alkylene group contains one to two carbon atoms ($C_1$-$C_2$ alkylene). In other embodiments, an alkylene group contains one carbon atom ($C_1$ alkylene).

As used herein, the term "cyclic group" broadly refers to any group that used alone or as part of a larger moiety, contains a saturated, partially saturated or aromatic ring system e.g., carbocyclic (cycloalkyl, cycloalkenyl), heterocyclic (heterocycloalkyl, heterocycloalkenyl), aryl and heteroaryl groups. Cyclic groups may have one or more (e.g., fused) ring systems. Thus, for example, a cyclic group can contain one or more carbocyclic, heterocyclic, aryl or heteroaryl groups.

As used herein, the term "carbocyclic" (also "carbocyclyl") refers to a group that used alone or as part of a larger moiety, contains a saturated, partially unsaturated, or aromatic ring system having 3 to 20 carbon atoms, that is alone or part of a larger moiety (e.g., an alkcarbocyclic group). The term carbocyclyl includes mono-, bi-, tri-, fused, bridged, and spiro-ring systems, and combinations thereof. In one embodiment, carbocyclyl includes 3 to 15 carbon atoms ($C_3$-$C_{15}$). In one embodiment, carbocyclyl includes 3 to 12 carbon atoms ($C_3$-$C_{12}$). In another embodiment, carbocyclyl includes $C_3$-$C_8$, $C_3$-$C_{10}$ or $C_5$-$C_{10}$. In another embodiment, carbocyclyl, as a monocycle, includes $C_3$-$C_8$, $C_3$-$C_6$ or $C_5$-$C_6$. In some embodiments, carbocyclyl, as a bicycle, includes $C_7$-$C_{12}$. In another embodiment, carbocyclyl, as a Spiro system, includes $C_5$-$C_{12}$. Representative examples of monocyclic carbocyclyls include cyclopropyl, cyclobutyl, cyclopentyl, 1-cyclopent-1-enyl, 1-cyclopent-2-enyl, 1-cyclopent-3-enyl, cyclohexyl, perdeuteriocyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, phenyl, and cyclododecyl; bicyclic carbocyclyls having 7 to 12 ring atoms include [4,3], [4,4], [4,5], [5,5], [5,6] or [6,6] ring systems, such as for example bicyclo[2.2.1]heptane, bicyclo[2.2.2]octane, naphthalene, and bicyclo[3.2.2]nonane. Representative examples of spiro carbocyclyls include spiro[2.2]pentane, spiro[2.3]hexane, spiro[2.4]heptane, spiro[2.5]octane and spiro[4.5]decane. The term carbocyclyl includes aryl ring systems as defined herein. The term carbocycyl also includes cycloalkyl rings (e.g., saturated or partially unsaturated mono-, bi-, or spiro-carbocycles). The term carbocyclic group also includes a carbocyclic ring fused to one or more (e.g., 1, 2 or 3) different cyclic groups (e.g., aryl or heterocyclic rings), where the radical or point of attachment is on the carbocyclic ring.

Thus, the term carbocyclic also embraces carbocyclylalkyl groups which as used herein refer to a group of the formula —R$^c$-carbocyclyl where W is an alkylene chain. The term carbocyclic also embraces carbocyclylalkoxy groups which as used herein refer to a group bonded through an oxygen atom of the formula —O—R$^c$-carbocyclyl where R$^c$ is an alkylene chain.

As used herein, the term "heterocyclyl" refers to a "carbocyclyl" that used alone or as part of a larger moiety, contains a saturated, partially unsaturated or aromatic ring system, wherein one or more (e.g., 1, 2, 3, or 4) carbon atoms have been replaced with a heteroatom (e.g., O, N, N(O), S, S(O), or S(O)$_2$). The term heterocyclyl includes mono-, bi-, tri-, fused, bridged, and spiro-ring systems, and combinations thereof. In some embodiments, a heterocyclyl refers to a 3 to 15 membered heterocyclyl ring system. In some embodiments, a heterocyclyl refers to a 3 to 12 membered heterocyclyl ring system. In some embodiments, a heterocyclyl refers to a saturated ring system, such as a 3 to 12 membered saturated heterocyclyl ring system. In some embodiments, a heterocyclyl refers to a heteroaryl ring system, such as a 5 to 14 membered heteroaryl ring system. The term heterocyclyl also includes C$_3$-C$_8$ heterocycloalkyl, which is a saturated or partially unsaturated mono-, bi-, or spiro-ring system containing 3-8 carbons and one or more (1, 2, 3 or 4) heteroatoms.

In some embodiments, a heterocyclyl group includes 3-12 ring atoms and includes monocycles, bicycles, tricycles and spiro ring systems, wherein the ring atoms are carbon, and one to 5 ring atoms is a heteroatom such as nitrogen, sulfur or oxygen. In some embodiments, heterocyclyl includes 3- to 7-membered monocycles having one or more heteroatoms selected from nitrogen, sulfur or oxygen. In some embodiments, heterocyclyl includes 4- to 6-membered monocycles having one or more heteroatoms selected from nitrogen, sulfur or oxygen. In some embodiments, heterocyclyl includes 3-membered monocycles. In some embodiments, heterocyclyl includes 4-membered monocycles. In some embodiments, heterocyclyl includes 5-6 membered monocycles. In some embodiments, the heterocyclyl group includes 0 to 3 double bonds. In any of the foregoing embodiments, heterocyclyl includes 1, 2, 3 or 4 heteroatoms. Any nitrogen or sulfur heteroatom may optionally be oxidized (e.g., NO, SO, SO$_2$), and any nitrogen heteroatom may optionally be quaternized (e.g., [NR$_4$]$^+$Cl$^-$, [NR$_4$]$^+$OH$^-$). Representative examples of heterocyclyls include oxiranyl, aziridinyl, thiiranyl, azetidinyl, oxetanyl, thietanyl, 1,2-dithietanyl, 1,3-dithietanyl, pyrrolidinyl, dihydro-1H-pyrrolyl, dihydrofuranyl, tetrahydropyranyl, dihydrothienyl, tetrahydrothienyl, imidazolidinyl, piperidinyl, piperazinyl, morpholinyl, thiomorpholinyl, 1,1-dioxo-thiomorpholinyl, dihydropyranyl, tetrahydropyranyl, hexahydrothiopyranyl, hexahydropyrimidinyl, oxazinanyl, thiazinanyl, thioxanyl, homopiperazinyl, homopiperidinyl, azepanyl, oxepanyl, thiepanyl, oxazepinyl, oxazepanyl, diazepanyl, 1,4-diazepanyl, diazepinyl, thiazepinyl, thiazepanyl, tetrahydrothiopyranyl, oxazolidinyl, thiazolidinyl, isothiazolidinyl, 1,1-dioxoisothiazolidinonyl, oxazolidinonyl, imidazolidinonyl, 4,5,6,7-tetrahydro[2H]indazolyl, tetrahydrobenzoimidazolyl, 4,5,6,7-tetrahydrobenzo[d]imidazolyl, 1,6-dihydroimidazol[4,5-d]pyrrolo[2,3-b]pyridinyl, thiazinyl, thiophenyl, oxazinyl, thiadiazinyl, oxadiazinyl, dithiazinyl, dioxazinyl, oxathiazinyl, thiatriazinyl, oxatriazinyl, dithiadiazinyl, imidazolinyl, dihydropyrimidyl, tetrahydropyrimidyl, 1-pyrrolinyl, 2-pyrrolinyl, 3-pyrrolinyl, indolinyl, thiapyranyl, 2H-pyranyl, 4H-pyranyl, dioxanyl, 1,3-dioxolanyl, pyrazolinyl, pyrazolidinyl, dithianyl, dithiolanyl, pyrimidinonyl, pyrimidindionyl, pyrimidin-2,4-dionyl, piperazinonyl, piperazindionyl, pyrazolidinylimidazolinyl, 3-azabicyclo[3.1.0]hexanyl, 3,6-diazabicyclo[3.1.1]heptanyl, 6-azabicyclo[3.1.1]heptanyl, 3-azabicyclo[3.1.1]heptanyl, 3-azabicyclo[4.1.0]heptanyl, azabicyclo[2.2.2]hexanyl, 2-azabicyclo[3.2.1]octanyl, 8-azabicyclo[3.2.1]octanyl, 2-azabicyclo[2.2.2]octanyl, 8-azabicyclo[2.2.2]octanyl, 7-oxabicyclo[2.2.1]heptane, azaspiro[3.5]nonanyl, azaspiro[2.5]octanyl, azaspiro[4.5]decanyl, 1-azaspiro[4.5]decan-2-only, azaspiro[5.5]undecanyl, tetrahydroindolyl, octahydroindolyl, tetrahydroisoindolyl, tetrahydroindazolyl, 1,1-dioxohexahydrothiopyranyl. Examples of 5-membered heterocyclyls containing a sulfur or oxygen atom and one to three nitrogen atoms are thiazolyl, including thiazol-2-yl and thiazol-2-yl N-oxide, thiadiazolyl, including 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Example 5-membered ring heterocyclyls containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Representative examples of benzo-fused 5-membered heterocyclyls are benzoxazol-2-yl, benzthiazol-2-yl and benzimidazol-2-yl. Example 6-membered heterocyclyls contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are yet other examples of heterocyclyl groups. In some embodiments, a heterocyclic group includes a heterocyclic ring fused to one or more (e.g., 1, 2 or 3) different cyclic groups (e.g., carbocyclic rings or heterocyclic rings), where the radical or point of attachment is on the heterocyclic ring, and in some embodiments wherein the point of attachment is a heteroatom contained in the heterocyclic ring.

Thus, the term heterocyclic embraces N-heterocyclyl groups which as used herein refer to a heterocyclyl group containing at least one nitrogen and where the point of attachment of the heterocyclyl group to the rest of the molecule is through a nitrogen atom in the heterocyclyl group. Representative examples of N-heterocyclyl group include 1-morpholinyl, 1-piperidinyl, 1-piperazinyl, 1-pyrrolidinyl, pyrazolidinyl, imidazolinyl and imidazolidinyl. The term heterocyclic also embraces C-heterocyclyl groups which as used herein refer to a heterocyclyl group containing at least one heteroatom and where the point of attachment of the heterocyclyl group to the rest of the molecule is through a carbon atom in the heterocyclyl group. Representative examples of C-heterocyclyl radicals include 2-morpholinyl, 2- or 3- or 4-piperidinyl, 2-piperazinyl, and 2- or 3-pyrrolidinyl. The term heterocyclic also embraces heterocyclylalkyl groups which as disclosed above refer to a group of the formula —R$^c$-heterocyclyl where R$^c$ is an alkylene chain. The term heterocyclic also embraces heterocyclylalkoxy groups which as used herein refer to a radical bonded through an oxygen atom of the formula —O—R$^c$-heterocyclyl where R$^c$ is an alkylene chain.

As used herein, the term "aryl" used alone or as part of a larger moiety (e.g., "aralkyl", wherein the terminal carbon atom on the alkyl group is the point of attachment, e.g., a benzyl group), "aralkoxy" wherein the oxygen atom is the point of attachment, or "aroxyalkyl" wherein the point of attachment is on the aryl group) refers to a group that includes monocyclic, bicyclic or tricyclic, carbon ring system, that includes fused rings, wherein at least one ring in the system is aromatic. In some embodiments, the aralkoxy group is a benzoxy group. The term "aryl" may be used interchangeably with the term "aryl ring". In one embodiment, aryl includes groups having 6-18 carbon atoms. In another embodiment, aryl includes groups having 6-10 carbon atoms. Examples of aryl groups include phenyl, naphthyl, anthracyl, biphenyl, phenanthrenyl, naphthacenyl, 1,2,3,4-tetrahydronaphthalenyl, 1H-indenyl, 2,3-dihydro-1H-indenyl, naphthyridinyl, and the like, which may be substituted or independently substituted by one or more substituents described herein. A particular aryl is phenyl. In some embodiments, an aryl group includes an aryl ring fused to one or more (e.g., 1, 2 or 3) different cyclic groups (e.g., carbocyclic rings or heterocyclic rings), where the radical or point of attachment is on the aryl ring.

Thus, the term aryl embraces aralkyl groups (e.g., benzyl) which as disclosed above refer to a group of the formula —$R^c$-aryl where $R^c$ is an alkylene chain such as methylene or ethylene. In some embodiments, the aralkyl group is an optionally substituted benzyl group. The term aryl also embraces aralkoxy groups which as used herein refer to a group bonded through an oxygen atom of the formula —O—$R^c$-aryl where $R^c$ is an alkylene chain such as methylene or ethylene.

As used herein, the term "heteroaryl" used alone or as part of a larger moiety (e.g., "heteroarylalkyl" (also "heteroaralkyl"), or "heteroarylalkoxy" (also "heteroaralkoxy"), refers to a monocyclic, bicyclic or tricyclic ring system having 5 to 14 ring atoms, wherein at least one ring is aromatic and contains at least one heteroatom. In one embodiment, heteroaryl includes a 5-6 membered monocyclic aromatic groups where one or more ring atoms is nitrogen, sulfur or oxygen. Representative examples of heteroaryl groups include thienyl, furyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, imidazopyridyl, pyrazinyl, pyridazinyl, triazinyl, tetrazinyl, tetrazolo[1,5-b]pyridazinyl, purinyl, deazapurinyl, benzoxazolyl, benzofuryl, benzothiazolyl, benzothiadiazolyl, benzotriazolyl, benzoimidazolyl, indolyl, 1,3-thiazol-2-yl, 1,3,4-triazol-5-yl, 1,3-oxazol-2-yl, 1,3,4-oxadiazol-5-yl, 1,2,4-oxadiazol-5-yl, 1,3,4-thiadiazol-5-yl, 1H-tetrazol-5-yl, 1,2,3-triazol-5-yl, and pyrid-2-yl N-oxide. The term "heteroaryl" also includes groups in which a heteroaryl is fused to one or more cyclic (e.g., carbocyclyl, or heterocyclyl) rings, where the radical or point of attachment is on the heteroaryl ring. Nonlimiting examples include indolyl, indolizinyl, isoindolyl, benzothienyl, benzothiophenyl, methylenedioxyphenyl, benzofuranyl, dibenzofuranyl, indazolyl, benzimidazolyl, benzodioxazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl and pyrido[2,3-b]-1,4-oxazin-3(4H)-one. A heteroaryl group may be mono-, bi- or tri-cyclic. In some embodiments, a heteroaryl group includes a heteroaryl ring fused to one or more (e.g., 1, 2 or 3) different cyclic groups (e.g., carbocyclic rings or heterocyclic rings), where the radical or point of attachment is on the heteroaryl ring, and in some embodiments wherein the point of attachment is a heteroatom contained in the heterocyclic ring.

Thus, the term heteroaryl embraces N-heteroaryl groups which as used herein refer to a heteroaryl group as defined above containing at least one nitrogen and where the point of attachment of the heteroaryl group to the rest of the molecule is through a nitrogen atom in the heteroaryl group. The term heteroaryl also embraces C-heteroaryl groups which as used herein refer to a heteroaryl group as defined above and where the point of attachment of the heteroaryl group to the rest of the molecule is through a carbon atom in the heteroaryl group. The term heteroaryl also embraces heteroarylalkyl groups which as disclosed above refer to a group of the formula —$R^c$-heteroaryl, wherein $R^c$ is an alkylene chain as defined above. The term heteroaryl also embraces heteroaralkoxy (or heteroarylalkoxy) groups which as used herein refer to a group bonded through an oxygen atom of the formula —O—$R^c$-heteroaryl, where $R^c$ is an alkylene group as defined above.

Any of the groups described herein may be substituted or unsubstituted. As used herein, the term "substituted" broadly refers to all permissible substituents with the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc. Representative substituents include halogens, hydroxyl groups, and any other organic groupings containing any number of carbon atoms, e.g., 1-14 carbon atoms, and which may include one or more (e.g., 1, 2, 3, or 4) heteroatoms such as oxygen, sulfur, and nitrogen grouped in a linear, branched, or cyclic structural format.

Representative examples of substituents may thus include alkyl, substituted alkyl (e.g., $C_1$-$C_6$, $C_1$-$C_5$, $C_1$-$C_4$, $C_1$-$C_3$, $C_1$-$C_2$, $C_1$), alkoxy (e.g., $C_1$-$C_6$, $C_1$-$C_5$, $C_1$-$C_4$, $C_1$-$C_3$, $C_1$-$C_2$, $C_1$), substituted alkoxy (e.g., $C_1$-$C_6$, $C_1$-$C_5$, $C_1$-$C_4$, $C_1$-$C_3$, $C_1$-$C_2$, haloalkyl (e.g., $CF_3$), alkenyl (e.g., $C_2$-$C_6$, $C_2$-$C_5$, $C_2$-$C_4$, $C_2$-$C_3$, $C_2$), substituted alkenyl (e.g., $C_2$-$C_6$, $C_2$-$C_5$, $C_2$-$C_4$, $C_2$-$C_3$, $C_2$), alkynyl (e.g., $C_2$-$C_6$, $C_2$-$C_5$, $C_2$-$C_4$, $C_2$-$C_3$, $C_2$), substituted alkynyl (e.g., $C_2$-$C_6$, $C_2$-$C_5$, $C_2$-$C_4$, $C_2$-$C_3$, $C_2$), cyclic (e.g., $C_3$-$C_{12}$, $C_5$-$C_6$), substituted cyclic (e.g., $C_3$-$C_{12}$, $C_5$-$C_6$), carbocyclic (e.g., $C_3$-$C_{12}$, $C_5$-$C_6$), substituted carbocyclic (e.g., $C_3$-$C_{12}$, $C_5$-$C_6$), heterocyclic (e.g., $C_3$-$C_{12}$, $C_5$-$C_6$), substituted heterocyclic (e.g., $C_3$-$C_{12}$, $C_5$-$C_6$), aryl (e.g., benzyl and phenyl), substituted aryl (e.g., substituted benzyl or phenyl), heteroaryl (e.g., pyridyl or pyrimidyl), substituted heteroaryl (e.g., substituted pyridyl or pyrimidyl), aralkyl (e.g., benzyl), substituted aralkyl (e.g., substituted benzyl), halo, hydroxyl, aryloxy (e.g., $C_6$-$C_{12}$, $C_6$), substituted aryloxy (e.g., $C_6$-$C_{12}$, $C_6$), alkylthio (e.g., $C_1$-$C_6$), substituted alkylthio (e.g., $C_1$-$C_6$), arylthio (e.g., $C_6$-$C_{12}$, $C_6$), substituted arylthio (e.g., $C_6$-$C_{12}$, $C_6$), cyano, carbonyl, substituted carbonyl, carboxyl, substituted carboxyl, amino, substituted amino, amido, substituted amido, thio, substituted thio, sulfinyl, substituted sulfinyl, sulfonyl, substituted sulfonyl, sulfinamide, substituted sulfinamide, sulfonamide, substituted sulfonamide, urea, substituted urea, carbamate, substituted carbamate, amino acid, and peptide groups.

Broadly, the compounds of the invention are represented by a structure of formula I:

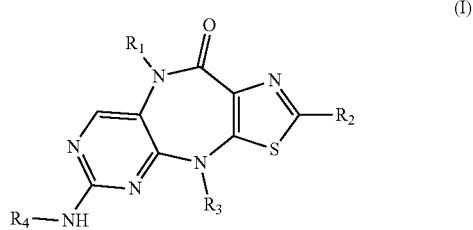

(I)

wherein:
R₁ is hydrogen, optionally substituted alkyl, optionally substituted carbocyclyl, or optionally substituted heterocyclyl;
R₂ is hydrogen, optionally substituted alkyl, optionally substituted carbocyclyl, or optionally substituted heterocyclyl;
R₃ is hydrogen, optionally substituted alkyl, optionally substituted carbocyclyl, or optionally substituted heterocyclyl;
R₄ is optionally substituted pyrazolyl, optionally substituted pyridinyl, optionally substituted benzopiperidinyl,

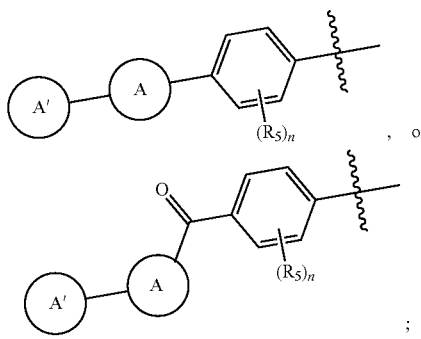

each R₅ is independently H, OH, CN, alkyl, alkoxy, halo, haloalkyl, haloalkoxy, amino, acyl, or amide;
n is 0, 1, or 2;

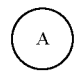

is an optionally substituted amide or an optionally substituted heterocycle;

is absent if

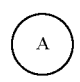

is an optionally substituted amide, and if

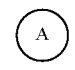

is optionally substituted heterocycle,

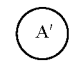

is absent, optionally substituted piperidinyl or optionally substituted piperazinyl;
or a pharmaceutically acceptable salt or stereoisomer thereof.

In some embodiments, R₄ is optionally substituted pyrazolyl and the compounds of the present invention have a structure represented by formula (Ia):

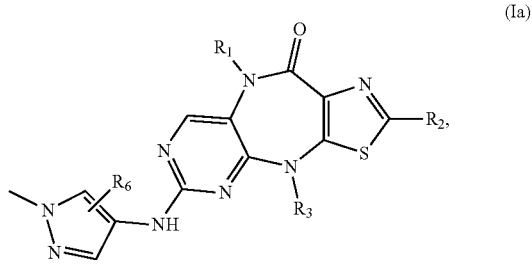

(Ia)

wherein
R₆ is H, alkyl, or alkoxy,
or a pharmaceutically acceptable salt or stereoisomer thereof.

In some embodiments, R₄ is optionally substituted pyridinyl and the compounds of the present invention have a structure represented by formula (Ib):

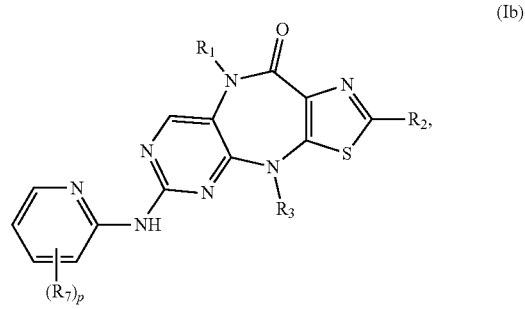

(Ib)

wherein
each R₇ is independently alkyl, alkoxy, or optionally substituted heterocyclyl; and
p is 0, 1, or 2,
or a pharmaceutically acceptable salt or stereoisomer thereof.

In some embodiments, R₄ is optionally substituted benzopiperidinyl and the compounds of the present invention have a structure represented by formula (Ic):

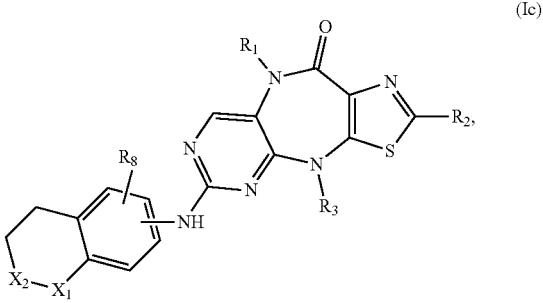

(Ic)

wherein $R_8$ is H, alkyl, or alkoxy;

$X_1$ represents NH or $CH_2$; and $X_2$ represents C=O or NMe;

provided that when $X_1$ represents NH, $X_2$ represents C=O, and when $X_1$ represents $CH_2$, $X_2$ represents NMe;

or a pharmaceutically acceptable salt or stereoisomer thereof.

In some embodiments, $R_4$ is

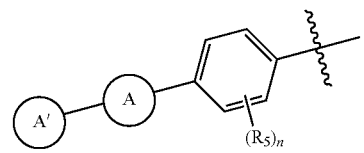

and the compounds of the present invention have a structure represented by formula (Id):

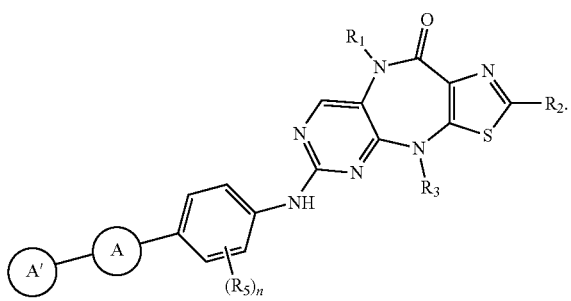

(Id)

In some embodiments,

is an amide and

is absent and the compounds of the present invention have a structure represented by formula (Id1):

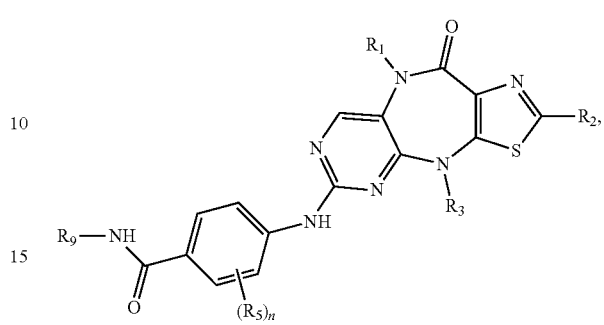

(Id1)

wherein $R_9$ is $C_1$-$C_6$ alkyl, or a pharmaceutically acceptable salt or stereoisomer thereof.

In some embodiments,

is an optionally substituted heterocycle and

is absent and the compounds of the present invention have a structure represented by formula (Id2):

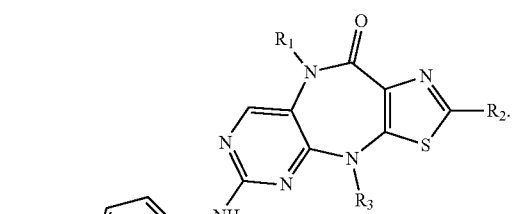

(Id2)

In some embodiments,

is optionally substituted piperidinyl and the compounds of the present invention have a structure represented by formula (Id2a):

(Id2a)

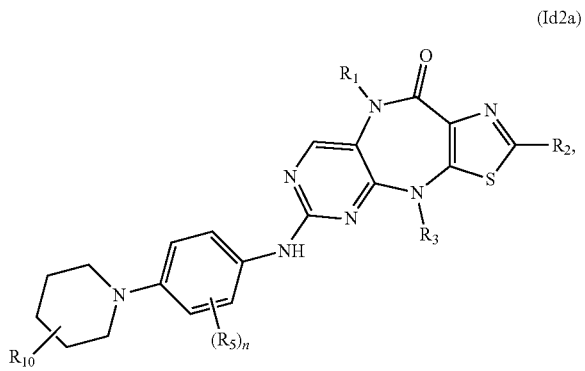

$R_{10}$ is H, OH, $C_1$-$C_6$ alkyl, $C_1$-$C_6$ alkoxy, or halo;
or a pharmaceutically acceptable salt or stereoisomer thereof.

In some embodiments,

Ⓐ is piperazinyl and the compounds of the present invention have a structure represented by formula (Id2b):

(Id2b)

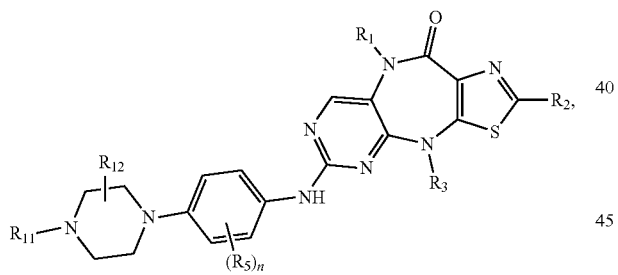

$R_{11}$ is H, $SO_2Me$, or optionally substituted $C_1$-$C_4$ alkyl; and $R_{12}$ is H or $C_1$-$C_6$ alkyl;
or a pharmaceutically acceptable salt or stereoisomer thereof.

In some embodiments,

Ⓐ is optionally substituted piperidinyl and the compounds of the present invention have a structure represented by formula (Id2c):

(Id2c)

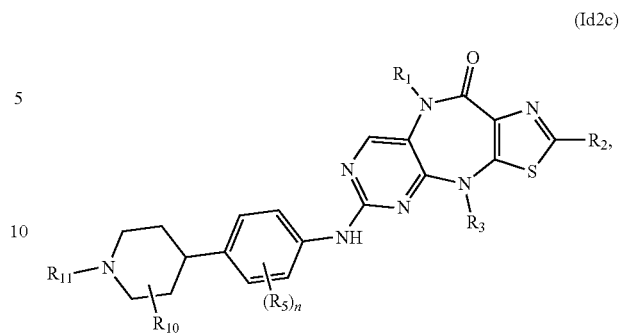

$R_{10}$ is H, OH, $C_1$-$C_6$ alkyl, $C_1$-$C_6$ alkoxy, or halo; and
$R_{11}$ is H, $SO_2Me$, or optionally substituted $C_1$-$C_4$ alkyl;
or a pharmaceutically acceptable salt or stereoisomer thereof.

In some embodiments,

Ⓐ is an optionally substituted heterocycle and

Ⓐ' is piperazinyl and the compounds of the present invention have a structure represented by formula (Id3):

(Id3)

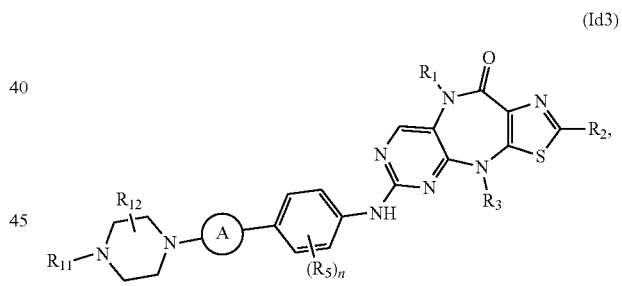

$R_{11}$ is H, $SO_2Me$, or optionally substituted $C_1$-$C_4$ alkyl; and $R_{12}$ is H or $C_1$-$C_6$ alkyl;
or a pharmaceutically acceptable salt or stereoisomer thereof.

In some embodiments,

Ⓐ is piperidinyl and

Ⓐ' is piperazinyl and the compounds of the present invention have a structure represented by formula (Id3a):

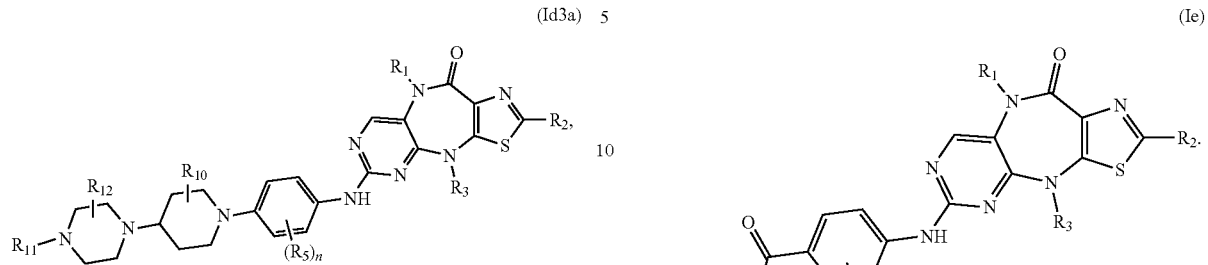
(Id3a)

$R_{10}$ is H, $C_1$-$C_6$ alkyl, $C_1$-$C_6$ alkoxy, or halo;
$R_{11}$ is H, $SO_2Me$, or optionally substituted $C_1$-$C_4$ alkyl; and
$R_{12}$ is H or $C_1$-$C_6$ alkyl;
or a pharmaceutically acceptable salt or stereoisomer thereof.

In some embodiments,

is piperazinyl and


is piperidinyl and the compounds of the present invention have a structure represented by formula (Id3b):

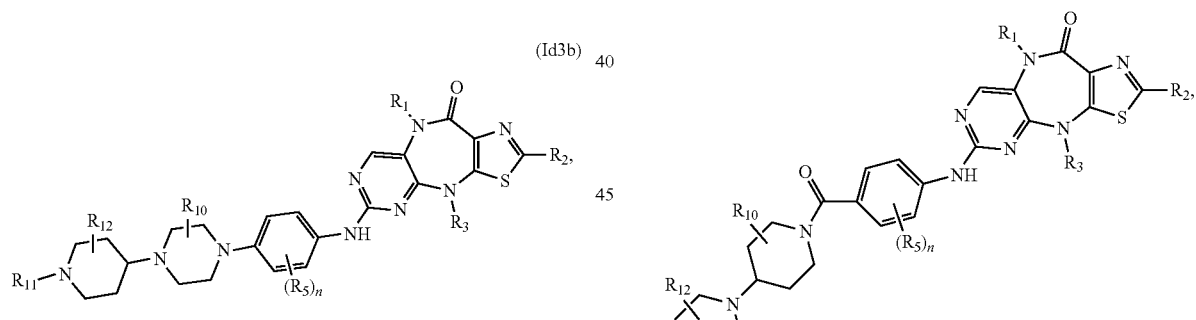
(Id3b)

$R_{10}$ is H, $C_1$-$C_6$ alkyl, $C_1$-$C_6$ alkoxy, or halo;
$R_{11}$ is H, $SO_2Me$, or optionally substituted $C_1$-$C_4$ alkyl; and
$R_{12}$ is H or $C_1$-$C_6$ alkyl;
or a pharmaceutically acceptable salt or stereoisomer thereof.

In some embodiments, $R_4$ is

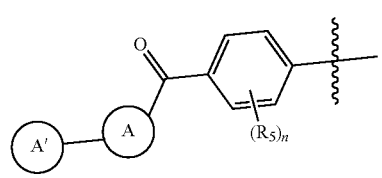

and the compounds of the present invention have a structure represented by formula (Ie):

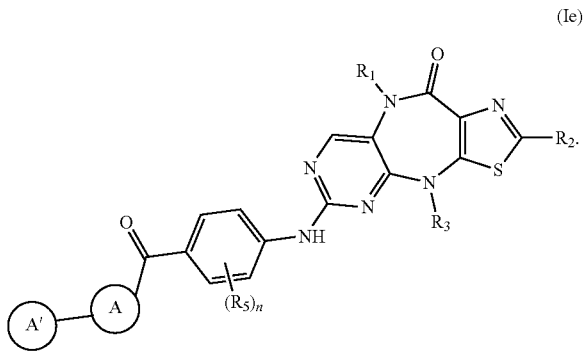
(Ie)

In some embodiments,


is piperidinyl and

is piperazinyl and the compounds of the present invention have a structure represented by formula (Ie1):

(Ie1)

$R_{10}$ is H, $C_1$-$C_6$ alkyl, $C_1$-$C_6$ alkoxy, or halo;
$R_{11}$ is H, $SO_2Me$, or optionally substituted $C_1$-$C_4$ alkyl; and
$R_{12}$ is H or $C_1$-$C_6$ alkyl;
or a pharmaceutically acceptable salt or stereoisomer thereof.

In some embodiments,

is an optionally substituted heterocycle and is substituted with 0-4 substituents, independently selected from Me, OH, (Ia)-(Ie), may be independently Me, Et, i-Pr, n-Pr, OH, Ph, OMe, OEt, CF$_3$, CH$_2$CF$_3$, OCH$_2$CF$_3$.

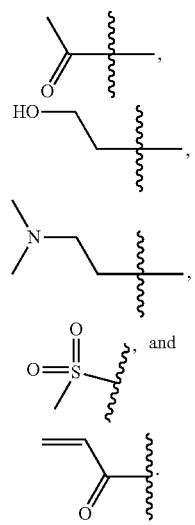

In some embodiments, R$_5$ is OH, CN, alkyl, alkoxy, halo, haloalkyl, haloalkoxy, amino, acyl, or amide.

In certain embodiments, R$_5$ is Me, OMe, OEt, n-Pr, OCH$_2$CF$_3$,

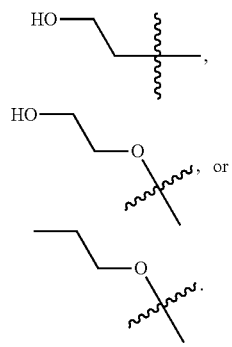

In some embodiments, R$_3$ is H, methyl, ethyl, i-Pr, n-Pr, or CH$_2$CF$_3$.

In some embodiments, R$_2$ is H, methyl, ethyl, i-Pr, CH$_2$CF$_3$, or Ph.

In some embodiments, R$_1$ is H, methyl, ethyl, i-Pr, n-Pr, or CH$_2$CF$_3$.

In certain embodiments, R$_2$ and R$_3$ are methyl. In certain embodiments, R$_1$ and R$_3$ are methyl. In certain embodiments, R$_2$ and R$_3$ are methyl and R$_1$ is H. In other embodiments, R$_1$, R$_2$, and R$_3$ each are methyl.

In some embodiments, R$_6$ is H or Me.

In some embodiments, R$_7$ is OMe or

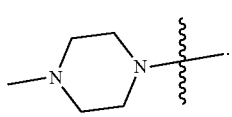 [SMILES: *N1CCN(C)CC1]

In some embodiments, R$_8$ is H or OMe.

In some embodiments, the optional substituents for any of the aforementioned groups in any of formulae (I), e.g.,

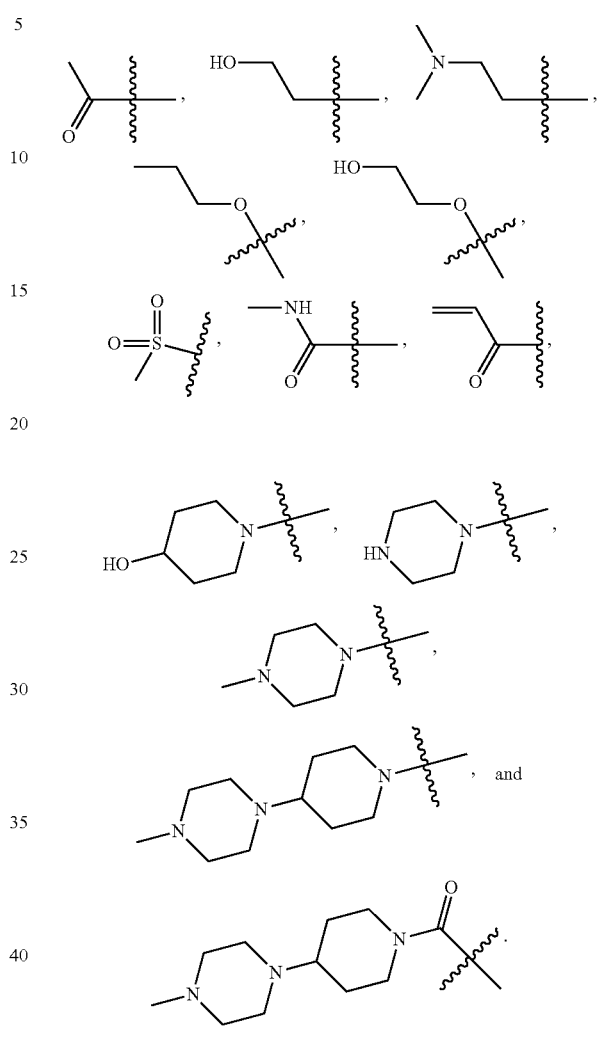

In some embodiments, the compounds of the present invention are represented by any of the following structures:

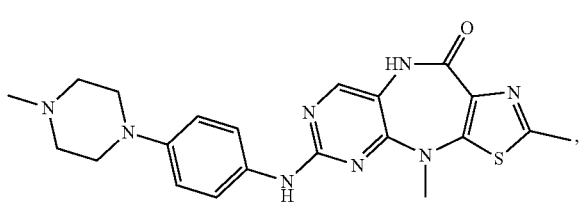

(1)

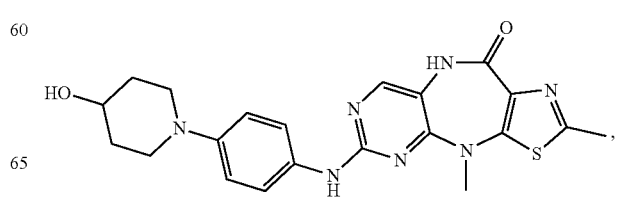

(2)

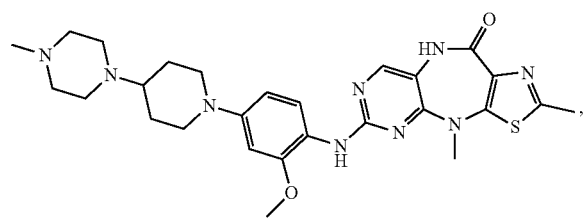
(3)
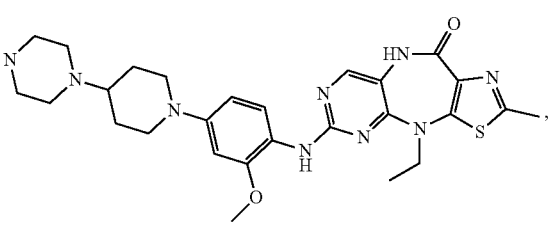
(9)
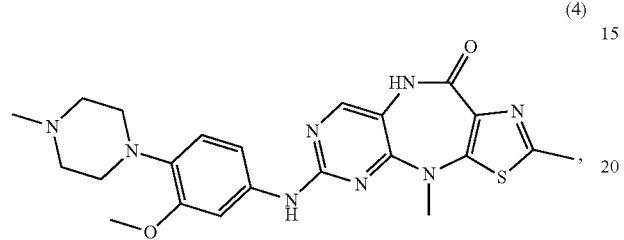
(4)
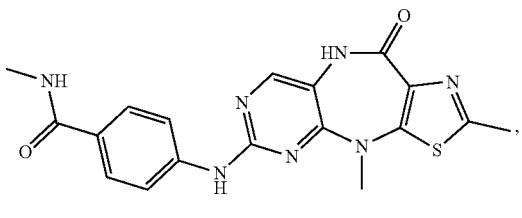
(10)
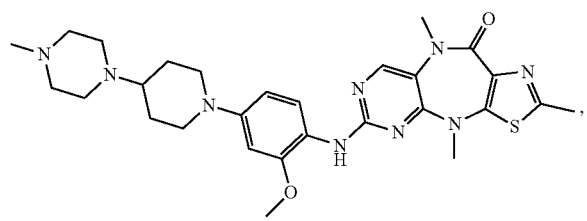
(5)
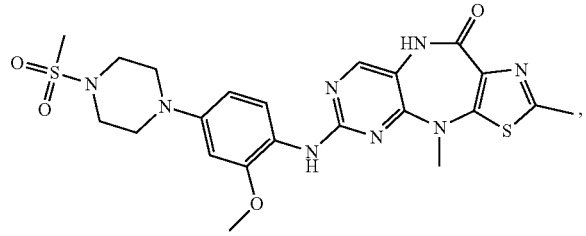
(11)
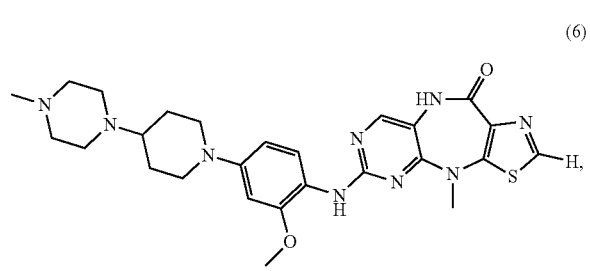
(6)
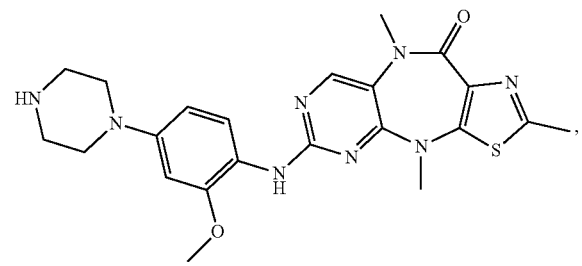
(12)
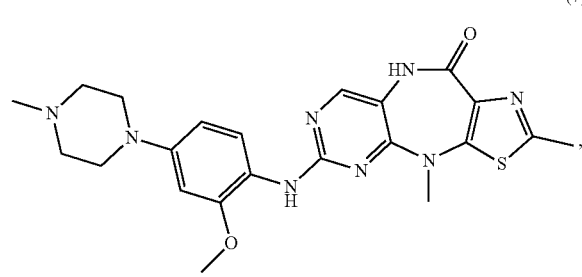
(7)
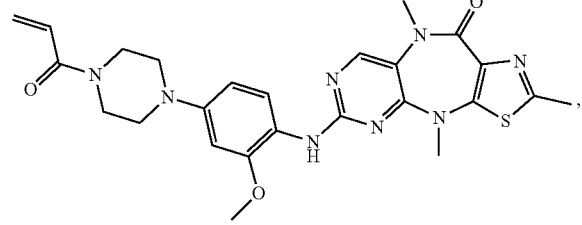
(13)
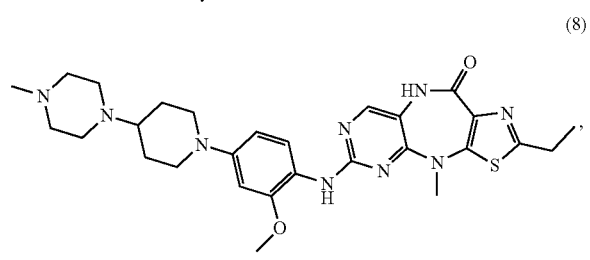
(8)
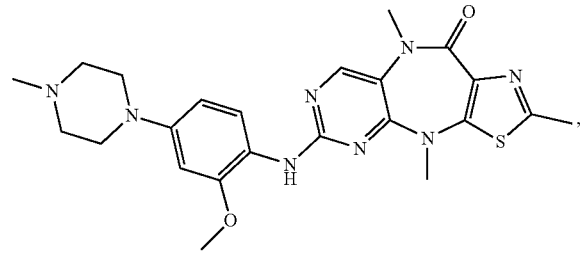
(14)

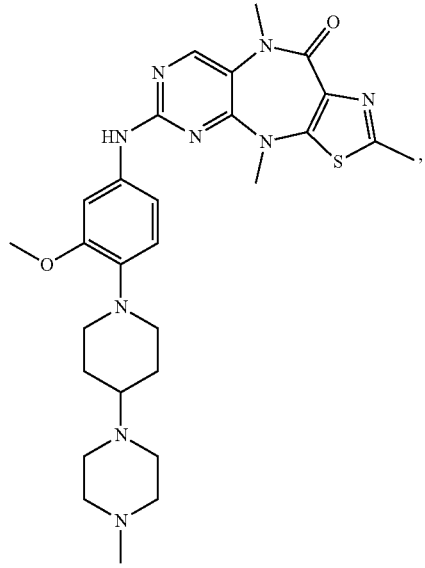
(15)
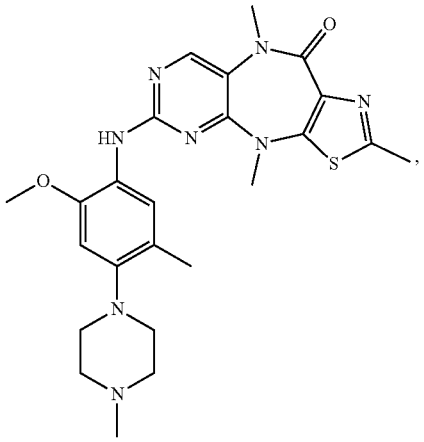
(18)
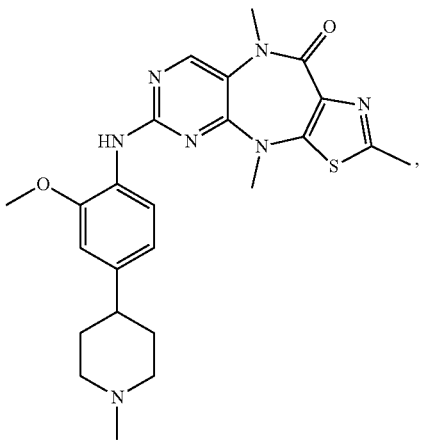
(19)
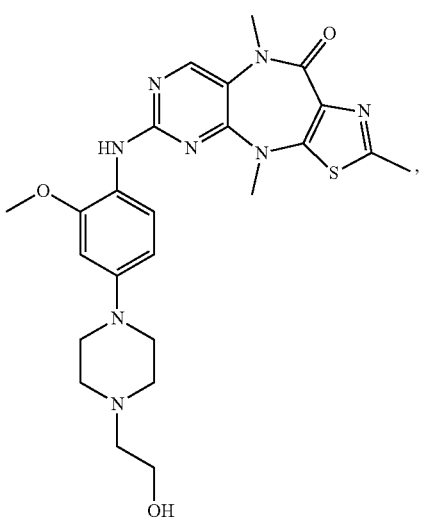
(16)
(17)
(20)

-continued
(21)
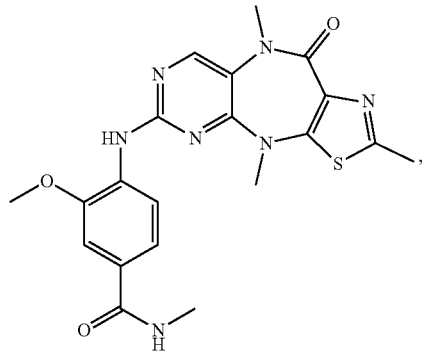
(22)
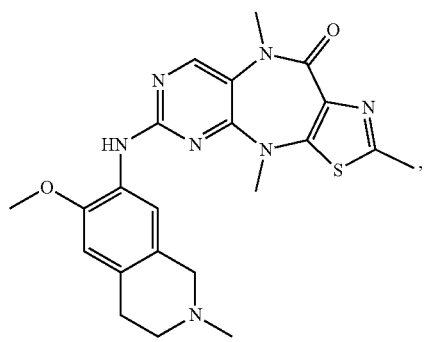
(23)
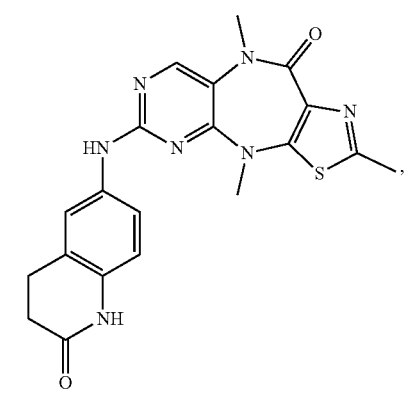
(24)
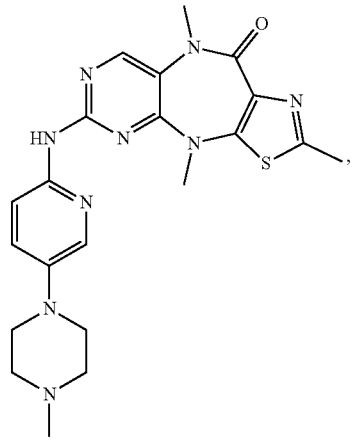
-continued
(25)
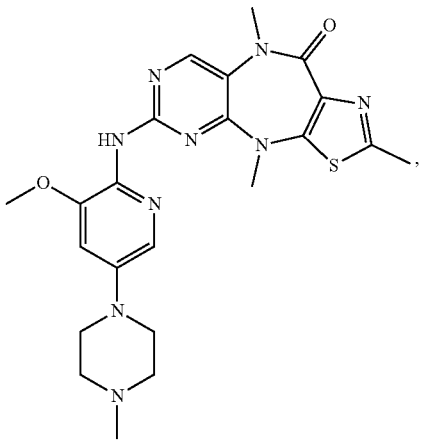
(26)
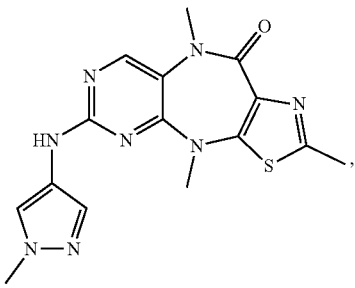
(27)
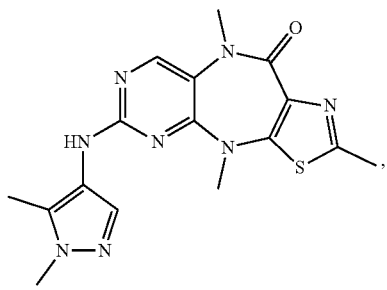
(28)
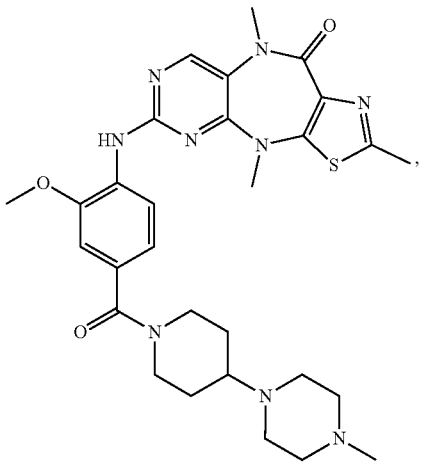

(29)
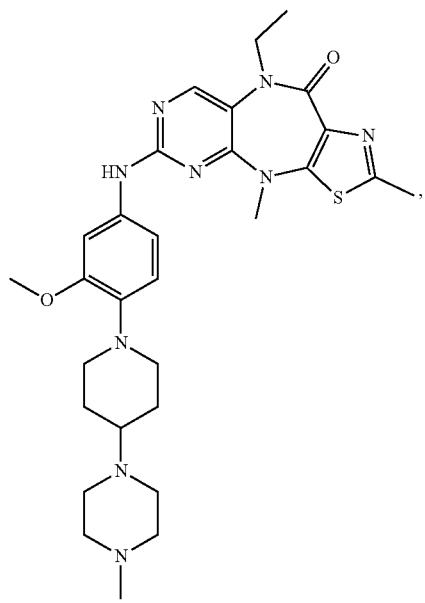
(30)
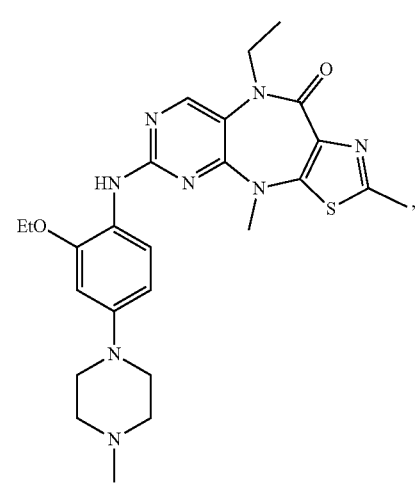
(31)
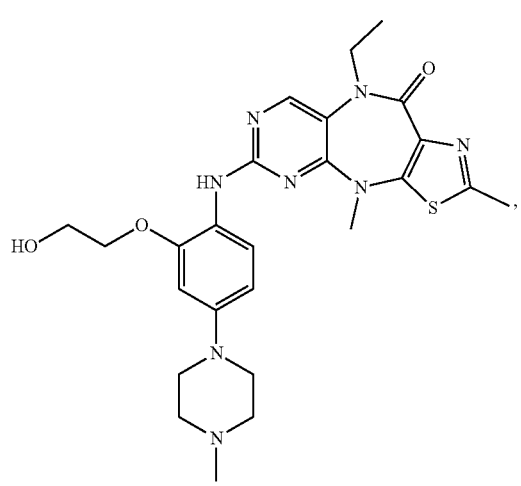
(32)
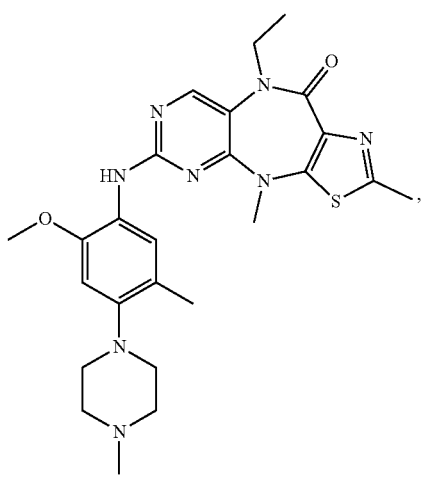
(33)
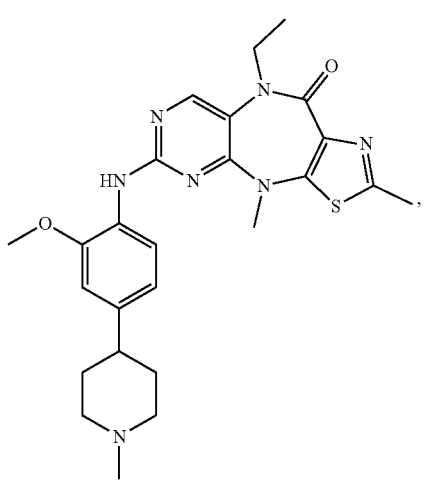
(34)
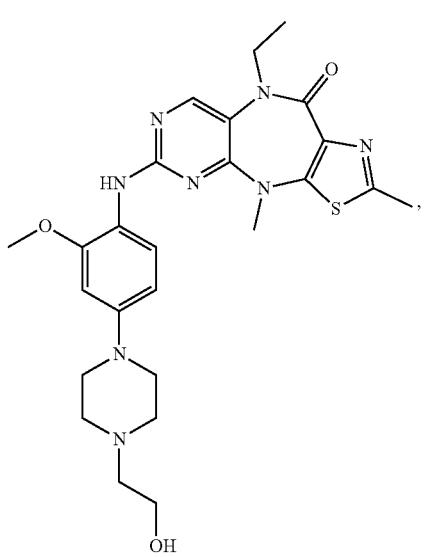

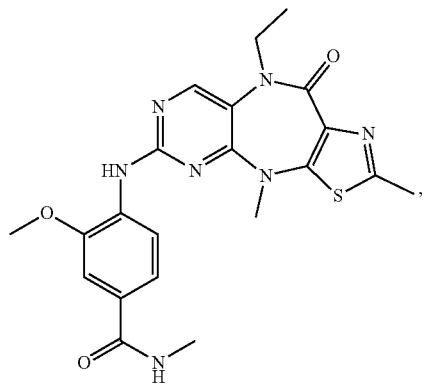
(35)
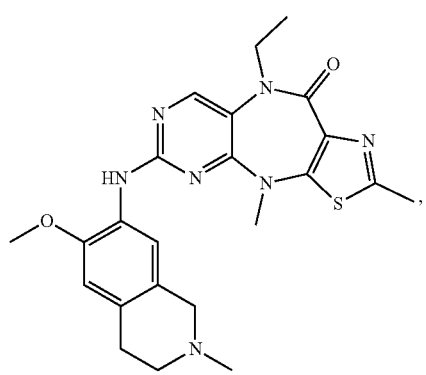
(36)
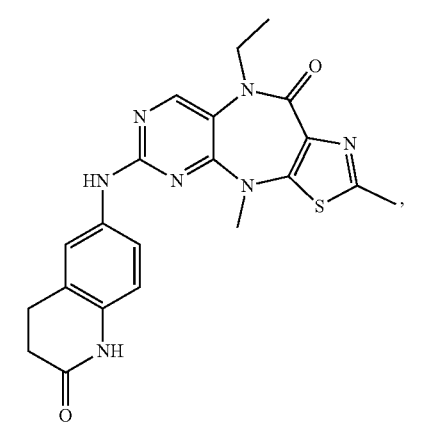
(37)
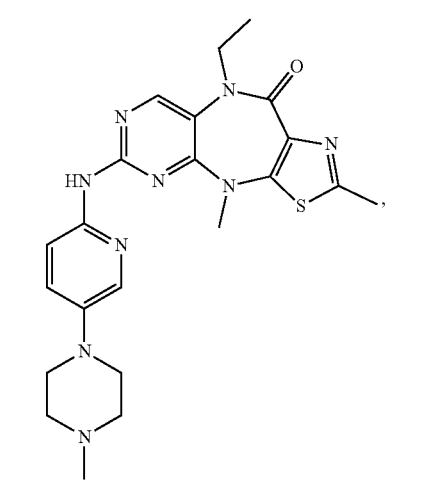
(38)
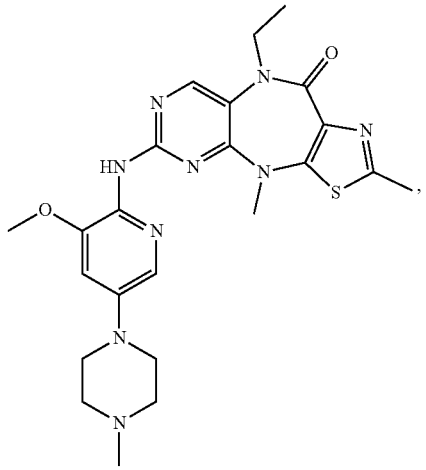
(39)
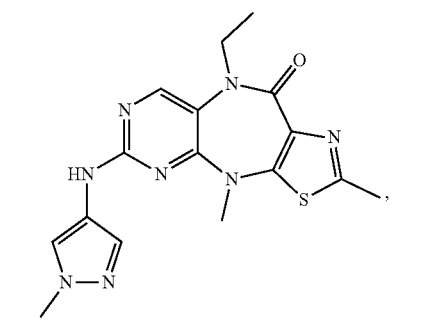
(40)
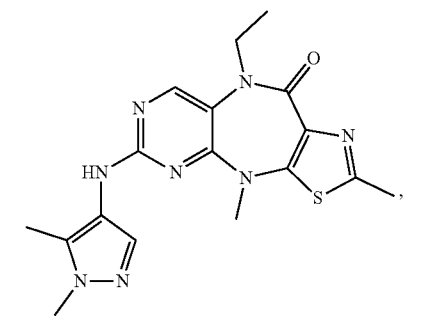
(41)
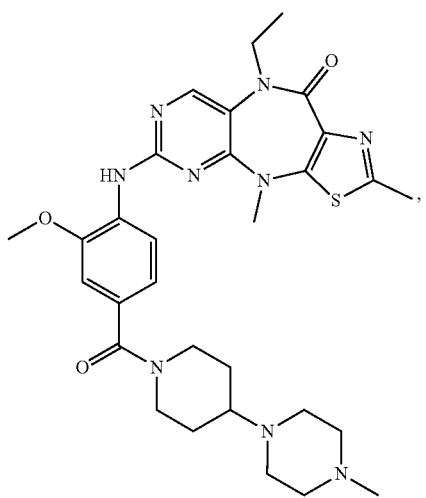
(42)

(43)
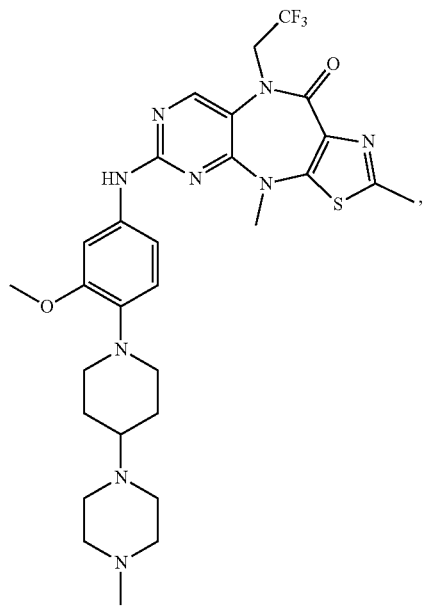
(44)
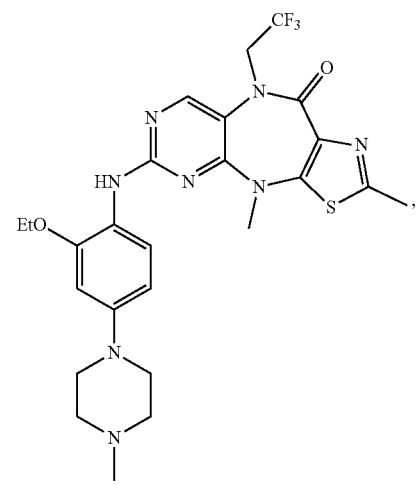
(45)
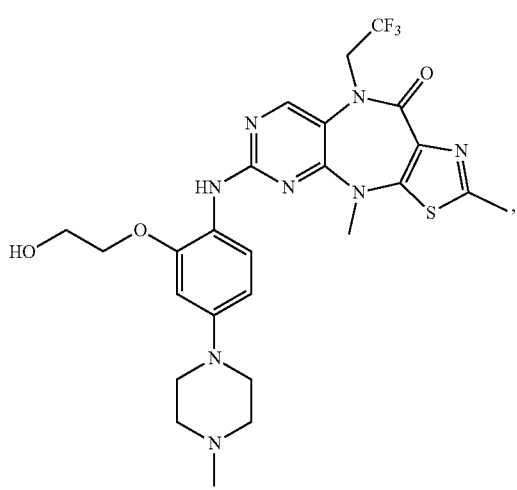
(46)
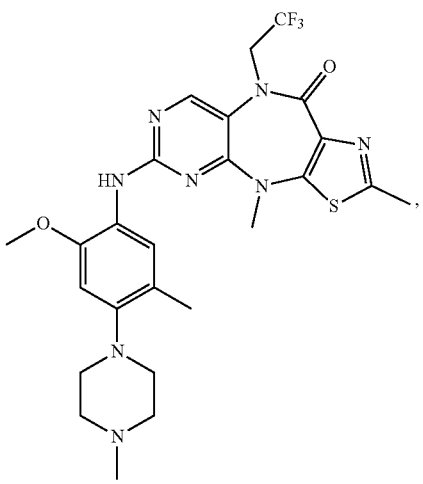
(47)
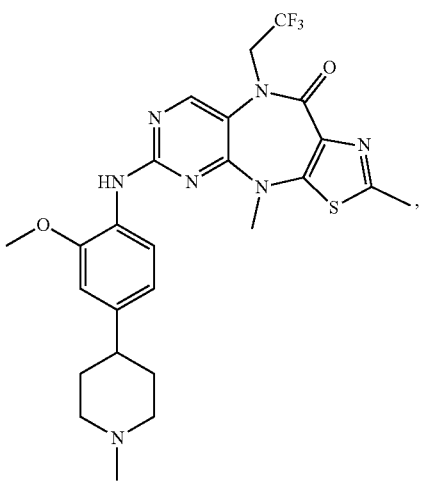
(48)
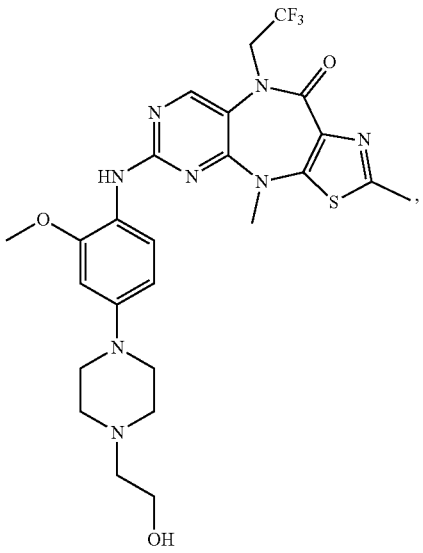

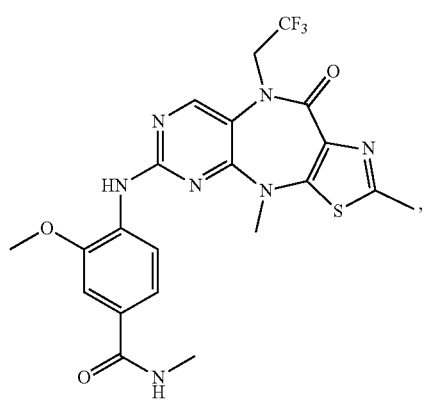
(49)
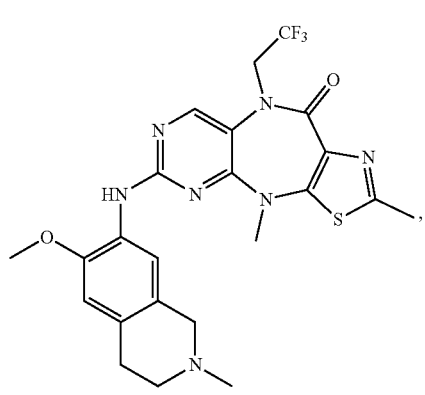
(50)
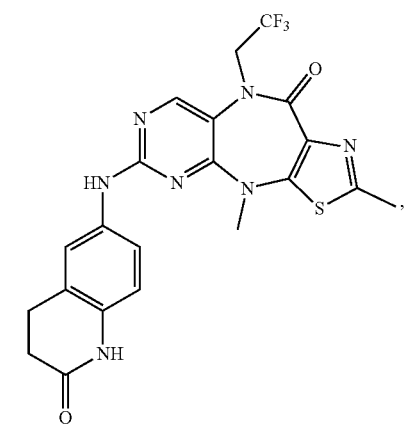
(51)
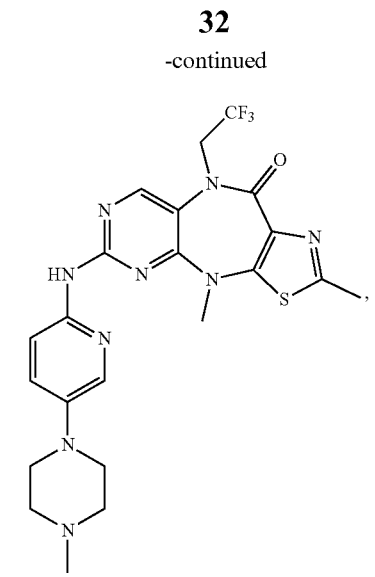
(52)
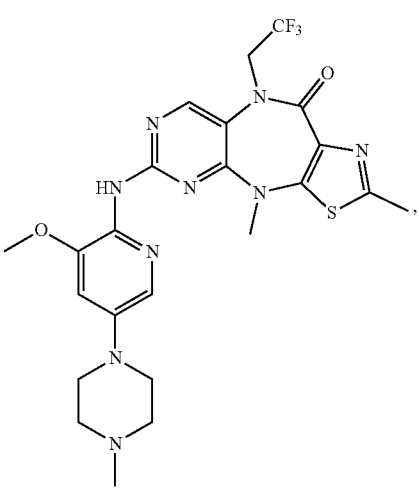
(56)
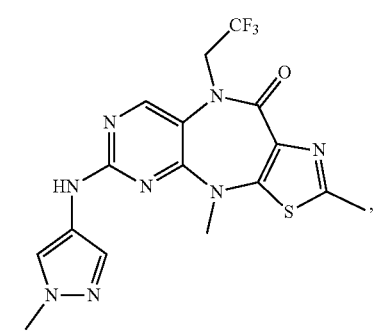
(57)
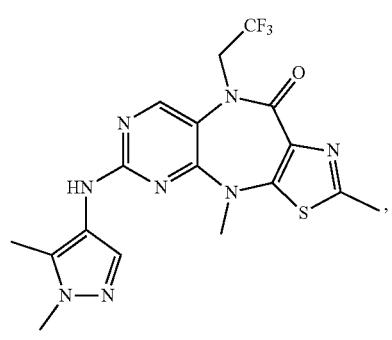
(58)

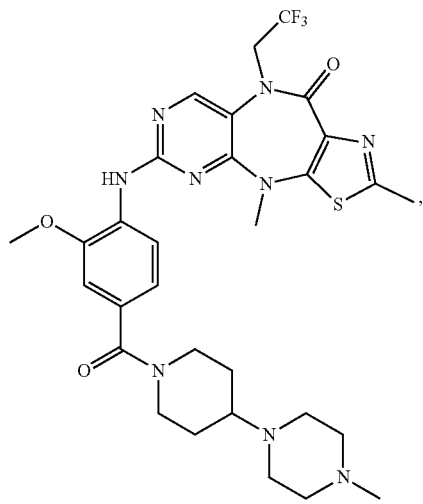
(59)
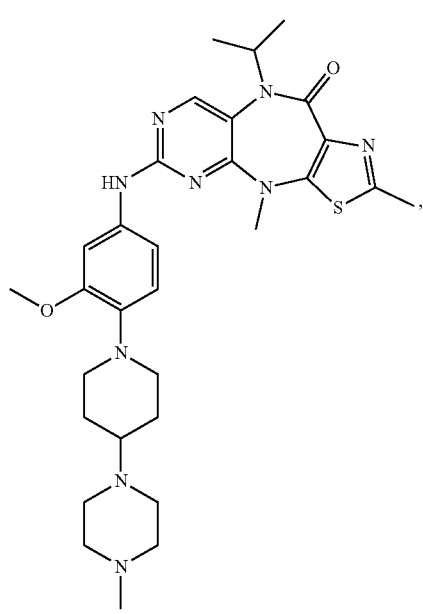
(60)
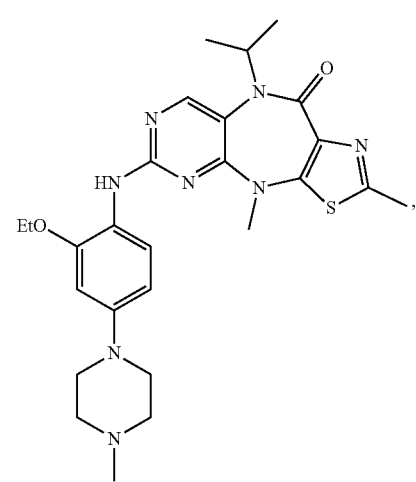
(61)
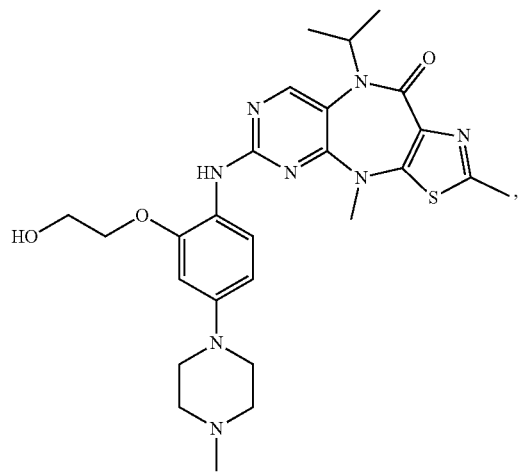
(62)
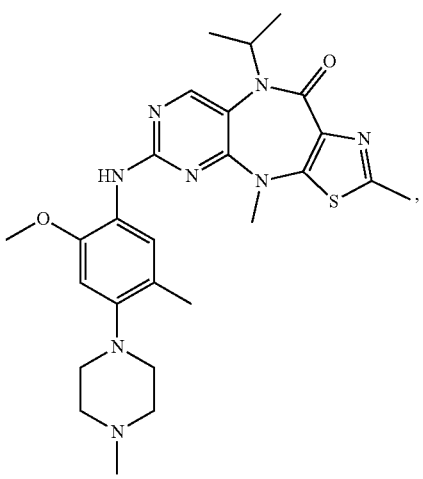
(63)
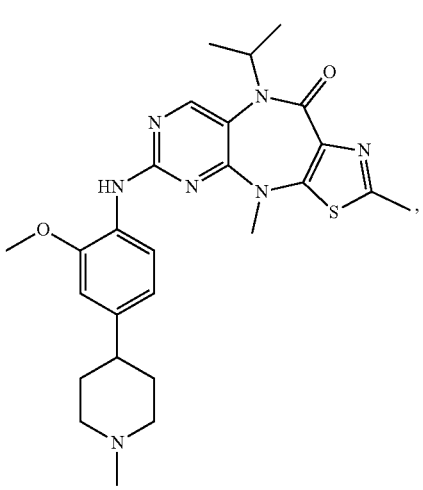
(64)

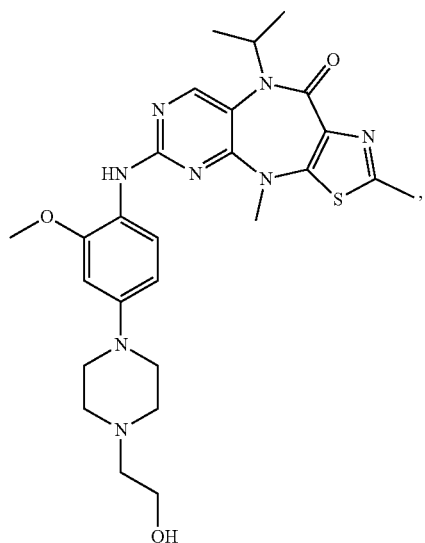
(65)
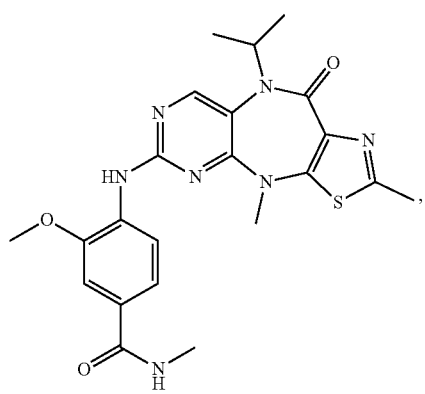
(66)
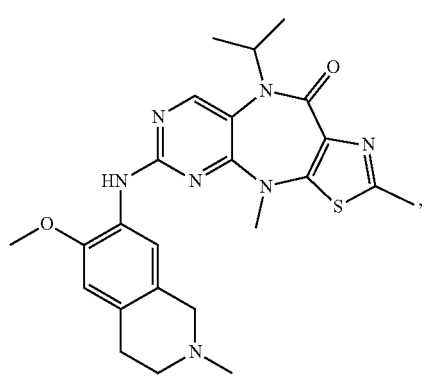
(67)
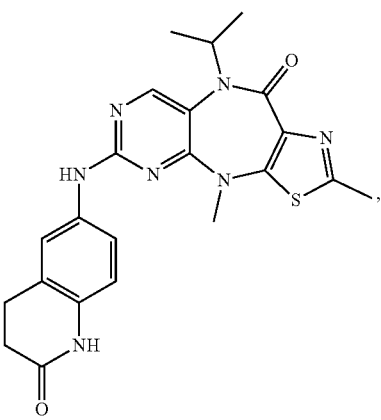
(68)
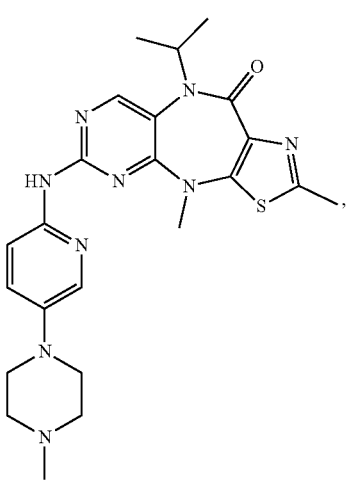
(69)
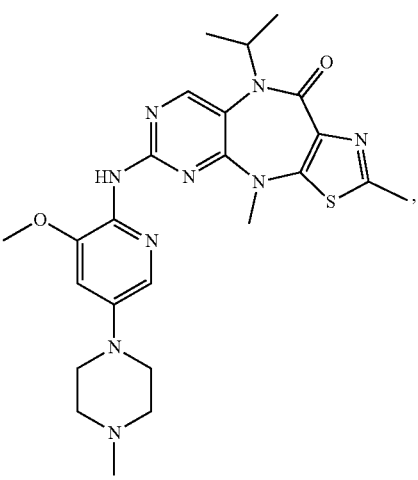
(70)

(71) 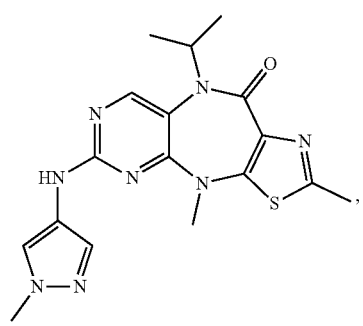
(72) 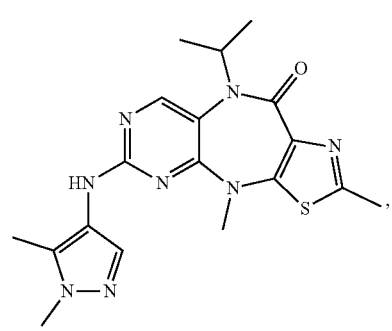
(73) 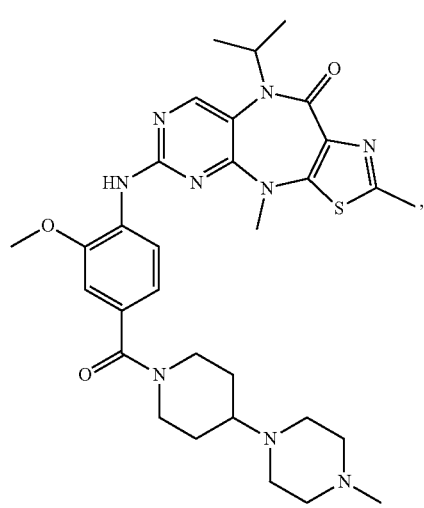
(74) 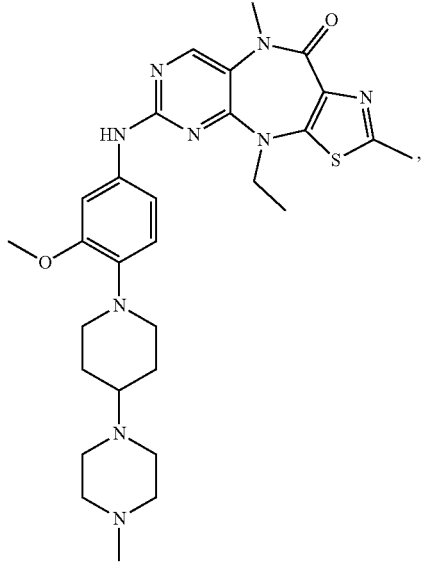
(75) 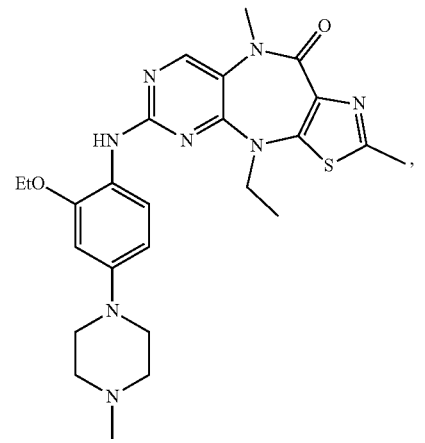
(76) 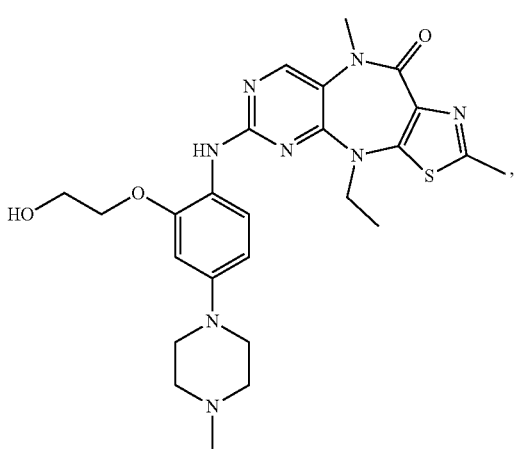

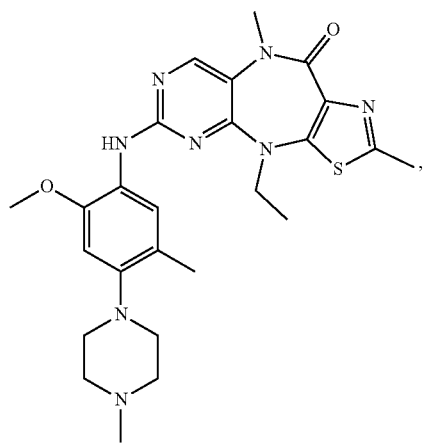
(77)
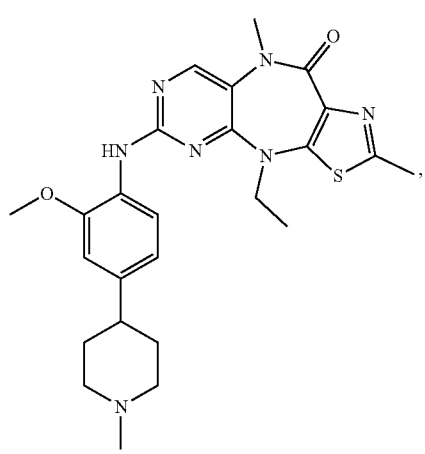
(78)
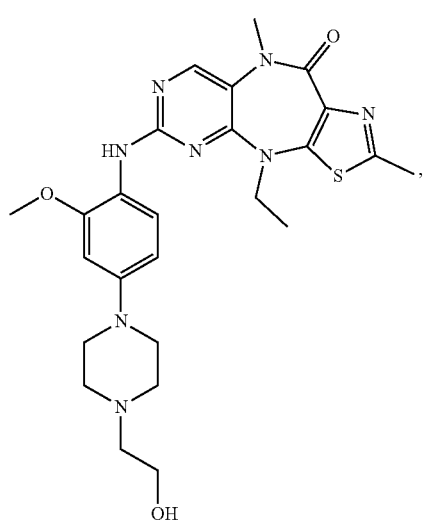
(79)
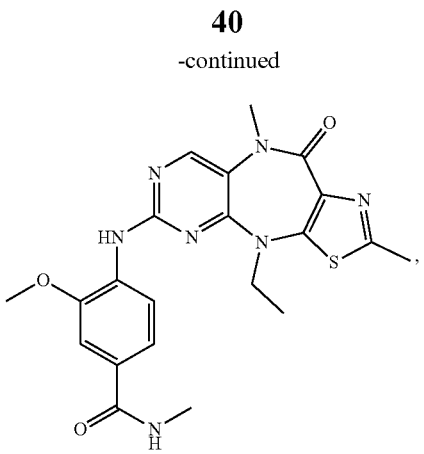
(80)
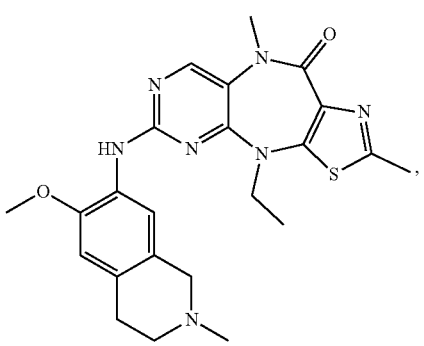
(81)
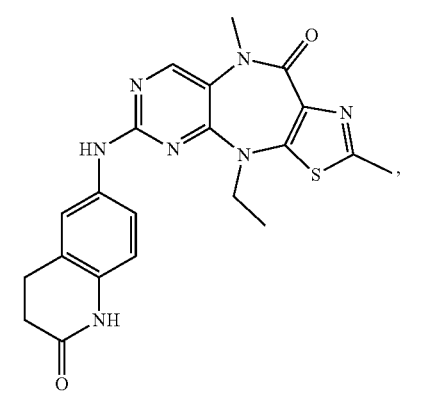
(82)
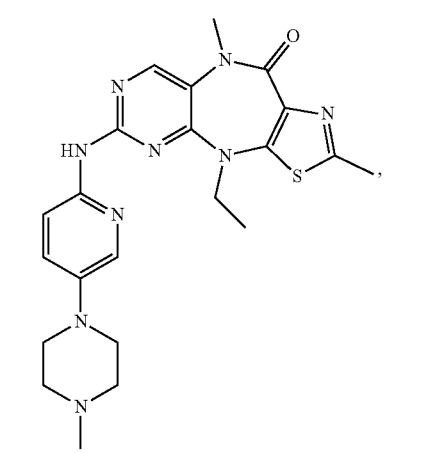
(83)

-continued
(84)
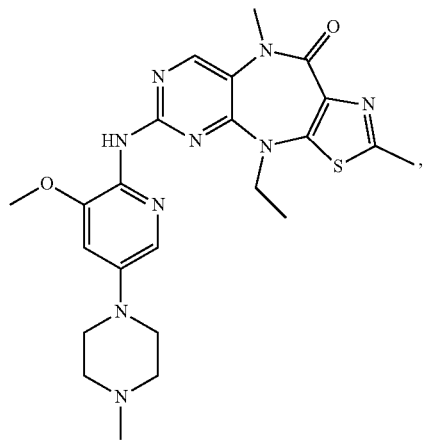
(85)
(86)
(87)
-continued
(88)
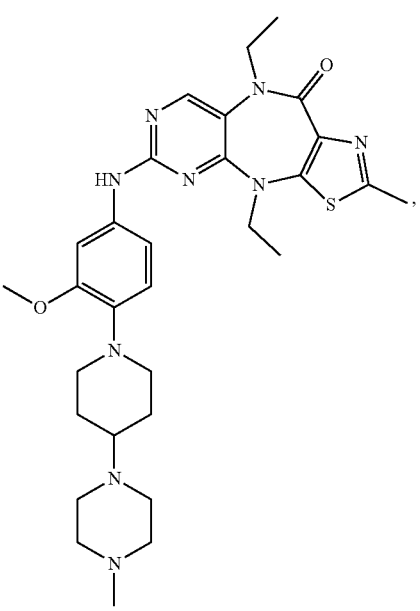
(89)
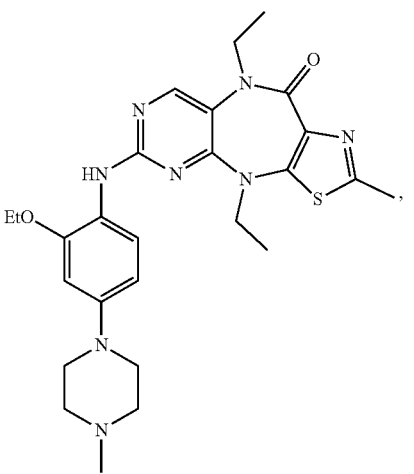
(90)
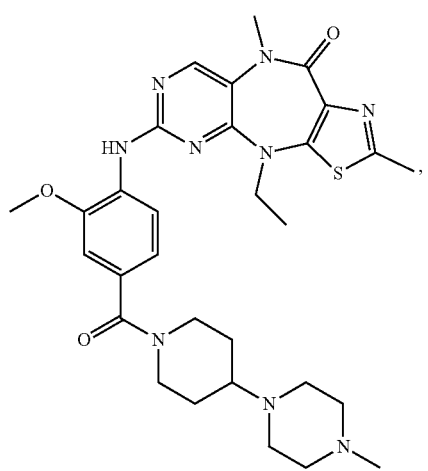

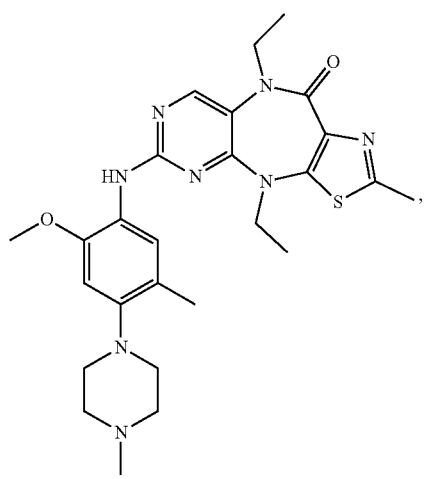
(91)
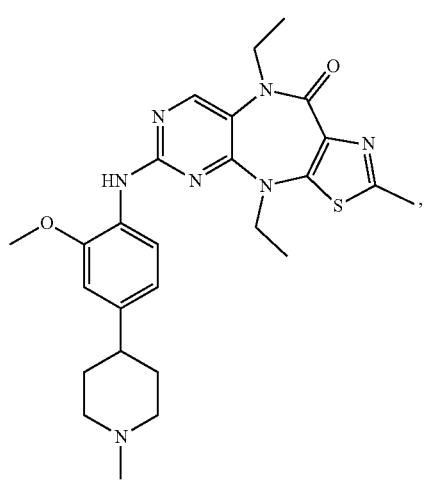
(92)
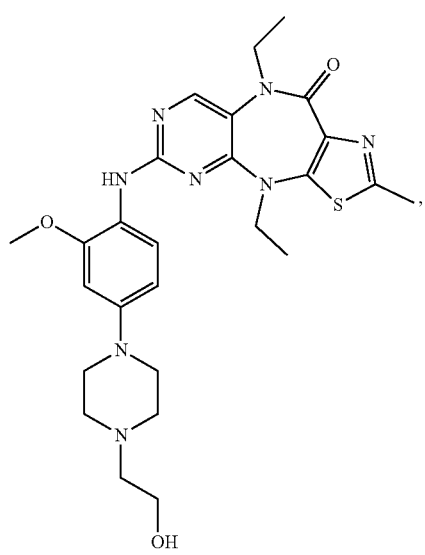
(93)
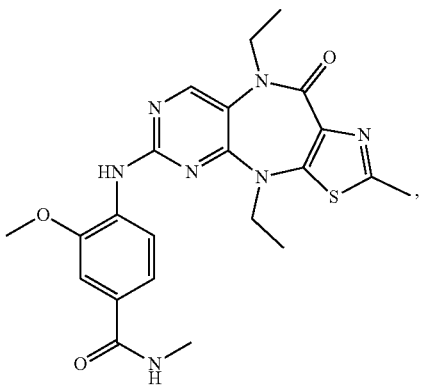
(94)
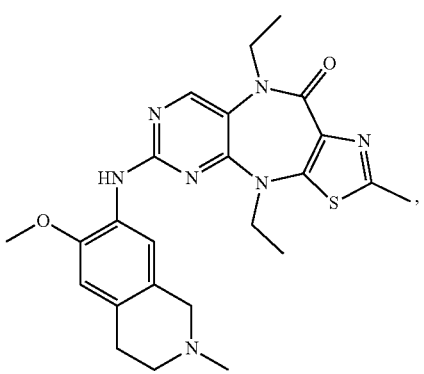
(95)
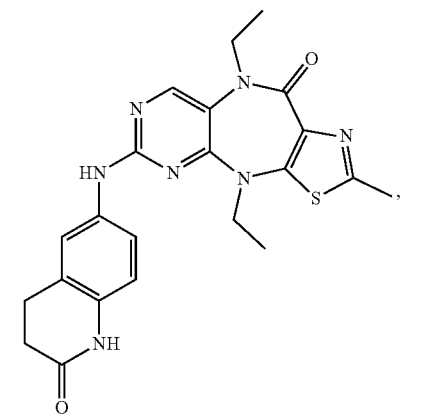
(96)
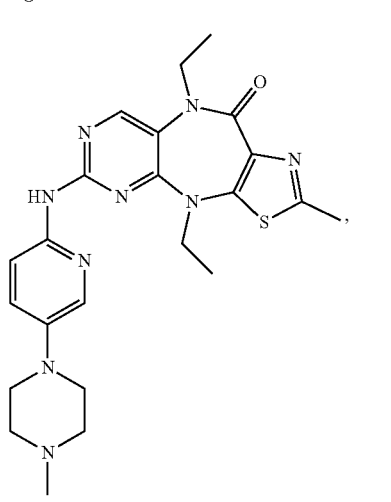
(97)

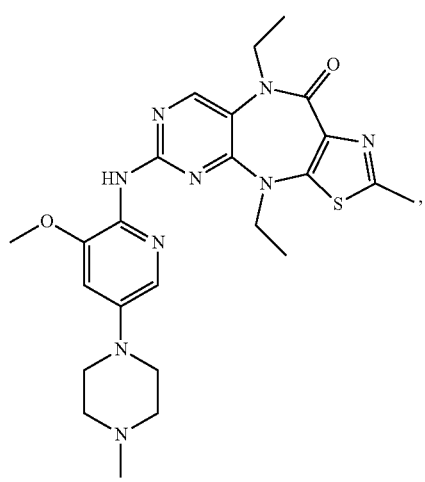
(98)
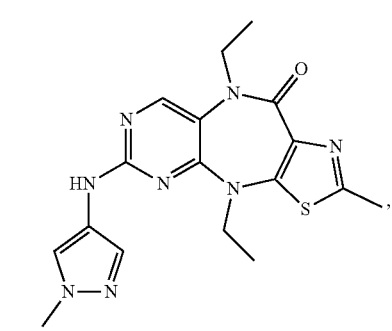
(99)
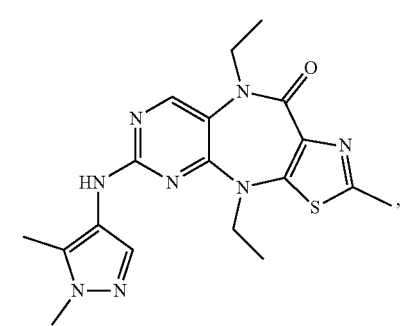
(100)
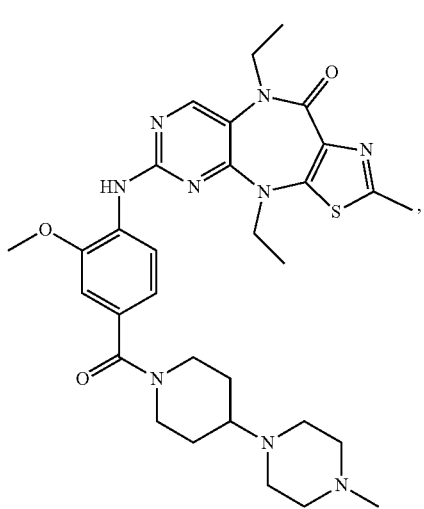
(101)
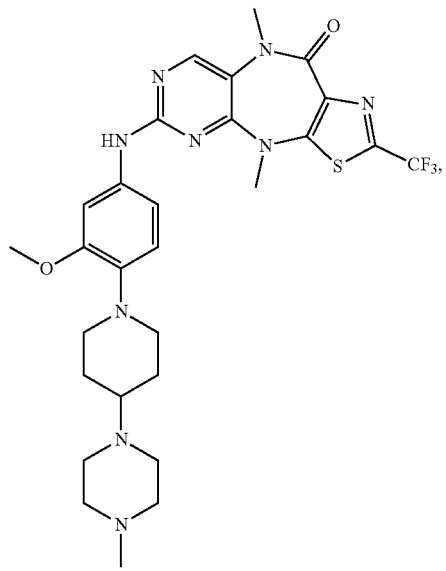
(102)
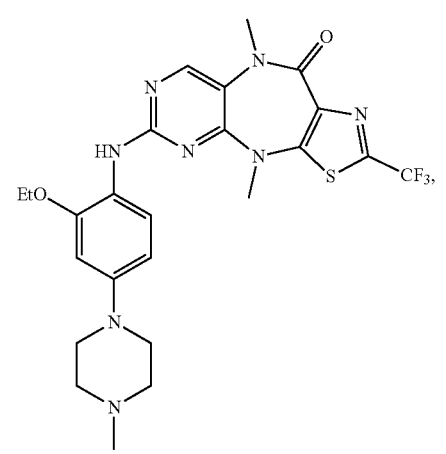
(103)
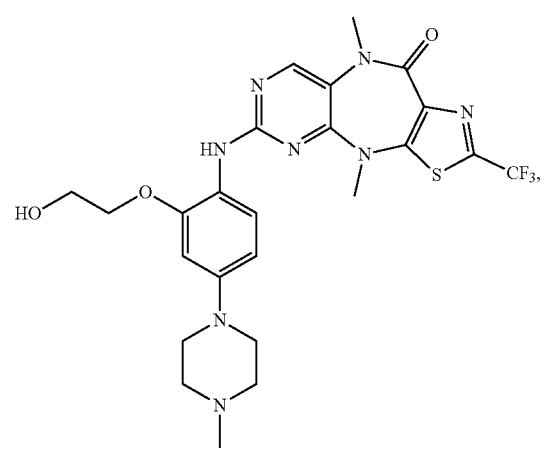
(104)

(105)
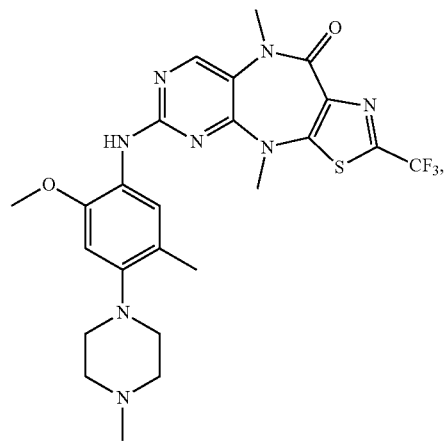
(106)
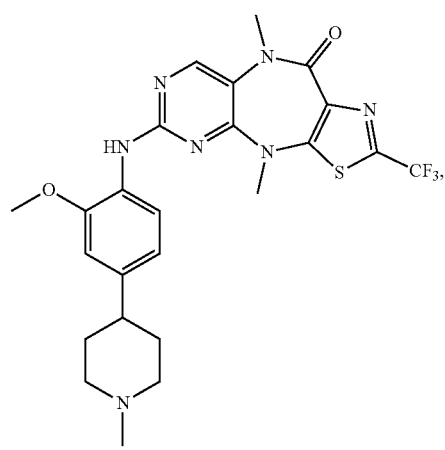
(107)
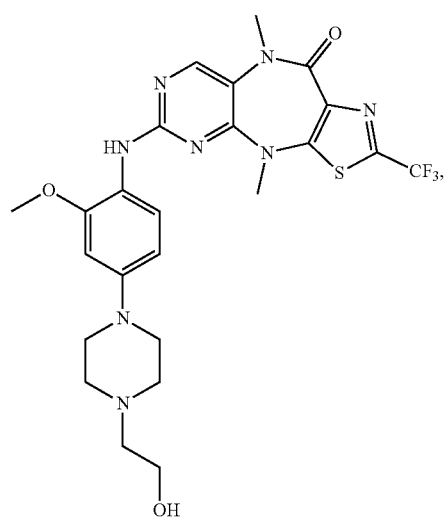
(108)
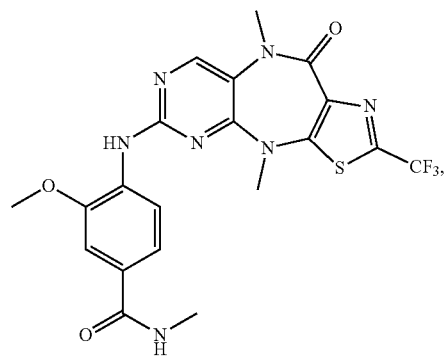
(109)
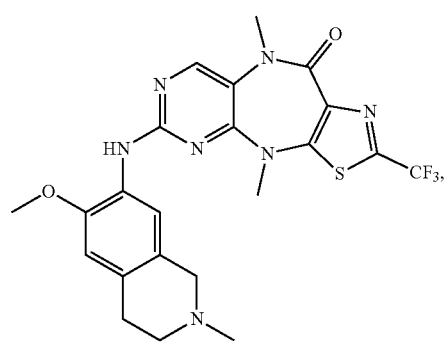
(110)
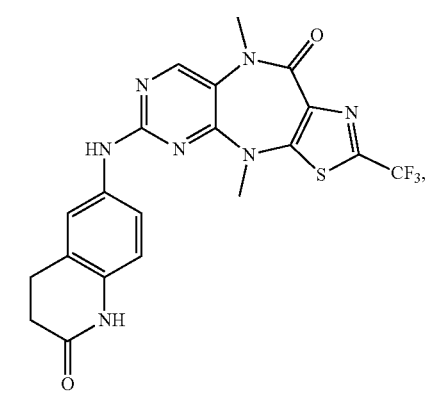
(111)
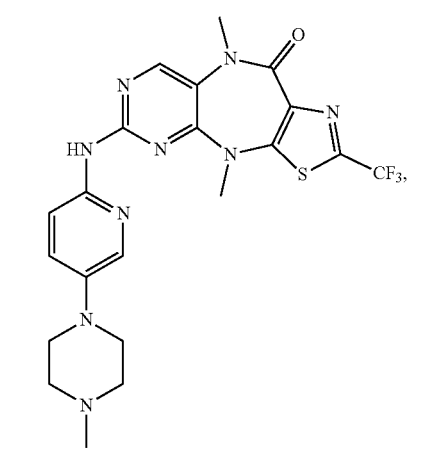

(112)
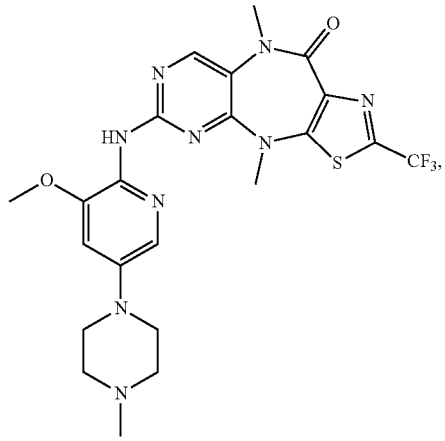
(113)
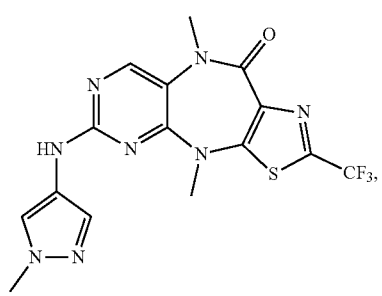
(114)
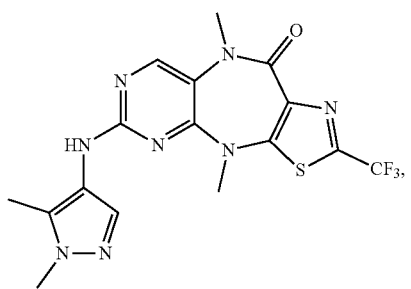
(115)
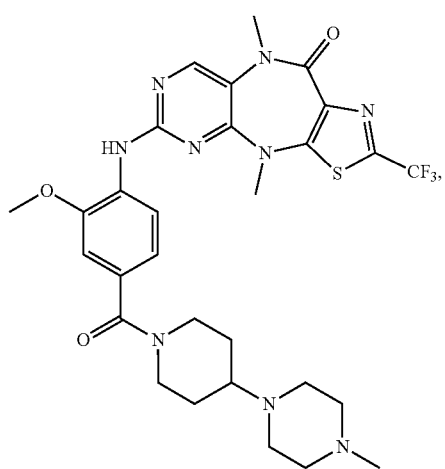
(116)
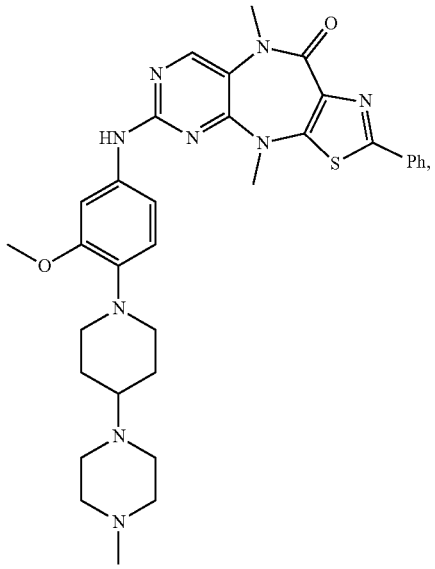
(117)
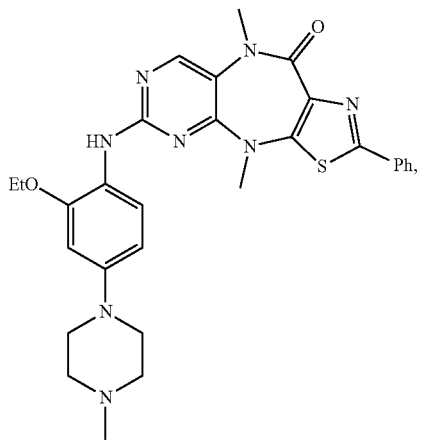
(118)
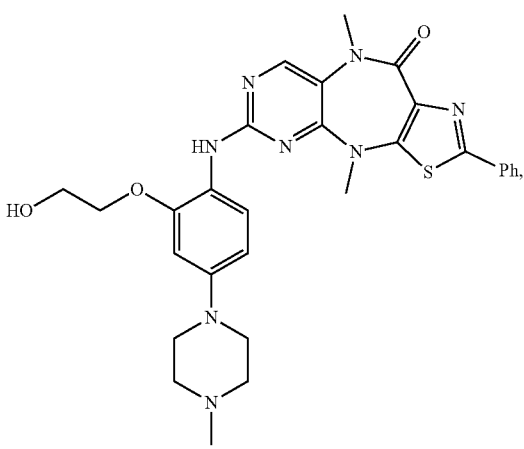

(119)
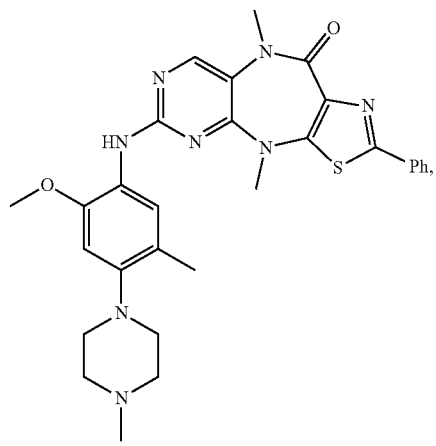
(120)
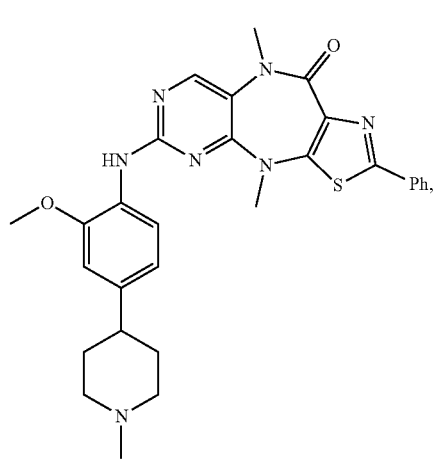
(121)
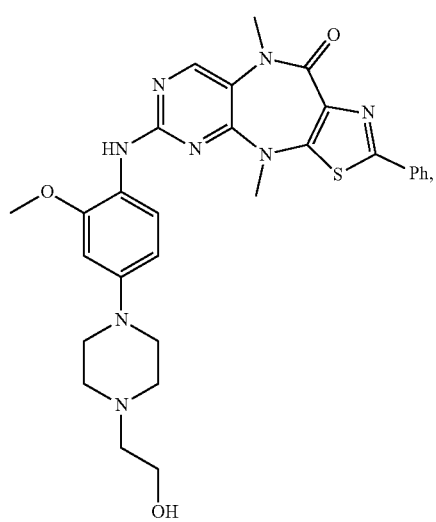
(122)
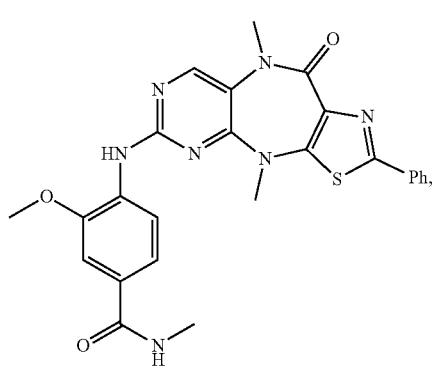
(123)
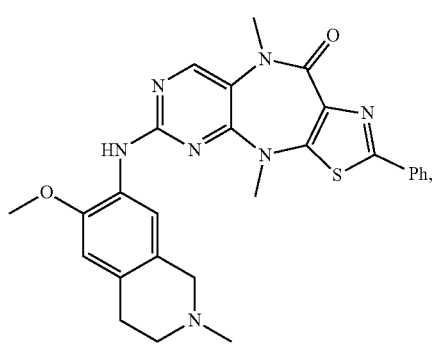
(124)
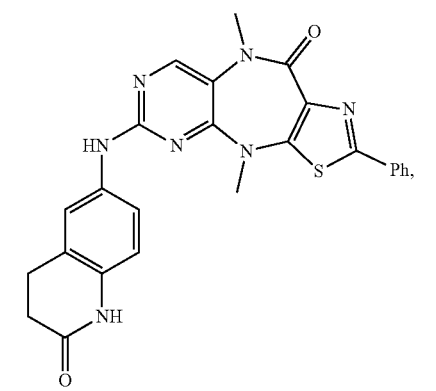
(125)
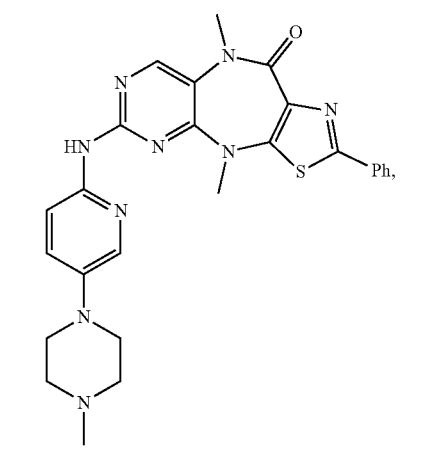

-continued
(126)
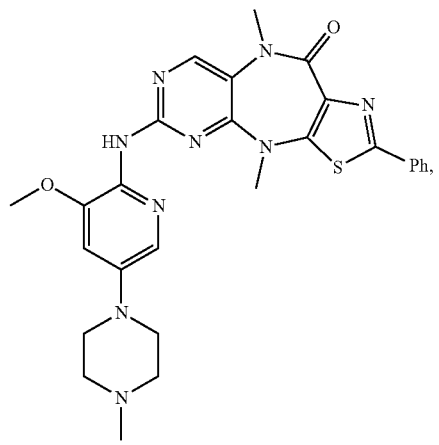
(127)
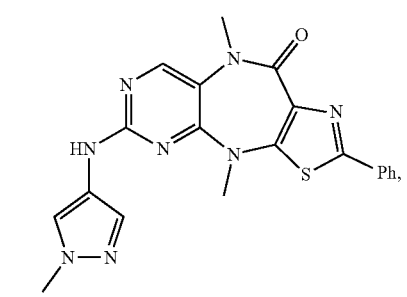
(128)
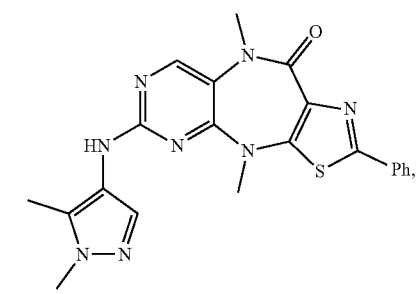
(129)
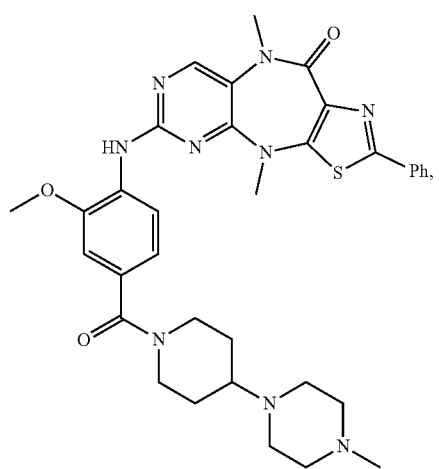
-continued
(130)
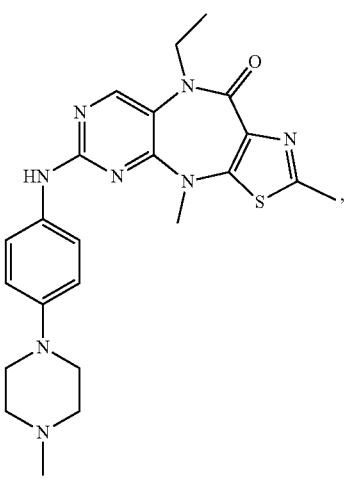
(131)
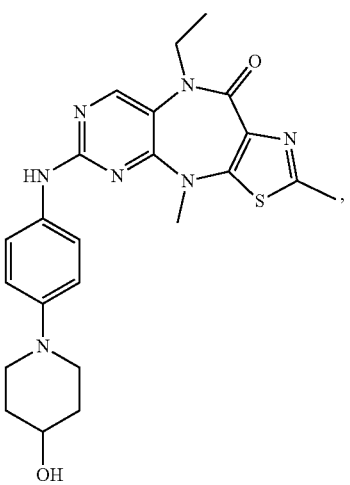
(132)
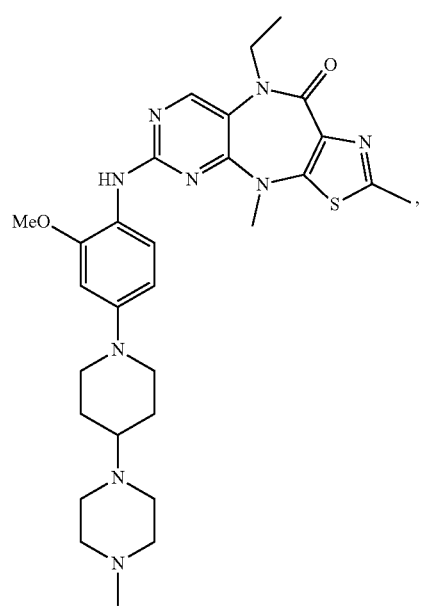

(133)
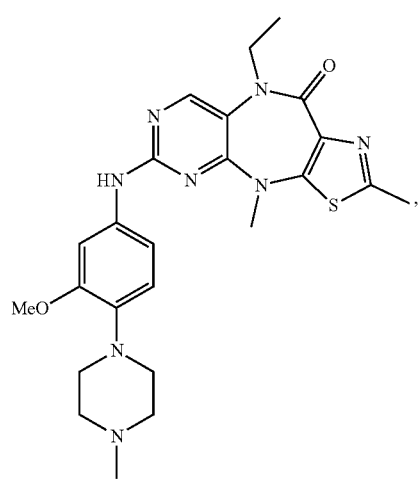
(134)
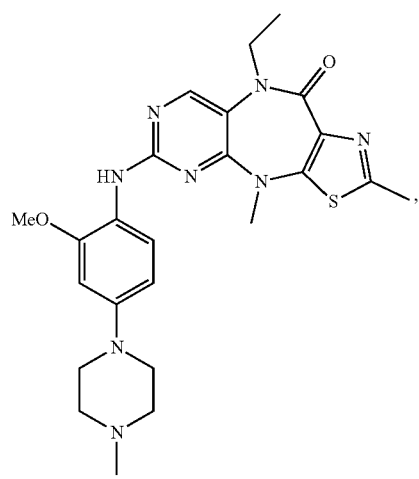
(135)
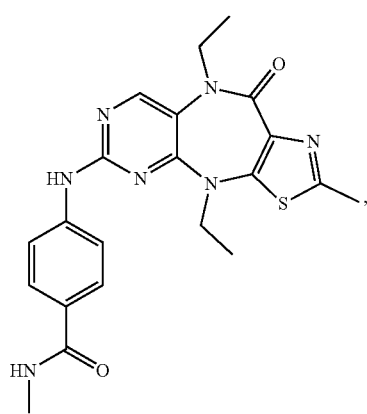
(136)
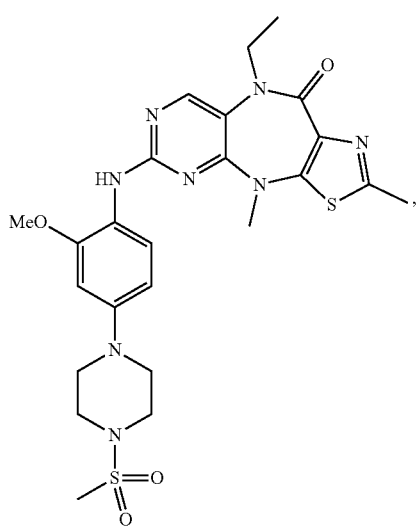
(137)
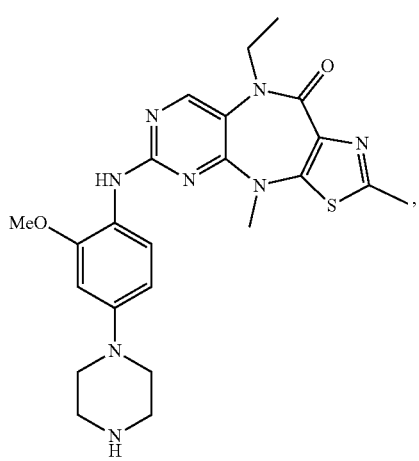
(138)
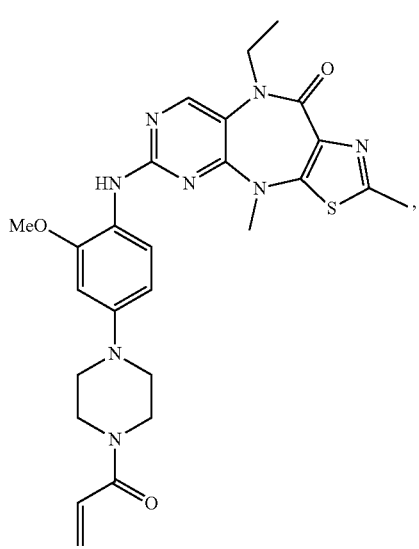

-continued
(139)
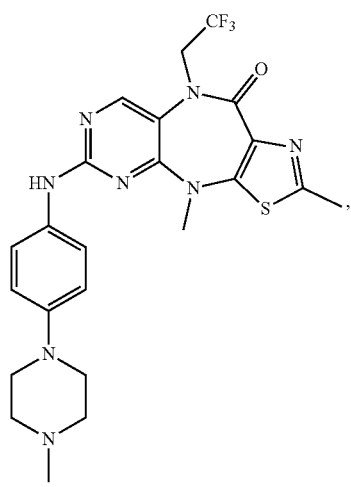
(140)
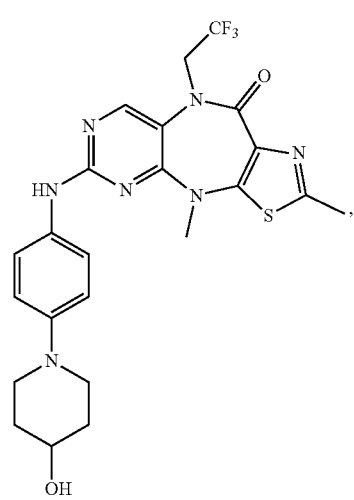
(141)
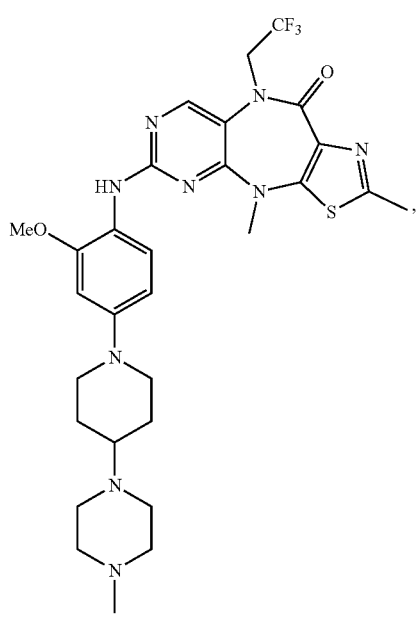
-continued
(142)
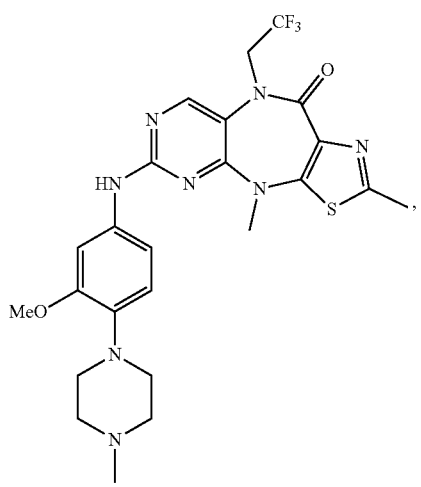
(143)
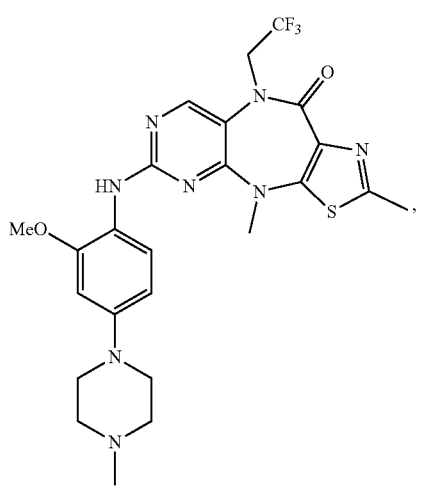
(144)
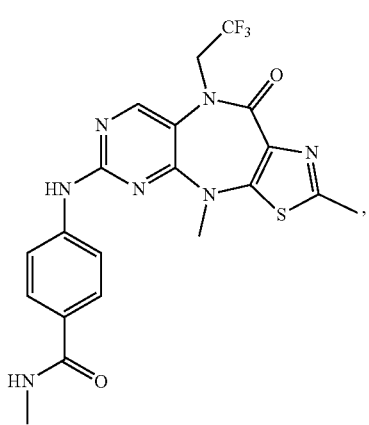

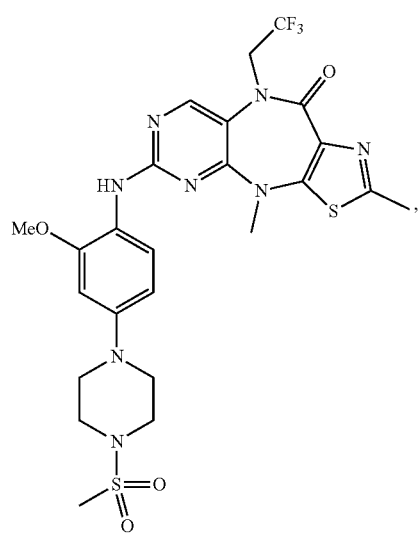
(145)
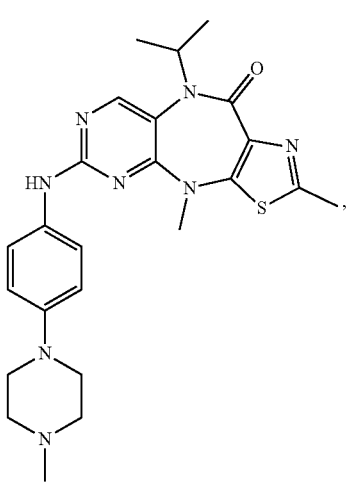
(148)
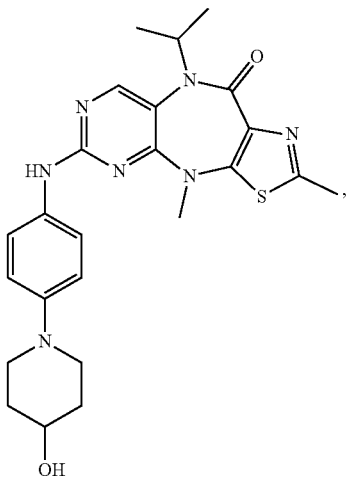
(149)
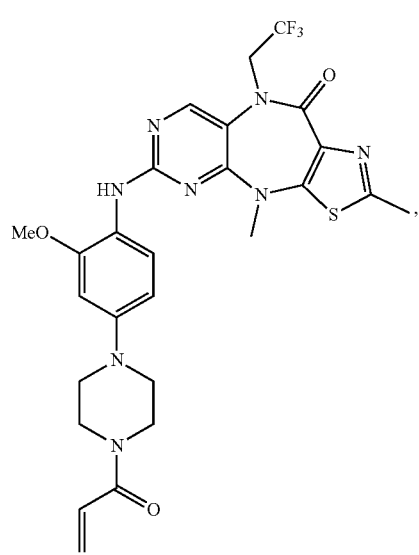
(146)
(147)
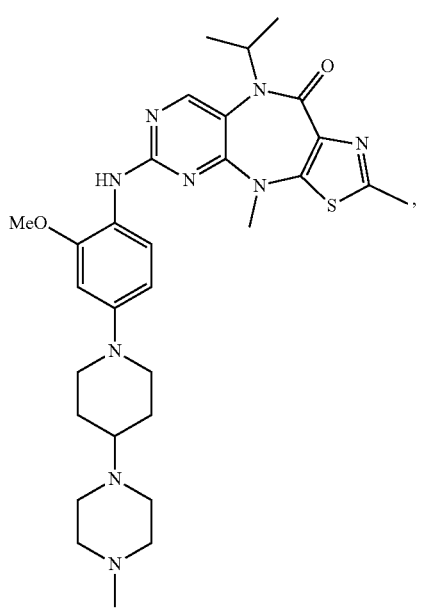
(150)

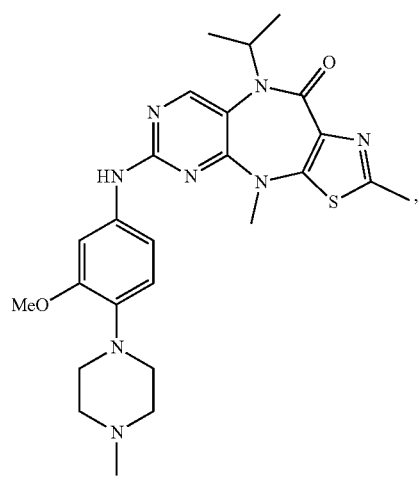
(151)
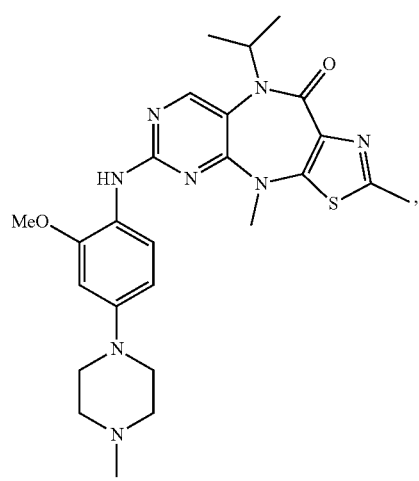
(152)
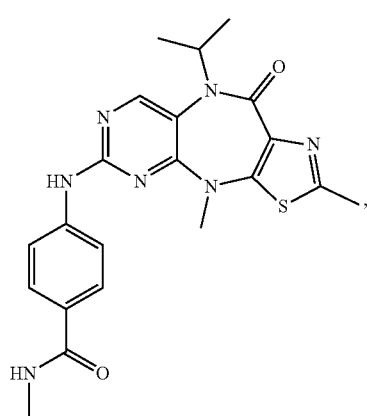
(153)
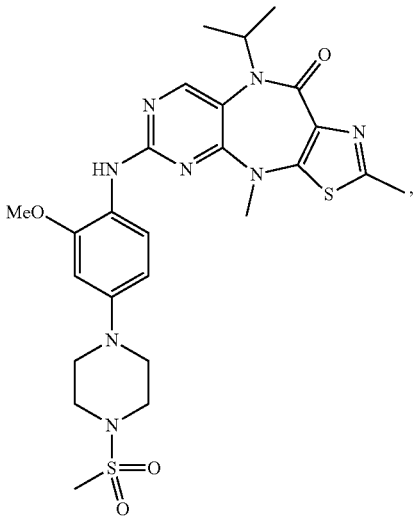
(154)
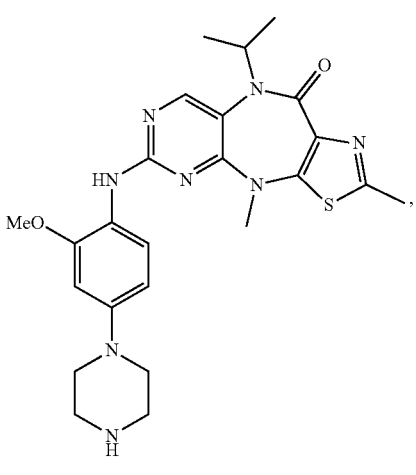
(155)
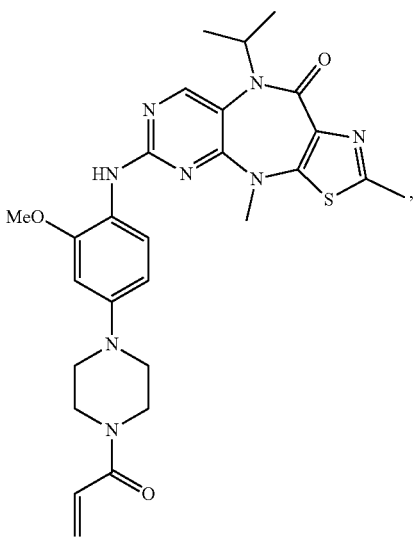
(156)

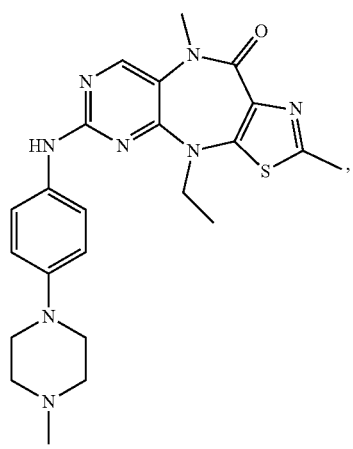
(157)
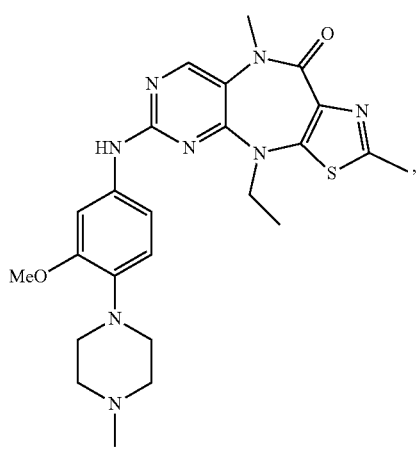
(160)
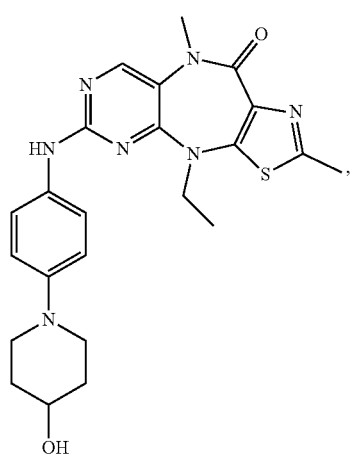
(158)
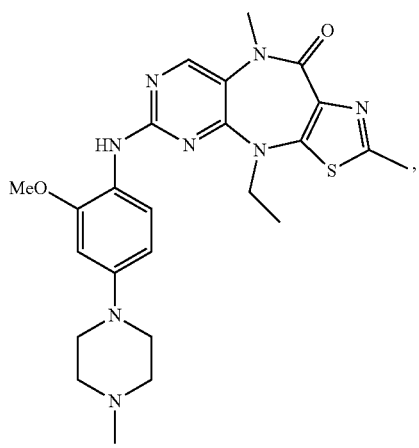
(161)
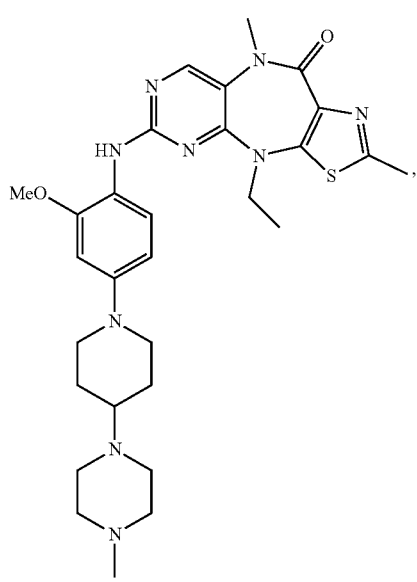
(159)
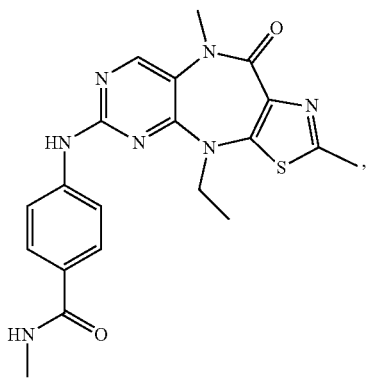
(162)

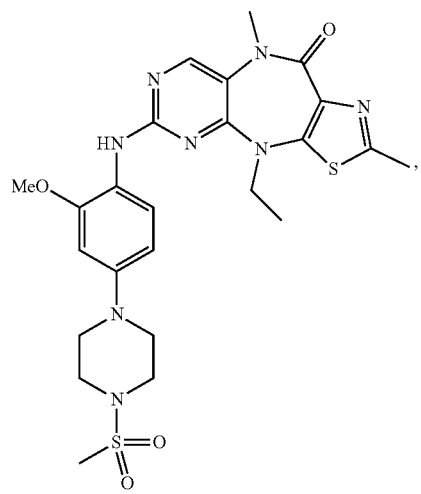
(163)
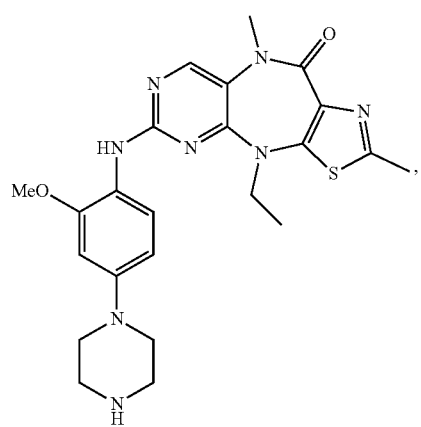
(164)
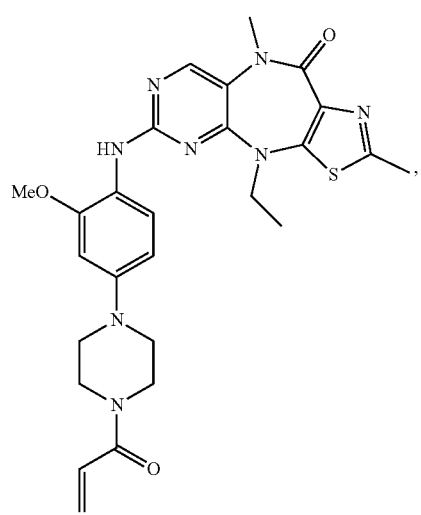
(165)
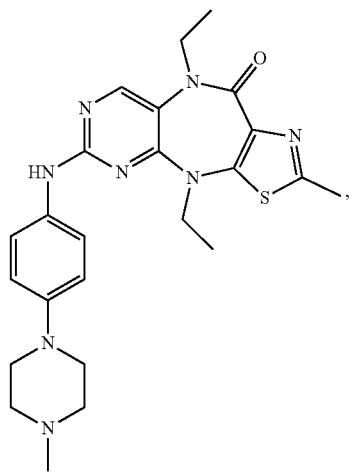
(166)
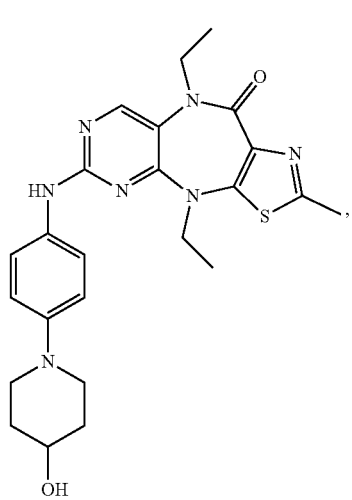
(167)
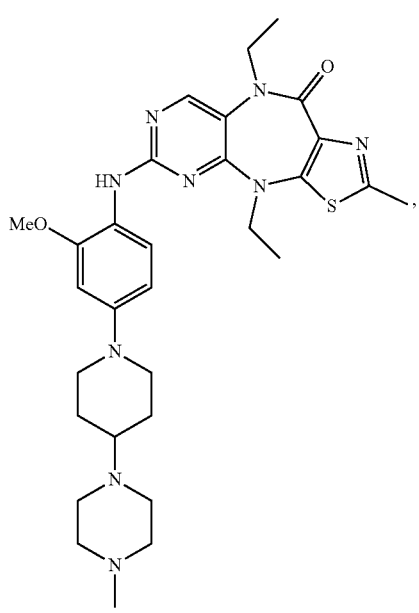
(168)

-continued
(169)
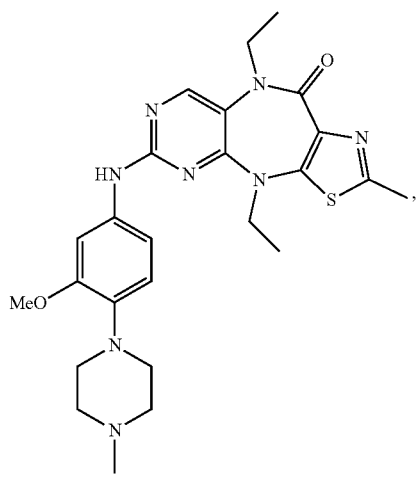
(170)
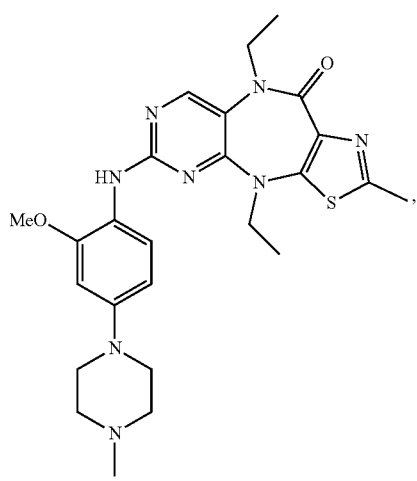
(171)
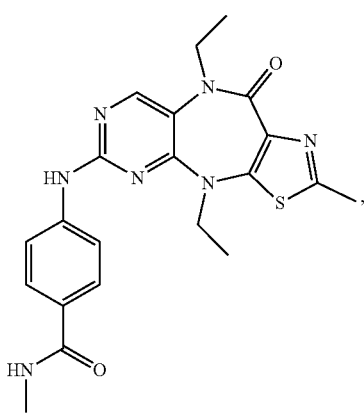
-continued
(172)
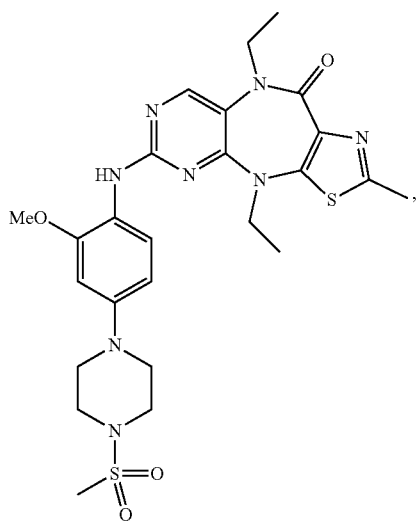
(173)
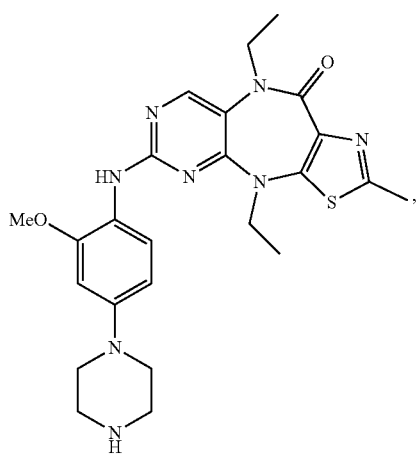
(174)
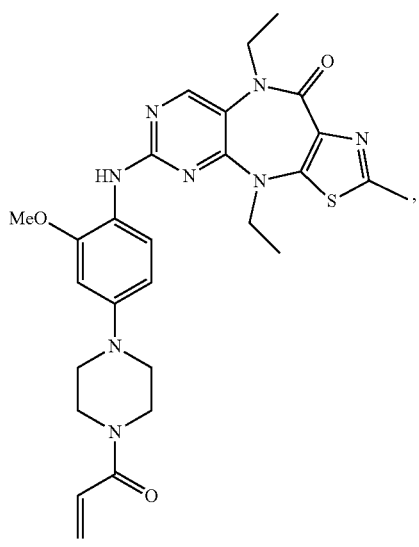

69
-continued
(175) 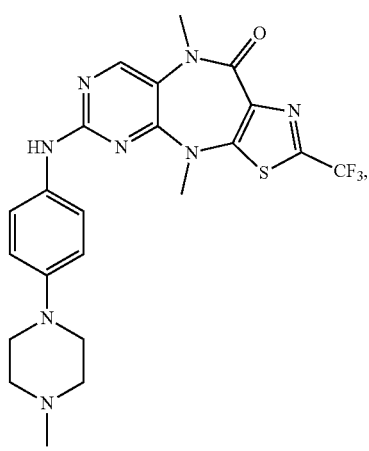
(176) 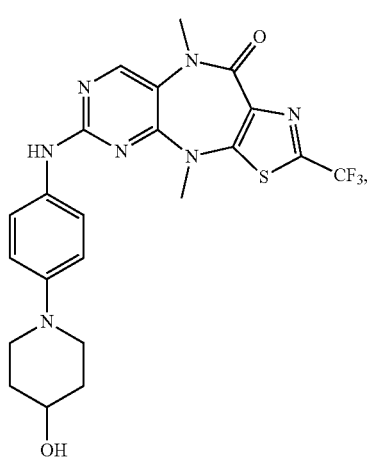
(177) 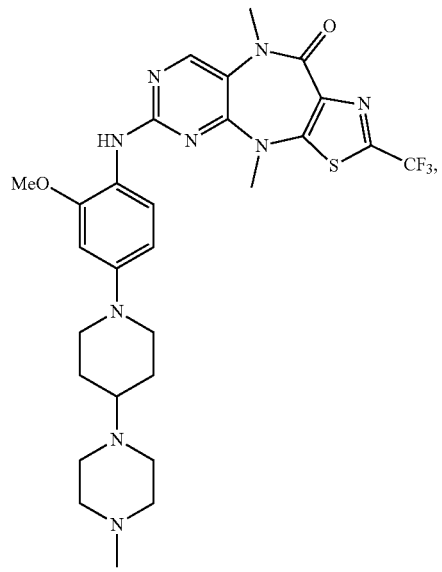
70
-continued
(178) 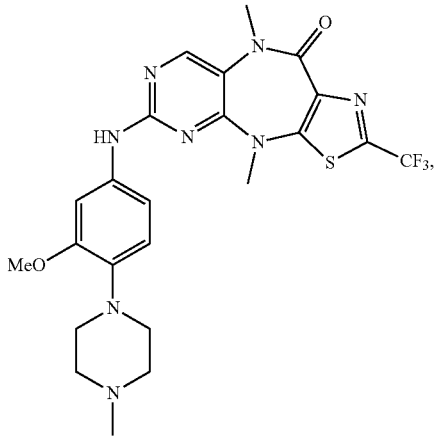
(179) 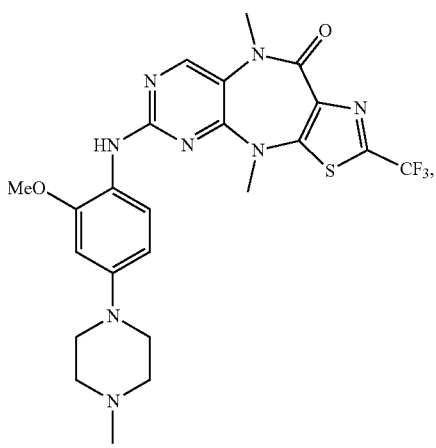
(180) 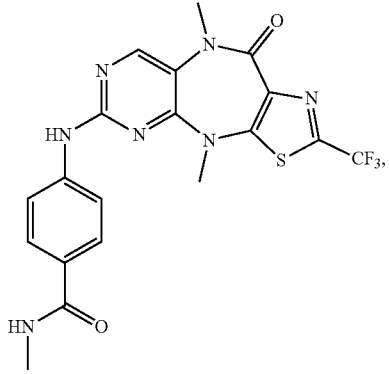

-continued
(181)
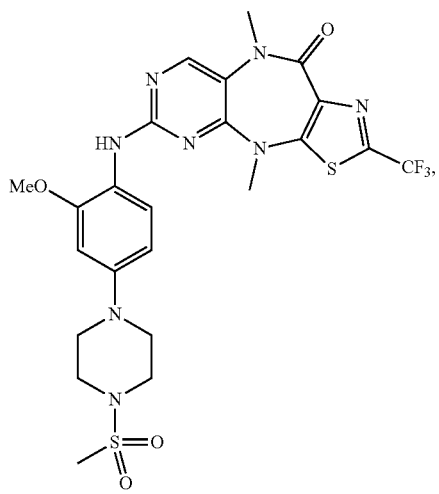
(182)
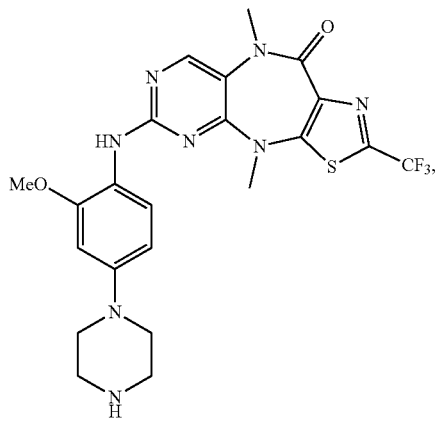
(183)
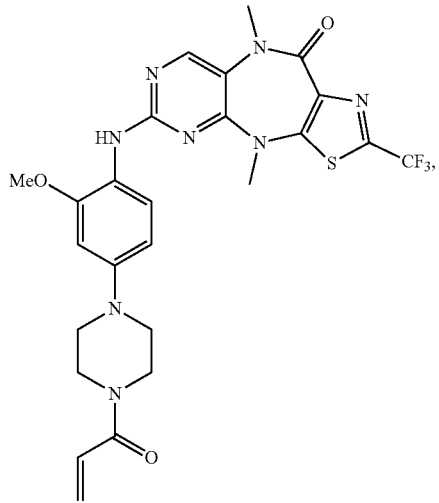
-continued
(184)
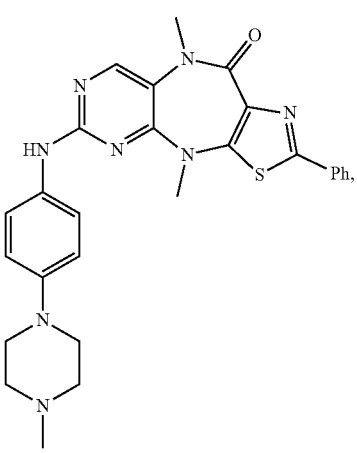
(185)
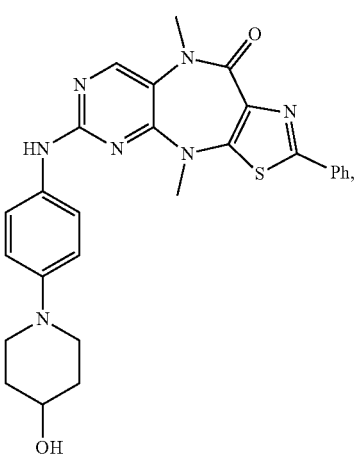
(186)
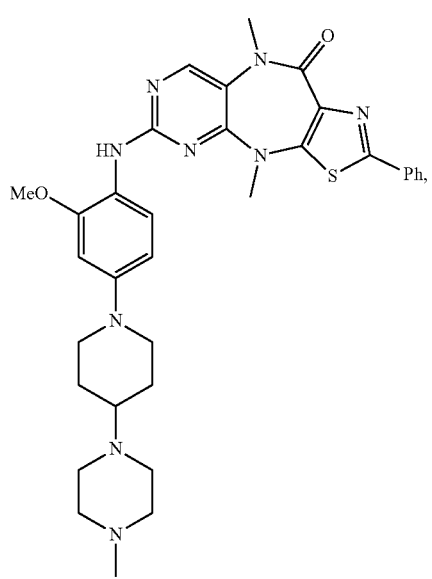

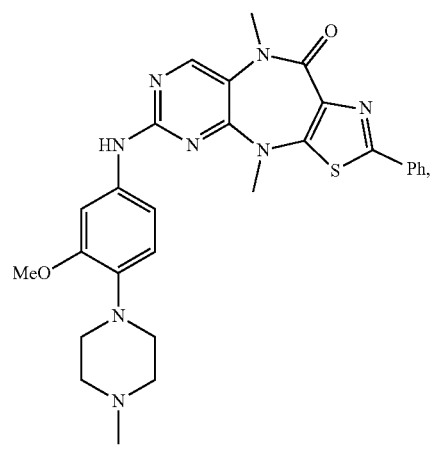
(187)
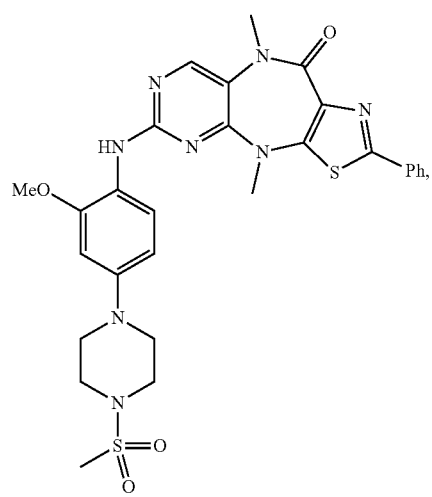
(190)
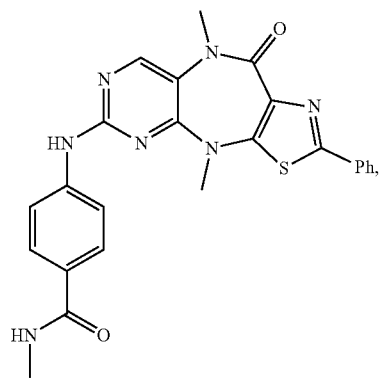
(188)
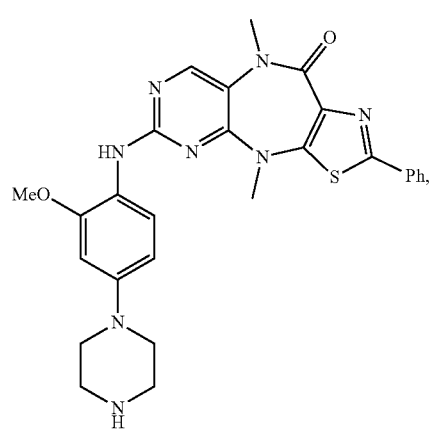
(191)
(189)
(192)

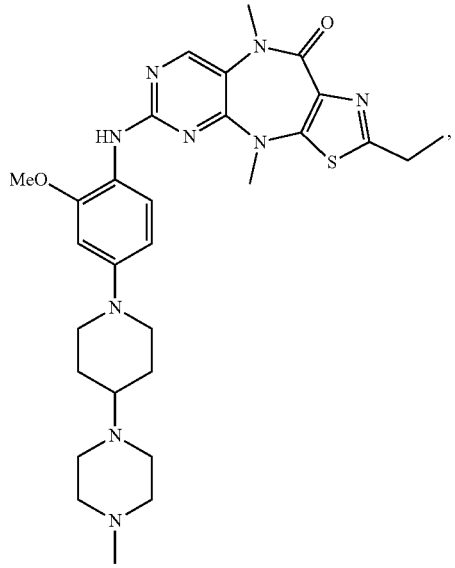
(193)
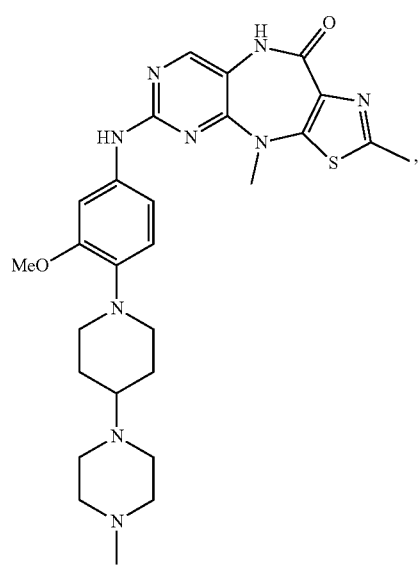
(194)
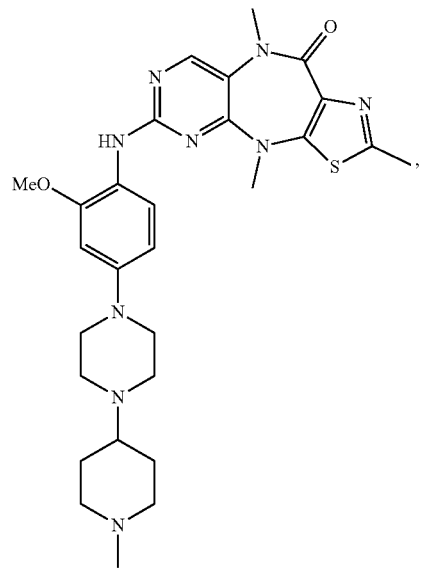
(195)
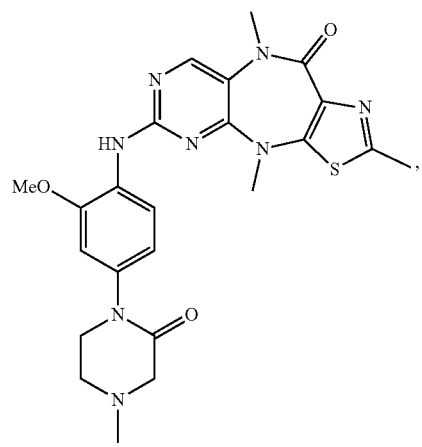
(196)
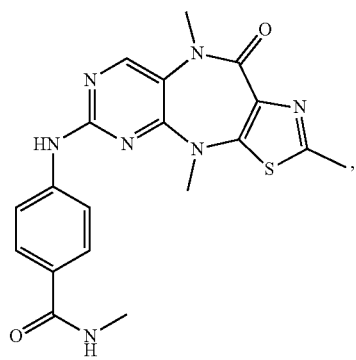
(197)

-continued
(198)
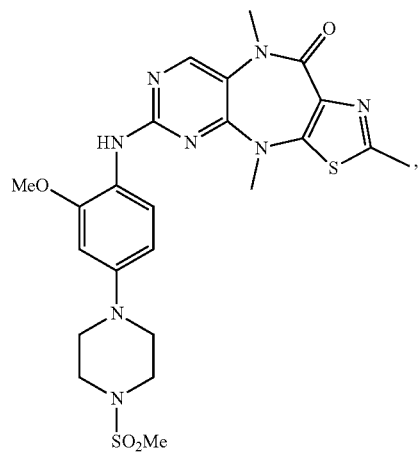
(199)
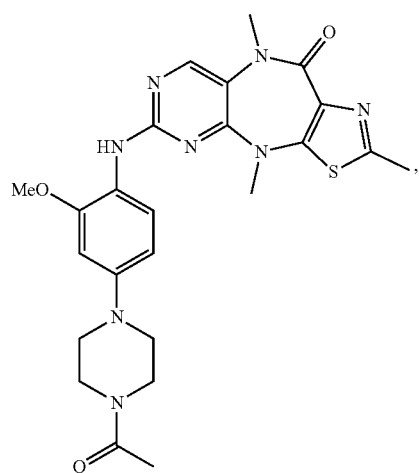
(200)
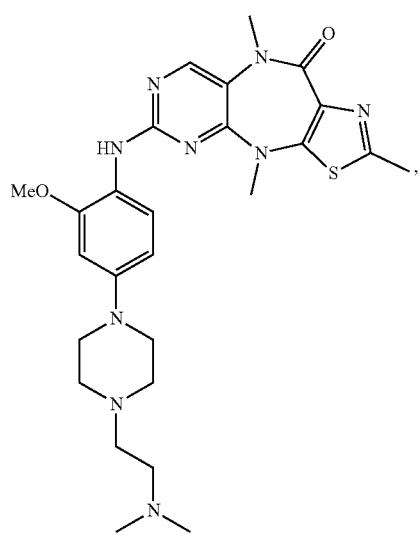
-continued
(201)
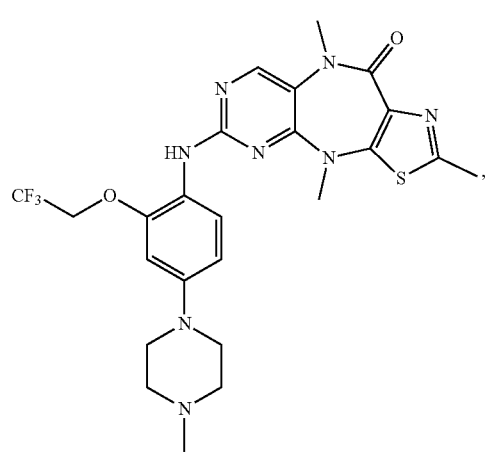
(202)
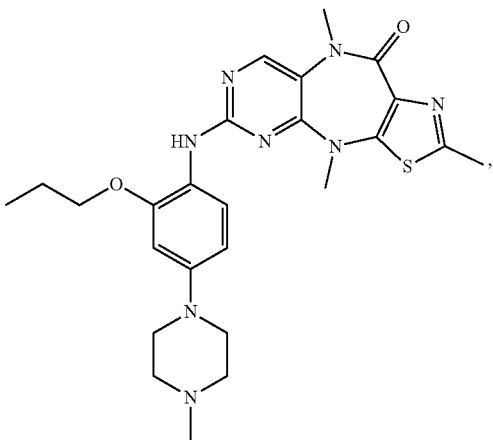
(203)
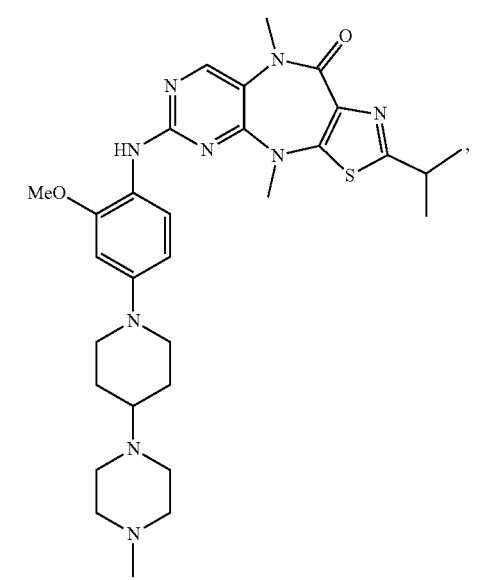

(204)

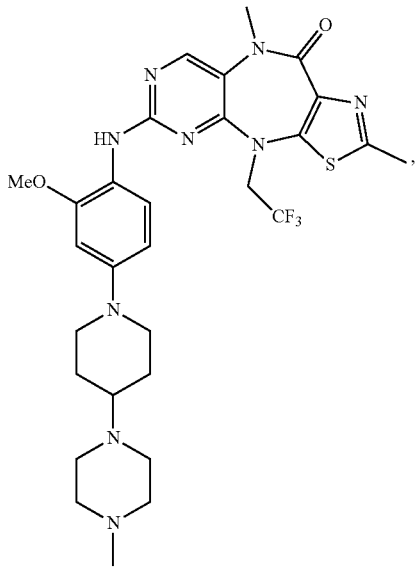

(205)

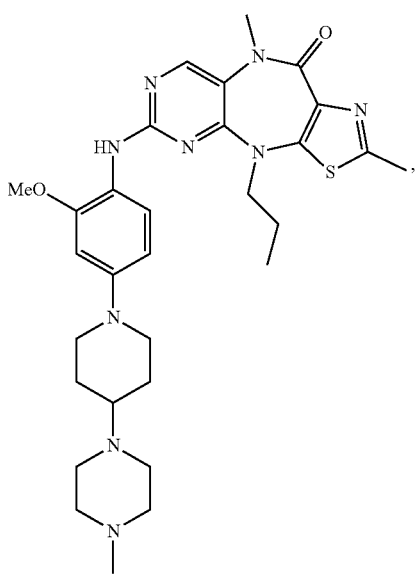

or a pharmaceutically acceptable salt or stereoisomer thereof.

Compounds of the present invention may be in the form of a free acid or free base, or a pharmaceutically acceptable salt. As used herein, the term "pharmaceutically acceptable" refers to a material, such as a carrier or diluent, which does not abrogate the biological activity or properties of the compound, and is relatively non-toxic, i.e., the material may be administered to a subject without causing undesirable biological effects (such as dizziness or gastric upset) or interacting in a deleterious manner with any of the components of the composition in which it is contained. The term "pharmaceutically acceptable salt" refers to a product obtained by reaction of the compound of the present invention with a suitable acid or a base. Examples of pharmaceutically acceptable salts of the compounds of this invention include those derived from suitable inorganic bases such as Li, Na, K, Ca, Mg, Fe, Cu, Al, Zn and Mn salts. Examples of pharmaceutically acceptable, nontoxic acid addition salts are salts of an amino group formed with inorganic acids such as hydrochloride, hydrobromide, hydroiodide, nitrate, sulfate, bisulfate, phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, 4-methylbenzenesulfonate or p-toluenesulfonate salts and the like. Certain compounds of the invention can form pharmaceutically acceptable salts with various organic bases such as lysine, arginine, guanidine, diethanolamine or metformin.

In some embodiments, the compound is an isotopic derivative in that it has at least one desired isotopic substitution of an atom, at an amount above the natural abundance of the isotope, i.e., enriched. In one embodiment, the compound includes deuterium or multiple deuterium atoms. Substitution with heavier isotopes such as deuterium, i.e. $^{2}H$, may afford certain therapeutic advantages resulting from greater metabolic stability, for example, increased in vivo half-life or reduced dosage requirements, and thus may be advantageous in some circumstances.

Compounds of the present invention may have at least one chiral center and thus may be in the form of a stereoisomer, which as used herein, embraces all isomers of individual compounds that differ only in the orientation of their atoms in space. The term stereoisomer includes mirror image isomers (enantiomers which include the (R—) or (S—) configurations of the compounds), mixtures of mirror image isomers (physical mixtures of the enantiomers, and racemates or racemic mixtures) of compounds, geometric (cis/trans or E/Z, R/S) isomers of compounds and isomers of compounds with more than one chiral center that are not mirror images of one another (diastereoisomers). The chiral centers of the compounds may undergo epimerization in vivo; thus, for these compounds, administration of the compound in its (R—) form is considered equivalent to administration of the compound in its (S—) form. Accordingly, the compounds of the present invention may be made and used in the form of individual isomers and substantially free of other isomers, or in the form of a mixture of various isomers, e.g., racemic mixtures of stereoisomers.

Methods of Synthesis

In another aspect, the present invention is directed to a method for making a compound of formula (I), or a pharmaceutically acceptable salt or stereoisomer thereof. Broadly, the inventive compounds or pharmaceutically-acceptable salts or stereoisomers thereof may be prepared by any process known to be applicable to the preparation of chemically related compounds. The compounds of the present invention will be better understood in connection with the synthetic schemes that described in various working examples and which illustrate non-limiting methods by which the compounds of the invention may be prepared.

Pharmaceutical Compositions

Another aspect of the present invention is directed to a pharmaceutical composition that includes a therapeutically effective amount of a compound of formula (I) or a pharmaceutically acceptable salt or stereoisomer thereof, and a pharmaceutically acceptable carrier. The term "pharmaceutically acceptable carrier," as known in the art, refers to a pharmaceutically acceptable material, composition or vehicle, suitable for administering compounds of the present invention to mammals. Suitable carriers may include, for example, liquids (both aqueous and non-aqueous alike, and combinations thereof), solids, encapsulating materials, gases, and combinations thereof (e.g., semi-solids), and gases, that function to carry or transport the compound from one organ, or portion of the body, to another organ, or portion of the body. A carrier is "acceptable" in the sense of being physiologically inert to and compatible with the other ingredients of the formulation and not injurious to the subject or patient. Depending on the type of formulation, the composition may also include one or more pharmaceutically acceptable excipients.

Broadly, compounds of formula (I) and their pharmaceutically acceptable salts and stereoisomers may be formulated into a given type of composition in accordance with conventional pharmaceutical practice such as conventional mixing, dissolving, granulating, dragee-making, levigating, emulsifying, encapsulating, entrapping and compression processes (see, e.g., Remington: *The Science and Practice of Pharmacy* (20th ed.), ed. A. R. Gennaro, Lippincott Williams & Wilkins, 2000 and *Encyclopedia of Pharmaceutical Technology*, eds. J. Swarbrick and J. C. Boylan, 1988-1999, Marcel Dekker, New York). The type of formulation depends on the mode of administration which may include enteral (e.g., oral, buccal, sublingual and rectal), parenteral (e.g., subcutaneous (s.c.), intravenous (i. v.), intramuscular (i.m.), and intrasternal injection, or infusion techniques, intra-ocular, intra-arterial, intramedullary, intrathecal, intraventricular, transdermal, interdermal, intravaginal, intraperitoneal, mucosal, nasal, intratracheal instillation, bronchial instillation, and inhalation) and topical (e.g., transdermal). In general, the most appropriate route of administration will depend upon a variety of factors including, for example, the nature of the agent (e.g., its stability in the environment of the gastrointestinal tract), and/or the condition of the subject (e.g., whether the subject is able to tolerate oral administration). For example, parenteral (e.g., intravenous) administration may also be advantageous in that the compound may be administered relatively quickly such as in the case of a single-dose treatment and/or an acute condition.

In some embodiments, the compounds are formulated for oral or intravenous administration (e.g., systemic intravenous injection).

Accordingly, compounds of formula (I) may be formulated into solid compositions (e.g., powders, tablets, dispersible granules, capsules, cachets, and suppositories), liquid compositions (e.g., solutions in which the compound is dissolved, suspensions in which solid particles of the compound are dispersed, emulsions, and solutions containing liposomes, micelles, or nanoparticles, syrups and elixirs); semi-solid compositions (e.g., gels, suspensions and creams); and gases (e.g., propellants for aerosol compositions). Compounds may also be formulated for rapid, intermediate or extended release.

Solid dosage forms for oral administration include capsules, tablets, pills, powders, and granules. In such solid dosage forms, the active compound is mixed with a carrier such as sodium citrate or dicalcium phosphate and an additional carrier or excipient such as a) fillers or extenders such as starches, lactose, sucrose, glucose, mannitol, and silicic acid, b) binders such as, for example, methylcellulose, microcrystalline cellulose, hydroxypropylmethylcellulose, carboxymethylcellulose, sodium carboxymethylcellulose, alginates, gelatin, polyvinylpyrrolidinone, sucrose, and acacia, c) humectants such as glycerol, d) disintegrating agents such as crosslinked polymers (e.g., crosslinked polyvinylpyrrolidone (crospovidone), crosslinked sodium carboxymethyl cellulose (croscarmellose sodium), sodium starch glycolate, agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also include buffering agents. Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings. They may further contain an opacifying agent.

In some embodiments, compounds of formula (I) may be formulated in a hard or soft gelatin capsule. Representative excipients that may be used include pregelatinized starch, magnesium stearate, mannitol, sodium stearyl fumarate, lactose anhydrous, microcrystalline cellulose and croscarmellose sodium. Gelatin shells may include gelatin, titanium dioxide, iron oxides and colorants.

Liquid dosage forms for oral administration include solutions, suspensions, emulsions, micro-emulsions, syrups and elixirs. In addition to the compound, the liquid dosage forms may contain an aqueous or non-aqueous carrier (depending upon the solubility of the compounds) commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Oral compositions may also include an excipients such as wetting agents, suspending agents, coloring, sweetening, flavoring, and perfuming agents.

Injectable preparations for parenteral administration may include sterile aqueous solutions or oleaginous suspensions. They may be formulated according to standard techniques using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The effect of the compound may be prolonged by slowing its absorption, which may be accomplished by the use of a liquid suspension or crystalline or amorphous material with poor water solubility. Prolonged absorption of the compound from a parenterally administered formulation may also be accomplished by suspending the compound in an oily vehicle.

In certain embodiments, compounds of formula (I) may be administered in a local rather than systemic manner, for example, via injection of the conjugate directly into an organ, often in a depot preparation or sustained release formulation. In specific embodiments, long acting formulations are administered by implantation (for example subcutaneously or intramuscularly) or by intramuscular injection. Injectable depot forms are made by forming microencapsule matrices of the compound in a biodegradable polymer, e.g., polylactide-polyglycolides, poly(orthoesters) and poly(anhydrides). The rate of release of the compound may be controlled by varying the ratio of compound to polymer and the nature of the particular polymer employed. Depot injectable formulations are also prepared by entrapping the compound in liposomes or microemulsions that are compatible with body tissues. Furthermore, in other embodiments, the compound is delivered in a targeted drug delivery system, for example, in a liposome coated with organ-specific antibody. In such embodiments, the liposomes are targeted to and taken up selectively by the organ.

The compositions may be formulated for buccal or sublingual administration, examples of which include tablets, lozenges and gels.

The compounds of formula (I) may be formulated for administration by inhalation. Various forms suitable for administration by inhalation include aerosols, mists or powders. Pharmaceutical compositions may be delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In some embodiments, the dosage unit of a pressurized aerosol may be determined by providing a valve to deliver a metered amount. In some embodiments, capsules and cartridges including gelatin, for example, for use in an inhaler or insufflator, may be formulated containing a powder mix of the compound and a suitable powder base such as lactose or starch.

Compounds of formula (I) may be formulated for topical administration which as used herein, refers to administration intradermally by invention of the formulation to the epidermis. These types of compositions are typically in the form of ointments, pastes, creams, lotions, gels, solutions and sprays.

Representative examples of carriers useful in formulating compounds for topical application include solvents (e.g., alcohols, poly alcohols, water), creams, lotions, ointments, oils, plasters, liposomes, powders, emulsions, microemulsions, and buffered solutions (e.g., hypotonic or buffered saline). Creams, for example, may be formulated using saturated or unsaturated fatty acids such as stearic acid, palmitic acid, oleic acid, palmito-oleic acid, cetyl, or oleyl alcohols. Creams may also contain a non-ionic surfactant such as polyoxy-40-stearate.

In some embodiments, the topical formulations may also include an excipient, an example of which is a penetration enhancing agent. These agents are capable of transporting a pharmacologically active compound through the stratum corneum and into the epidermis or dermis, preferably, with little or no systemic absorption. A wide variety of compounds have been evaluated as to their effectiveness in enhancing the rate of penetration of drugs through the skin. See, for example, *Percutaneous Penetration Enhancers*, Maibach H. I. and Smith H. E. (eds.), CRC Press, Inc., Boca Raton, Fla. (1995), which surveys the use and testing of various skin penetration enhancers, and Buyuktimkin et al., *Chemical Means of Transdermal Drug Permeation Enhancement in Transdermal and Topical Drug Delivery Systems*, Gosh T. K., Pfister W. R., Yum S. I. (Eds.), Interpharm Press Inc., Buffalo Grove, Ill. (1997). Representative examples of penetration enhancing agents include triglycerides (e.g., soybean oil), aloe compositions (e.g., aloe-vera gel), ethyl alcohol, isopropyl alcohol, octolyphenylpolyethylene glycol, oleic acid, polyethylene glycol 400, propylene glycol, N-decylmethylsulfoxide, fatty acid esters (e.g., isopropyl myristate, methyl laurate, glycerol monooleate, and propylene glycol monooleate), and N-methylpyrrolidone.

Representative examples of yet other excipients that may be included in topical as well as in other types of formulations (to the extent they are compatible), include preservatives, antioxidants, moisturizers, emollients, buffering agents, solubilizing agents, skin protectants, and surfactants. Suitable preservatives include alcohols, quaternary amines, organic acids, parabens, and phenols. Suitable antioxidants include ascorbic acid and its esters, sodium bisulfite, butylated hydroxytoluene, butylated hydroxyanisole, tocopherols, and chelating agents like EDTA and citric acid. Suitable moisturizers include glycerin, sorbitol, polyethylene glycols, urea, and propylene glycol. Suitable buffering agents include citric, hydrochloric, and lactic acid buffers. Suitable solubilizing agents include quaternary ammonium chlorides, cyclodextrins, benzyl benzoate, lecithin, and polysorbates. Suitable skin protectants include vitamin E oil, allatoin, dimethicone, glycerin, petrolatum, and zinc oxide.

Transdermal formulations typically employ transdermal delivery devices and transdermal delivery patches wherein the compound is formulated in lipophilic emulsions or buffered, aqueous solutions, dissolved and/or dispersed in a polymer or an adhesive. Patches may be constructed for continuous, pulsatile, or on demand delivery of pharmaceutical agents. Transdermal delivery of the compounds may be accomplished by means of an iontophoretic patch. Transdermal patches may provide controlled delivery of the compounds wherein the rate of absorption is slowed by using rate-controlling membranes or by trapping the compound within a polymer matrix or gel. Absorption enhancers may be used to increase absorption, examples of which include absorbable pharmaceutically acceptable solvents that assist passage through the skin.

Ophthalmic formulations include eye drops.

Formulations for rectal administration include enemas, rectal gels, rectal foams, rectal aerosols, and retention enemas, which may contain conventional suppository bases such as cocoa butter or other glycerides, as well as synthetic polymers such as polyvinylpyrrolidone, PEG, and the like. Compositions for rectal or vaginal administration may also be formulated as suppositories which can be prepared by mixing the compound with suitable non-irritating carriers and excipients such as cocoa butter, mixtures of fatty acid glycerides, polyethylene glycol, suppository waxes, and combinations thereof, all of which are solid at ambient temperature but liquid at body temperature and therefore melt in the rectum or vaginal cavity and release the compound.

Dosage Amounts

As used herein, the term, "therapeutically effective amount" refers to an amount of a compound of formula (I) or a pharmaceutically acceptable salt or a stereoisomer thereof; or a composition including a compound of formula (I) or a pharmaceutically acceptable salt or a stereoisomer thereof, that is effective in producing the desired therapeutic response in a particular patient suffering from a disease or disorder mediated by aberrant FAK. The term "therapeutically effective amount" thus includes the amount of the compound of the invention or a pharmaceutically acceptable salt or a stereoisomer thereof, that when administered, induces a positive modification in the disease or disorder to be treated, or is sufficient to prevent development or progression of the disease or disorder, or alleviate to some extent, one or more of the symptoms of the disease or disorder being treated in a subject, or which simply kills or inhibits the growth of diseased (e.g., cancer) cells, or reduces the amounts of FAK in diseased cells.

The total daily dosage of the compounds and usage thereof may be decided in accordance with standard medical practice, e.g., by the attending physician using sound medical judgment. The specific therapeutically effective dose for any particular subject may depend upon a variety of factors including the disease or disorder being treated and the severity thereof (e.g., its present status); the age, body weight, general health, sex and diet of the subject; the time of administration, route of administration, and rate of excretion of the specific compound employed; the duration of the treatment; drugs used in combination or coincidental with the compound; and like factors well known in the medical arts (see, for example, *Goodman and Gilman's, The Pharmacological Basis of Therapeutics*, 10th Edition, A. Gilman, J. Hardman and L. Limbird, eds., McGraw-Hill Press, 155-173, 2001).

Compounds of formula (I) and their pharmaceutically acceptable salts and stereoisomers may be effective over a wide dosage range. In some embodiments, the total daily dosage (e.g., for adult humans) may range from about 0.001 to about 1600 mg, from 0.01 to about 1600 mg, from 0.01 to about 500 mg, from about 0.01 to about 100 mg, from about 0.5 to about 100 mg, from 1 to about 100-400 mg per day, from about 1 to about 50 mg per day, and from about 5 to about 40 mg per day, or in yet other embodiments from about 10 to about 30 mg per day. In some embodiments, the total daily dosage may range from 400 mg to 600 mg. Individual dosages may be formulated to contain the desired dosage amount depending upon the number of times the compound is administered per day. By way of example, capsules may be formulated with from about 1 to about 200 mg of compound (e.g., 1, 2, 2.5, 3, 4, 5, 10, 15, 20, 25, 50, 100, 150, and 200 mg). In some embodiments, individual dosages may be formulated to contain the desired dosage amount depending upon the number of times the compound is administered per day.

Methods of Use

In some aspects, the present invention is directed to methods of treating diseases or disorders involving aberrant (e.g., dysfunctional or dysregulated) FAK activity, that entails administration of a therapeutically effective amount of a compound of formula (I) or a pharmaceutically acceptable salt or stereoisomer thereof, to a subject in need thereof.

The diseases or disorders may be said to be characterized or mediated by aberrant FAK activity (e.g., elevated levels of the proteins or otherwise functionally abnormal relative to a non-pathological state). A "disease" is generally regarded as a state of health of a subject wherein the subject cannot maintain homeostasis, and wherein if the disease is not ameliorated then the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. In some embodiments, compounds of the invention may be useful in the treatment of cell proliferative diseases and disorders (e.g., cancer or benign neoplasms). As used herein, the term "cell proliferative disease or disorder" refers to the conditions characterized by deregulated or abnormal cell growth, or both, including noncancerous conditions such as neoplasms, precancerous conditions, benign tumors, and cancer.

The term "subject" (or "patient") as used herein includes all members of the animal kingdom prone to or suffering from the indicated disease or disorder. In some embodiments, the subject is a mammal, e.g., a human or a non-human mammal. The methods are also applicable to companion animals such as dogs and cats as well as livestock such as cows, horses, sheep, goats, pigs, and other domesticated and wild animals. A subject "in need of" treatment according to the present invention may be "suffering from or suspected of suffering from" a specific disease or disorder may have been positively diagnosed or otherwise presents with a sufficient number of risk factors or a sufficient number or combination of signs or symptoms such that a medical professional could diagnose or suspect that the subject was suffering from the disease or disorder. Thus, subjects suffering from, and suspected of suffering from, a specific disease or disorder are not necessarily two distinct groups.

In some embodiments, the methods are directed to treating subjects having cancer. Broadly, the compounds of the present invention may be effective in the treatment of carcinomas (solid tumors including both primary and metastatic tumors), sarcomas, melanomas, and hematological cancers (cancers affecting blood including lymphocytes, bone marrow and/or lymph nodes) such as leukemia, lymphoma and multiple myeloma. Adult tumors/cancers and pediatric tumors/cancers are included. The cancers may be vascularized, or not yet substantially vascularized, or non-vascularized tumors.

Representative examples of cancers includes adrenocortical carcinoma, AIDS-related cancers (e.g., Kaposi's and AIDS-related lymphoma), appendix cancer, childhood cancers (e.g., childhood cerebellar astrocytoma, childhood cerebral astrocytoma), basal cell carcinoma, skin cancer (non-melanoma), biliary cancer, extrahepatic bile duct cancer, intrahepatic bile duct cancer, bladder cancer, urinary bladder cancer, brain cancer (e.g., gliomas and glioblastomas such as brain stem glioma, gestational trophoblastic tumor glioma, cerebellar astrocytoma, cerebral astrocytoma/malignant glioma, ependymoma, medulloblastoma, supratentorial primitive neuroectodeimal tumors, visual pathway and hypothalamic glioma), breast cancer, bronchial adenomas/carcinoids, carcinoid tumor, nervous system cancer (e.g., central nervous system cancer, central nervous system lymphoma), cervical cancer, chronic myeloproliferative disorders, colorectal cancer (e.g., colon cancer, rectal cancer), lymphoid neoplasm, mycosis fungoids, Sezary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastrointestinal cancer (e.g., stomach cancer, small intestine cancer, gastrointestinal carcinoid tumor, gastrointestinal stromal tumor (GIST)), cholangiocarcinoma, germ cell tumor, ovarian germ cell tumor, head and neck cancer, neuroendocrine tumors, Hodgkin's lymphoma, Ann Arbor stage III and stage IV childhood Non-Hodgkin's lymphoma, ROS1-positive refractory Non-Hodgkin's lymphoma, leukemia, lymphoma, multiple myeloma, hypopharyngeal cancer, intraocular melanoma, ocular cancer, islet cell tumors (endocrine pancreas), renal cancer (e.g., Wilm's Tumor, renal cell carcinoma), liver cancer, lung cancer (e.g., non-small cell lung cancer and small cell lung cancer), ALK-positive anaplastic large cell lymphoma, ALK-positive advanced malignant solid neoplasm, Waldenstrom's macroglobulinema, melanoma, intraocular (eye) melanoma, merkel cell carcinoma, mesothelioma, metastatic squamous neck cancer with occult primary, multiple endocrine neoplasia (MEN), myelodysplastic syndromes, myelodysplastic/myeloproliferative diseases, nasopharyngeal cancer, neuroblastoma, oral cancer (e.g., mouth cancer, lip cancer, oral cavity cancer, tongue cancer, oropharyngeal cancer, throat cancer, laryngeal cancer), ovarian cancer (e.g., ovarian epithelial cancer, ovarian germ cell tumor, ovarian low malignant potential tumor), pancreatic cancer, islet cell pancreatic cancer, paranasal sinus and nasal cavity cancer, parathyroid cancer, penile cancer, pharyngeal cancer, pheochromocytoma, pineoblastoma, metastatic anaplastic thyroid cancer, undifferentiated thyroid cancer, papillary thyroid cancer, pituitary tumor, plasma cell neoplasm/multiple myeloma, pleuropulmonary blastoma, prostate cancer, retinoblastoma, rhabdomyosarcoma, salivary gland cancer, uterine cancer (e.g., endometrial uterine cancer, uterine sarcoma, uterine corpus cancer), squamous cell carcinoma, testicular cancer, thymoma, thymic carcinoma, thyroid cancer, juvenile xanthogranuloma, transitional cell cancer of the renal pelvis and ureter and other urinary organs, urethral cancer, gestational trophoblastic tumor, vaginal cancer, vulvar cancer, hepatoblastoma, rhabdoid tumor, and Wilms tumor.

Sarcomas that may be treatable with compounds of the present invention include both soft tissue and bone cancers alike, representative examples of which include osteosarcoma or osteogenic sarcoma (bone) (e.g., Ewing's sarcoma), chondrosarcoma (cartilage), leiomyosarcoma (smooth muscle), rhabdomyosarcoma (skeletal muscle), mesothelial sarcoma or mesothelioma (membranous lining of body cavities), fibrosarcoma (fibrous tissue), angiosarcoma or hemangioendothelioma (blood vessels), liposarcoma (adipose tissue), glioma or astrocytoma (neurogenic connective tissue found in the brain), myxosarcoma (primitive embryonic connective tissue) and mesenchymous or mixed mesodermal tumor (mixed connective tissue types), and histiocytic sarcoma (immune cancer).

In some embodiments, methods of the present invention entail treatment of subjects having cell proliferative diseases or disorders of the hematological system, liver, brain, lung, colon, pancreas, prostate, skin, ovary, breast, skin and endometrium.

As used herein, "cell proliferative diseases or disorders of the hematological system" include lymphoma, leukemia, myeloid neoplasms, mast cell neoplasms, myelodysplasia, benign monoclonal gammopathy, lymphomatoid papulosis, polycythemia vera, chronic myelocytic leukemia, agnogenic myeloid metaplasia, and essential thrombocythemia. Representative examples of hematologic cancers may thus include multiple myeloma, lymphoma (including T-cell lymphoma, Hodgkin's lymphoma, non-Hodgkin's lymphoma (diffuse large B-cell lymphoma (DLBCL), follicular lymphoma (FL), mantle cell lymphoma (MCL) and ALK+ anaplastic large cell lymphoma (e.g., B-cell non-Hodgkin's lymphoma selected from diffuse large B-cell lymphoma (e.g., germinal center B-cell-like diffuse large B-cell lymphoma or activated B-cell-like diffuse large B-cell lymphoma), Burkitt's lymphoma/leukemia, mantle cell lymphoma, mediastinal (thymic) large B-cell lymphoma, follicular lymphoma, marginal zone lymphoma, lymphoplasmacytic lymphoma/Waldenstrom macroglobulinemia, metastatic pancreatic adenocarcinoma, refractory B-cell non-Hodgkin's lymphoma, and relapsed B-cell non-Hodgkin's lymphoma, childhood lymphomas, and lymphomas of lymphocytic and cutaneous origin, e.g., small lymphocytic lymphoma, leukemia, including childhood leukemia, hairy-cell leukemia, acute lymphocytic leukemia, acute myelocytic leukemia, acute myeloid leukemia (e.g., acute monocytic leukemia), chronic lymphocytic leukemia, small lymphocytic leukemia, chronic myelocytic leukemia, chronic myelogenous leukemia, and mast cell leukemia, myeloid neoplasms and mast cell neoplasms.

As used herein, "cell proliferative diseases or disorders of the liver" include all forms of cell proliferative disorders affecting the liver. Cell proliferative disorders of the liver may include liver cancer (e.g., hepatocellular carcinoma, intrahepatic cholangiocarcinoma and hepatoblastoma), a precancer or precancerous condition of the liver, benign growths or lesions of the liver, and malignant growths or lesions of the liver, and metastatic lesions in tissue and organs in the body other than the liver. Cell proliferative disorders of the liver may include hyperplasia, metaplasia, and dysplasia of the liver.

As used herein, "cell proliferative diseases or disorders of the brain" include all forms of cell proliferative disorders affecting the brain. Cell proliferative disorders of the brain may include brain cancer (e.g., gliomas, glioblastomas, meningiomas, pituitary adenomas, vestibular schwannomas, and primitive neuroectodermal tumors (medulloblastomas)), a precancer or precancerous condition of the brain, benign growths or lesions of the brain, and malignant growths or lesions of the brain, and metastatic lesions in tissue and organs in the body other than the brain. Cell proliferative disorders of the brain may include hyperplasia, metaplasia, and dysplasia of the brain.

As used herein, "cell proliferative diseases or disorders of the lung" include all forms of cell proliferative disorders affecting lung cells. Cell proliferative disorders of the lung include lung cancer, precancer and precancerous conditions of the lung, benign growths or lesions of the lung, hyperplasia, metaplasia, and dysplasia of the lung, and metastatic lesions in the tissue and organs in the body other than the lung. Lung cancer includes all forms of cancer of the lung, e.g., malignant lung neoplasms, carcinoma in situ, typical carcinoid tumors, and atypical carcinoid tumors. Lung cancer includes small cell lung cancer ("SLCL"), non-small cell lung cancer ("NSCLC"), squamous cell carcinoma, adenocarcinoma, small cell carcinoma, large cell carcinoma, squamous cell carcinoma, and mesothelioma. Lung cancer can include "scar carcinoma", bronchioveolar carcinoma, giant cell carcinoma, spindle cell carcinoma, and large cell neuroendocrine carcinoma. Lung cancer also includes lung neoplasms having histologic and ultrastructural heterogeneity (e.g., mixed cell types). In some embodiments, a compound of the present invention may be used to treat non-metastatic or metastatic lung cancer (e.g., NSCLC, ALK-positive NSCLC, NSCLC harboring ROS1 Rearrangement, Lung Adenocarcinoma, and Squamous Cell Lung Carcinoma).

As used herein, "cell proliferative diseases or disorders of the colon" include all forms of cell proliferative disorders affecting colon cells, including colon cancer, a precancer or precancerous conditions of the colon, adenomatous polyps of the colon and metachronous lesions of the colon. Colon cancer includes sporadic and hereditary colon cancer, malignant colon neoplasms, carcinoma in situ, typical carcinoid tumors, and atypical carcinoid tumors, adenocarcinoma, squamous cell carcinoma, and squamous cell carcinoma. Colon cancer can be associated with a hereditary syndrome such as hereditary nonpolyposis colorectal cancer, familiar adenomatous polyposis, MYH associated polyposis, Gardner's syndrome, Peutz-Jeghers syndrome, Turcot's syndrome and juvenile polyposis. Cell proliferative disorders of the colon may also be characterized by hyperplasia, metaplasia, or dysplasia of the colon.

As used herein, "cell proliferative diseases or disorders of the pancreas" include all forms of cell proliferative disorders affecting pancreatic cells. Cell proliferative disorders of the pancreas may include pancreatic cancer, a precancer or precancerous condition of the pancreas, hyperplasia of the pancreas, dysplasia of the pancreas, benign growths or lesions of the pancreas, and malignant growths or lesions of the pancreas, and metastatic lesions in tissue and organs in the body other than the pancreas. Pancreatic cancer includes all forms of cancer of the pancreas, including ductal adenocarcinoma, adenosquamous carcinoma, pleomorphic giant cell carcinoma, mucinous adenocarcinoma, osteoclast-like giant cell carcinoma, mucinous cystadenocarcinoma, acinar carcinoma, unclassified large cell carcinoma, small cell carcinoma, pancreatoblastoma, papillary neoplasm, mucinous cystadenoma, papillary cystic neoplasm, and serous cystadenoma, and pancreatic neoplasms having histologic and ultrastructural heterogeneity (e.g., mixed cell).

As used herein, "cell proliferative diseases or disorders of the prostate" include all forms of cell proliferative disorders affecting the prostate. Cell proliferative disorders of the prostate may include prostate cancer, a precancer or precancerous condition of the prostate, benign growths or lesions of the prostate, and malignant growths or lesions of the prostate, and metastatic lesions in tissue and organs in the body other than the prostate. Cell proliferative disorders of the prostate may include hyperplasia, metaplasia, and dysplasia of the prostate.

As used herein, "cell proliferative diseases or disorders of the ovary" include all forms of cell proliferative disorders affecting cells of the ovary. Cell proliferative disorders of the ovary may include a precancer or precancerous condition of the ovary, benign growths or lesions of the ovary, ovarian cancer, and metastatic lesions in tissue and organs in the body other than the ovary. Cell proliferative disorders of the ovary may include hyperplasia, metaplasia, and dysplasia of the ovary.

As used herein, "cell proliferative diseases or disorders of the breast" include all forms of cell proliferative disorders affecting breast cells. Cell proliferative disorders of the breast may include breast cancer, a precancer or precancerous condition of the breast, benign growths or lesions of the breast, and metastatic lesions in tissue and organs in the body other than the breast. Cell proliferative disorders of the breast may include hyperplasia, metaplasia, and dysplasia of the breast.

As used herein, "cell proliferative diseases or disorders of the skin" include all forms of cell proliferative disorders affecting skin cells. Cell proliferative disorders of the skin may include a precancer or precancerous condition of the skin, benign growths or lesions of the skin, melanoma, malignant melanoma or other malignant growths or lesions of the skin, and metastatic lesions in tissue and organs in the body other than the skin. Cell proliferative disorders of the skin may include hyperplasia, metaplasia, and dysplasia of the skin.

As used herein, "cell proliferative diseases or disorders of the endometrium" include all forms of cell proliferative disorders affecting cells of the endometrium. Cell proliferative disorders of the endometrium may include a precancer or precancerous condition of the endometrium, benign growths or lesions of the endometrium, endometrial cancer, and metastatic lesions in tissue and organs in the body other than the endometrium. Cell proliferative disorders of the endometrium may include hyperplasia, metaplasia, and dysplasia of the endometrium.

The compounds of formula (I) and their pharmaceutically acceptable salts and stereoisomers may be administered to a patient, e.g., a cancer patient, as a monotherapy or by way of combination therapy. Therapy may be "front/first-line", i.e., as an initial treatment in patients who have undergone no prior anti-cancer treatment regimens, either alone or in combination with other treatments; or "second-line", as a treatment in patients who have undergone a prior anti-cancer treatment regimen, either alone or in combination with other treatments; or as "third-line", "fourth-line", etc. treatments, either alone or in combination with other treatments. Therapy may also be given to patients who have had previous treatments which have been unsuccessful, or partially successful but who have become intolerant to the particular treatment. Therapy may also be given as an adjuvant treatment, i.e., to prevent reoccurrence of cancer in patients with no currently detectable disease or after surgical removal of a tumor. Thus, in some embodiments, the compound may be administered to a patient who has received prior therapy, such as chemotherapy, radioimmunotherapy, surgical therapy, immunotherapy, radiation therapy, targeted therapy or any combination thereof.

The methods of the present invention may entail administration of a compound of formula (I) or a pharmaceutical composition thereof to the patient in a single dose or in multiple doses (e.g., 1, 2, 3, 4, 5, 6, 7, 8, 10, 15, 20, or more doses). For example, the frequency of administration may range from once a day up to about once every eight weeks. In some embodiments, the frequency of administration ranges from about once a day for 1, 2, 3, 4, 5, or 6 weeks, and in other embodiments entails a 28-day cycle which includes daily administration for 3 weeks (21 days) followed by a 7-day "off" period. In other embodiments, the compound may be dosed twice a day (BID) over the course of two and a half days (for a total of 5 doses) or once a day (QD) over the course of two days (for a total of 2 doses). In other embodiments, the compound may be dosed once a day (QD) over the course of 5 days.

Combination Therapy

Compounds of formula (I) and their pharmaceutically acceptable salts and stereoisomers may be used in combination or concurrently with at least one other active agent, e.g., anti-cancer agent or regimen, in treating diseases and disorders. The terms "in combination" and "concurrently" in this context mean that the agents are co-administered, which includes substantially contemporaneous administration, by way of the same or separate dosage forms, and by the same or different modes of administration, or sequentially, e.g., as part of the same treatment regimen, or by way of successive treatment regimens. Thus, if given sequentially, at the onset of administration of the second compound, the first of the two compounds is in some cases still detectable at effective concentrations at the site of treatment. The sequence and time interval may be determined such that they can act together (e.g., synergistically) to provide an increased benefit than if they were administered otherwise. For example, the therapeutics may be administered at the same time or sequentially in any order at different points in time; however, if not administered at the same time, they may be administered sufficiently close in time so as to provide the desired therapeutic effect, which may be in a synergistic fashion. Thus, the terms are not limited to the administration of the active agents at exactly the same time.

In some embodiments, the treatment regimen may include administration of a compound of formula (I) in combination with one or more additional therapeutics known for use in treating the disease or condition (e.g., cancer). The dosage of the additional anticancer therapeutic may be the same or even lower than known or recommended doses. See, Hardman et al., eds., *Goodman & Gilman's The Pharmacological Basis Of Basis Of Therapeutics,* 10th ed., McGraw-Hill, New York, 2001; Physician's Desk Reference 60th ed., 2006. For example, anti-cancer agents that may be suitable for use in combination with the inventive compounds are known in the art. See, e.g., U.S. Pat. No. 9,101,622 (Section 5.2 thereof) and U.S. Pat. No. 9,345,705 B2 (Columns 12-18 thereof). Representative examples of additional active agents and treatment regimens include radiation therapy, chemotherapeutics (e.g., mitotic inhibitors, angiogenesis inhibitors, anti-hormones, autophagy inhibitors, alkylating agents, intercalating antibiotics, growth factor inhibitors, anti-androgens, signal transduction pathway inhibitors, anti-microtubule agents, platinum coordination complexes, HDAC inhibitors, proteasome inhibitors, and topoisomerase inhibitors), immunomodulators, therapeutic antibodies (e.g., mono-specific and bispecific antibodies) and CAR-T therapy.

In some embodiments, a compound of formula (I) and the additional (e.g., anticancer) therapeutic may be administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. The two or more (e.g., anticancer) therapeutics may be administered within the same patient visit.

When the active components of the combination are not administered in the same pharmaceutical composition, it is understood that they can be administered in any order to a subject in need thereof. For example, a compound of the present invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various aspects, the anticancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one example, the (e.g., anticancer) therapeutics are administered within the same office visit. In another example, the combination anticancer therapeutics may be administered at 1 minute to 24 hours apart.

In some embodiments involving cancer treatment, a compound of formula (I) and the additional anti-cancer agent or therapeutic are cyclically administered. Cycling therapy involves the administration of one anticancer therapeutic for a period of time, followed by the administration of a second anti-cancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies. In one example, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

Pharmaceutical Kits

The present compounds and/or compositions containing them may be assembled into kits or pharmaceutical systems. Kits or pharmaceutical systems according to this aspect of the invention include a carrier or package such as a box, carton, tube or the like, having in close confinement therein one or more containers, such as vials, tubes, ampoules, or bottles, which contain a compound of formula (I) or a pharmaceutical composition thereof. The kits or pharmaceutical systems of the invention may also include printed instructions for using the compounds and compositions.

These and other aspects of the present invention will be further appreciated upon consideration of the following Examples, which are intended to illustrate certain particular embodiments of the invention but are not intended to limit its scope, as defined by the claims.

EXAMPLES

These and other aspects of the present invention will be further appreciated upon consideration of the following Examples, which are intended to illustrate certain particular embodiments of the invention but are not intended to limit its scope, as defined by the claims.

Example 1: Synthesis of Tricyclic Core for Compounds 1-4, 7, 10, and 11

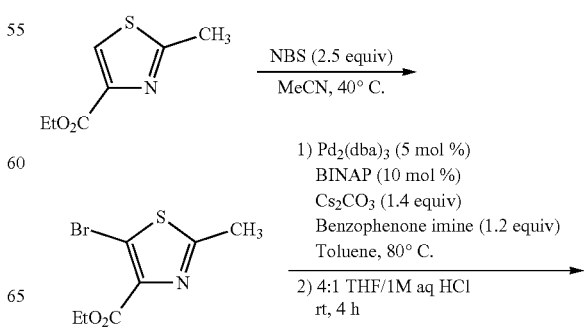

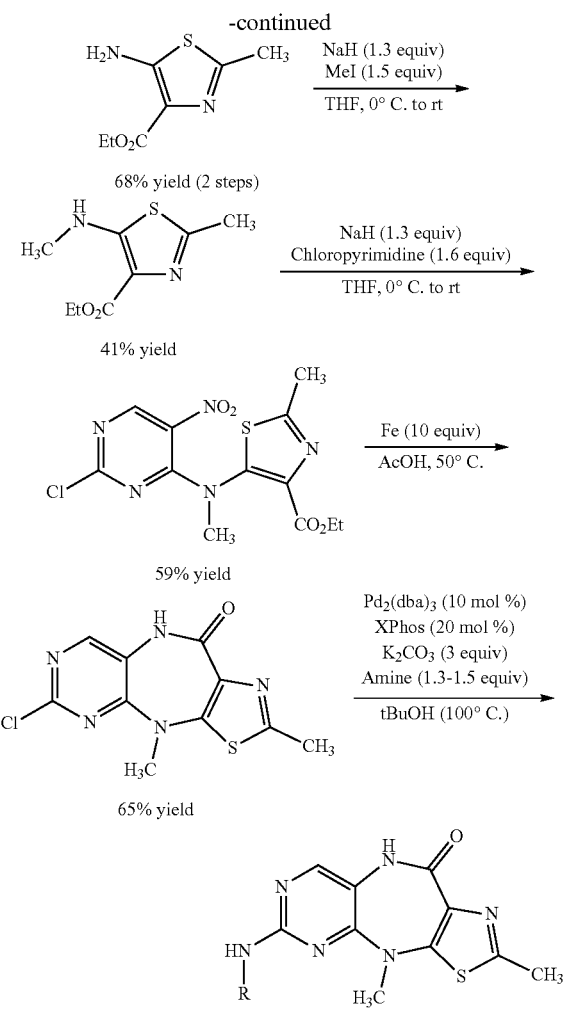

68% yield (2 steps)

41% yield

59% yield

65% yield

To a solution of 2-methylthiazole-4-carboxylate (2.417 g, 14 mmol, 1 equiv) in acetonitrile (50 mL) was added N-bromosuccinimide (6.265 g, 35 mmol, 2.5 equiv). The mixture was heated to 40° C. for 2 days. The reaction was then diluted with DCM (100 mL) and water (200 mL). The organic layer was removed, and the aqueous layer extracted with DCM (3×75 mL). The combined organic layers were washed twice with water, once with brine, dried over MgSO$_4$, filtered and then concentrated to provide a dark, viscous oil. ISCO flash chromatography (40 g silica, 20-80% EtOAc/hexanes, 20 min gradient) provided ethyl 5-bromo-2-methylthiazole-4-carboxylate as a light yellow solid (2.174 g, 61% yield). $^1$H NMR (500 MHz, CDCl$_3$) δ 4.44 (q, J=7.2 Hz, 2H), 2.71 (s, 3H), 1.42 (t, J=7.2 Hz, 3H). MS (ESI) 249.78, 251.87 (M+H)$^+$.

A mixture of ethyl 5-bromo-2-methylthiazole-4-carboxylate (2.010 g, 8.0 mmol, 1 equiv), Pd$_2$(dba)$_3$ (368 mg, 0.40 mmol, 0.05 equiv), (±)-BINAP (495 mg, 0.80 mmol, 0.10 equiv), and cesium carbonate (3.685 g, 11.2 mmol, 1.4 equiv), and benzophenone imine (1.61 mL, 9.6 mmol, 1.2 equiv) in anhydrous toluene (35 mL) was sparged with N$_2$ for 10 minutes. The reaction was heated to 80° C. for 20 hours, and then cooled to room temperature, diluted with EtOAc (100 mL) and filtered through Celite®. Solvents were removed in vacuo to provide a dark red syrup. The intermediate ethyl 5-((diphenylmethylene)amino)-2-methylthiazole-4-carboxylate was carried on directly to hydrolysis. MS (ESI) 350.87 (M+H)$^+$.

Crude ethyl 5-((diphenylmethylene)amino)-2-methylthiazole-4-carboxylate was dissolved in 20 mL THF and 5 mL 1 M HCl. The mixture was stirred at room temperature for 4 hours, at which point ultra-performance liquid chromatography-mass spectrometry (UPLC-MS) analysis showed complete hydrolysis of the imine. The reaction was diluted with 50 mL EtOAc and then extracted with 1 M HCl (4×50 mL). The combined aqueous layers were neutralized to pH>12 and then extracted with DCM (5×50 mL). The combined DCM layers were washed with saturated aqueous NaHCO$_3$, dried over MgSO$_4$, filtered and concentrated to provide ethyl 5-amino-2-methylthiazole-4-carboxylate as a light yellow solid (1.011 g, 68% yield over 2 steps). The product was sufficiently pure and did not require further purification. $^1$H NMR (500 MHz, CDCl$_3$) δ 5.87 (s, 2H), 4.38 (q, J=7.1 Hz, 2H), 2.53 (s, 3H), 1.40 (t, J=7.1 Hz, 3H). MS (ESI) 186.87 (M+H)$^+$.

A 250 mL round-bottom flask was dried with a heat gun. Sodium hydride (331 mg, 7.8 mmol, 1.3 equiv, 60% dispersion in mineral oil) was added and washed (2×8 mL) with hexanes. Anhydrous THF (40 mL) was added and the flask was cooled on an ice bath. To this suspension, a solution of ethyl 5-amino-2-methylthiazole-4-carboxylate (1.120 g, 6.0 mmol, 1.0 equiv) in 30 mL THF was added over 10 minutes. The reaction was stirred for 1 hour and then iodomethane (0.56 mL, 9.0 mmol, 1.5 equiv) was added dropwise. The reaction was stirred for 20 hours, slowly warming to room temperature. The reaction was quenched with water (50 mL). The aqueous layer was extracted with EtOAc (4×50 mL). The combined organic layers were washed with brine, dried over MgSO$_4$, filtered and concentrated. ISCO flash chromatography (20-80% EtOAC/hex, 18 minutes, 40 g silica) provided ethyl 2-methyl-5-(methylamino)thiazole-4-carboxylate as a light yellow solid (502 mg, 41% yield). $^1$H NMR (500 MHz, CDCl$_3$) δ 7.21 (s, 1H), 4.36 (q, J=7.1 Hz, 2H), 3.00 (d, J=5.2 Hz, 3H), 2.54 (s, 3H), 1.38 (t, J=7.1 Hz, 3H). MS (ESI) 200.87 (M+H)$^+$.

A 100 mL round-bottom flask was dried with a heat gun. Sodium hydride (132 mg, 3.12 mmol, 1.3 equiv, 60% dispersion in mineral oil) was added and washed (2×5 mL) with hexanes. Anhydrous THF (15 mL) was added and the flask was cooled on an ice bath. To this suspension, a solution of ethyl 2-methyl-5-(methylamino)thiazole-4-carboxylate (480 mg, 2.4 mmol, 1.0 equiv) in 13 mL THF was added over 10 minutes. The reaction was stirred at 0° C. for 1 hour and then 2,4-dichloro-5-nitropyrimidine (746 mg, 3.85 mmol, 1.6 equiv) was added. The reaction was stirred for 5 hours, slowly warming to room temperature. UPLC-MS analysis showed full consumption of starting material. The reaction was quenched with water (50 mL). The aqueous layer was extracted with EtOAc (3×30 mL). The combined organic layers were washed with brine, dried over MgSO$_4$, filtered and concentrated. ISCO flash chromatography (20-80% EtOAC/hex, 18 minutes, 40 g silica) provided ethyl 5-((2-chloro-5-nitropyrimidin-4-yl)(methyl)amino)-2-methylthiazole-4-carboxylate as a yellow oil that partially solidified on standing (508 mg, 59% isolated yield). $^1$H NMR (500 MHz, CDCl$_3$) δ 8.59 (s, 1H), 4.26 (q, J=7.1 Hz, 2H), 3.63 (s, 3H), 2.73 (s, 3H), 1.25 (t, J=7.1 Hz, 3H). MS (ESI) 357.77 (M+H)$^+$.

A suspension of ethyl 5-((2-chloro-5-nitropyrimidin-4-yl)(methyl)amino)-2-methylthiazole-4-carboxylate (499 mg, 1.4 mmol, 1.0 equiv) and iron powder (784 mg, 14.0 mmol, 10 equiv) in glacial acetic acid (20 mL) was heated to 50° C. for 16 hours. The reaction was cooled to room temperature and residual iron was removed with a magnetic wand. The crude reaction mixture was poured into a beaker with 150 mL water and stirred at room temperature for 30 minutes. The resulting precipitate was collected by suction filtration, washing with ~100 mL water, and dried in vacuo to provide 6-chloro-2,4-dimethyl-4,9-dihydro-10H-pyrimido[5,4-b]thiazolo[5,4-e][1,4]diazepin-10-one as a beige solid (258 mg, 65% isolated yield). $^1$H NMR (500 MHz, MeOD) δ 8.09 (s, 1H), 3.46 (s, 3H), 2.60 (s, 3H). MS (ESI) 282.07. (M+H)$^+$.

Example 2: General Palladium (Pd) Coupling Conditions

To a 1-dram vial with a stir bar were added 6-chloro-2,4-dimethyl-4,9-dihydro-10H-pyrimido[5,4-b]thiazolo[5,4-e][1,4]diazepin-10-one (1.0 equiv), Pd$_2$(dba)$_3$ (0.10 equiv), XPhos (0.20 equiv), K$_2$CO$_3$ (3.0 equiv) and the desired aniline (1.30-1.50 equiv). Tert-butanol (0.08 M) was added, the flask was sealed with a septum-lined cap, and the suspension was sparged with nitrogen for 10 minutes. The reaction was heated to 100° C. overnight, and then diluted with EtOAc (10 mL), filtered through Celite®, concentrated in vacuo, and purified by reverse-phase preparative HPLC using a water (0.035% TFA)/methanol (0.035%) or water (0.035% TFA)/acetonitrile (0.035%) gradient.

Example 3: Synthesis of 2,4-dimethyl-6-((4-(4-methylpiperazin-1-yl)phenyl)amino)-4,9-dihydro-10H-pyrimido[5,4-b]thiazolo[5,4-e][1,4]diazepin-10-one (1)

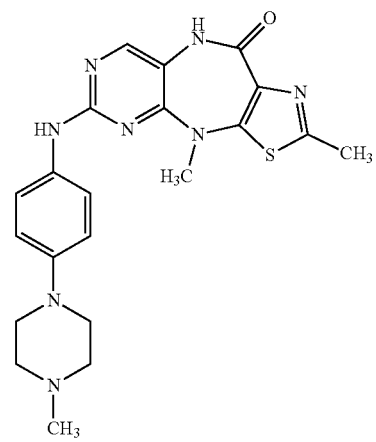 [SMILES: Cc1nc2c(s1)N(C)c1nc(Nc3ccc(N4CCN(C)CC4)cc3)ncc1NC2=O]

General Pd coupling was run on 0.05 mmol scale using 4-(4-methylpiperazin-1-yl)aniline (14.0 mg, 0.075 mmol, 1.5 equiv). The reaction mixture was purified by reverse-phase prep HPLC (100-40% H$_2$O/MeOH, 20 mL/min, 45 min). Lyophilization from H$_2$O/MeCN provided the title compound as a yellow powder (8.1 mg TFA salt). $^1$H-NMR (500 MHz, DMSO-d$_6$) δ 9.96 (s, 1H), 9.53 (s, 1H), 9.38 (s, 1H), 7.98 (s, 1H), 7.57 (d, J=8.8 Hz, 2H), 6.95 (d, J=8.8 Hz, 2H), 3.72 (d, J=13.2 Hz, 2H), 3.36 (s, 3H), 3.16 (m, 2H), 2.88 (m, 5H), 2.53 (s, 3H). MS (ESI) 437.28 (M+H)$^+$.

Example 4: Synthesis of 6-((4-(4-hydroxypiperidin-1-yl)phenyl)amino)-2,4-dimethyl-4,9-dihydro-10H-pyrimido[5,4-b]thiazolo[5,4-e][1,4]diazepin-10-one (2)

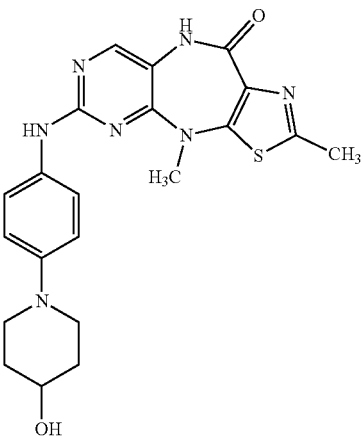 [SMILES: Cc1nc2c(s1)N(C)c1nc(Nc3ccc(N4CCC(O)CC4)cc3)ncc1NC2=O]

General Pd coupling was run on 0.05 mmol scale using 1-(4-aminophenyl)piperidin-4-ol (14.4 mg, 0.075 mmol, 1.5 equiv). The reaction mixture was purified by reverse-phase prep HPLC (100-40% H$_2$O/MeOH, 20 mL/min, 45 min). Lyophilization from H$_2$O/MeCN provided the title compound as a yellow powder (6.3 mg TFA salt). MS (ESI) 438.28 (M+H)$^+$.

Example 5: Synthesis of 6-((2-methoxy-4-(4-(4-methylpiperazin-1-yl)piperidin-1-yl)phenyl)amino)-2,4-dimethyl-4,9-dihydro-10H-pyrimido[5,4-b]thiazolo[5,4-e][1,4]diazepin-10-one (3)

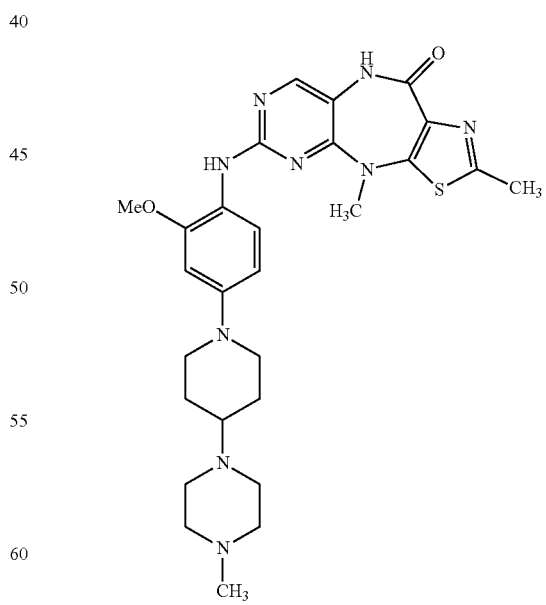

General Pd coupling was run on 0.05 mmol scale using 2-methoxy-4-(4-(4-methylpiperazin-1-yl)piperidin-1-yl)aniline (21.1 mg, 0.070 mmol, 1.4 equiv). The reaction mixture was purified by reverse-phase prep HPLC (100-40%

H₂O/MeOH, 20 mL/min, 45 min). Lyophilization from H₂O/MeCN provided the title compound as a beige powder (8.8 mg TFA salt). $^1$H NMR (500 MHz, DMSO-$d_6$) δ 9.51 (s, 1H), 7.95 (s, 1H), 7.93 (s, 1H), 7.72 (d, J=8.7 Hz, 1H), 6.70 (s, 1H), 6.56 (d, J=8.6 Hz, 1H), 3.81 (s, 3H), 3.79-3.65 (m, 8H), 3.31 (s, 3H), 2.76 (s, 3H), 2.53 (s, 3H), 2.04-1.92 (m, 2H), 1.71-1.59 (m, 2H). MS (ESI) 550.39 (M+H)⁺.

Example 6: Synthesis of 6-((3-methoxy-4-(4-methylpiperazin-1-yl)phenyl)amino)-2,4-dimethyl-4,9-dihydro-10H-pyrimido[5,4-b]thiazolo[5,4-e][1,4]diazepin-10-one (4)

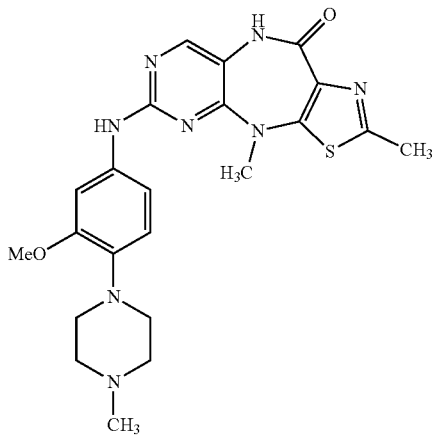 [SMILES: COc1cc(Nc2ncc3c(n2)N(C)c2sc(C)nc2C(=O)N3)ccc1N1CCN(C)CC1]

General Pd coupling was run on 0.05 mmol scale using 3-methoxy-4-(4-methylpiperazin-1-yl)aniline (16.5 mg, 0.075 mmol, 1.5 equiv). The reaction mixture was purified by reverse-phase prep HPLC (90-40% H₂O/MeOH, 20 mL/min, 45 min). Lyophilization from H₂O/MeCN provided the title compound as a yellow powder (16.0 mg TFA salt). $^1$H NMR (500 MHz, DMSO-$d_6$) δ 9.62 (s, 1H), 9.55 (s, 1H), 9.45 (s, 1H), 8.00 (s, 1H), 7.46 (d, J=2.3 Hz, 1H), 7.21 (dd, J=8.6, 2.4 Hz, 1H), 6.87 (d, J=8.6 Hz, 1H), 3.79 (s, 3H), 3.48 (d, J=11.8 Hz, 2H), 3.40 (s, 5H), 3.19 (q, J=11.0 Hz, 2H), 2.91-2.80 (m, 5H), 2.54 (s, 3H). MS (ESI) 467.38 (M+H)⁺.

Example 7: Synthesis of 6-((2-methoxy-4-(4-methylpiperazin-1-yl)phenyl)amino)-2,4-dimethyl-4,9-dihydro-10H-pyrimido[5,4-b]thiazolo[5,4-e][1,4]diazepin-10-one (7)

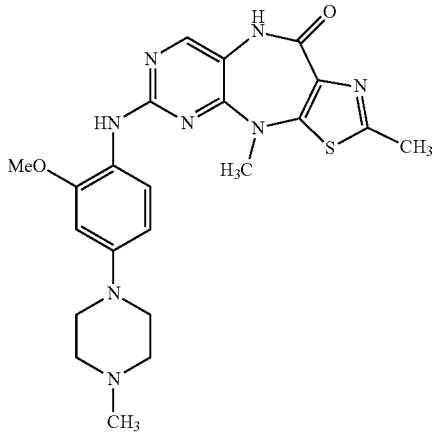 [SMILES: COc1cc(N2CCN(C)CC2)ccc1Nc1ncc2c(n1)N(C)c1sc(C)nc1C(=O)N2]

General Pd coupling was run on 0.08 mmol scale using 2-methoxy-4-(4-methylpiperazin-1-yl)aniline (27.2 mg, 0.120 mmol, 1.5 equiv). The reaction mixture was purified by reverse-phase prep HPLC (100-30% H₂O/MeCN, 20 mL/min, 28 min). Lyophilization from H₂O/MeCN provided the title compound as a light brown powder (3.9 mg TFA salt). $^1$H NMR (500 MHz, DMSO-$d_6$) δ 9.87 (s, 1H), 9.51 (s, 1H), 7.96 (s, 1H), 7.93 (s, 1H), 7.74 (d, J=8.8 Hz, 1H), 6.70 (d, J=2.6 Hz, 1H), 6.54 (dd, J=8.8, 2.6 Hz, 1H), 3.82 (s, 3H), 3.53 (d, J=12.4 Hz, 2H), 3.31 (s, 3H), 3.24-3.11 (m, 2H), 2.93 (t, J=12.5 Hz, 2H), 2.87 (s, 3H), 2.53 (s, 3H). MS (ESI) 467.18 (M+H)⁺.

Example 8: Synthesis of 4-((2,4-dimethyl-10-oxo-9,10-dihydro-4H-pyrimido[5,4-b]thiazolo[5,4-e][1,4]diazepin-6-yl)amino)-N-methylbenzamide (10)

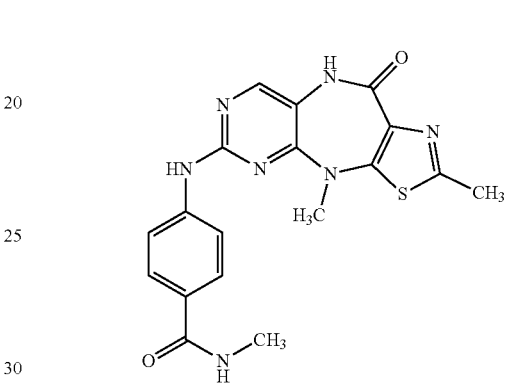

General Pd coupling was run on 0.08 mmol scale using 4-amino-N-methylbenzamide (18.3 mg, 0.12 mmol, 1.5 equiv). The reaction mixture was purified by reverse-phase prep HPLC (100-40% H₂O/MeCN, 20 mL/min, 45 min). Lyophilization from H₂O/MeCN provided the title compound as a light yellow powder (12.9 mg TFA salt). $^1$H NMR (500 MHz, DMSO-$d_6$) δ 9.82 (s, 1H), 9.60 (s, 1H), 8.23 (q, J=4.4 Hz, 1H), 8.05 (s, 1H), 7.76 (s, 4H), 3.41 (s, 3H), 2.76 (d, J=4.5 Hz, 3H), 2.54 (s, 3H). MS (ESI) 396.27 (M+H)⁺.

Example 9: Synthesis of 6-((2-methoxy-4-(4-(methylsulfonyl)piperazin-1-yl)phenyl)amino)-2,4-dimethyl-4,9-dihydro-10H-pyrimido[5,4-b]thiazolo[5,4-e][1,4]diazepin-10-one (11)

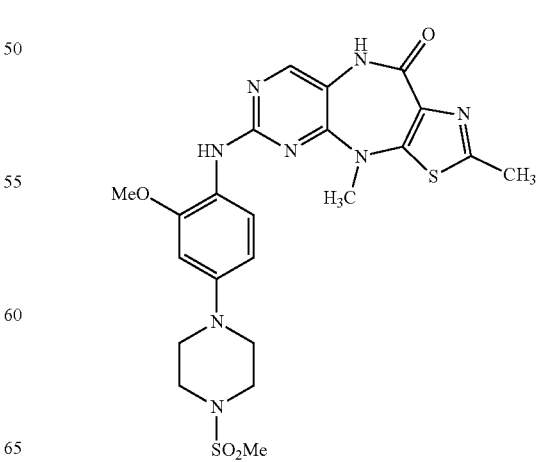

General Pd coupling was run on 0.08 mmol scale using 2-methoxy-4-(4-(methylsulfonyl)piperazin-1-yl)aniline (36.2 mg, 0.12 mmol, 1.5 equiv). The reaction mixture was purified by reverse-phase prep HPLC (100-40% H₂O/MeCN, 20 mL/min, 45 min). Lyophilization from H₂O/MeCN provided the title compound as a light brown powder (2.5 mg TFA salt). $^1$H NMR (500 MHz, DMSO-d$_6$) δ 9.53 (s, 1H), 8.15 (br s, 1H), 7.91 (s, 1H), 7.69 (d, J=8.7 Hz, 1H), 6.69 (d, J=2.5 Hz, 1H), 6.54 (dd, J=8.8, 2.6 Hz, 1H), 3.81 (s, 3H), 3.33 (s, 3H), 3.28-3.21 (m, 8H), 2.93 (s, 3H), 2.53 (s, 3H). MS (ESI) 531.28 (M+H)⁺.

Example 10: Synthesis of Tricyclic Core for Compounds 5 and 12-14

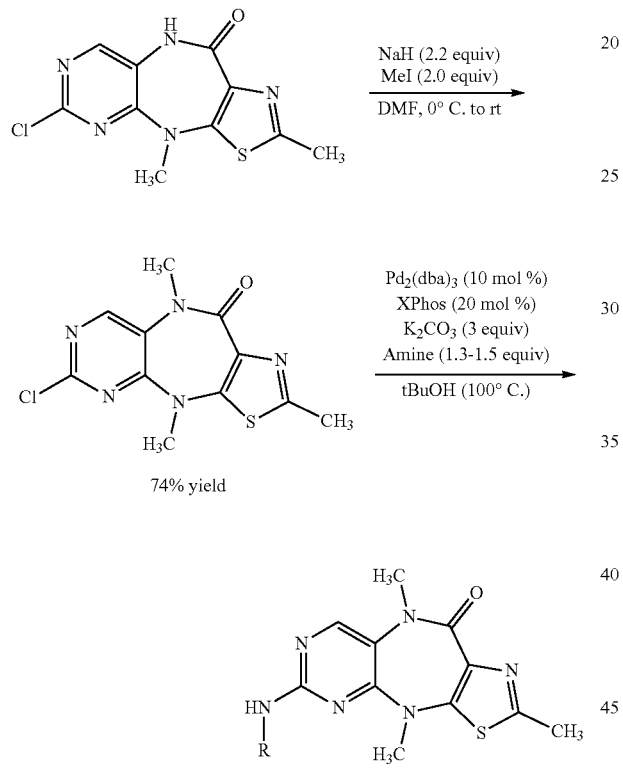

74% yield

To a suspension of 6-chloro-2,4-dimethyl-4,9-dihydro-10H-pyrimido[5,4-b]thiazolo[5,4-e][1,4]diazepin-10-one (267 mg, 0.95 mmol, 1.0 equiv) and iodomethane (0.130 mL, 2.0 mmol, 2.1 equiv) in anhydrous DMF (12 mL) at 0° C., NaH (97.3 mg, 2.4 mmol, 2.5 equiv, 60% dispersion in mineral oil) was added in a single portion. The reaction was stirred for 2 hours, at which point UPLC-MS analysis showed complete consumption of starting material. The reaction was then quenched with water (20 mL) and extracted with EtOAc (4×40 mL). The combined organic layers were washed twice with water, once with brine, dried over MgSO₄, filtered and concentrated. ISCO flash chromatography (24 g silica, 0-10% MeOH/DCM, 14 min gradient) provided 6-chloro-2,4,9-trimethyl-4,9-dihydro-10H-pyrimido[5,4-b]thiazolo[5,4-e][1,4]diazepin-10-one as a light yellow solid (219.7 mg, 74% yield). $^1$H NMR (500 MHz, CDCl₃) δ 8.23 (s, 1H), 3.45 (s, 3H), 3.43 (s, 3H), 2.62 (s, 3H). MS (ESI) 295.77 (M+H)⁺.

Example 11: Synthesis of 6-((2-methoxy-4-(4-(4-methylpiperazin-1-yl)piperidin-1-yl)phenyl)amino)-2,4,9-trimethyl-4,9-dihydro-10H-pyrimido[5,4-b]thiazolo[5,4-e][1,4]diazepin-10-one (5)

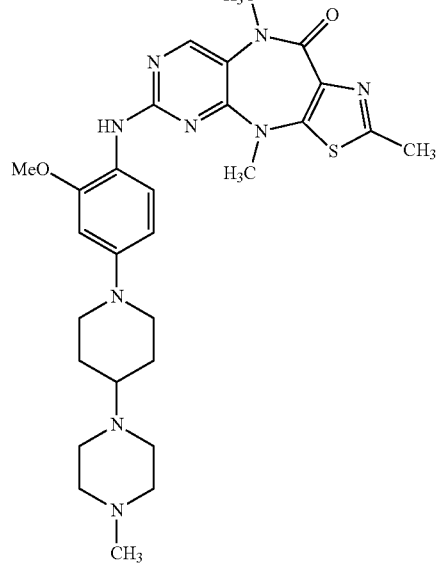

General Pd coupling was run on 0.05 mmol scale using 2-methoxy-4-(4-(4-methylpiperazin-1-yl)piperidin-1-yl)aniline (21.6 mg, 0.07 mmol, 1.4 equiv). The reaction mixture was purified by reverse-phase prep HPLC (100-50% H₂O/MeCN, 20 mL/min, 45 min). Lyophilization from H₂O/MeCN provided the title compound as a white powder (4.2 mg TFA salt). $^1$H NMR (500 MHz, DMSO-d$_6$) δ 8.30 (s, 1H), 8.06 (s, 1H), 7.64 (d, J=8.7 Hz, 1H), 6.61 (d, J=2.6 Hz, 1H), 6.48 (dd, J=8.8, 2.6 Hz, 1H), 3.79 (s, 3H), 3.68 (d, J=12.2 Hz, 2H), 3.28 (s, 3H), 3.26 (s, 3H), 2.63 (td, J=12.1, 2.3 Hz, 3H), 2.53 (s, 4H), 2.38 (m, 4H), 2.22 (s, 3H), 1.84 (d, J=12.3 Hz, 2H), 1.58-1.44 (m, 2H). MS (ESI) 564.49 (M+H)⁺.

Example 12: Synthesis of 6-((2-methoxy-4-(piperazin-1-yl)phenyl)amino)-2,4,9-trimethyl-4,9-dihydro-10H-pyrimido[5,4-b]thiazolo[5,4-e][1,4]diazepin-10-one (12)

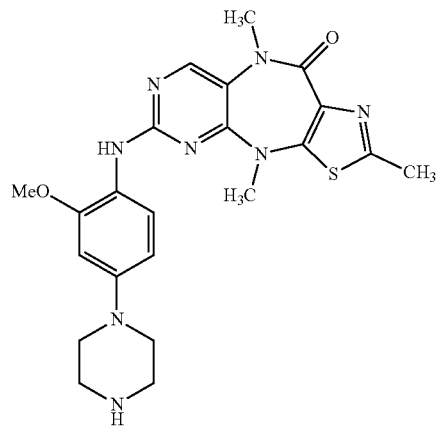 [SMILES: COc1cc(N2CCNCC2)ccc1Nc1ncc2c(n1)N(C)c1sc(C)nc1C(=O)N2C]

General Pd coupling was run on 0.13 mmol scale using tert-butyl 4-(4-amino-3-methoxyphenyl)piperazine-1-carboxylate. ISCO flash chromatography (12 g silica, 0-10% MeOH/DCM, 12 min gradient) provided tert-butyl 4-(3-methoxy-4-((2,4,9-trimethyl-10-oxo-9,10-dihydro-4H-pyrimido[5,4-b]thiazolo[5,4-e][1,4]diazepin-6-yl)amino)phenyl)piperazine-1-carboxylate as a yellow solid (29.4 mg, 40% yield). $^1$H NMR (500 MHz, DMSO-$d_6$) δ 8.31 (s, 1H), 8.09 (s, 1H), 7.68 (d, J=8.7 Hz, 1H), 6.66 (d, J=2.6 Hz, 1H), 6.51 (dd, J=8.8, 2.6 Hz, 1H), 3.80 (s, 3H), 3.46 (t, J=5.1 Hz, 4H), 3.29 (s, 3H), 3.26 (s, 3H), 3.07 (t, J=5.2 Hz, 4H), 2.53 (s, 3H), 1.42 (s, 9H). MS (ESI) 567.39 (M+H)$^+$.

The Boc-protected intermediate (29.4 mg, 0.052 mmol, 1.0 equiv) was dissolved in DCM (0.8 mL) and TFA (0.2 mL). The mixture was stirred at room temp for 3 hours; UPLC-MS analysis showed complete deprotection. Volatiles were removed in vacuo; Lyophilization from H$_2$O/MeCN provided the title compound as a yellow powder (44.4 mg, 2×TFA salt). $^1$H NMR (500 MHz, DMSO-$d_6$) δ 8.78 (s, 2H), 8.31 (s, 1H), 8.14 (s, 1H), 7.72 (d, J=8.7 Hz, 1H), 6.69 (d, J=2.6 Hz, 1H), 6.54 (dd, J=8.8, 2.6 Hz, 1H), 3.81 (s, 3H), 3.35-3.31 (m, 4H), 3.30 (s, 3H), 3.27 (s, 3H), 3.26-3.20 (m, 4H), 2.53 (s, 3H). MS (ESI) 466.88 (M+H)$^+$.

Example 13: Synthesis of 6-((4-(4-acryloylpiperazin-1-yl)-2-methoxyphenyl)amino)-2,4,9-trimethyl-4,9-dihydro-10H-pyrimido[5,4-b]thiazolo[5,4-e][1,4]diazepin-10-one (13)

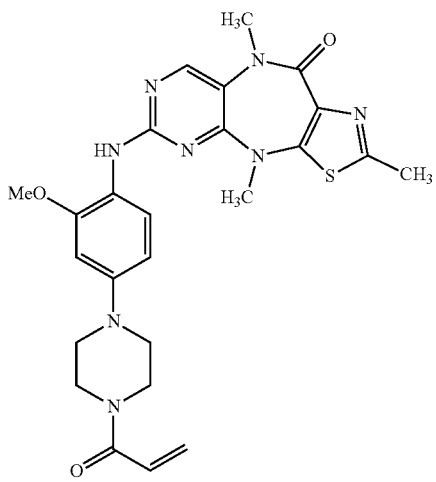 [SMILES: C=CC(=O)N1CCN(c2ccc(Nc3ncc4c(n3)N(C)c3sc(C)nc3C(=O)N4C)c(OC)c2)CC1]

To a suspension of 12 (26.1 mg, 0.045 mmol, 1.0 equiv) in DCM (1.0 mL) at room temperature were added triethylamine (30.00 µL, 0.215 mmol, 4.8 equiv) and then acryloyl chloride (6.00 µL, 0.074 mmol, 1.6 equiv). The reaction was stirred for 2 hours, at which point UPLC-MS analysis showed full conversion of 12. The mixture was quenched with water (5 mL) and extracted with DCM (5×5 mL). The combined organic layers were washed with saturated aqueous NaHCO$_3$ and then brine, dried over MgSO$_4$, filtered and concentrated. Reverse-phase prep HPLC purification (100-25% H$_2$O/MeCN, 20 mL/min, 45 min) and lyophilization from H$_2$O/MeCN provided the title compound as a yellow oil (2.8 mg TFA salt). $^1$H NMR (500 MHz, DMSO-$d_6$) δ 8.31 (s, 1H), 8.11 (s, 1H), 7.69 (d, J=8.7 Hz, 1H), 6.86 (dd, J=16.7, 10.5 Hz, 1H), 6.68 (d, J=2.6 Hz, 1H), 6.52 (dd, J=8.7, 2.6 Hz, 1H), 6.14 (dd, J=16.7, 2.5 Hz, 1H), 5.71 (dd, J=10.5, 2.3 Hz, 1H), 3.81 (s, 3H), 3.74-3.64 (m, 4H), 3.29 (s, 3H), 3.26 (s, 3H), 3.16-3.08 (m, 4H), 2.53 (s, 3H). MS (ESI) 520.88 (M+H)$^+$.

Example 14: Synthesis of 6-((2-methoxy-4-(4-methylpiperazin-1-yl)phenyl)amino)-2,4,9-trimethyl-4,9-dihydro-10H-pyrimido[5,4-b]thiazolo[5,4-e][1,4]diazepin-10-one (14)

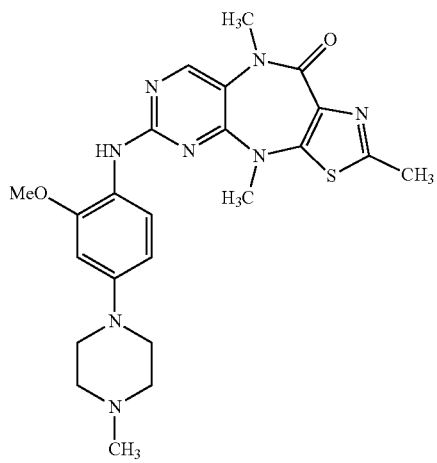 [SMILES: COc1cc(N2CCN(C)CC2)ccc1Nc1ncc2c(n1)N(C)c1sc(C)nc1C(=O)N2C]

General Pd coupling was run on 0.055 mmol scale using 2-methoxy-4-(4-methylpiperazin-1-yl)aniline (21.7 mg, 0.098 mmol, 1.8 equiv). The reaction mixture was purified by reverse-phase prep HPLC (100-40% H$_2$O/MeCN, 20 mL/min, 45 min). The material was further purified by prep TLC (10% MeOH/DCM). Lyophilization from H$_2$O/MeCN provided the title compound as a light yellow powder (10.1 mg TFA salt). $^1$H NMR (500 MHz, DMSO-$d_6$) δ 9.77 (s, 1H), 8.31 (s, 1H), 8.12 (s, 1H), 7.72 (d, J=8.7 Hz, 1H), 6.69 (d, J=2.6 Hz, 1H), 6.54 (dd, J=8.7, 2.6 Hz, 1H), 3.81 (s, 3H), 3.32 (br s, 8H), 3.29 (s, 3H), 3.27 (s, 3H), 2.79 (s, 3H), 2.53 (s, 3H). MS (ESI) 480.88 (M+H)$^+$.

Example 15: Synthesis of Tricyclic Core for Compound 6

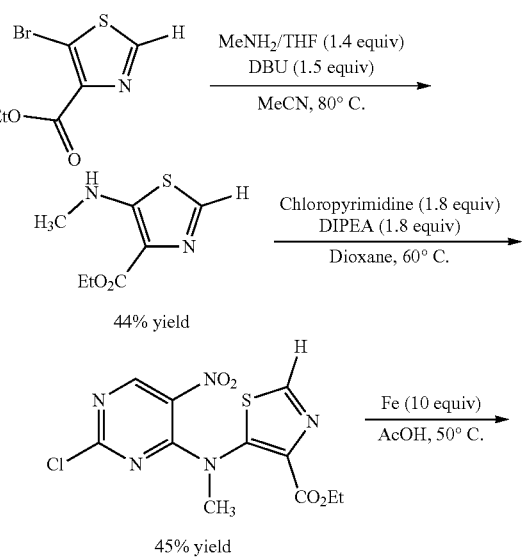

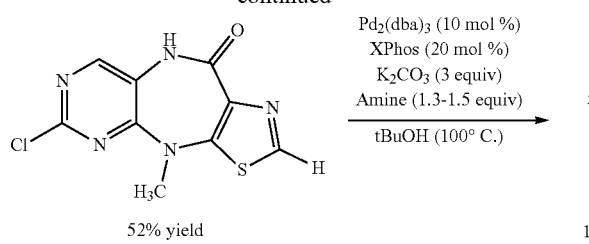

52% yield

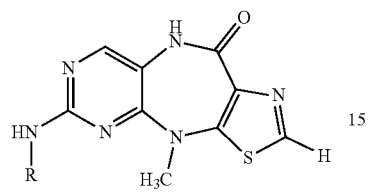

To a solution of ethyl 5-bromothiazole-4-carboxylate (1.191 g, 5.0 mmol, 1.0 equiv) in anhydrous acetonitrile (12 mL) were added methylamine (2.0 M in THF, 3.6 mL, 7.2 mmol, 1.44 equiv) and DBU (1.120 mL, 7.5 mmol, 1.5 equiv). The mixture was heated to 80° C. for 4 hours, and then cooled to room temperature. The reaction was diluted with 50 mL each EtOAc and water. The organic layer was removed and the aqueous was extracted with EtOAc (3×40 mL). The combined organic layers were washed with brine, dried over MgSO$_4$, filtered and concentrated. ISCO flash chromatography (24 g silica, 25 to 80% EtOAc/hexanes gradient, 18 minutes) provided ethyl 5-(methylamino)thiazole-4-carboxylate as a white solid (412 mg, 44% yield). $^1$H NMR (500 MHz, CDCl$_3$) δ 7.85 (d, J=1.0 Hz, 1H), 7.31 (s, 1H), 4.37 (q, J=7.1 Hz, 2H), 3.05 (d, J=5.1 Hz, 3H), 1.41 (t, J=7.0 Hz, 3H). MS (ESI) 187.19 (M+H)$^+$.

A mixture of ethyl 5-(methylamino)thiazole-4-carboxylate (377 mg, 2.0 mmol, 1.0 equiv), 2,4-dichloro-5-nitropyrimidine (696 mg, 3.6 mmol, 1.8 equiv), and DIPEA (0.65 mL, 3.6 mmol, 1.8 equiv) in dioxane (8 mL) was heated to 80° C. for 2 days. The reaction was diluted with 50 mL EtOAc and 100 mL water. The organic layer was removed and the aqueous was extracted with EtOAc (5×40 mL). The combined organic layers were washed twice with water and twice with brine, dried over MgSO$_4$, filtered and concentrated. ISCO flash chromatography (40 g silica, 20 to 80% EtOAc/hexanes gradient, 18 minutes) provided ethyl 5-((2-chloro-5-nitropyrimidin-4-yl)(methyl)amino)thiazole-4-carboxylate as a dark red solid (311 mg, 45% isolated yield). $^1$H NMR (500 MHz, CDCl$_3$) δ 8.76 (s, 1H), 8.62 (s, 1H), 4.28 (q, J=7.1 Hz, 2H), 3.67 (s, 3H), 1.29 (t, J=7.1 Hz, 3H). MS (ESI) 344.07 (M+H)$^+$.

A suspension of ethyl 5-((2-chloro-5-nitropyrimidin-4-yl) (methyl)amino)thiazole-4-carboxylate (311 mg, 0.90 mmol, 1.0 equiv) and iron powder (488 mg, 9.0 mmol, 10 equiv) in glacial acetic acid (12 mL) was heated to 50° C. for 16 hours. The reaction was cooled to room temperature and residual iron was removed with a magnetic wand. The crude reaction mixture was poured into a beaker with 40 mL water and stirred at room temperature for 30 minutes. The resulting precipitate was collected by suction filtration, washing with ~100 mL water, and dried in vacuo to provide 6-chloro-4-methyl-4,9-dihydro-10H-pyrimido[5,4-b]thiazolo[5,4-e][1,4]diazepin-10-one as a light tan solid (127.6 mg, 52% yield). MS (ESI) 268.07 (M+H)$^+$.

Example 16: Synthesis of 6-((2-methoxy-4-(4-(4-methylpiperazin-1-yl)piperidin-1-yl)phenyl)amino)-4-methyl-4,9-dihydro-10H-pyrimido[5,4-b]thiazolo[5,4-e][1,4]diazepin-10-one (6)

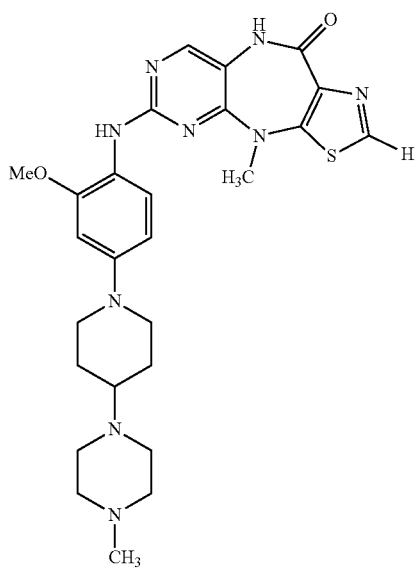 [SMILES: COc1cc(N2CCC(N3CCN(C)CC3)CC2)ccc1Nc1ncc2c(n1)N(C)c1scnc1C(=O)N2]

General Pd coupling was run on 0.08 mmol scale using 2-methoxy-4-(4-(4-methylpiperazin-1-yl)piperidin-1-yl) aniline (34.6 mg, 0.11 mmol, 1.4 equiv). The reaction mixture was purified by reverse-phase prep HPLC (100-30% H$_2$O/MeCN, 20 mL/min, 28 min). The material was further purified by prep TLC (10% MeOH/DCM). Lyophilization from H$_2$O/MeCN provided the title compound as a dark gray powder (3.4 mg TFA salt). $^1$H NMR (500 MHz, DMSO-d$_6$) δ 9.62 (s, 1H), 8.67 (s, 1H), 8.02 (s, 1H), 7.95 (s, 1H), 7.75 (d, J=8.7 Hz, 1H), 6.75 (s, 1H), 6.61 (s, 1H), 3.82 (s, 3H), 3.80-3.74 (m, 3H), 3.66-3.44 (m, 5H), 3.36 (s, 3H), 2.81 (br s, 7H), 2.08-2.00 (m, 3H), 1.75-1.64 (m, 3H). MS (ESI) 536.38 (M+H)$^+$.

Example 17: Synthesis of Tricyclic Core for Compound 8

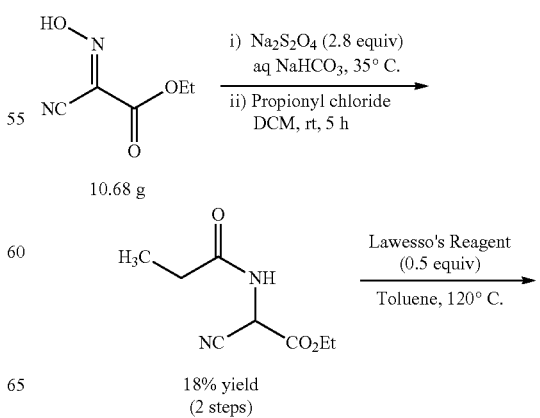

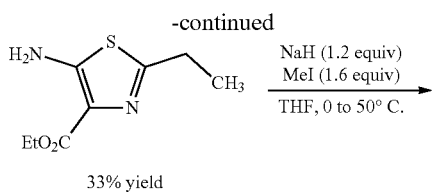

33% yield

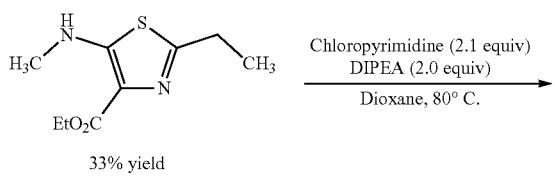

33% yield

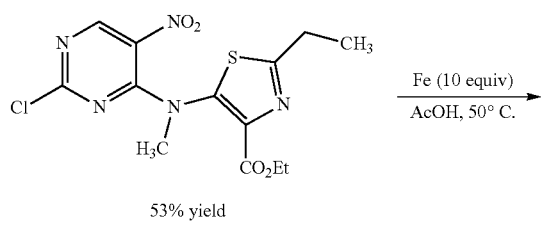

53% yield

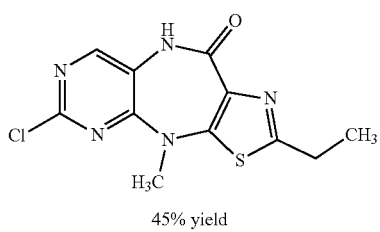

45% yield

To a stirred solution of ethyl cyano(hydroxyimino)acetate (8.590 g, 60 mmol, 1.0 equiv) in 180 mL saturated aqueous NaHCO$_3$, sodium hydrosulfite (34.3 g, 168 mmol, 2.8 equiv) was added portion-wise over 5 minutes. The reaction was heated to 35° C. for 1 hour, and then cooled to room temperature and extracted with DCM (5×100 mL). The combined organic layers were washed with brine, dried over MgSO$_4$, filtered and concentrated to provide a clear, orange oil (1.790 g, 23% yield). The crude ethyl cyanoglycine was further reacted without purification. $^1$H NMR (500 MHz, CDCl$_3$) δ 4.43 (s, 1H), 4.34 (q, J=7.2 Hz, 2H), 1.95 (s, 2H), 1.35 (t, J=7.1 Hz, 3H).

To a solution of ethyl cyanoglycine (512 mg, 4.0 mmol, 1.0 equiv) in DCM (8 mL), propionyl chloride (0.49 mL, 5.6 mmol, 1.4 equiv) was added dropwise, followed by triethylamine (0.89 mL, 6.4 mmol, 1.6 equiv). The reaction was stirred at room temperature overnight, and then diluted with DCM and saturated aqueous NaHCO$_3$ (25 mL each). The organic layer was removed, and the aqueous layer extracted with DCM (2×20 mL). The combined organic layers were washed with brine, dried over MgSO$_4$, filtered and concentrated. ISCO flash chromatography (40 g silica, 50 to 80% EtOAc/hexanes gradient) provided ethyl 2-cyano-2-propionamidoacetate as an off-white solid (577 mg, 78% yield). $^1$H NMR (500 MHz, CDCl$_3$) δ 6.30 (s, 1H), 5.54 (d, J=7.7 Hz, 1H), 4.36 (q, J=7.1 Hz, 2H), 2.35 (q, J=7.6 Hz, 2H), 1.37 (t, J=7.1 Hz, 3H), 1.20 (t, J=7.6 Hz, 3H).

To a 50 mL round-bottom flask were added ethyl 2-cyano-2-propionamidoacetate (554 mg, 3.0 mmol, 1.0 equiv), anhydrous toluene (16 mL), Lawesson's reagent (739 mg, 1.8 mmol, 0.6 equiv), and 3 Å molecular sieves (powder, 130 mg). The suspension was flushed with nitrogen, sealed and heated overnight. The reaction was then cooled to room temperature, filtered and washed with 50 mL EtOAc. The title product was isolated by acidic extraction (extracted crude material 4×25 mL 1 M HCl, neutralized aqueous component, and extracted 4×50 mL EtOAc) and concentrated to provide ethyl 5-amino-2-ethylthiazole-4-carboxylate as a light brown solid (202 mg, 33% yield). MS (ESI) 200.26 (M+H)$^+$. The material was carried on to the next step without further purification.

Ethyl 5-amino-2-ethylthiazole-4-carboxylate (199 mg, 1.0 mmol, 1.0 equiv) was subjected to N-methylation conditions as described in Example 1. Modification: the reaction was heated to 50° C. for 15 hours. ISCO flash chromatography (12 g silica, 25-80% EtOAc/hexanes, 16 min gradient) provided ethyl 2-ethyl-5-(methylamino)thiazole-4-carboxylate as a clear yellow oil (70.1 mg, 33% yield). $^1$H NMR (500 MHz, CDCl$_3$) δ 7.24 (s, 1H), 4.37 (q, J=7.1 Hz, 2H), 3.02 (d, J=5.1 Hz, 3H), 2.89 (q, J=7.6 Hz, 2H), 1.39 (t, J=7.1 Hz, 3H), 1.31 (t, J=7.6 Hz, 3H). MS (ESI) 215.28 (M+H)$^+$.

Ethyl 2-ethyl-5-(methylamino)thiazole-4-carboxylate (70.1 mg, 0.33 mmol, 1.0 equiv) was subjected to S$_N$Ar conditions with 2,4-dichloro-5-nitropyrimidine (135.8 mg, 0.70 mmol, 2.1 equiv) as described in Example 15. Modifications: reaction was run at 80° C. for 22 hours. ISCO flash chromatography (12 g silica, 20-80% EtOAc/hexanes, 15 min gradient) provided ethyl 5-((2-chloro-5-nitropyrimidin-4-yl)(methyl)amino)-2-ethylthiazole-4-carboxylate (66.0 mg, 53% yield) as a clear yellow-orange oil. $^1$H NMR (500 MHz, CDCl$_3$) δ 8.58 (s, 1H), 4.26 (q, J=7.1 Hz, 2H), 3.63 (s, 3H), 3.04 (q, J=7.6 Hz, 2H), 1.40 (t, J=7.6 Hz, 3H), 1.25 (t, J=7.1 Hz, 3H). MS (ESI) 372.07 (M+H)$^+$.

Ethyl 5-((2-chloro-5-nitropyrimidin-4-yl)(methyl) amino)-2-ethylthiazole-4-carboxylate (66.0 mg, 0.177 mmol, 1.0 equiv) was subjected to reductive lactamization as described in Example 1. Modified isolation: after the precipitate settled, the supernatant was removed by decantation. The precipitate was washed with water (2×3 mL, decantation) and dried at 45° C. under a stream of N$_2$ to provide 6-chloro-2-ethyl-4-methyl-4,9-dihydro-10H-pyrimido[5,4-b]thiazolo[5,4-e][1,4]diazepin-10-one as a yellow solid (21.3 mg, 45% yield). $^1$H NMR (500 MHz, CDCl$_3$) δ 9.15 (s, 1H), 8.17 (s, 1H), 3.45 (s, 3H), 2.93 (s, 2H), 1.33 (s, 3H) (signals broadened due to paramagnetism of residual Fe). MS (ESI) 296.07 (M+H)$^+$.

Example 18: 2-ethyl-6-((2-methoxy-4-(4-(4-methylpiperazin-1-yl)piperidin-1-yl)phenyl)amino)-4-methyl-4,9-dihydro-10H-pyrimido[5,4-b]thiazolo[5,4-e][1,4]diazepin-10-one (8)

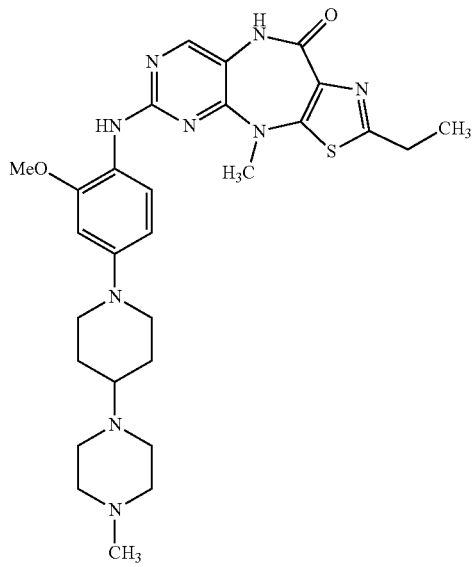 [SMILES: CCc1nc2c(s1)N(C)c1nc(Nc3ccc(N4CCC(N5CCN(C)CC5)CC4)cc3OC)ncc1NC2=O]

General Pd coupling was run on 0.08 mmol scale using 2-methoxy-4-(4-(4-methylpiperazin-1-yl)piperidin-1-yl)aniline (31.3 mg, 0.104 mmol, 1.3 equiv). The reaction mixture was purified by reverse-phase prep HPLC (100-30% $H_2O$/MeCN, 20 mL/min, 28 min). The material was further purified by prep TLC (10% MeOH/DCM). Lyophilization from $H_2O$/MeCN provided the title compound as a light yellow powder (15.6 mg TFA salt). $^1$H NMR (500 MHz, DMSO-$d_6$) δ 9.51 (s, 1H), 7.92 (s, 1H), 7.87 (s, 1H), 7.66 (d, J=8.7 Hz, 1H), 6.61 (d, J=2.6 Hz, 1H), 6.48 (dd, J=8.8, 2.6 Hz, 1H), 3.79 (s, 3H), 3.69 (d, J=12.0 Hz, 2H), 2.86 (q, J=7.5 Hz, 2H), 2.34 (s, 3H), 1.86 (d, J=12.2 Hz, 2H), 1.52 (dt, J=12.6, 11.2 Hz, 2H), 1.24 (t, J=7.5 Hz, 3H). MS (ESI) 564.39 (M+H)$^+$.

Example 19: Synthesis of Tricyclic Core for Compound 9

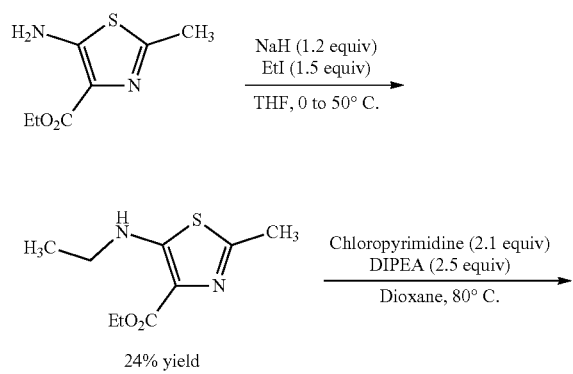

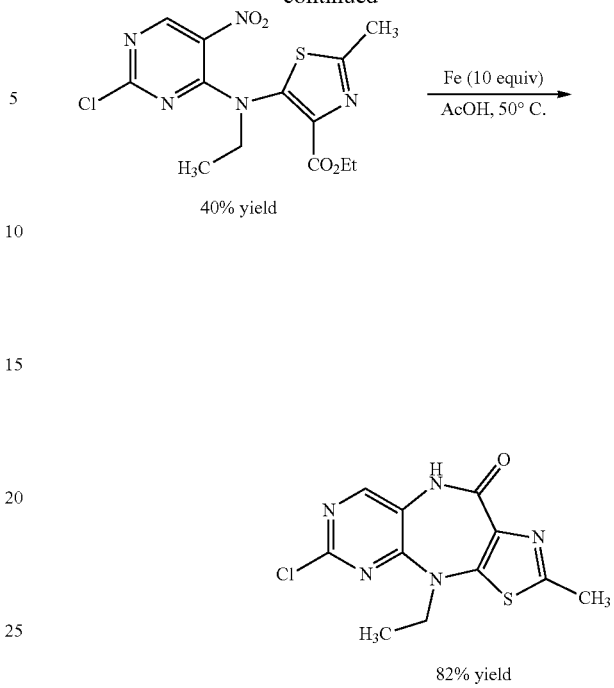

Ethyl 5-amino-2-methylthiazole-4-carboxylate (191.5 mg, 1.03 mmol, 1.0 equiv) was subjected to N-alkylation conditions as described in Example 1. Modification: the reaction used iodoethane (0.120 mL, 1.5 mmol, 1.5 equiv) and was heated to 50° C. for 15 hours. ISCO flash chromatography (12 g silica, 25-80% EtOAc/hexanes, 16 min gradient) provided ethyl 5-(ethylamino)-2-methylthiazole-4-carboxylate as a red-orange oil (52.9 mg, 24% yield). $^1$H NMR (500 MHz, CDCl$_3$) δ 7.24 (s, 1H), 4.37 (q, J=7.1 Hz, 2H), 3.24 (qd, J=7.2, 5.6 Hz, 2H), 2.55 (s, 3H), 1.39 (t, J=7.1 Hz, 3H), 1.31 (t, J=7.2 Hz, 3H). MS (ESI) 215.18 (M+H)$^+$.

Ethyl 5-(ethylamino)-2-methylthiazole-4-carboxylate (52.9 mg, 0.25 mmol, 1.0 equiv) was subjected to $S_N$Ar conditions with 2,4-dichloro-5-nitropyrimidine (104.6 mg, 0.54 mmol, 2.1 equiv) as described in Example 15. Modifications: reaction was run at 80° C. for 22 hours. ISCO flash chromatography (12 g silica, 20-80% EtOAc/hexanes, 15 min gradient) provided ethyl 5-((2-chloro-5-nitropyrimidin-4-yl)(ethyl)amino)-2-methylthiazole-4-carboxylate as a yellow-orange waxy solid (38.0 mg, 40% yield). $^1$H NMR (500 MHz, CDCl$_3$) δ 8.55 (s, 1H), 4.31-4.05 (m, 4H), 2.72 (s, 3H), 1.29 (t, J=7.1 Hz, 3H), 1.23 (t, J=7.1 Hz, 3H). MS (ESI) 372.07 (M+H)$^+$.

Ethyl 5-((2-chloro-5-nitropyrimidin-4-yl)(ethyl)amino)-2-methylthiazole-4-carboxylate (38.0 mg, 0.10 mmol, 1.0 equiv) was subjected to reductive lactamization as described in Example 1. Modified isolation: the reaction was diluted with 5 mL water, residual Fe was removed with a magnet, and then the aqueous component was extracted with DCM (4×8 mL) The combined DCM layers were washed with brine, dried over MgSO$_4$, filtered and concentrated to provide 6-chloro-4-ethyl-2-methyl-4,9-dihydro-10H-pyrimido[5,4-b]thiazolo[5,4-e][1,4]diazepin-10-one as a light yellow solid (24.5 mg, 82% yield). $^1$H NMR (500 MHz, CDCl$_3$) δ 9.21 (s, 1H), 8.13 (s, 1H), 4.00 (q, J=7.1 Hz, 2H), 2.61 (s, 3H), 1.43 (t, J=7.1 Hz, 3H). MS (ESI) 296.07 (M+H)$^+$.

Example 20: Synthesis of 4-ethyl-6-((2-methoxy-4-(4-(4-methylpiperazin-1-yl)piperidin-1-yl)phenyl)amino)-2-methyl-4,9-dihydro-10H-pyrimido[5,4-b]thiazolo[5,4-e][1,4]diazepin-10-one (9)

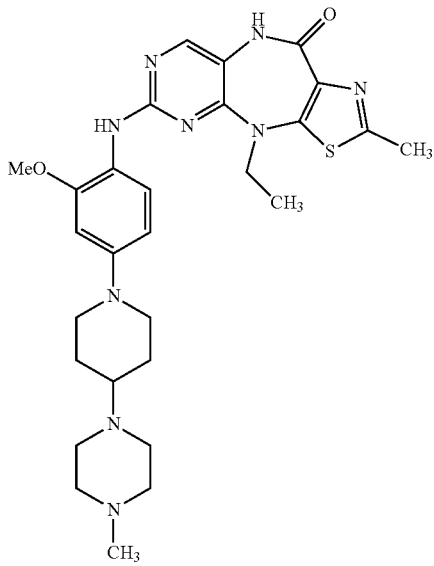 [SMILES: CCN1c2nc(Nc3ccc(N4CCC(N5CCN(C)CC5)CC4)cc3OC)ncc2NC(=O)c2nc(C)sc21]

General Pd coupling was run on 0.08 mmol scale using 2-methoxy-4-(4-(4-methylpiperazin-1-yl)piperidin-1-yl)aniline (33.0 mg, 0.108 mmol, 1.35 equiv). The reaction mixture was purified by reverse-phase prep HPLC (100-30% H$_2$O/MeCN, 20 mL/min, 28 min). The material was further purified by prep TLC (10% MeOH/DCM). Lyophilization from H$_2$O/MeCN provided the title compound as a yellow powder (4.7 mg TFA salt). $^1$H NMR (500 MHz, DMSO-d$_6$) δ 9.50 (s, 1H), 7.92 (s, 1H), 7.91 (s, 1H), 7.56 (d, J=8.7 Hz, 1H), 6.60 (d, J=2.6 Hz, 1H), 6.47 (dd, J=8.7, 2.6 Hz, 1H), 3.83 (q, J=7.1 Hz, 2H), 3.78 (s, 3H), 3.68 (d, J=12.1 Hz, 2H), 2.63 (t, J=11.0 Hz, 2H), 2.52 (s, 3H), 2.23 (s, 3H), 1.84 (d, J=12.3 Hz, 2H), 1.59-1.45 (m, 2H), 1.29 (t, J=7.0 Hz, 3H). MS (ESI) 564.39 (M+H)$^+$.

Example 21: Synthesis of 6-((2-ethoxy-4-(4-methylpiperazin-1-yl)phenyl)amino)-2,4,9-trimethyl-4,9-dihydro-10H-pyrimido[5,4-b]thiazolo[5,4-e][1,4]diazepin-10-one (16)

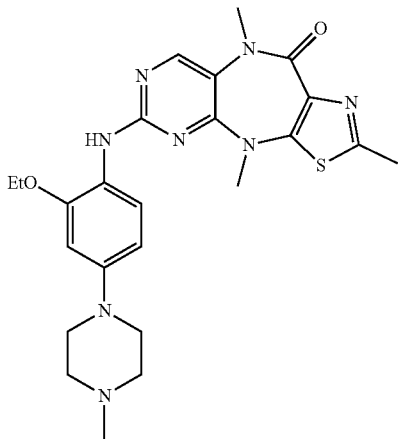 [SMILES: CCOc1cc(N2CCN(C)CC2)ccc1Nc1ncc2c(n1)N(C)c1sc(C)nc1C(=O)N2C]

General Pd coupling was run on 0.05 mmol scale using 2-ethoxy-4-(4-methylpiperazin-1-yl)aniline (18.3 mg, 0.08 mmol, 1.6 equiv). The reaction mixture was purified by reverse-phase prep HPLC (100-50% H$_2$O/MeCN, 20 mL/min, 45 min). Lyophilization from H$_2$O/MeCN provided the title compound as a yellow oil (5.5 mg free base). $^1$H NMR (500 MHz, DMSO-d$_6$) δ 8.31 (s, 1H), 8.00 (s, 1H), 7.70 (d, J=8.8 Hz, 1H), 6.61 (d, J=2.6 Hz, 1H), 6.48 (dd, J=8.8, 2.6 Hz, 1H), 4.07 (q, J=7.0 Hz, 2H), 3.29 (s, 3H), 3.27 (s, 3H), 3.10 (t, J=5.0 Hz, 4H), 2.53 (s, 3H), 2.45 (t, J=5.0 Hz, 4H), 2.22 (s, 3H), 1.29 (t, J=7.0 Hz, 3H). MS (ESI) 494.98 (M+H)$^+$.

Example 22: Synthesis of 6-((2-(2-hydroxyethoxy)-4-(4-methylpiperazin-1-yl)phenyl)amino)-2,4,9-trimethyl-4,9-dihydro-10H-pyrimido[5,4-b]thiazolo[5,4-e][1,4]diazepin-10-one (17)

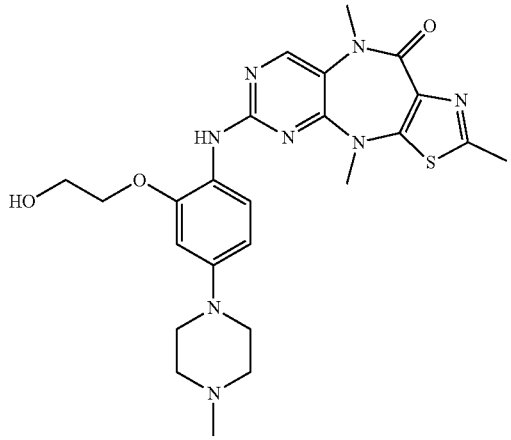 [SMILES: Cc1nc2c(s1)N(C)c1nc(Nc3ccc(N4CCN(C)CC4)cc3OCCO)ncc1N(C)C2=O]

General Pd coupling was run on 0.05 mmol scale using 2-(2-amino-5-(4-methylpiperazin-1-yl)phenoxy)ethan-1-ol (20.2 mg, 0.08 mmol, 1.6 equiv). The reaction mixture was purified by reverse-phase prep HPLC (100-50% H$_2$O/MeCN, 20 mL/min, 45 min). Lyophilization from H$_2$O/MeCN provided the title compound as a light pink powder (7.0 mg free base). $^1$H NMR (500 MHz, DMSO-d$_6$) δ 9.64 (s, 1H), 8.42 (s, 1H), 8.35 (s, 1H), 7.91 (d, J=8.8 Hz, 1H), 6.70 (d, J=2.6 Hz, 1H), 6.57 (dd, J=8.8, 2.6 Hz, 1H), 5.11 (s, 1H), 4.03 (q, J=4.5 Hz, 2H), 3.81 (d, J=12.9 Hz, 2H), 3.71 (t, J=4.7 Hz, 2H), 3.51 (s, 3H), 3.28 (s, 3H), 3.21-3.09 (m, 3H), 2.95-2.88 (m, 2H), 2.87 (s, 3H), 2.54 (s, 3H). MS (ESI) 510.68 (M+H)$^+$.

Example 23: Synthesis of 6-((2-methoxy-5-methyl-4-(4-methylpiperazin-1-yl)phenyl)amino)-2,4,9-trimethyl-4,9-dihydro-10H-pyrimido[5,4-b]thiazolo[5,4-e][1,4]diazepin-10-one (18)

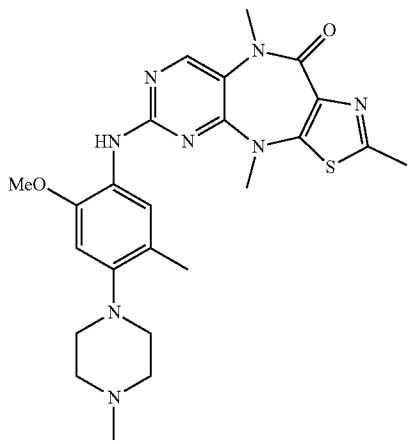 [SMILES: COc1cc(N2CCN(C)CC2)c(C)cc1Nc1ncc2c(n1)N(C)c1sc(C)nc1C(=O)N2C]

General Pd coupling was run on 0.05 mmol scale using 2-methoxy-5-methyl-4-(4-methylpiperazin-1-yl)aniline (16.4 mg, 0.07 mmol, 1.4 equiv). The reaction mixture was purified by reverse-phase prep HPLC (100-45% H$_2$O/MeCN, 20 mL/min, 45 min). Lyophilization from H$_2$O/MeCN provided the title compound as a light yellow powder (15.2 mg TFA salt). $^1$H NMR (500 MHz, DMSO-d$_6$) δ 8.34 (s, 1H), 8.07 (s, 1H), 7.74 (s, 1H), 6.71 (s, 1H), 3.80 (s, 3H), 3.27 (s, 3H), 2.86 (t, J=4.8 Hz, 4H), 2.53 (s, 3H), 2.28 (s, 3H), 2.18 (s, 3H). MS (ESI) 494.88 (M+H)$^+$.

Example 24: Synthesis of 6-((2-methoxy-4-(1-methylpiperidin-4-yl)phenyl)amino)-2,4,9-trimethyl-4,9-dihydro-10H-pyrimido[5,4-b]thiazolo[5,4-e][1,4]diazepin-10-one (19)

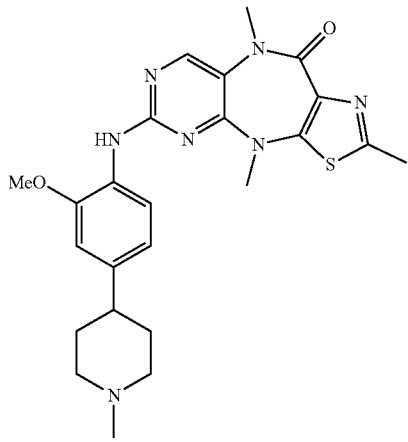 [SMILES: COc1cc(C2CCN(C)CC2)ccc1Nc1ncc2c(n1)N(C)c1sc(C)nc1C(=O)N2C]

General Pd coupling was run on 0.06 mmol scale using 2-methoxy-4-(1-methylpiperidin-4-yl)aniline (18.3 mg, 0.083 mmol, 1.4 equiv). The reaction mixture was purified by reverse-phase prep HPLC (100-40% H$_2$O/MeCN, 20 mL/min, 45 min). Lyophilization from H$_2$O/MeCN provided the title compound as a white powder (8.7 mg TFA salt). $^1$H NMR (500 MHz, DMSO-d$_6$) δ 9.47 (s, 1H), 8.35 (s, 1H), 8.16 (s, 1H), 7.96 (d, J=8.2 Hz, 1H), 6.90 (d, J=1.9 Hz, 1H), 6.81 (dd, J=8.3, 1.9 Hz, 1H), 3.84 (s, 3H), 3.33 (s, 3H), 3.27 (s, 3H), 3.12-3.00 (m, 2H), 2.81 (s, 3H), 2.53 (s, 3H), 2.03 (d, J=13.9 Hz, 2H), 1.89-1.77 (m, 2H). MS (ESI) 479.98 (M+H)$^+$.

Example 25: Synthesis of 6-((4-(4-(2-hydroxyethyl)piperazin-1-yl)-2-methoxyphenyl)amino)-2,4,9-trimethyl-4,9-dihydro-10H-pyrimido[5,4-b]thiazolo[5,4-e][1,4]diazepin-10-one (20)

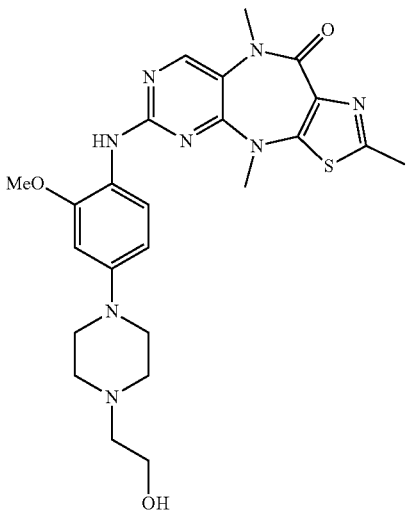 [SMILES: COc1cc(N2CCN(CCO)CC2)ccc1Nc1ncc2c(n1)N(C)c1sc(C)nc1C(=O)N2C]

General Pd coupling was run on 0.06 mmol scale using 2-(4-(4-amino-3-methoxyphenyl)piperazin-1-yl)ethan-1-ol (20.6 mg, 0.082 mmol, 1.4 equiv). The reaction mixture was purified by reverse-phase prep HPLC (100-40% H$_2$O/MeCN, 20 mL/min, 45 min). Lyophilization from H$_2$O/MeCN provided the title compound as a brown powder (15.6 mg TFA salt). $^1$H NMR (500 MHz, DMSO-d$_6$) δ 9.68 (s, 1H), 8.31 (s, 1H), 8.13 (s, 1H), 7.72 (d, J=8.7 Hz, 1H), 6.70 (d, J=2.6 Hz, 1H), 6.55 (dd, J=8.8, 2.6 Hz, 1H), 5.42 (s, 1H), 3.82 (s, 3H), 3.78 (t, J=5.4 Hz, 2H), 3.66-3.52 (m, 2H), 3.30 (s, 3H), 3.27 (s, 3H), 3.21 (s, 2H), 3.05 (d, J=13.3 Hz, 2H), 2.53 (s, 3H). MS (ESI) 510.88 (M+H)$^+$.

Example 26: Synthesis of 3-methoxy-N-methyl-4-((2,4,9-trimethyl-10-oxo-9,10-dihydro-4H-pyrimido[5,4-b]thiazolo[5,4-e][1,4]diazepin-6-yl)amino)benzamide (21)

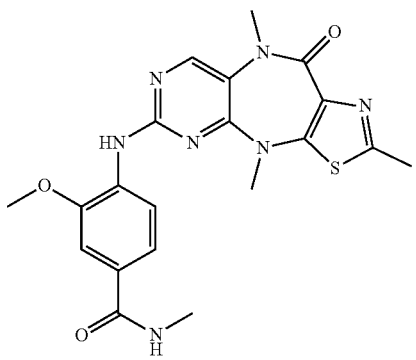

General Pd coupling was run on 0.05 mmol scale using 4-amino-3-methoxy-N-methylbenzamide (12.8 mg, 0.07 mmol, 1.4 equiv). The reaction mixture was purified by reverse-phase prep HPLC (100-50% H$_2$O/MeCN, 20 mL/min, 45 min). Further purification by prep TLC (10% MeOH/2% NEt$_3$/DCM) and lyophilization from H$_2$O/MeCN provided the title compound as a tan powder (5.4 mg free base). $^1$H NMR (500 MHz, DMSO-d$_6$) δ 8.44 (s, 1H), 8.36 (q, J=4.5 Hz, 1H), 8.28-8.21 (m, 2H), 7.52-7.47 (m, 2H), 3.92 (s, 3H), 3.37 (s, 3H), 3.29 (s, 3H), 2.78 (d, J=4.4 Hz, 3H), 2.54 (s, 3H). MS (ESI) 439.98 (M+H)$^+$.

Example 27: Synthesis of 6-((6-methoxy-2-methyl-1,2,3,4-tetrahydroisoquinolin-7-yl)amino)-2,4,9-trimethyl-4,9-dihydro-10H-pyrimido[5,4-b]thiazolo[5,4-e][1,4]diazepin-10-one (22)

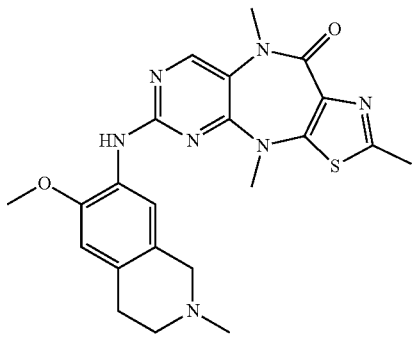

General Pd coupling was run on 0.05 mmol scale using 6-methoxy-2-methyl-1,2,3,4-tetrahydroisoquinolin-7-amine (12.7 mg, 0.065 mmol, 1.3 equiv). The reaction mixture was purified by reverse-phase prep HPLC (100-45% H$_2$O/MeCN, 20 mL/min, 45 min). Lyophilization from H$_2$O/MeCN provided the title compound as a yellow powder (11.3 mg TFA salt). $^1$H NMR (500 MHz, DMSO-d$_6$) δ 8.37 (s, 1H), 8.08 (s, 1H), 7.74 (s, 1H), 6.77 (s, 1H), 3.80 (s, 3H), 3.49 (s, 2H), 3.28 (s, 3H), 2.80 (t, J=6.0 Hz, 2H), 2.69-2.60 (m, 2H), 2.54 (s, 3H), 2.38 (s, 3H). MS (ESI) 451.88 (M+H)$^+$.

Example 28: Synthesis of 2,4,9-trimethyl-6-((2-oxo-1,2,3,4-tetrahydroquinolin-6-yl)amino)-4,9-dihydro-10H-pyrimido[5,4-b]thiazolo[5,4-e][1,4]diazepin-10-one (23)

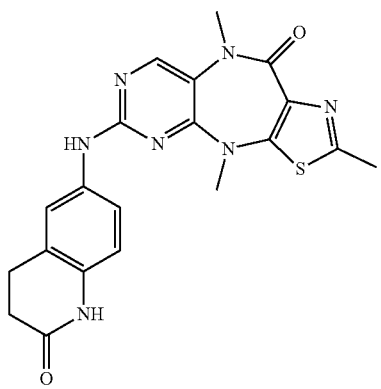 [SMILES: Cc1nc2c(s1)N(C)c1nc(Nc3ccc4c(c3)CCC(=O)N4)ncc1N(C)C2=O]

A solution of 6-chloro-2,4,9-trimethyl-4,9-dihydro-10H-pyrimido[5,4-b]thiazolo[5,4-e][1,4]diazepin-10-one (17.6 mg, 0.060 mmol, 1.0 equiv) and 6-amino-3,4-dihydroquinolin-2(1H)-one (34.5 mg, 0.210 mmol, 3.5 equiv) in 4 M HCl/dioxane (0.60 mL) was stirred at 100° C. for 3 days. The reaction mixture was diluted with DCM and filtered through Celite®, washing with 10 mL MeOH, and then purified by reverse-phase prep HPLC (100-50% H$_2$O/MeCN, 20 mL/min, 45 min). Further purification by prep TLC (10% MeOH/2% NEt$_3$/DCM) and lyophilization from H$_2$O/MeCN provided the title compound as a beige powder (1.6 mg free base). MS (ESI) 421.87 (M+H)$^+$.

Example 29: Synthesis of 2,4,9-trimethyl-6-((5-(4-methylpiperazin-1-yl)pyridin-2-yl)amino)-4,9-dihydro-10H-pyrimido[5,4-b]thiazolo[5,4-e][1,4]diazepin-10-one (24)

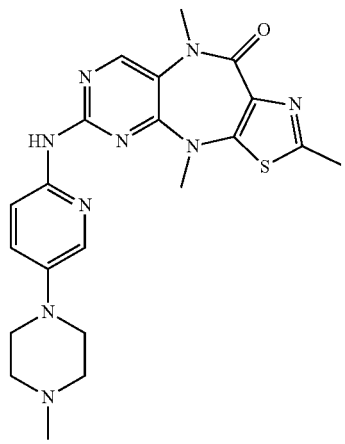 [SMILES: Cc1nc2c(s1)N(C)c1nc(Nc3ccc(N4CCN(C)CC4)cn3)ncc1N(C)C2=O]

General Pd coupling was run on 0.08 mmol scale using 5-(4-methylpiperazin-1-yl)pyridin-2-amine (21.6 mg, 0.11 mmol, 1.4 equiv). The reaction mixture was purified by reverse-phase prep HPLC (100-50% H$_2$O/MeCN, 20 mL/min, 45 min). Lyophilization from H$_2$O/MeCN provided the title compound as a white powder (XX mg TFA salt).

Further purification by prep TLC (10% MeOH/2% NEt₃/DCM) and lyophilization from H₂O/MeCN provided the title compound as a beige powder (1.7 mg free base). MS (ESI) 451.88 (M+H)⁺.

Example 30: Synthesis of 2,4,9-trimethyl-6-((1-methyl-1H-pyrazol-4-yl)amino)-4,9-dihydro-10H-pyrimido[5,4-b]thiazolo[5,4-e][1,4]diazepin-10-one (26)

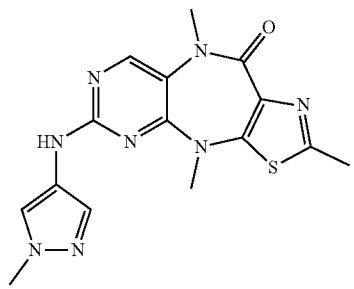

General Pd coupling was run on 0.06 mmol scale using 1-methyl-1H-pyrazol-4-amine (12.6 mg, 0.13 mmol, 2.15 equiv). The reaction mixture was purified by reverse-phase prep HPLC (100-50% H₂O/MeCN, 20 mL/min, 45 min). Lyophilization from H₂O/MeCN provided the title compound as a white powder (5.3 mg TFA salt). ¹H NMR (500 MHz, DMSO-d₆) δ 9.58 (s, 1H), 8.35 (s, 1H), 7.82 (s, 1H), 7.48 (s, 1H), 3.81 (s, 3H), 3.27 (s, 3H), 3.17 (s, 3H), 2.54 (s, 3H). MS (ESI) 356.97 (M+H)⁺.

Example 31: Synthesis of 6-((2-methoxy-4-(4-(4-methylpiperazin-1-yl)piperidine-1-carbonyl)phenyl)amino)-2,4,9-trimethyl-4,9-dihydro-10H-pyrimido[5,4-b]thiazolo[5,4-e][1,4]diazepin-10-one (28)

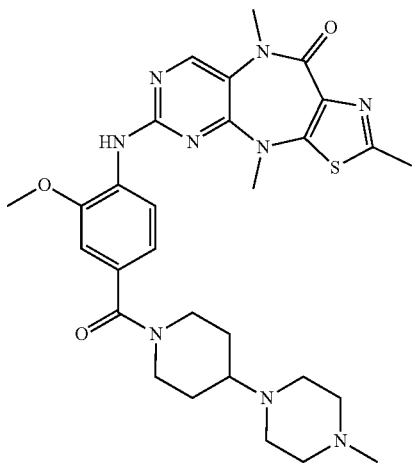

General Pd coupling was run on 0.06 mmol scale using (4-amino-3-methoxyphenyl)-(4-(4-methylpiperazin-1-yl)piperidin-1-yl)methanone (38.1 mg, 0.115 mmol, 1.9 equiv). The reaction mixture was purified by reverse-phase prep HPLC (100-50% H₂O/MeCN, 20 mL/min, 45 min). Lyophilization from H₂O/MeCN provided the title compound as a white powder (6.4 mg TFA salt). ¹H NMR (500 MHz, DMSO-d₆) δ 8.42 (s, 1H), 8.26 (s, 1H), 8.18 (d, J=8.2 Hz, 1H), 7.01 (dd, J=8.2, 1.8 Hz, 1H), 3.89 (s, 3H), 3.36 (s, 3H), 3.29 (s, 3H), 2.75 (s, 3H), 2.54 (s, 3H), 1.96-1.78 (m, 2H), 1.54-1.38 (m, 2H) (Piperazine resonances obscured under water peak). MS (ESI) 591.89 (M+H)⁺.

Example 32: Synthesis of Tricyclic Core for Compound 132

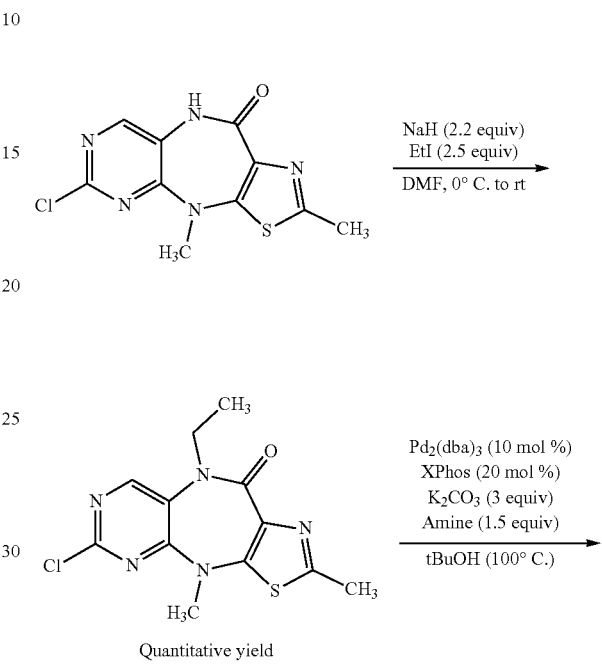

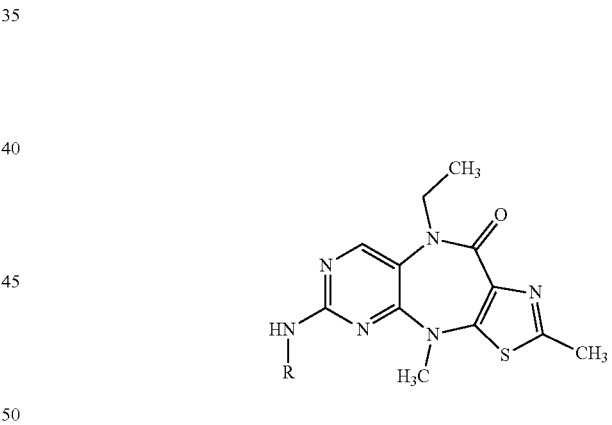

To a suspension of 6-chloro-2,4-dimethyl-4,9-dihydro-10H-pyrimido[5,4-b]thiazolo[5,4-e][1,4]diazepin-10-one (29.5 mg, 0.10 mmol, 1.0 equiv) and iodoethane (20.0 µL, 0.25 mmol, 2.5 equiv) in anhydrous DMF (1.5 mL) at 0° C., NaH (10.1 mg, 0.22 mmol, 2.2 equiv, 60% dispersion in mineral oil) was added in a single portion. The reaction was stirred overnight, and UPLC-MS analysis showed complete consumption of starting material. The reaction was then quenched with water (10 mL) and extracted with EtOAc (4×10 mL). The combined organic layers were washed twice with water, once with brine, dried over MgSO₄, filtered and concentrated. ISCO flash chromatography (12 g silica, 0-10% MeOH/DCM, 10 min gradient) provided 6-chloro-9-ethyl-2,4-dimethyl-4,9-dihydro-10H-pyrimido[5,4-b]thiazolo[5,4-e][1,4]diazepin-10-one as an amber oil (35.0 mg, quantitative yield). MS (ESI) 309.77 (M+H)⁺.

Example 33: Synthesis of 9-ethyl-6-((2-methoxy-4-(4-(4-methylpiperazin-1-yl)piperidin-1-yl)phenyl)amino)-2,4-dimethyl-4,9-dihydro-10H-pyrimido[5,4-b]thiazolo[5,4-e][1,4]diazepin-10-one (132)

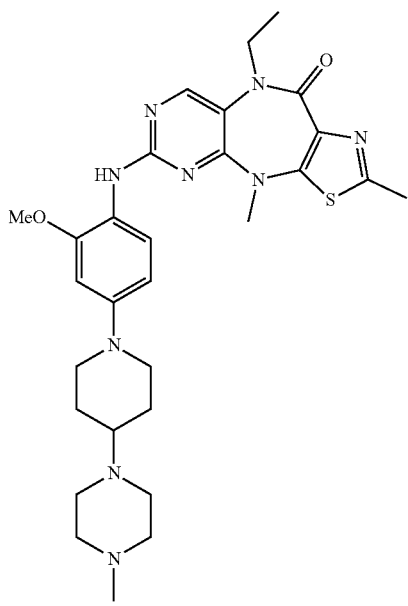 [SMILES: CCN1C(=O)c2nc(C)sc2N(C)c2nc(Nc3ccc(N4CCC(N5CCN(C)CC5)CC4)cc3OC)ncc21]

General Pd coupling was run on 0.05 mmol scale using 2-methoxy-4-(4-(4-methylpiperazin-1-yl)piperidin-1-yl)aniline (23.1 mg, 0.076 mmol, 1.5 equiv). The reaction mixture was purified by reverse-phase prep HPLC (100-50% H$_2$O/MeCN, 20 mL/min, 45 min). Further purification by prep TLC (10% MeOH/2% NEt$_3$/DCM) and lyophilization from H$_2$O/MeCN provided the title compound as a white powder (1.0 mg free base). $^1$H NMR (500 MHz, DMSO-d$_6$) δ 8.33 (s, 1H), 8.12 (s, 1H), 7.65 (d, J=8.7 Hz, 1H), 6.64 (s, 1H), 6.51 (d, J=8.8 Hz, 1H), 3.83 (q, J=7.0 Hz, 2H), 3.80 (s, 3H), 3.74 (br s, 2H), 2.67 (t, J=12.1 Hz, 2H), 2.53 (s, 3H), 2.02-1.81 (m, 2H), 1.57 (br s, 2H), 1.08 (t, J=7.1 Hz, 3H). MS (ESI) 577.99 (M+H)$^+$.

Example 34: Synthesis of Tricyclic Core for Compound 159

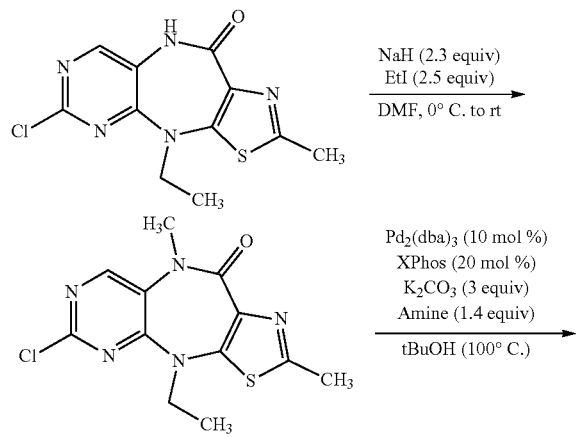

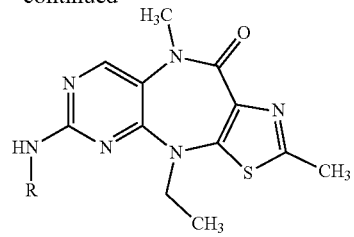

To a suspension of 6-chloro-4-ethyl-2-methyl-4,9-dihydro-10H-pyrimido[5,4-b]thiazolo[5,4-e][1,4]diazepin-10-one (38.4 mg, 0.13 mmol, 1.0 equiv) and iodomethane (20.0 μL, 0.32 mmol, 2.5 equiv) in anhydrous DMF (1.6 mL) at 0° C., NaH (12.0 mg, 0.30 mmol, 2.3 equiv, 60% dispersion in mineral oil) was added in a single portion. The reaction was stirred for 1 hour, and UPLC-MS analysis showed complete consumption of starting material. The reaction was then quenched with water (5 mL) and extracted with EtOAc (5×8 mL). The combined organic layers were washed twice with water, once with brine, dried over MgSO$_4$, filtered and concentrated. ISCO flash chromatography (12 g silica, 0-10% MeOH/DCM, 12 min gradient) provided 6-chloro-4-ethyl-2,9-dimethyl-4,9-dihydro-10H-pyrimido[5,4-b]thiazolo[5,4-e][1,4]diazepin-10-one as a yellow oil (31.0 mg, 77% yield). MS (ESI) 309.77 (M+H)$^+$.

Example 35: Synthesis of 4-ethyl-6-((2-methoxy-4-(4-(4-methylpiperazin-1-yl)piperidin-1-yl)phenyl)amino)-2,9-dimethyl-4,9-dihydro-10H-pyrimido[5,4-b]thiazolo[5,4-e][1,4]diazepin-10-one (159)

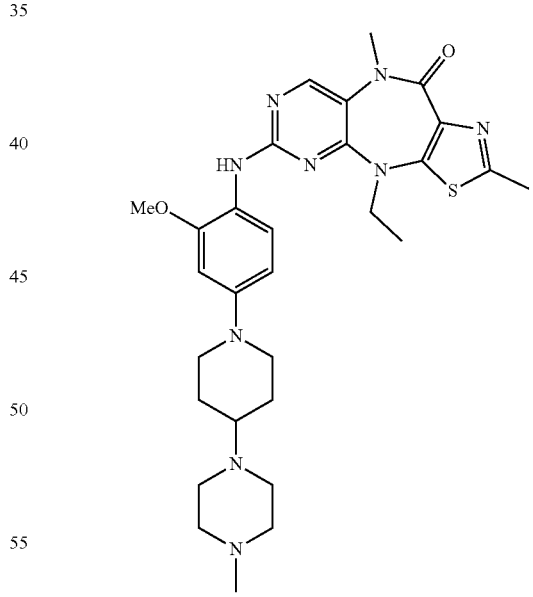

General Pd coupling was run on 0.08 mmol scale using 2-methoxy-4-(4-(4-methylpiperazin-1-yl)piperidin-1-yl)aniline (34.5 mg, 0.11 mmol, 1.4 equiv). The reaction mixture was purified by reverse-phase prep HPLC (100-50% H$_2$O/MeCN, 20 mL/min, 45 min). Further purification by prep TLC (10% MeOH/2% NEt$_3$/DCM) and lyophilization from H$_2$O/MeCN provided the title compound as a white powder (4.0 mg free base). $^1$H NMR (500 MHz, DMSO-d$_6$) δ 8.30 (s, 1H), 8.11 (s, 1H), 7.56 (d, J=8.7 Hz, 1H), 6.61 (d, J=2.6 Hz, 1H), 6.49 (dd, J=8.8, 2.6 Hz, 1H), 3.82-3.75 (m, 5H), 3.72 (d, J=12.0 Hz, 2H), 3.27 (s, 3H), 3.09 (q, J=7.3 Hz, 1H), 2.65 (t, J=12.2 Hz, 2H), 2.53 (s, 3H), 1.96-1.80 (m, 2H), 1.61-1.48 (m, 2H), 1.30 (t, J=7.1 Hz, 3H). MS (ESI) 578.09 (M+H)+.

Example 36: Synthesis of Tricyclic Core for Compound 177

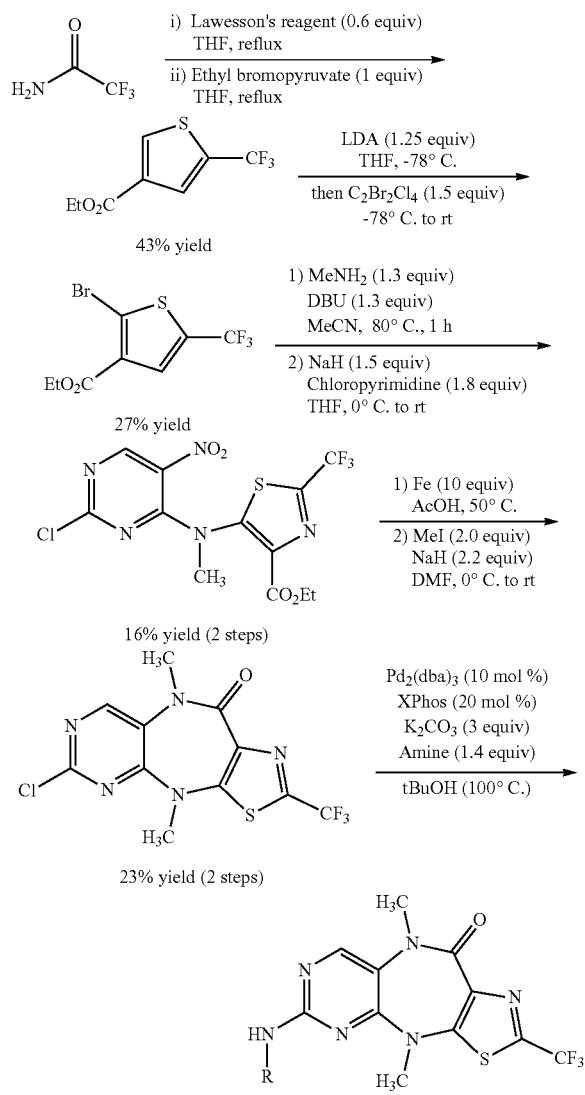

A suspension of trifluoroacetamide (2.267 g, 20.0 mmol, 1.0 equiv) and Lawesson's reagent (4.835 g, 12.0 mmol, 0.6 equiv) in anhydrous THF (40 mL) was heated to 70° C. for 2 days. The reaction flask was removed from the heat, cooled to room temperature, and ethyl bromopyruvate (2.60 mL, 20.0 mmol, 1.0 equiv) was added, and then the reaction was returned to 70° C. for 18 hours. The reaction mixture was then cooled to room temperature, quenched with water (100 mL), and extracted with EtOAc (3×75 mL). The combined organic layers were washed with brine, dried over MgSO₄, filtered and concentrated. Purification with ISCO flash chromatography (80 g silica, 10-60% EtOAc/Hex, 28 min gradient) provided ethyl 2-(trifluoromethyl)thiazole-4-carboxylate as a yellow-orange solid (1.936 g, 43% yield). ¹H NMR (500 MHz, CDCl₃) δ 8.38 (s, 1H), 4.46 (q, J=7.1 Hz, 2H), 1.42 (t, J=7.1 Hz, 3H). ¹⁹F NMR (471 MHz, CDCl₃) δ-61.02. MS (ESI) 225.88 (M+H)+.

A 250 mL round-bottom flask was dried with a heat gun under vacuum. Under N₂ atmosphere, a solution of anhydrous THF (40 mL) and LDA (2 M in THF, 4.70 mL, 9.40 mmol, 1.25 equiv) was cooled to −78° C. A solution of ethyl 2-(trifluoromethyl)thiazole-4-carboxylate (1.688 g, 7.5 mmol, 1.0 equiv) in THF (20 mL) was added dropwise over 12 minutes, and then stirred at −78° C. for 30 minutes. A solution of 1,2-dibromotetrachloroethane (3.663 g, 11.25 mmol, 1.5 equiv) in THF (15 mL) was added dropwise over 7 minutes. The reaction was stirred at −78° C. for 1 hour, and then at room temperature for 1 hour. The reaction was quenched with saturated aqueous NH₄Cl (25 mL) and diluted with water (100 mL), then extracted with EtOAc (3×75 mL). The combined organic layers were washed with brine, dried over MgSO₄, filtered and concentrated. Purification with ISCO flash chromatography (40 g silica, 0-40% EtOAc/Hex, 18 min gradient) provided ethyl 5-bromo-2-(trifluoromethyl)thiazole-4-carboxylate as a yellow-orange semi-solid (636 mg, 28% yield). ¹H NMR (500 MHz, CDCl₃) δ 4.47 (q, J=7.1 Hz, 2H), 1.43 (t, J=7.2 Hz, 3H). 19F NMR (471 MHz, CDCl₃) δ-61.16. MS (ESI) 303.67, 305.67 (M+H, M+2+H)+.

To a solution of ethyl 5-bromo-2-(trifluoromethyl)thiazole-4-carboxylate (632 mg, 2.1 mmol, 1.0 equiv) in anhydrous acetonitrile (10.5 mL) were added methylamine (2.0 M in THF, 1.30 mL, 2.6 mmol, 1.24 equiv) and DBU (0.40 mL, 2.8 mmol, 1.3 equiv). The mixture was heated to 80° C. for 2 hours, and then cooled to room temperature. The reaction was diluted with 1:1 EtOAc:water (100 mL). The organic layer was removed and the aqueous was extracted with EtOAc (3×50 mL). The combined organic layers were washed with brine, dried over MgSO₄, filtered and concentrated. UPLC-MS analysis showed ethyl 5-(methylamino)-2-(trifluoromethyl)thiazole-4-carboxylate in approx. 30% yield, and the crude mixture was carried on to the next step without purification. MS (ESI) 254.87 (M+H)+.

The entirety of the crude methylamination mixture in anhydrous THF (12 mL) was cooled to 0° C. NaH (78.5 mg, 1.95 mmol, 1.3 equiv) was added in a single portion, and the reaction was stirred for 30 minutes. A solution of 2,4-dichloro-5-nitropyrimidine (449.3 mg, 2.30 mmol, 1.6 equiv) in THF (3 mL) was added dropwise over 3 minutes. The reaction was stirred, warming to room temperature overnight, and then quenched with aqueous NH₄Cl (50 mL). The aqueous layer was extracted with EtOAc (4×25 mL). The combined organic layers were washed with brine, dried over MgSO₄, filtered and concentrated. Purification with ISCO flash chromatography (24 g silica, 0 to 40% EtOAc/hexanes gradient, 20 minutes) provided ethyl 5-((2-chloro-5-nitropyrimidin-4-yl)(methyl)amino)-2-(trifluoromethyl)thiazole-4-carboxylate as a clear yellow oil (143.7 mg, 16% yield over 2 steps). ¹H NMR (500 MHz, CDCl₃) δ 8.71 (s, 1H), 4.29 (q, J=7.1 Hz, 2H), 3.71 (s, 3H), 1.28 (t, J=7.2 Hz, 3H). ¹⁹F NMR (471 MHz, CDCl₃) δ-61.82. MS (ESI) 411.87 (M+H)+.

A suspension of ethyl 5-((2-chloro-5-nitropyrimidin-4-yl)(methyl)amino)-2-(trifluoromethyl)thiazole-4-carboxylate (136.2 mg, 0.33 mmol, 1.0 equiv) and iron powder (182 mg, 3.30 mmol, 10 equiv) in glacial acetic acid (4.5 mL) was heated to 50° C. for 16 hours. The reaction was diluted with water (5 mL) and extracted with DCM (5×5 mL). The combined organic layers were washed with sat. aqueous NaHCO₃ (3×15 mL) and then brine, dried over MgSO₄, filtered and concentrated to provide 6-chloro-4-methyl-2-(trifluoromethyl)-4,9-dihydro-10H-pyrimido[5,4-b]thiazolo[5,4-e][1,4]diazepin-10-one as a yellow solid (97.1 mg, 88% yield). $^1$H NMR (500 MHz, DMSO-$d_6$) δ 10.30 (s, 1H), 8.20 (s, 1H), 3.47 (s, 3H). $^{19}$F NMR (471 MHz, DMSO) δ-60.55. MS (ESI) 335.77 (M+H)$^+$.

NaH (21.0 mg, 0.53 mmol, 2.2 equiv, 60% dispersion in mineral oil) was added in a single portion to a suspension of 6-chloro-4-methyl-2-(trifluoromethyl)-4,9-dihydro-10H-pyrimido[5,4-b]thiazolo[5,4-e][1,4]diazepin-10-one (81.3 mg, 0.24 mmol, 1.0 equiv) and iodomethane (30.0 μL, 0.48 mmol, 2.0 equiv) in anhydrous DMF (3.0 mL) at 0° C. The reaction was stirred for 2 hours, and UPLC-MS analysis showed complete consumption of starting material. The reaction was then quenched with water (5 mL) and extracted with DCM (5×5 mL). The combined organic layers were washed three times with water, once with brine, dried over MgSO$_4$, filtered and concentrated. Purification with ISCO flash chromatography (12 g silica, 0-5% MeOH/DCM, 12 min gradient) provided 6-chloro-4,9-dimethyl-2-(trifluoromethyl)-4,9-dihydro-10H-pyrimido[5,4-b]thiazolo[5,4-e][1,4]diazepin-10-one as a yellow solid (32.6 mg, 39% yield). $^1$H NMR (500 MHz, CDCl$_3$) δ 8.33 (s, 1H), 3.54 (s, 3H), 3.47 (s, 3H). $^{19}$F NMR (471 MHz, CDCl$_3$) δ-61.28. MS (ESI) 349.77 (M+H)$^+$.

Example 37: Synthesis of 6-((2-methoxy-4-(4-(4-methylpiperazin-1-yl)piperidin-1-yl)phenyl)amino)-4,9-dimethyl-2-(trifluoromethyl)-4,9-dihydro-10H-pyrimido[5,4-b]thiazolo[5,4-e][1,4]diazepin-10-one (177)

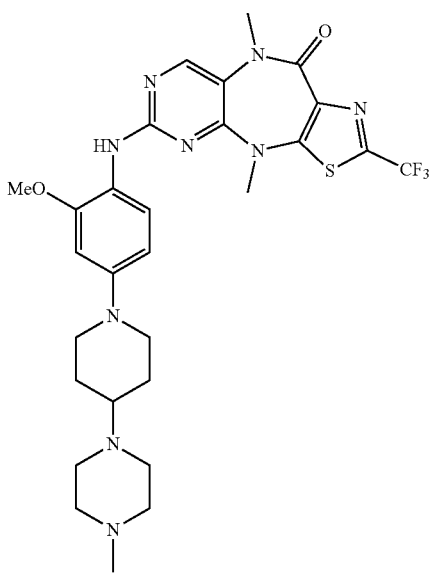 [SMILES: COc1cc(N2CCC(N3CCN(C)CC3)CC2)ccc1Nc1ncc2c(n1)N(C)c1sc(C(F)(F)F)nc1C(=O)N2C]

General Pd coupling was run on 0.05 mmol scale using 2-methoxy-4-(4-(4-methylpiperazin-1-yl)piperidin-1-yl)aniline (23.1 mg, 0.076 mmol, 1.5 equiv). The reaction mixture was purified by reverse-phase prep HPLC (100-40% H$_2$O/MeCN, 20 mL/min, 45 min). Further purification by prep TLC (10% MeOH/2% NEt$_3$/DCM) and lyophilization from H$_2$O/MeCN provided the title compound as a yellow solid (11.1 mg free base). $^1$H NMR (500 MHz, DMSO-$d_6$) δ 8.38 (s, 1H), 8.26 (s, 1H), 7.60 (d, J=8.7 Hz, 1H), 6.64 (d, J=2.6 Hz, 1H), 6.52 (dd, J=8.8, 2.6 Hz, 1H), 3.80 (s, 3H), 3.75 (d, J=12.3 Hz, 2H), 3.32 (s, 3H), 2.74-2.62 (m, 5H), 1.91 (s, 2H), 1.67-1.52 (m, 2H). $^{19}$F NMR (471 MHz, DMSO) δ-64.35. MS (ESI) 617.89 (M+H)$^+$.

Example 38: Synthesis of Tricyclic Core for Compounds 184 and 186

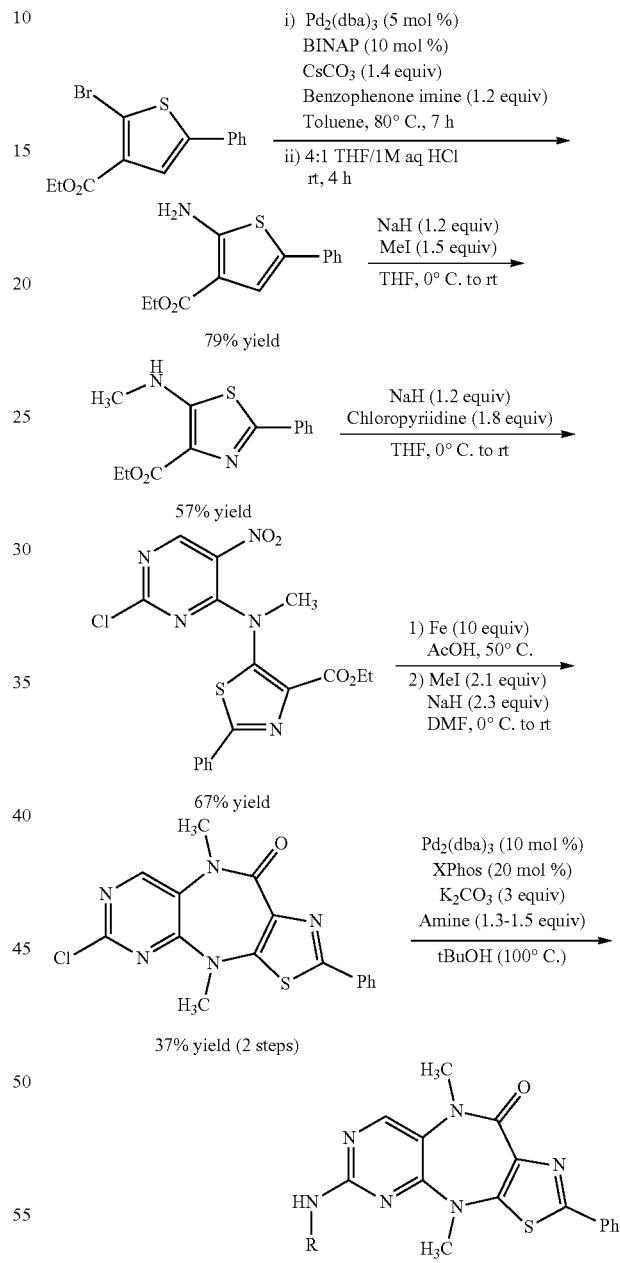

A mixture of ethyl 5-bromo-2-phenylthiazole-4-carboxylate (2.015 g, 6.5 mmol, 1.0 equiv), Pd$_2$(dba)$_3$ (298 mg, 0.33 mmol, 0.05 equiv), (±)-BINAP (405 mg, 0.65 mmol, 0.10 equiv), and cesium carbonate (2.965 g, 9.1 mmol, 1.4 equiv), and benzophenone imine (1.31 mL, 7.8 mmol, 1.2 equiv) in anhydrous toluene (25 mL) was sparged with Na for 10 minutes. The reaction was heated to 80° C. for 19 hours, and then cooled to room temperature, diluted with EtOAc (100 mL) and filtered through Celite®. Solvents were removed in vacuo to provide a dark red syrup. The intermediate ethyl 5-((diphenylmethylene)amino)-2-phenylthiazole-4-carboxylate was carried on directly to hydrolysis. MS (ESI) 412.87 (M+H)$^+$.

Crude ethyl 5-((diphenylmethylene)amino)-2-phenylthiazole-4-carboxylate was dissolved in THF (25 mL) and 1 M HCl (8 mL). The mixture was stirred at room temperature for 5 hours, at which point UPLC-MS analysis showed complete hydrolysis of the imine. The reaction was diluted with EtOAc (100 mL), neutralized to pH~10, washed twice with water and once with brine, dried over MgSO$_4$, filtered and concentrated. Purification with ISCO flash chromatography (40 g silica, 25-80% EtOAc/Hex, 20 min gradient) provided ethyl 5-amino-2-phenylthiazole-4-carboxylate as a yellow solid (1.273 g, 79% yield over 2 steps). $^1$H NMR (500 MHz, CDCl$_3$) δ 7.82-7.76 (m, 2H), 7.43-7.33 (m, 3H), 5.89 (br s, 2H), 4.43 (q, J=7.1 Hz, 2H), 1.44 (t, J=7.1 Hz, 3H). MS (ESI) 248.88 (M+H)$^+$.

A 100 mL round-bottom flask was dried with a heat gun. A suspension of sodium hydride (192 mg, 4.8 mmol, 1.2 equiv, 60% dispersion in mineral oil) in anhydrous THF (30 mL) was added and the flask was cooled on an ice bath. To this suspension, a solution of ethyl 5-amino-2-phenylthiazole-4-carboxylate (1.018 g, 4.0 mmol, 1.0 equiv) in THF (10 mL) was added over 5 minutes. The reaction was stirred for 30 minutes and then iodomethane (0.37 mL, 6.0 mmol, 1.5 equiv) was added dropwise. The reaction was stirred for 3 hours, slowly warming to room temperature. The reaction was quenched with water (50 mL). The aqueous layer was extracted with EtOAc (4×50 mL). The combined organic layers were washed twice with water, once with brine, dried over MgSO$_4$, filtered and concentrated. Purification with ISCO flash chromatography (25-80% EtOAC/hex, 19 minutes, 40 g silica) provided ethyl 5-(methylamino)-2-phenylthiazole-4-carboxylate as a yellow viscous oil (620 mg, 57% yield). $^1$H NMR (500 MHz, CDCl$_3$) δ 7.87-7.75 (m, 2H), 7.43-7.34 (m, 3H), 6.08 (s, 1H), 4.41 (t, J=7.1 Hz, 2H), 3.11 (s, 3H), 1.43 (t, J=7.1 Hz, 3H). MS (ESI) 262.87 (M+H)$^+$.

A 100 mL round-bottom flask was dried with a heat gun. A suspension of sodium hydride (112 mg, 2.76 mmol, 1.2 equiv, 60% dispersion in mineral oil) in anhydrous THF (12 mL) was added and the flask was cooled on an ice bath. To this suspension, a solution of ethyl 5-(methylamino)-2-phenylthiazole-4-carboxylate (620 mg, 2.3 mmol, 1.0 equiv) in THF (5 mL) was added over 4 minutes. The reaction was stirred at 0° C. for 20 minutes and then 2,4-dichloro-5-nitropyrimidine (796 mg, 4.14 mmol, 1.8 equiv) was added. The reaction was stirred overnight, slowly warming to room temperature. The reaction was quenched with aqueous NH$_4$Cl (40 mL), and the aqueous layer was extracted with EtOAc (4×30 mL). The combined organic layers were washed twice with water and once with brine, dried over MgSO$_4$, filtered and concentrated. Purification with ISCO flash chromatography (20-70% EtOAC/hex, 18 minutes, 24 g silica) provided ethyl 5-((2-chloro-5-nitropyrimidin-4-yl)(methyl)amino)-2-phenylthiazole-4-carboxylate as a yellow-orange foam (655 mg, 67% isolated yield). $^1$H NMR (500 MHz, CDCl$_3$) δ 8.62 (s, 1H), 7.97-7.90 (m, 2H), 7.52-7.44 (m, 3H), 4.28 (q, J=7.1 Hz, 2H), 3.69 (s, 3H), 1.28 (t, J=7.1 Hz, 3H). MS (ESI) 419.77 (M+H)$^+$.

A suspension of ethyl 5-((2-chloro-5-nitropyrimidin-4-yl)(methyl)amino)-2-phenylthiazole-4-carboxylate (655 mg, 1.50 mmol, 1.0 equiv) and iron powder (824 mg, 15.0 mmol, 10 equiv) in glacial acetic acid (22 mL) was heated to 50° C. for 16 hours. The reaction was cooled to room temperature and residual iron was removed with a magnetic wand. The crude reaction mixture was poured into a beaker with water (50 mL) and stirred at room temperature for 45 minutes. The resulting precipitate was collected by suction filtration, washing with water (50 mL), and dried in vacuo to provide 6-chloro-4-methyl-2-phenyl-4,9-dihydro-10H-pyrimido[5,4-b]thiazolo[5,4-e][1,4]diazepin-10-one as a yellow solid (321 mg, 60% yield). $^1$H NMR (500 MHz, DMSO-d$_6$) δ 10.09 (s, 1H), 8.16 (s, 1H), 7.89-7.77 (m, 2H), 7.64-7.35 (m, 3H), 3.46 (s, 3H). MS (ESI) 343.77 (M+H)$^+$.

NaH (63.5 mg, 1.54 mmol, 2.2 equiv, 60% dispersion in mineral oil) was added in a single portion to a suspension of 6-chloro-4-methyl-2-phenyl-4,9-dihydro-10H-pyrimido[5,4-b]thiazolo[5,4-e][1,4]diazepin-10-one (246 mg, 0.70 mmol, 1.0 equiv) and iodomethane (0.090 mL, 1.40 mmol, 2.0 equiv) in anhydrous DMF (10 mL) at 0° C. The reaction was stirred for 2 hours, and UPLC-MS analysis showed complete consumption of starting material. The reaction was then quenched with water (20 mL) and extracted with DCM (5×10 mL). The combined organic layers were washed three times with water, once with brine, dried over MgSO$_4$, filtered and concentrated. Purification with ISCO flash chromatography (12 g silica, 0-10% MeOH/DCM, 12 min gradient) provided 6-chloro-4,9-dimethyl-2-phenyl-4,9-dihydro-10H-pyrimido[5,4-b]thiazolo[5,4-e][1,4]diazepin-10-one as a red-orange solid (156.4 mg, 62% yield). $^1$H NMR (500 MHz, DMSO-d$_6$) δ 8.63 (s, 1H), 7.88-7.81 (m, 2H), 7.53-7.44 (m, 3H), 3.47 (s, 3H), 3.35 (s, 3H). MS (ESI) 357.77 (M+H)$^+$.

Example 39: Synthesis of 4,9-dimethyl-6-((4-(4-methylpiperazin-1-yl)phenyl)amino)-2-phenyl-4,9-dihydro-10H-pyrimido[5,4-b]thiazolo[5,4-e][1,4]diazepin-10-one (184)

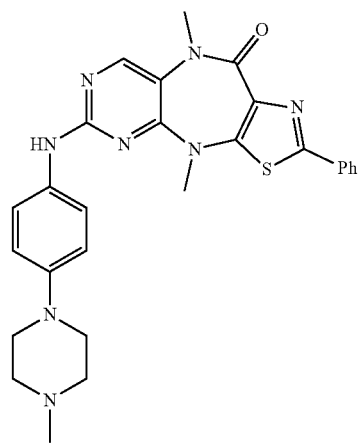 [SMILES: CN1CCN(c2ccc(Nc3ncc4c(n3)N(C)c3sc(-c5ccccc5)nc3C(=O)N4C)cc2)CC1]

General Pd coupling was run on 0.070 mmol scale using 4-(4-methylpiperazin-1-yl)aniline (20.2 mg, 0.105 mmol, 1.5 equiv). The reaction mixture was purified by reverse-phase prep HPLC (100-40% H$_2$O/MeCN, 20 mL/min, 45 min). Lyophilization from H$_2$O/MeCN provided the title compound as a white powder (12.9 mg TFA salt). $^1$H NMR (500 MHz, DMSO-d$_6$) δ 9.74 (s, 1H), 9.58 (s, 1H), 8.41 (s, 1H), 7.90-7.79 (m, 2H), 7.63-7.58 (m, 2H), 7.54-7.46 (m, 3H), 7.00-6.95 (m, 2H), 3.74 (d, J=13.2 Hz, 2H), 3.46 (s, 3H), 3.33 (s, 3H), 3.23-3.11 (m, 2H), 2.95-2.83 (m, 5H). MS (ESI) 512.88 (M+H)$^+$.

Example 40: Synthesis of 6-((2-methoxy-4-(4-(4-methylpiperazin-1-yl)piperidin-1-yl)phenyl)amino)-4,9-dimethyl-2-phenyl-4,9-dihydro-10H-pyrimido[5,4-b]thiazolo[5,4-e][1,4]diazepin-10-one (186)

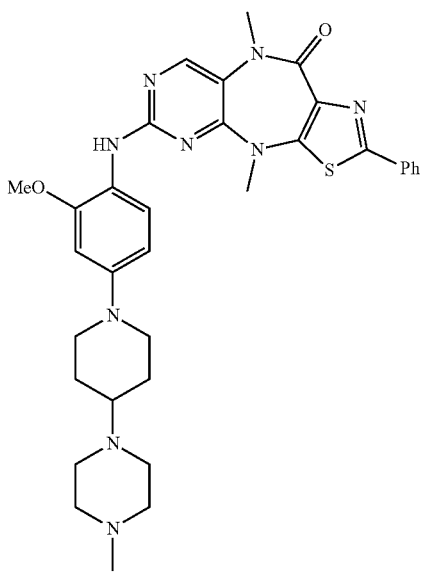 [SMILES: COc1cc(N2CCC(N3CCN(C)CC3)CC2)ccc1Nc1ncc2c(n1)N(C)c1sc(-c3ccccc3)nc1C(=O)N2C]

General Pd coupling was run on 0.065 mmol scale using 2-methoxy-4-(4-(4-methylpiperazin-1-yl)piperidin-1-yl) aniline (27.8 mg, 0.091 mmol, 1.4 equiv). The reaction mixture was purified by reverse-phase prep HPLC (100-50% H$_2$O/MeCN, 20 mL/min, 45 min). Further purification by prep TLC (10% MeOH/2% NEt$_3$/DCM) and lyophilization from H$_2$O/MeCN provided the title compound as a yellow solid (8.1 mg free base). $^1$H NMR (500 MHz, DMSO-d$_6$) δ 8.34 (s, 1H), 8.14 (d, J=1.4 Hz, 1H), 7.87-7.80 (m, 2H), 7.64 (d, J=8.7 Hz, 1H), 7.54-7.44 (m, 3H), 6.63 (s, 1H), 6.54-6.46 (m, 1H), 3.80 (s, 3H), 3.72 (s, 2H), 3.39 (s, 3H), 3.31 (s, 3H), 2.80-2.59 (m, 5H), 2.07-1.80 (m, 2H), 1.63-1.39 (m, 2H). MS (ESI) 625.99 (M+H)$^+$.

Example 41: Synthesis of Tricyclic Core for Compound 193

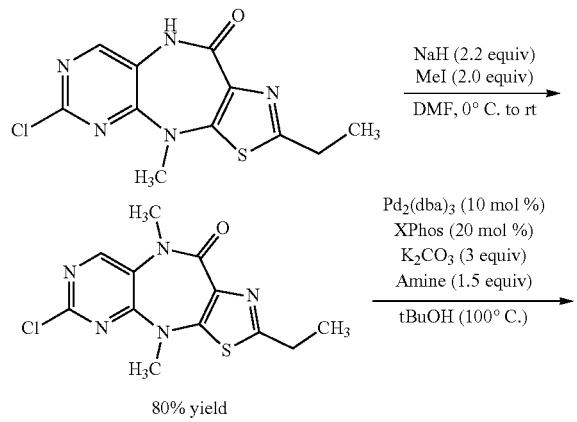

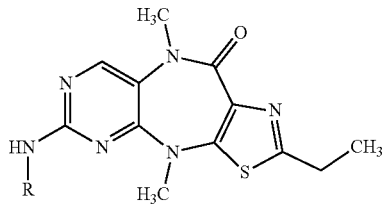

NaH (18.4 mg, 0.44 mmol, 2.2 equiv, 60% dispersion in mineral oil) was added in a single portion to a suspension of 6-chloro-2-ethyl-4-methyl-4,9-dihydro-10H-pyrimido[5,4-b]thiazolo[5,4-e][1,4]diazepin-10-one (63.0 mg, 0.20 mmol, 1.0 equiv) and iodomethane (25.0 µL, 0.40 mmol, 2.0 equiv) in anhydrous DMF (2.5 mL) at 0° C. The reaction was stirred for 3 hours, at which point UPLC-MS analysis showed complete consumption of starting material. The reaction was then quenched with water (5 mL) and extracted with EtOAc (4×5 mL). The combined organic layers were washed three times with water, once with brine, dried over MgSO$_4$, filtered and concentrated. Purification with ISCO flash chromatography (12 g silica, 0-5% MeOH/DCM, 12 min gradient) provided 6-chloro-2-ethyl-4,9-dimethyl-4,9-dihydro-10H-pyrimido[5,4-b]thiazolo[5,4-e][1,4]diazepin-10-one as a light yellow solid (49.8 mg, 80% yield). $^1$H NMR (500 MHz, DMSO-d$_6$) δ 8.58 (s, 1H), 3.37 (s, 3H), 3.31 (s, 3H), 2.88 (q, J=7.5 Hz, 2H), 1.24 (t, J=7.5 Hz, 3H). MS (ESI) 309.87 (M+H)$^+$.

Example 42: Synthesis of 2-ethyl-6-((2-methoxy-4-(4-(4-methylpiperazin-1-yl)piperidin-1-yl)phenyl) amino)-4,9-dimethyl-4,9-dihydro-10H-pyrimido[5,4-b]thiazolo[5,4-e][1,4]diazepin-10-one (193)

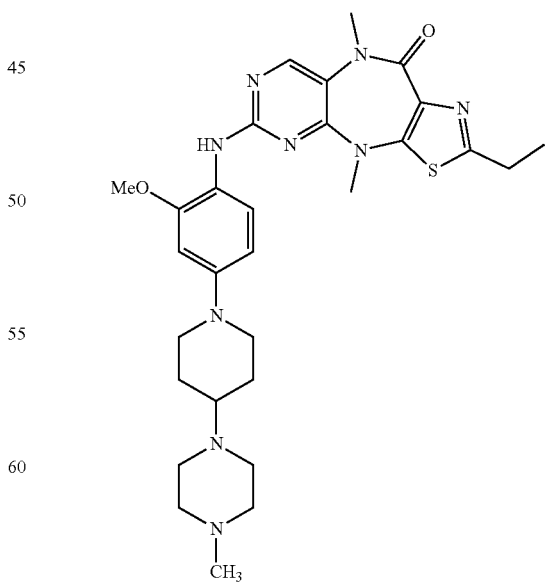

General Pd coupling was run on 0.16 mmol scale using 2-methoxy-4-(4-(4-methylpiperazin-1-yl)piperidin-1-yl)aniline (70.9 mg, 0.23 mmol, 1.5 equiv). The reaction mixture was purified by reverse-phase prep HPLC (85-15% H$_2$O/MeCN, 40 mL/min, 60 min). Further purification by prep TLC (10% MeOH/DCM) and lyophilization from H$_2$O/MeCN provided the title compound as a light yellow powder (19.2 mg TFA salt). $^1$H NMR (500 MHz, DMSO-d$_6$) δ 8.31 (s, 1H), 8.14 (s, 1H), 7.70 (d, J=8.7 Hz, 1H), 6.71 (s, 1H), 6.58 (d, J=8.6 Hz, 1H), 3.84-3.74 (m, 9H), 3.31 (s, 3H), 3.27 (s, 3H), 2.86 (q, J=7.5 Hz, 2H), 2.78 (br s, 5H), 2.06-1.96 (m, 2H), 1.65 (d, J=12.3 Hz, 2H), 1.23 (t, J=7.5 Hz, 3H). MS (ESI) 577.98 (M+H)$^+$.

Example 43: Synthesis of 6-((3-methoxy-4-(4-(4-methylpiperazin-1-yl)piperidin-1-yl)phenyl)amino)-2,4-dimethyl-4,9-dihydro-10H-pyrimido[5,4-b]thiazolo[5,4-e][1,4]diazepin-10-one (194)

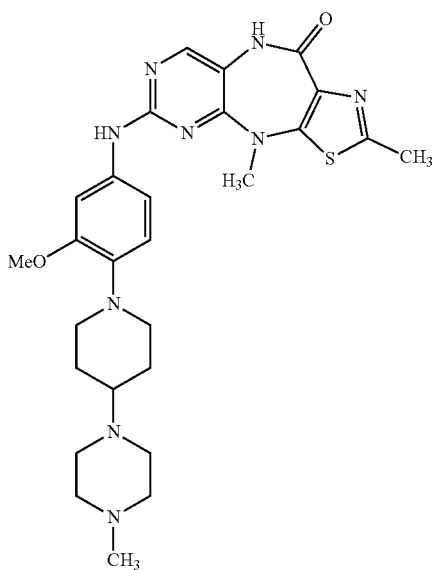 [SMILES: COc1cc(Nc2ncc3c(n2)N(C)c2sc(C)nc2C(=O)N3)ccc1N1CCC(N2CCN(C)CC2)CC1]

General Pd coupling was run on 0.08 mmol scale using 3-methoxy-4-(4-(4-methylpiperazin-1-yl)piperidin-1-yl)aniline (41.4 mg, 0.136 mmol, 1.7 equiv). The reaction mixture was purified by reverse-phase prep HPLC (100-40% H$_2$O/MeCN, 20 mL/min, 45 min). Lyophilization from H$_2$O/MeCN provided the title compound as a light yellow powder (30.7 mg TFA salt). $^1$H NMR (500 MHz, DMSO-d$_6$) δ 9.58 (s, 2H), 8.02 (s, 1H), 7.57 (s, 1H), 7.24 (d, J=6.8 Hz, 1H), 3.85 (s, 3H), 3.54-3.44 (m, 3H), 3.41 (s, 3H), 3.19-2.88 (m, 4H), 2.80 (s, 3H), 2.54 (s, 3H), 2.10-1.98 (m, 2H), 1.82 (s, 2H). MS (ESI) 550.27 (M+H)$^+$.

Example 44: Synthesis of 6-((2-methoxy-4-(4-(1-methylpiperidin-4-yl)piperazin-1-yl)phenyl)amino)-2,4,9-trimethyl-4,9-dihydro-10H-pyrimido[5,4-b]thiazolo[5,4-e][1,4]diazepin-10-one (195)

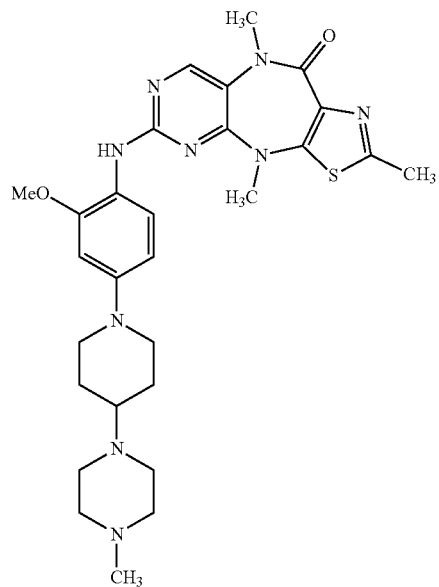 [SMILES: COc1cc(N2CCC(N3CCN(C)CC3)CC2)ccc1Nc1ncc2c(n1)N(C)c1sc(C)nc1C(=O)N2C]

General Pd coupling was run on 0.07 mmol scale using 2-methoxy-4-(4-(1-methylpiperidin-4-yl)piperazin-1-yl)aniline (29.5 mg, 0.105 mmol, 1.5 equiv). The reaction mixture was purified by reverse-phase prep HPLC (100-50% H$_2$O/MeCN, 20 mL/min, 45 min). Further purification by prep TLC (10% MeOH/DCM) and lyophilization from H$_2$O/MeCN provided the title compound as a white powder (13.7 mg TFA salt). $^1$H NMR (500 MHz, DMSO-d$_6$) δ 8.31 (s, 1H), 8.11 (s, 1H), 7.70 (d, J=6.6 Hz, 1H), 6.68 (s, 1H), 6.53 (d, J=8.6 Hz, 1H), 3.81 (s, 3H), 3.62-3.48 (m, 2H), 3.29 (s, 3H), 3.27 (s, 3H), 3.02-2.90 (m, 2H), 2.77 (s, 3H), 2.53 (s, 3H). MS (ESI) 563.99 (M+H)$^+$.

Example 45: Synthesis of 6-((2-methoxy-4-(4-methyl-2-oxopiperazin-1-yl)phenyl)amino)-2,4,9-trimethyl-4,9-dihydro-10H-pyrimido[5,4-b]thiazolo[5,4-e][1,4]diazepin-10-one (196)

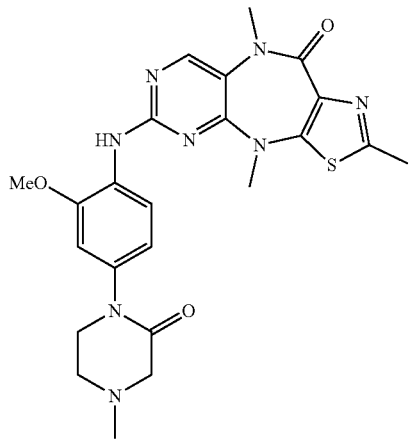 [SMILES: COc1cc(N2CCN(C)CC2=O)ccc1Nc1ncc2c(n1)N(C)c1sc(C)nc1C(=O)N2C]

General Pd coupling was run on 0.05 mmol scale using 1-(4-amino-3-methoxyphenyl)-4-methylpiperazin-2-one (16.0 mg, 0.065 mmol, 1.3 equiv). The reaction mixture was purified by reverse-phase prep HPLC (100-50% H$_2$O/MeCN, 20 mL/min, 45 min). Lyophilization from H$_2$O/MeCN provided the title compound as a white powder (4.8 mg TFA salt). $^1$H NMR (500 MHz, DMSO-d$_6$) δ 8.39 (s, 1H), 8.22 (s, 1H), 8.02 (d, J=8.6 Hz, 1H), 7.01 (d, J=2.2 Hz, 1H), 6.88 (dd, J=8.6, 2.2 Hz, 1H), 3.83 (s, 3H), 3.65 (dd, J=6.3, 4.6 Hz, 2H), 3.34 (s, 2H), 3.28 (s, 3H), 3.10 (s, 2H), 2.75-2.70 (m, 2H), 2.54 (s, 3H), 2.29 (s, 3H). MS (ESI) 494.88 (M+H)$^+$.

Example 46: Synthesis of N-methyl-4-((2,4,9-trimethyl-10-oxo-9,10-dihydro-4H-pyrimido[5,4-b]thiazolo[5,4-e][1,4]diazepin-6-yl)amino)benzamide (197)

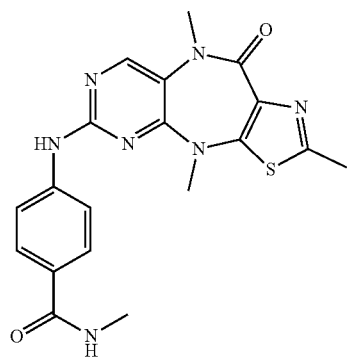 [SMILES: CNC(=O)c1ccc(Nc2ncc3c(n2)N(C)c2sc(C)nc2C(=O)N3C)cc1]

General Pd coupling was run on 0.05 mmol scale using 4-amino-N-methylbenzamide (13.0 mg, 0.086 mmol, 1.7 equiv). The reaction mixture was purified by reverse-phase prep HPLC (100-50% H$_2$O/MeCN, 20 mL/min, 45 min). Further purification by prep TLC (10% MeOH/2% NEt$_3$/DCM) and lyophilization from H$_2$O/MeCN provided the title compound as a white powder (6.6 mg free base). $^1$H NMR (500 MHz, DMSO-d$_6$) δ 9.97 (s, 1H), 8.46 (s, 1H), 8.24 (q, J=4.2 Hz, 1H), 7.78 (s, 4H), 3.40 (s, 3H), 3.30 (s, 3H), 2.76 (d, J=4.4 Hz, 3H), 2.54 (s, 3H). MS (ESI) 409.87 (M+H)$^+$.

Example 47: Synthesis of 6-((2-methoxy-4-(4-(methylsulfonyl)piperazin-1-yl)phenyl)amino)-2,4,9-trimethyl-4,9-dihydro-10H-pyrimido[5,4-b]thiazolo[5,4-e][1,4]diazepin-10-one (198)

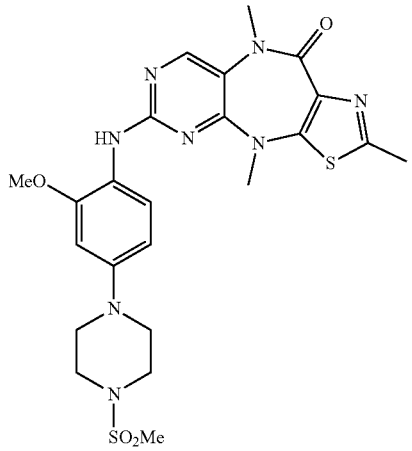 [SMILES: COc1cc(N2CCN(S(C)(=O)=O)CC2)ccc1Nc1ncc2c(n1)N(C)c1sc(C)nc1C(=O)N2C]

General Pd coupling was run on 0.05 mmol scale using 2-methoxy-4-(4-(methylsulfonyl)piperazin-1-yl)aniline (21.8 mg, 0.065 mmol, 1.3 equiv). The reaction mixture was purified by reverse-phase prep HPLC (100-50% H$_2$O/MeCN, 20 mL/min, 45 min). Further purification by prep TLC (10% MeOH/2% NEt$_3$/DCM) and lyophilization from H$_2$O/MeCN provided the title compound as a white powder (5.1 mg free base). $^1$H NMR (500 MHz, DMSO-d$_6$) δ 8.31 (s, 1H), 8.10 (s, 1H), 7.71 (d, J=8.8 Hz, 1H), 6.68 (d, J=2.6 Hz, 1H), 6.53 (dd, J=8.8, 2.6 Hz, 1H), 3.81 (s, 3H), 3.30 (s, 3H), 3.27 (s, 3H), 3.25-3.20 (m, 8H), 2.93 (s, 3H), 2.53 (s, 3H). MS (ESI) 544.79 (M+H)$^+$.

Example 48: Synthesis of 6-((4-(4-acetylpiperazin-1-yl)-2-methoxyphenyl)amino)-2,4,9-trimethyl-4,9-dihydro-10H-pyrimido[5,4-b]thiazolo[5,4-e][1,4]diazepin-10-one (199)

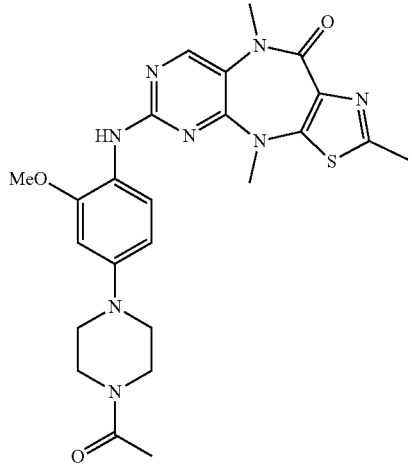 [SMILES: COc1cc(N2CCN(C(C)=O)CC2)ccc1Nc1ncc2c(n1)N(C)c1sc(C)nc1C(=O)N2C]

General Pd coupling was run on 0.06 mmol scale using 1-(4-(4-amino-3-methoxyphenyl)piperazin-1-yl)ethan-1-one (23.2 mg, 0.093 mmol, 1.5 equiv). The reaction mixture was purified by reverse-phase prep HPLC (100-50% H$_2$O/MeCN, 20 mL/min, 45 min). Lyophilization from H$_2$O/MeCN provided the title compound as a white powder (10.7 mg TFA salt). $^1$H NMR (500 MHz, DMSO-d$_6$) δ 8.31 (s, 1H), 8.15 (s, 1H), 7.69 (d, J=8.7 Hz, 1H), 6.69 (d, J=2.6 Hz, 1H), 6.53 (dd, J=8.8, 2.6 Hz, 1H), 3.81 (s, 3H), 3.29 (s, 3H), 3.26 (s, 3H), 3.15 (t, J=5.2 Hz, 2H), 3.09 (t, J=5.3 Hz, 2H), 2.54 (s, 4H), 2.53 (s, 3H), 2.05 (s, 3H). MS (ESI) 509.16 (M+H)$^+$.

Example 49: Synthesis of 6-((4-(4-(2-(dimethyl-amino)ethyl)piperazin-1-yl)-2-methoxyphenyl)amino)-2,4,9-trimethyl-4,9-dihydro-10H-pyrimido[5,4-b]thiazolo[5,4-e][1,4]diazepin-10-one (200)

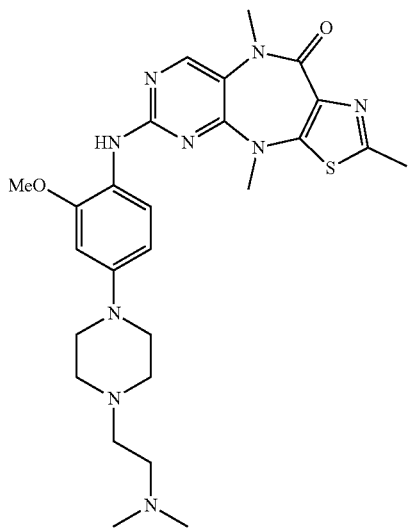 [SMILES: COc1cc(N2CCN(CCN(C)C)CC2)ccc1Nc1ncc2c(n1)N(C)c1sc(C)nc1C(=O)N2C]

General Pd coupling was run on 0.06 mmol scale using 4-(4-(2-(dimethylamino)ethyl)piperazin-1-yl)-2-methoxyaniline (25.4 mg, 0.091 mmol, 1.5 equiv). The reaction mixture was purified by reverse-phase prep HPLC (100-50% H$_2$O/MeCN, 20 mL/min, 45 min). Further purification by prep TLC (10% MeOH/2% NEt$_3$/DCM) and lyophilization from H$_2$O/MeCN provided the title compound as a white powder (14.7 mg free base). $^1$H NMR (500 MHz, DMSO-d$_6$) δ 9.10 (s, 1H), 8.30 (s, 1H), 8.12 (s, 1H), 7.69 (d, J=8.7 Hz, 1H), 6.67 (d, J=2.5 Hz, 1H), 6.53 (dd, J=8.8, 2.5 Hz, 1H), 3.81 (s, 3H), 3.29 (s, 3H), 3.27 (s, 3H), 2.83 (s, 6H), 2.53 (s, 3H). MS (ESI) 538.23 (M+H)$^+$.

Example 50: Synthesis of 2,4,9-trimethyl-6-((4-(4-methylpiperazin-1-yl)-2-(2,2,2-trifluoroethoxy)phenyl)amino)-4,9-dihydro-10H-pyrimido[5,4-b]thiazolo[5,4-e][1,4]diazepin-10-one (201)

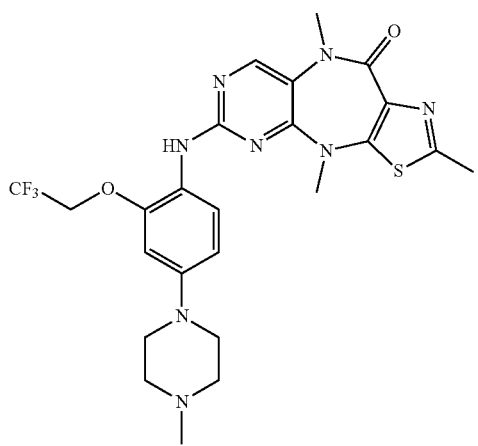 [SMILES: Cc1nc2c(s1)N(C)c1nc(Nc3ccc(N4CCN(C)CC4)cc3OCC(F)(F)F)ncc1N(C)C2=O]

General Pd coupling was run on 0.05 mmol scale using 4-(4-methylpiperazin-1-yl)-2-(2,2,2-trifluoroethoxy)aniline (20 mg, 0.069 mmol, 1.4 equiv). The reaction mixture was purified by reverse-phase prep HPLC (100-50% H$_2$O/MeCN, 20 mL/min, 45 min). Further purification by prep TLC (10% MeOH/DCM) and lyophilization from H$_2$O/MeCN provided the title compound as a white powder (2.6 mg TFA salt). $^1$H NMR (500 MHz, DMSO-d$_6$) δ 8.28 (s, 1H), 8.22 (s, 1H), 7.50 (d, J=8.8 Hz, 1H), 6.74 (d, J=2.6 Hz, 1H), 6.58 (dd, J=8.8, 2.6 Hz, 1H), 4.73 (q, J=8.9 Hz, 2H), 3.25 (s, 6H), 3.13 (t, J=5.0 Hz, 4H), 2.53 (s, 3H), 2.45 (t, J=5.1 Hz, 4H), 2.22 (s, 3H). $^{19}$F NMR (471 MHz, DMSO-d$_6$) δ-72.62 (t, J=8.9 Hz). MS (ESI) 548.89 (M+H)$^+$.

Example 51: Synthesis of 2,4,9-trimethyl-6-((4-(4-methylpiperazin-1-yl)-2-propoxyphenyl)amino)-4,9-dihydro-10H-pyrimido[5,4-b]thiazolo[5,4-e][1,4]diazepin-10-one (202)

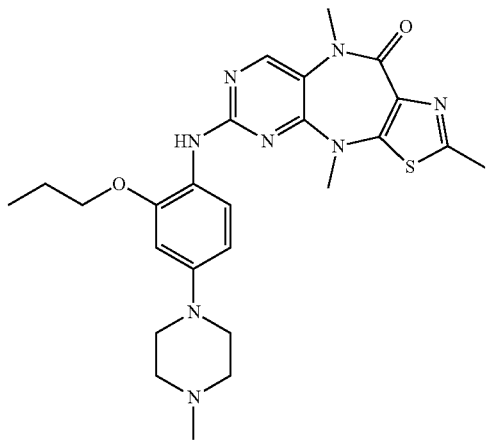 [SMILES: CCCOc1cc(N2CCN(C)CC2)ccc1Nc1ncc2c(n1)N(C)c1sc(C)nc1C(=O)N2C]

General Pd coupling was run on 0.05 mmol scale using 4-(4-methylpiperazin-1-yl)-2-propoxyaniline (17 mg, 0.068 mmol, 1.3 equiv). The reaction mixture was purified by reverse-phase prep HPLC (100-50% H$_2$O/MeCN, 20 mL/min, 45 min). Further purification by prep TLC (10% MeOH/DCM) and lyophilization from H$_2$O/MeCN provided the title compound as a white powder (6.8 mg TFA salt). $^1$H NMR (500 MHz, DMSO-d$_6$) δ 8.24 (s, 1H), 7.96 (s, 1H), 7.57 (d, J=8.8 Hz, 1H), 6.55 (d, J=2.6 Hz, 1H), 6.41 (dd, J=8.8, 2.6 Hz, 1H), 3.88 (t, J=6.5 Hz, 2H), 3.21 (s, 3H), 3.19 (s, 3H), 3.05 (s, 4H), 2.46 (s, 3H), 2.20 (br s, 2H), 1.67-1.56 (m, 2H), 0.82 (t, J=7.4 Hz, 3H). MS (ESI) 508.98 (M+H)$^+$.

Example 52: Synthesis of Tricyclic Core for Compound 203

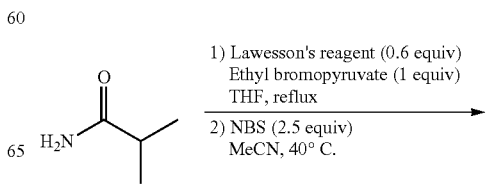

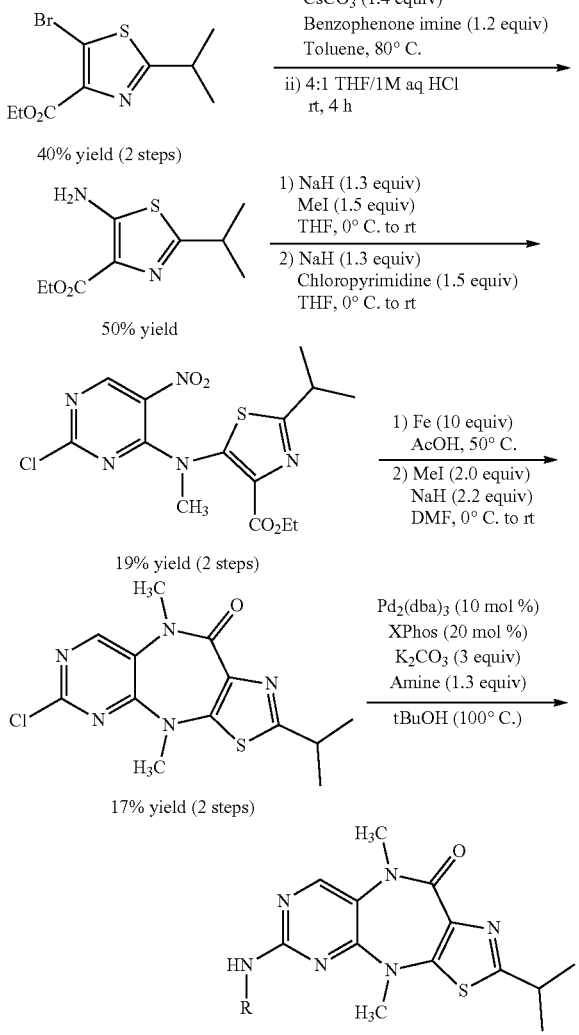

A suspension of isobutyramide (2.62 g, 30.0 mmol, 1.0 equiv) and Lawesson's reagent (7.23 g, 18.0 mmol, 0.6 equiv) in anhydrous THF (40 mL) was heated to 70° C. for 24 hours. The reaction flask was removed from the heat, cooled to room temperature, and ethyl bromopyruvate (3.75 mL, 30.0 mmol, 1.0 equiv) was added, and then the reaction was returned to 70° C. for 2 days. The reaction mixture was then cooled to room temperature, quenched with water (100 mL), and extracted with EtOAc (3×75 mL). The combined organic layers were washed with brine, dried over MgSO$_4$, filtered and concentrated. Purification with ISCO flash chromatography (80 g silica, 10-60% EtOAc/Hex, 28 min gradient) provided ethyl 2-isopropylthiazole-4-carboxylate as a yellow oil (7.3 g, quantitative yield, ~50% purity). $^1$H NMR (500 MHz, CDCl$_3$) δ 8.06 (s, 1H), 4.42 (q, J=7.1 Hz, 2H), 3.54-3.47 (m, 1H), 1.45-1.38 (m, 9H). MS (ESI) 200.08 (M+H)$^+$.

To the impure mixture of ethyl 2-isopropylthiazole-4-carboxylate (7.3 g, 18.3 mmol, 1 equiv) in acetonitrile (37 mL) was added N-bromosuccinimide (8.14 g, 45.8 mmol, 2.5 equiv). The mixture was heated to 40° C. for 24 hours. The reaction was then diluted with DCM (100 mL) and water (200 mL). The organic layer was removed, and the aqueous layer was extracted with DCM (3×75 mL). The combined organic layers were washed twice with water, once with brine, dried over MgSO$_4$, filtered and then concentrated to provide a dark, viscous oil. Purification with ISCO flash chromatography (40 g silica, 15-80% EtOAc/hexanes, 11 min gradient) provided ethyl 5-bromo-2-isopropylthiazole-4-carboxylate as a light yellow solid (3.35 g, 40% yield over 2 steps). MS (ESI) 277.77 (M+H)$^+$, 279.77 (M+2+H)$^+$.

A mixture of ethyl 5-bromo-2-isopropylthiazole-4-carboxylate (1.6 g, 5.75 mmol, 1.0 equiv), Pd$_2$(dba)$_3$ (262 mg, 0.29 mmol, 0.05 equiv), (±)-BINAP (358 mg, 0.58 mmol, 0.10 equiv), cesium carbonate (2.61 g, 8.0 mmol, 1.4 equiv), and benzophenone imine (1.16 mL, 6.9 mmol, 1.2 equiv) in anhydrous toluene (23 mL) was sparged with N$_2$ for 5 minutes. The reaction was heated to 80° C. overnight, and then cooled to room temperature, diluted with EtOAc (100 mL) and filtered through Celite®. Solvents were removed in vacuo to provide a dark red syrup. The intermediate ethyl 5-((diphenylmethylene)amino)-2-isopropylthiazole-4-carboxylate was carried on directly to hydrolysis. MS (ESI) 378.97 (M+H)$^+$.

Crude ethyl 5-((diphenylmethylene)amino)-2-isopropylthiazole-4-carboxylate was dissolved in THF (20 mL) and 1 M HCl (4 mL). The mixture was stirred at room temperature overnight, at which point UPLC-MS analysis showed complete hydrolysis of the imine. The reaction was diluted with EtOAc (100 mL), neutralized to pH~10, washed twice with water and once with brine, dried over MgSO$_4$, filtered and concentrated. Purification with ISCO flash chromatography (24 g silica, 25-80% EtOAc/hexanes, 10 min gradient) provided ethyl 5-amino-2-isopropylthiazole-4-carboxylate as a yellow-orange solid (660 mg, 50% yield). $^1$H NMR (500 MHz, CDCl$_3$) δ 5.87 (s, 2H), 4.39 (q, J=7.1 Hz, 2H), 3.25 (h, J=7.0 Hz, 1H), 1.40 (t, J=7.1 Hz, 3H), 1.32 (d, J=6.9 Hz, 6H). MS (ESI) 215.08 (M+H)$^+$.

A 100 mL round-bottom flask was dried with a heat gun. A suspension of sodium hydride (107 mg, 4.42 mmol, 1.3 equiv) in anhydrous THF (22 mL) was added and the flask was cooled on an ice bath. A solution of ethyl 5-amino-2-phenylthiazole-4-carboxylate (728 mg, 3.4 mmol, 1.0 equiv) in THF (10 mL) was added over 5 minutes to the solution. The reaction was stirred for 30 minutes and then iodomethane (0.31 mL, 5.1 mmol, 1.5 equiv) was added dropwise. The reaction was stirred overnight, slowly warming to room temperature. The reaction was quenched with water (50 mL). The aqueous layer was extracted with EtOAc (4×50 mL). The combined organic layers were washed twice with water, once with brine, dried over MgSO$_4$, filtered and concentrated. Purification with ISCO flash chromatography (20-80% EtOAC/hex, 10 minutes, 12 g silica) provided ethyl 2-isopropyl-5-(methylamino)thiazole-4-carboxylate as a yellow solid (205 mg, 26% yield). MS (ESI) 229.08 (M+H)$^+$.

A 100 mL round-bottom flask was dried with a heat gun. A suspension of sodium hydride (38 mg, 1.56 mmol, 1.3 equiv) in anhydrous THF (9 mL) was added and the flask was cooled on an ice bath. A solution of ethyl 2-isopropyl-5-(methylamino)thiazole-4-carboxylate (256 mg, 1.2 mmol, 1.0 equiv) in THF (3 mL) was added over 4 minutes to the suspension. The reaction was stirred at 0° C. for 20 minutes and then 2,4-dichloro-5-nitropyrimidine (350 mg, 1.8 mmol, 1.5 equiv) was added. The reaction was stirred overnight, slowly warming to room temperature. The reaction was quenched with aqueous NH$_4$Cl (40 mL), and the aqueous layer was extracted with EtOAc (4×30 mL). The combined organic layers were washed twice with water and once with brine, dried over MgSO₄, filtered and concentrated. Purification with ISCO flash chromatography (20-80% EtOAC/hex, 15 minutes, 40 g silica) provided ethyl 5-((2-chloro-5-nitropyrimidin-4-yl)(methyl)amino)-2-isopropylthiazole-4-carboxylate as a red-orange oil (350 mg, 75% isolated yield). MS (ESI) 385.87 (M+H)⁺.

A suspension of ethyl 5-((2-chloro-5-nitropyrimidin-4-yl)(methyl)amino)-2-isopropylthiazole-4-carboxylate (350 mg, 0.9 mmol, 1.0 equiv) and iron powder (502 mg, 9.0 mmol, 10 equiv) in glacial acetic acid (13 mL) was heated to 50° C. for 17 hours. The reaction was cooled to room temperature and residual iron was removed with a magnetic wand. The crude reaction mixture was poured into water (100 mL) and stirred for 30 minutes. The precipitate was collected by suction filtration, and washed with water (50 mL) to provide 6-chloro-2-isopropyl-4-methyl-4,9-dihydro-10H-pyrimido[5,4-b]thiazolo[5,4-e][1,4]diazepin-10-one as a yellow solid (110 mg, 39% yield). $^1$H NMR (500 MHz, DMSO-d$_6$) δ 9.95 (s, 1H), 8.11 (s, 1H), 3.37 (s, 3H), 3.16 (p, J=6.9 Hz, 1H), 1.28 (d, J=6.9 Hz, 6H). MS (ESI) 309.77 (M+H)⁺.

NaH (18.8 mg, 0.78 mmol, 2.1 equiv) was added in a single portion to a suspension of 6-chloro-2-isopropyl-4-methyl-4,9-dihydro-10H-pyrimido[5,4-b]thiazolo[5,4-e][1,4]diazepin-10-one (110 mg, 0.36 mmol, 1.0 equiv) and iodomethane (50.0 μL, 0.80 mmol, 2.2 equiv) in anhydrous DMF (3.5 mL) at 0° C. The reaction was stirred overnight and then quenched with water (20 mL) and extracted with EtOAc (5×10 mL). The combined organic layers were washed twice with water, once with brine, dried over MgSO₄, filtered and concentrated to provide 6-chloro-2-isopropyl-4,9-dimethyl-4,9-dihydro-10H-pyrimido[5,4-b]thiazolo[5,4-e][1,4]diazepin-10-one as a yellow oil (110 mg, 95% yield). The material was sufficiently pure by NMR analysis and not purified further. $^1$H NMR (500 MHz, DMSO-d$_6$) δ 8.57 (s, 1H), 3.38 (s, 3H), 3.31 (s, 3H), 3.17 (p, J=6.9 Hz, 1H), 1.27 (d, J=6.9 Hz, 6H). MS (ESI) 323.87 (M+H)⁺.

Example 53: Synthesis of 2-isopropyl-6-((2-methoxy-4-(4-(4-methylpiperazin-1-yl)piperidin-1-yl)phenyl)amino)-4,9-dimethyl-4,9-dihydro-10H-pyrimido[5,4-b]thiazolo[5,4-e][1,4]diazepin-10-one (203)

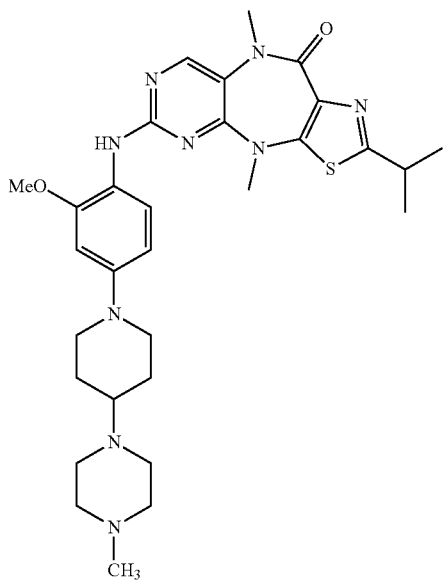 [SMILES: COc1cc(N2CCC(N3CCN(C)CC3)CC2)ccc1Nc1ncc2c(n1)N(C)c1sc(C(C)C)nc1C(=O)N2C]

General Pd coupling was run on 0.08 mmol scale using 2-methoxy-4-(4-(4-methylpiperazin-1-yl)piperidin-1-yl)aniline (31.6 mg, 0.104 mmol, 1.3 equiv). The reaction mixture was purified by reverse-phase prep HPLC (100-50% H₂O/MeCN, 20 mL/min, 45 min). Further purification by prep TLC (10% MeOH/DCM) and lyophilization from H₂O/MeCN provided the title compound as a white powder (8.5 mg TFA salt). $^1$H NMR (500 MHz, DMSO-d$_6$) δ 8.29 (s, 1H), 8.08 (s, 1H), 7.64 (d, J=8.7 Hz, 1H), 6.62 (s, 1H), 6.50 (d, J=8.8 Hz, 1H), 3.80 (s, 3H), 3.70 (s, 2H), 3.30 (s, 3H), 3.27 (s, 3H), 3.16 (p, J=6.9 Hz, 1H), 3.10-2.89 (m, 4H), 2.82-2.71 (m, 2H), 2.66 (t, J=12.0 Hz, 2H), 1.95-1.74 (m, 2H), 1.60-1.44 (m, 2H), 1.27 (d, J=6.9 Hz, 6H). MS (ESI) 591.99 (M+H)⁺.

Example 54: Synthesis of Tricyclic Core for Compound 204

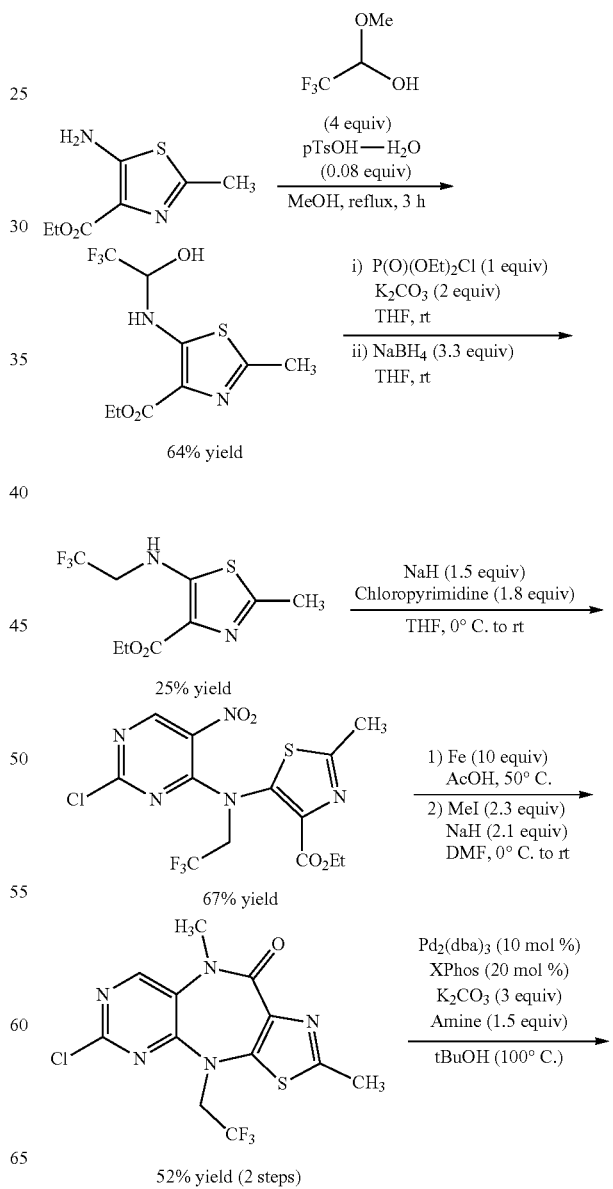

-continued

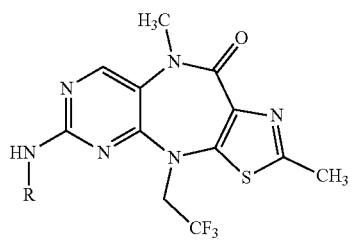

To a suspension of ethyl 5-amino-2-methylthiazole-4-carboxylate (701 mg, 3.5 mmol, 1.0 equiv) and p-toluenesulfonic acid monohydrate (52.5 mg, 0.28 mmol, 0.08 equiv) in methanol (9 mL), trifluoroacetaldehyde methyl hemiacetal (1.34 mL, 14.0 mmol, 4.0 equiv) was added and the mixture was heated to 70° C. for 3 hours. The reaction was then cooled, diluted with EtOAc (30 mL) and poured into saturated aqueous NaHCO$_3$ (100 mL). The organic layer was separated, and the aqueous component was extracted with EtOAc (2×30 mL). The combined organic layers were washed twice with water and once with brine, dried over MgSO$_4$, filtered and concentrated. Purification with ISCO flash chromatography (15-70% EtOAC/hex, 20 minutes, 40 g silica) provided ethyl 2-methyl-5-((2,2,2-trifluoro-1-hydroxyethyl)amino)thiazole-4-carboxylate as a viscous yellow oil (644 mg, 64% isolated yield). $^1$H NMR (500 MHz, CDCl$_3$) δ 7.88 (d, J=8.7 Hz, 1H), 5.08 (dq, J=8.7, 4.3 Hz, 1H), 4.75 (d, J=3.7 Hz, 1H), 4.39 (q, J=7.1 Hz, 2H), 2.56 (s, 3H), 1.39 (t, J=7.1 Hz, 3H). $^{19}$F NMR (471 MHz, CDCl$_3$) δ-82.02 (d, J=4.5 Hz). MS (ESI) 284.77 (M+H)$^+$.

To a suspension of ethyl 2-methyl-5-((2,2,2-trifluoro-1-hydroxyethyl)amino)thiazole-4-carboxylate (810 mg, 2.8 mmol, 1.0 equiv) and K$_2$CO$_3$ (781 mg, 5.6 mmol, 2.0 equiv) in anhydrous THF (15 mL), diethyl chlorophosphate (0.42 mL, 2.8 mmol, 1.0 equiv) was added at room temperature and the reaction was conducted for 14 hours. The mixture was then diluted with anhydrous THF (8 mL) and NaBH$_4$ (346 mg, 9.1 mmol, 3.3 equiv) was added. The reaction was stirred for 6 hours, and then quenched with dilute aqueous NH$_4$Cl. The aqueous component was extracted with EtOAc (3×25 mL). The combined organic layers were washed with water and brine, dried over MgSO$_4$, filtered and concentrated. Purification with ISCO flash chromatography (15-70% EtOAC/hex, 20 minutes, 24 g silica) provided ethyl 2-methyl-5-((2,2,2-trifluoroethyl)amino)thiazole-4-carboxylate as an off-white solid (189.8 mg, 25% yield). $^1$H NMR (500 MHz, CDCl$_3$) δ 7.66 (t, J=6.1 Hz, 1H), 4.40 (q, J=7.1 Hz, 2H), 3.80 (qd, J=8.5, 7.0 Hz, 2H), 2.58 (s, 3H), 1.41 (t, J=7.1 Hz, 3H). $^{19}$F NMR (471 MHz, CDCl$_3$) δ-72.46 (t, J=8.5 Hz). MS (ESI) 268.87 (M+H)$^+$.

A 25 mL round-bottom flask was dried with a heat gun. Sodium hydride (42.0 mg, 1.05 mmol, 1.5 equiv, 60% dispersion in mineral oil) was added to an ice-cold solution of ethyl 2-methyl-5-((2,2,2-trifluoroethyl)amino)thiazole-4-carboxylate (186.2 mg, 0.70 mmol, 1.0 equiv) in anhydrous THF (5.0 mL). The reaction was stirred at 0° C. for 10 minutes and then 2,4-dichloro-5-nitropyrimidine (245 mg, 1.26 mmol, 1.8 equiv) was added. The reaction was warmed to room temperature over 30 minutes, and then heated to 60° C. overnight. The reaction was quenched with dilute aqueous NH$_4$Cl (40 mL), and the aqueous layer was extracted with EtOAc (4×25 mL). The combined organic layers were washed twice with water and once with brine, dried over MgSO$_4$, filtered and concentrated. Purification with ISCO flash chromatography (15-60% EtOAC/hex, 16 minutes, 12 g silica) provided ethyl 5-((2-chloro-5-nitropyrimidin-4-yl)(2,2,2-trifluoroethyl)amino)-2-methylthiazole-4-carboxylate as a yellow oil (199.9 mg, 67% isolated yield). $^1$H NMR (500 MHz, CDCl$_3$) δ 8.63 (s, 1H), 4.77 (s, 2H), 4.27 (q, J=7.1 Hz, 2H), 2.74 (s, 3H), 1.26 (t, J=7.1 Hz, 3H). $^{19}$F NMR (471 MHz, CDCl$_3$) δ-68.21 (t, J=8.4 Hz). MS (ESI) 426.29 (M+H)$^+$.

A suspension of ethyl 5-((2-chloro-5-nitropyrimidin-4-yl)(2,2,2-trifluoroethyl)amino)-2-methylthiazole-4-carboxylate (195.9 mg, 0.48 mmol, 1.0 equiv) and iron powder (253 mg, 4.5 mmol, 9.4 equiv) in glacial acetic acid (6.0 mL) was heated to 50° C. for 18 hours. The reaction was cooled to room temperature and residual iron was removed with a magnetic wand. The crude reaction mixture was poured into water (50 mL) and extracted with DCM (4×10 mL). The combined organic layers were washed twice with sat. aqueous NaHCO$_3$ and then brine, dried over MgSO$_4$, filtered and concentrated to provide 6-chloro-2-methyl-4-(2,2,2-trifluoroethyl)-4,9-dihydro-10H-pyrimido[5,4-b]thiazolo[5,4-e][1,4]diazepin-10-one as a yellow foam (154.0 mg). $^1$H NMR (500 MHz, DMSO-d$_6$) δ 10.27 (s, 1H), 8.34 (s, 1H), 4.96 (q, J=8.8 Hz, 2H), 2.57 (s, 3H). $^{19}$F NMR (471 MHz, DMSO-d$_6$) δ-69.58 (t, J=8.9 Hz). MS (ESI) 349.77 (M+H)$^+$.

NaH (29.6 mg, 0.74 mmol, 2.1 equiv, 60% dispersion in mineral oil) was added in a single portion to a suspension of 6-chloro-2-methyl-4-(2,2,2-trifluoroethyl)-4,9-dihydro-10H-pyrimido[5,4-b]thiazolo[5,4-e][1,4]diazepin-10-one (122.8 mg, 0.35 mmol, 1.0 equiv) and iodomethane (50.0 µL, 0.80 mmol, 2.3 equiv) in anhydrous DMF (4.5 mL) at 0° C. The reaction was stirred for 2 hours, and UPLC-MS analysis showed complete consumption of starting material. The reaction was then quenched with water (20 mL) and extracted with DCM (4×10 mL). The combined organic layers were washed twice with water, once with brine, dried over MgSO$_4$, filtered and concentrated. Purification with ISCO flash chromatography (12 g silica, 0-10% MeOH/DCM, 12 min gradient) provided 6-chloro-2,9-dimethyl-4-(2,2,2-trifluoroethyl)-4,9-dihydro-10H-pyrimido[5,4-b]thiazolo[5,4-e][1,4]diazepin-10-one as a yellow oil (91.1 mg, 52% yield over 2 steps). $^1$H NMR (500 MHz, CDCl$_3$) δ 8.39 (s, 1H), 4.69 (q, J=8.1 Hz, 2H), 3.47 (s, 3H), 2.62 (s, 3H). $^{19}$F NMR (471 MHz, CDCl$_3$) δ-70.87 (t, J=8.1 Hz). MS (ESI) 363.77 (M+H)$^+$.

Example 55: Synthesis of 6-((2-methoxy-4-(4-(4-methylpiperazin-1-yl)piperidin-1-yl)phenyl)amino)-2,9-dimethyl-4-(2,2,2-trifluoroethyl)-4,9-dihydro-10H-pyrimido[5,4-b]thiazolo[5,4-e][1,4]diazepin-10-one (204)

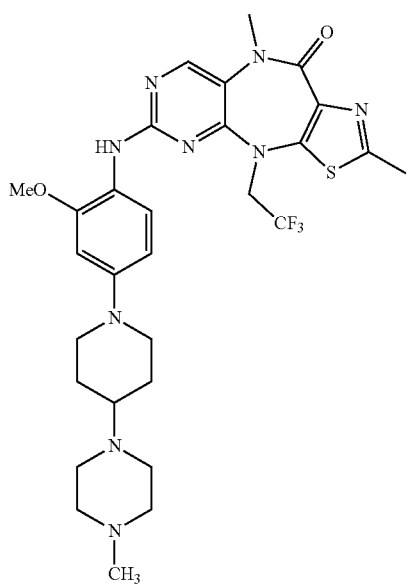 [SMILES: COc1cc(N2CCC(N3CCN(C)CC3)CC2)ccc1Nc1ncc2c(n1)N(CC(F)(F)F)c1sc(C)nc1C(=O)N2C]

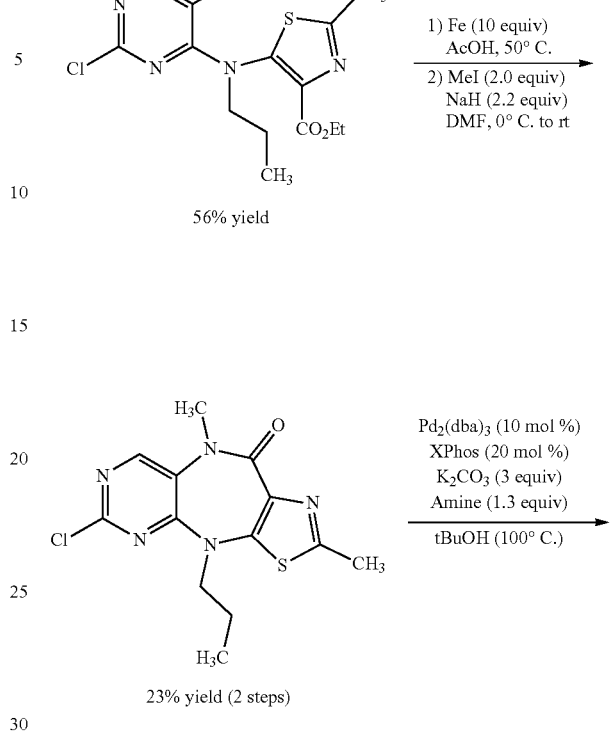

General Pd coupling was run on 0.07 mmol scale using 2-methoxy-4-(4-(4-methylpiperazin-1-yl)piperidin-1-yl)aniline (32.6 mg, 0.107 mmol, 1.5 equiv). The reaction mixture was purified by reverse-phase prep HPLC (100-50% H$_2$O/MeCN, 20 mL/min, 45 min). Lyophilization from H$_2$O/MeCN provided the title compound as a beige powder (2.5 mg TFA salt). $^1$H NMR (500 MHz, DMSO-d$_6$) δ 8.52 (s, 1H), 8.44 (s, 1H), 7.50 (d, J=8.6 Hz, 1H), 6.72 (s, 1H), 6.58 (d, J=8.5 Hz, 1H), 4.88 (br s, 2H), 3.80 (d, J=7.2 Hz, 3H), 3.33 (s, 3H), 2.85-2.72 (m, 7H), 2.56 (s, 3H), 2.08-1.98 (m, 2H), 1.75-1.59 (m, 2H). $^{19}$F NMR (471 MHz, DMSO-d$_6$) δ -73.58 (t, J=9.3 Hz). MS (ESI) 632.00 (M+H)$^+$.

Example 56: Synthesis of Tricyclic Core for Compound 205

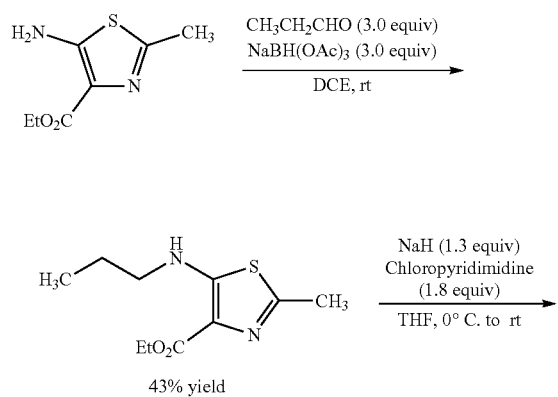

NaBH(OAc)$_3$ (2.260 g, 10.5 mmol, 3.0 equiv) was added portion-wise over 3 minutes at room temperature to a solution of ethyl 5-amino-2-methylthiazole-4-carboxylate (702 mg, 3.5 mmol, 1.0 equiv) and propionaldehyde (0.80 mL, 10.5 mmol, 3.0 equiv) in DCE (18 mL). The reaction was stirred for 4 hours, and then quenched with sat. NaHCO$_3$ (100 mL). The aqueous component was extracted with DCM (3×30 mL). The combined organic layers were washed with water and brine, dried over MgSO$_4$, filtered and concentrated. Purification with ISCO flash chromatography (24 g silica, 20-70% EtOAc/Hex, 15 min) provided ethyl 2-methyl-5-(propylamino)thiazole-4-carboxylate as a yellow oil (349 mg, 43% yield). $^1$H NMR (500 MHz, CDCl$_3$) δ 7.33 (s, 1H), 4.37 (q, J=7.1 Hz, 2H), 3.17 (td, J=7.0, 5.8 Hz, 2H), 2.54 (s, 3H), 1.70 (h, J=7.4 Hz, 2H), 1.39 (t, J=7.1 Hz, 3H), 0.99 (t, J=7.4 Hz, 3H). MS (ESI) 229.08 (M+H)$^+$.

A 50 mL round-bottom flask was dried with a heat gun. A suspension of sodium hydride (78.9 mg, 1.95 mmol, 1.3 equiv, 60% dispersion in mineral oil) in anhydrous THF (5.0 mL) was added and the flask was cooled on an ice bath. To this suspension, a solution of ethyl 2-methyl-5-(propylamino)thiazole-4-carboxylate (349 mg, 1.5 mmol, 1.0 equiv) in THF (5 mL) was added over 4 minutes. The reaction was stirred at 0° C. for 30 minutes and then 2,4-dichloro-5-nitropyrimidine (551 mg, 2.8 mmol, 1.8 equiv) was added. The reaction was warmed to room temperature over 1 hour, and then heated to 68° C. for 6 hours. The reaction was quenched with dilute aqueous $NH_4Cl$ (40 mL), and the aqueous layer was extracted with EtOAc (3×20 mL). The combined organic layers were washed twice with water and once with brine, dried over $MgSO_4$, filtered and concentrated. Purification with ISCO flash chromatography (20-70% EtOAC/hex, 17 minutes, 24 g silica) provided ethyl 5-((2-chloro-5-nitropyrimidin-4-yl)(propyl)amino)-2-methylthiazole-4-carboxylate as a red oil (327 mg, 56% isolated yield). $^1$H NMR (500 MHz, $CDCl_3$) δ 8.55 (s, 1H), 4.23 (q, J=7.2 Hz, 2H), 4.10-3.91 (m, 2H), 2.72 (s, 3H), 1.79-1.65 (m, 2H), 1.23 (t, J=7.1 Hz, 3H), 0.97 (t, J=7.4 Hz, 3H). MS (ESI) 385.87 $(M+H)^+$.

A suspension of ethyl 5-((2-chloro-5-nitropyrimidin-4-yl)(propyl)amino)-2-methylthiazole-4-carboxylate (327 mg, 0.84 mmol, 1.0 equiv) and iron powder (469 mg, 8.4 mmol, 10 equiv) in glacial acetic acid (12 mL) was heated to 50° C. for 18 hours. The reaction was cooled to room temperature and residual iron was removed with a magnetic wand. The crude reaction mixture was poured into water (100 mL) and extracted with DCM (5×20 mL). The combined organic layers were washed twice with sat. aqueous $NaHCO_3$ and then brine, dried over $MgSO_4$, filtered and concentrated to provide 6-chloro-2-methyl-4-propyl-4,9-dihydro-10H-pyrimido[5,4-b]thiazolo[5,4-e][1,4]diazepin-10-one as a yellow oil (245 mg, 94% yield). $^1$H NMR (500 MHz, $CDCl_3$) δ 8.09 (s, 1H), 3.93 (t, J=7.2 Hz, 2H), 2.62 (s, 3H), 1.84 (h, J=7.4 Hz, 2H), 1.00 (t, J=7.4 Hz, 3H). MS (ESI) 309.87 $(M+H)^+$.

NaH (70 mg, 1.76 mmol, 2.2 equiv, 60% dispersion in mineral oil) was added in a single portion to a suspension of 6-chloro-2-methyl-4-propyl-4,9-dihydro-10H-pyrimido[5,4-b]thiazolo[5,4-e][1,4]diazepin-10-one (245 mg, 0.80 mmol, 1.0 equiv) and iodomethane (0.10 mL, 1.60 mmol, 2.0 equiv) in anhydrous DMF (10 mL) at 0° C. The reaction was stirred for 1.5 hours. The reaction was then quenched with water (20 mL) and extracted with DCM (5×8 mL). The combined organic layers were washed twice with water, once with brine, dried over $MgSO_4$, filtered and concentrated. Purification with ISCO flash chromatography (12 g silica, 0-10% MeOH/DCM, 12 min gradient) provided 6-chloro-2,9-dimethyl-4-propyl-4,9-dihydro-10H-pyrimido[5,4-b]thiazolo[5,4-e][1,4]diazepin-10-one as a yellow semi-solid (64.9 mg, 25% yield). $^1$H NMR (500 MHz, $CDCl_3$) δ 8.09 (s, 1H), 3.93 (t, J=7.2 Hz, 2H), 2.62 (s, 3H), 1.84 (h, J=7.4 Hz, 2H), 1.00 (t, J=7.4 Hz, 3H). MS (ESI) 323.77 $(M+H)^+$.

Example 57: Synthesis of 6-((2-methoxy-4-(4-(4-methylpiperazin-1-yl)piperidin-1-yl)phenyl)amino)-2,9-dimethyl-4-propyl-4,9-dihydro-10H-pyrimido[5,4-b]thiazolo[5,4-e][1,4]diazepin-10-one (205)

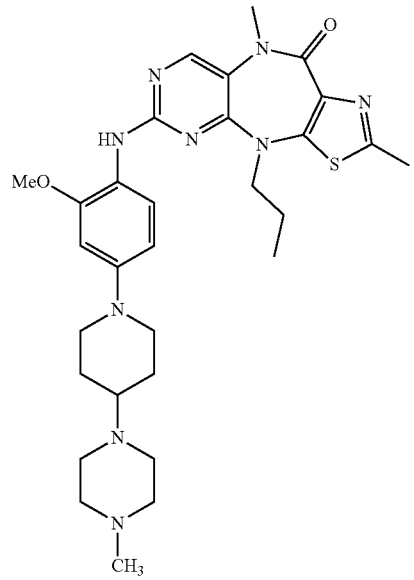 [SMILES: CCCN1c2nc(Nc3ccc(N4CCC(N5CCN(C)CC5)CC4)cc3OC)ncc2N(C)C(=O)c2nc(C)sc21]

General Pd coupling was run on 0.07 mmol scale using 2-methoxy-4-(4-(4-methylpiperazin-1-yl)piperidin-1-yl)aniline (30.1 mg, 0.105 mmol, 1.5 equiv). The reaction mixture was purified by reverse-phase prep HPLC (100-50% $H_2O$/MeCN, 20 mL/min, 45 min). Lyophilization from $H_2O$/MeCN provided the title compound as a white powder (8.0 mg TFA salt). $^1$H NMR (500 MHz, DMSO-$d_6$) δ 8.32 (s, 1H), 8.22 (s, 1H), 7.60 (d, J=8.4 Hz, 1H), 6.73 (s, 1H), 6.59 (d, J=8.8 Hz, 1H), 3.83-3.77 (m, 5H), 3.73 (t, J=7.2 Hz, 2H), 3.28 (s, 3H), 2.81 (s, 3H), 2.53 (s, 3H), 2.04 (d, J=11.9 Hz, 2H), 1.77-1.61 (m, 4H), 0.89 (t, J=7.3 Hz, 3H). MS (ESI) 592.09 $(M+H)^+$.

Example 58: $IC_{50}$ for FAK

Enzymatic $IC_{50}$ data was obtained through ThermoFisher Scientific SelectScreen™ Biochemical Kinase Profiling Service, using a Z'-LYTE™ kinase-specific assay, as described below. The results generated from the Assay are shown in Table 1 below.

Z'-LYTE Assay Conditions
Test Compounds

The test compounds were screened in 1% dimethyl sulfoxide (DMSO) (final) in the well. For 10 point titrations, 3-fold serial dilutions were conducted from the starting concentration.

Peptide/Kinase Mixtures

All peptide/kinase mixtures were diluted to a 2× working concentration in the appropriate kinase buffer (see section kinase specific assay conditions for a complete description).

ATP Solution

All ATP solutions were diluted to a 4× working concentration in kinase buffer (50 mM 4-(2-hydroxyethyl)-1-piperazineethanesulfonic acid (HEPES) pH 7.5, 0.01% BRIJ-35, 10 mM $MgCl_2$, 1 mM ethylene glycol-bis(β-aminoethyl ether)-N,N,N',N'-tetraacetic acid (EGTA)). ATP Km apparent was previously determined using a Z'-LYTE assay.

Development Reagent Solution

The development reagent was diluted in development buffer (see section kinase-specific assay conditions—direct and cascade for a complete description).

10× Novel PKC Lipid Mix 2 mg/ml phosphatidyl serine, 0.2 mg/ml diacylglycerol (DAG) in 20 mM HEPES, pH 7.4, 0.3% 3-((3-cholamidopropyl) dimethylammonio)-1-propanesulfonate (CHAPS)

For 5 mL 10× Novel PKC Lipid Mix:

10 mg phosphatidyl serine (Avanti Polar Lipids Part #8400032C or 840039C) and 1 mg DAG (Avanti Polar Lipids Part #800811C) were added to a glass tube. Chloroform was removed from the lipid mixture through evaporation to give a clear, thin film. Continuous rotation of the tube, at an angle to ensure maximum surface area of the lipid solution, promoted the thinnest film. Then 5 mL of resuspension buffer, 20 mM HEPES, and 0.3% CHAPS pH 7.4, was added to the dried lipid mixture which was then heated gently to 50-60° C. for 1-2 minutes. Vortexing in short intervals until the lipids were dissolved gave a clear or slightly hazy solution. The lipids were typically in solution after 2-3 heat/vortex cycles. The solution was then cooled to room temperature and aliquoted into single use volumes and stored at −20° C.

Assay Protocol

Using a bar-coded Corning, low volume NBS, black 384-well plate (Corning Cat. #4514), 100 nL of 100× test compound in 100% DMSO was added. Followed by 2.4 µL of kinase buffer, 5 µL of 2× peptide/kinase mixture, and 2.5 µL-4×ATP solution. The plate was then shaken for 30 seconds and held at room temperature for a 60 minute kinase reaction incubation period. At which point 5 µL of development reagent solution was added and the plate was shaken for 30 seconds. The plate was held again at room temperature for a 60 minute development reaction incubation period and then read on a fluorescence plate reader and analyzed.

Z'-LYTE Assay Controls

The following controls were made for each individual kinase and were located on the same plate as the kinase:

0% Phosphorylation Control (100% Inhibition Control)

The maximum emission ratio was established by the 0% phosphorylation control (100% inhibition control), which contained no ATP and therefore exhibited no kinase activity. This control yielded 100% cleaved peptide in the development reaction.

100% Phosphorylation Control

The 100% phosphorylation control, which consisted of a synthetically phosphorylated peptide of the same sequence as the peptide substrate, was designed to allow for the calculation of percent phosphorylation. This control yielded a very low percentage of cleaved peptide in the development reaction.

The 0% phosphorylation and 100% phosphorylation controls allowed one to calculate the percent phosphorylation achieved in a specific reaction well. Control wells did not include any kinase inhibitors.

0% Inhibition Control

The minimum emission ratio in a screen was established by the 0% inhibition control, which contained active kinase. This control was designed to produce a 10-50%* phosphorylated peptide in the kinase reaction.

* Cascade assays may produce up to 70% phosphorylated peptide.

Known Inhibitor

A known inhibitor control standard curve, 10 point titration was run for each individual kinase on the same plate as the kinase to ensure the kinase was inhibited within an expected $IC_{50}$ range previously determined.

The following controls were prepared for each concentration of test compound assayed:

Development Reaction Interference

The development reaction interference was established by comparing the test compound control wells that did not contain ATP versus the 0% phosphorylation control (which did not contain the test compound). The expected value for a non-interfering compound should be 100%. Any value outside of 90% to 110% was flagged.

Test Compound Fluorescence Interference

The test compound fluorescence interference was determined by comparing the test compound control wells that did not contain the kinase/peptide mixture (zero peptide control) versus the 0% inhibition control. The expected value for a non-fluorescence compound should be 0%. Any value>20% is flagged.

Kinase-Specific Assay Conditions—Direct Format

The 2×PTK2 (FAK)/Tyr 07 mixture was prepared in 50 mM HEPES pH 7.5, 0.01% BRIJ-35, 10 mM $MgCl_2$, 1 mM EGTA. The final 10 µL kinase reaction consisted of 12.5-100 ng PTK2 (FAK) and 2 µM Tyr 07 in 50 mM HEPES pH 7.5, 0.01% BRIJ-35, 10 mM $MgCl_2$, 1 mM EGTA. After the 1 hour kinase reaction incubation period, 5 µL of a 1:16 dilution of development reagent B was added.

Graphing Software

SelectScreen Kinase Profiling Service uses XLfit from ID Business Solutions (IDBS). The dose response curve was curve fit to model number 205 (sigmoidal dose-response model). If the bottom of the curve did not fit between −20% & 20% inhibition, it was set to 0% inhibition. If the top of the curve did not fit between 70% and 130% inhibition, it was set to 100% inhibition. Initial evaluations of the secondary amides demonstrated that an ortho-methoxy substituent on the aniline tail improved the FAK $IC_{50}$ (Table 1; 1, 2, 4 vs 3). Other modifications to the aniline component (7, 10, 11, 194) were tolerated, with sulfonamide-substituted 11 being most potent. Removal of the thiazole 2-methyl (6) led to an 8-fold loss in potency relative to 3. N-Methylation of the diazepinone amide (5) improved potency 3-fold relative to 3. The N-alkylated series was selected for further development as the tertiary amides typically possess a better PK profile than secondary amides. A variety of modifications incorporating H-bond acceptors or donors, or seeking to reduce the molecular weight led to inhibitors with biochemical $IC_{50}$s in the 30-80 nM range (12-14, 16, 18-22, 28, 195, 196, 198-201), but did not improve upon the potency of lead compound 5. Notably, other aminoheterocyclic substituents such as dihydroquinolinone 23, pyridine 24, or pyrazole 26 showed significantly reduced potency. Likewise, modifications to the tricyclic core generally led to decreased potency. Increased alkyl substitution at the thiazole 2-position was tolerated with a small loss in potency, up to isopropyl (8, 193, 203), whereas a phenyl substituent abrogated activity (184, 186). An electron-deficient thiazole 177 showed nearly 10-fold lower potency relative to 5. Finally, although an ethyl group was tolerated at either nitrogen of the diazepinone (132, 159), other substituents (204, 205) were slightly less potent.

TABLE 1

Enzymatic IC$_{50}$ data

| Compound | FAK IC$_{50}$ (nM) |
|---|---|
| 1 | 228 |
| 2 | 580 |
| 3 | 62.2 |
| 4 | 90.4 |
| 5 | 18.3 |
| 6 | 510 |
| 7 | 48.7 |
| 8 | 32.1 |
| 9 | 45.1 |
| 10 | 129 |
| 11 | 17.6 |
| 12 | 43.5 |
| 13 | 53.6 |
| 14 | 30.3 |
| 16 | 54.5 |
| 17 | 465 |
| 18 | 31.5 |
| 19 | 51.9 |
| 20 | 73.9 |
| 21 | 45.4 |
| 22 | 37.8 |
| 23 | 670 |
| 24 | 196 |
| 26 | 666 |
| 28 | 77.7 |
| 132 | 18.8 |
| 159 | 22.9 |
| 177 | 134 |
| 184 | >10000 |
| 186 | >10000 |
| 193 | 31.7 |
| 194 | 55.7 |
| 195 | 62.9 |
| 196 | 82.4 |
| 197 | 173 |
| 198 | 46.9 |
| 199 | 45.7 |
| 200 | 67.2 |
| 201 | 83.5 |
| 202 | 155 |
| 203 | 58.8 |
| 204 | 68.3 |
| 205 | 46.6 |

Example 59: KINOMEscan® of Compound 3

Selectivity profiling of compound 3 among a panel of kinases was performed with KINOMEscan® as set forth below. The KINOMEscan® screening platform employs an active site-directed competition binding assay to quantitatively measure interactions between a test compound, e.g., compound 3, and more than 450 kinases and disease-relevant mutant variants.

Screening of compound 3 was conducted at a concentration of 10 µM by Eurofins DiscoverX. Activity is measured as the ability of compound 3 to displace the kinase from a solid support relative to a negative control (i.e., DMSO). The output is % control. Compounds that do not engage the kinase are reported as 100% signal relative to control, while compounds that completely engage the kinase and displace it from the support are reported as 0% signal relative to the control. Accordingly, low numbers signify more potent kinase binding of compound 3.

As shown in FIG. 1, for compound 3, five non-mutant kinases out of 403 non-mutant kinases displayed <35% relative to control. Specifically, compound 3 successfully engaged FAK, cyclin G-associated kinase (GAK), Abelson (ABL) kinase, tyrosine kinase non-receptor 2 (TNK2), and mitogen-activated protein kinase kinase 5 (MEK5). The raw data presented in Table 2 shows the specific engagement levels for each kinase examined in the KINOMEscan®. Specifically, as shown in Table 2, FAK, GAK, ABL, TNK2, and MEK5, displayed 0.55%, 4.2%, 17%, 20%, and 22%, relative to a control, respectively.

The selectivity score (S-Score) refers to the number of non-mutant kinases that display a % control below a specific number, divided by the number of non-mutant kinases that were examined. As shown in FIG. 1, compound 3 had an S-Score (35) of 0.02, which illustrates the selective nature of compound 3 for FAK amongst all the kinases examined.

TABLE 2

Compound 3 engagement levels in the KinomeScan ®.

| DiscoveRX Gene Symbol | Entrez Gene Symbol | Percent Control | Compound Concentration (nM) |
|---|---|---|---|
| AAK1 | AAK1 | 48 | 10000 |
| ABL1(E255K)-phosphorylated | ABL1 | 17 | 10000 |
| ABL1(F317I)-nonphosphorylated | ABL1 | 3.8 | 10000 |
| ABL1(F317I)-phosphorylated | ABL1 | 14 | 10000 |
| ABL1(F317L)-nonphosphorylated | ABL1 | 3.9 | 10000 |
| ABL1(F317L)-phosphorylated | ABL1 | 10 | 10000 |
| ABL1(H396P)-nonphosphorylated | ABL1 | 4.3 | 10000 |
| ABL1(H396P)-phosphorylated | ABL1 | 19 | 10000 |
| ABL1(M351T)-phosphorylated | ABL1 | 19 | 10000 |
| ABL1(Q252H)-nonphosphorylated | ABL1 | 7.8 | 10000 |
| ABL1(Q252H)-phosphorylated | ABL1 | 9.7 | 10000 |
| ABL1(T315I)-nonphosphorylated | ABL1 | 100 | 10000 |
| ABL1(T315I)-phosphorylated | ABL1 | 93 | 10000 |
| ABL1(Y253F)-phosphorylated | ABL1 | 47 | 10000 |
| ABL1-nonphosphorylated | ABL1 | 25 | 10000 |
| ABL1-phosphorylated | ABL1 | 17 | 10000 |
| ABL2 | ABL2 | 69 | 10000 |
| ACVR1 | ACVR1 | 93 | 10000 |
| ACVR1B | ACVR1B | 80 | 10000 |
| ACVR2A | ACVR2A | 76 | 10000 |
| ACVR2B | ACVR2B | 92 | 10000 |
| ACVRL1 | ACVRL1 | 96 | 10000 |
| ADCK3 | CABC1 | 54 | 10000 |

TABLE 2-continued

Compound 3 engagement levels in the KinomeScan®.

| DiscoveRX Gene Symbol | Entrez Gene Symbol | Percent Control | Compound Concentration (nM) |
|---|---|---|---|
| ADCK4 | ADCK4 | 83 | 10000 |
| AKT1 | AKT1 | 89 | 10000 |
| AKT2 | AKT2 | 75 | 10000 |
| AKT3 | AKT3 | 100 | 10000 |
| ALK | ALK | 100 | 10000 |
| ALK(C1156Y) | ALK | 100 | 10000 |
| ALK(L1196M) | ALK | 80 | 10000 |
| AMPK-alpha1 | PRKAA1 | 79 | 10000 |
| AMPK-alpha2 | PRKAA2 | 83 | 10000 |
| ANKK1 | ANKK1 | 80 | 10000 |
| ARK5 | NUAK1 | 86 | 10000 |
| ASK1 | MAP3K5 | 74 | 10000 |
| ASK2 | MAP3K6 | 100 | 10000 |
| AURKA | AURKA | 92 | 10000 |
| AURKB | AURKB | 100 | 10000 |
| AURKC | AURKC | 95 | 10000 |
| AXL | AXL | 100 | 10000 |
| BIKE | BMP2K | 73 | 10000 |
| BLK | BLK | 55 | 10000 |
| BMPR1A | BMPR1A | 81 | 10000 |
| BMPR1B | BMPR1B | 88 | 10000 |
| BMPR2 | BMPR2 | 100 | 10000 |
| BMX | BMX | 76 | 10000 |
| BRAF | BRAF | 86 | 10000 |
| BRAF(V600E) | BRAF | 100 | 10000 |
| BRK | PTK6 | 66 | 10000 |
| BRSK1 | BRSK1 | 69 | 10000 |
| BRSK2 | BRSK2 | 78 | 10000 |
| BTK | BTK | 100 | 10000 |
| BUB1 | BUB1 | 100 | 10000 |
| CAMK1 | CAMK1 | 100 | 10000 |
| CAMK1B | PNCK | 95 | 10000 |
| CAMK1D | CAMK1D | 98 | 10000 |
| CAMK1G | CAMK1G | 74 | 10000 |
| CAMK2A | CAMK2A | 76 | 10000 |
| CAMK2B | CAMK2B | 81 | 10000 |
| CAMK2D | CAMK2D | 82 | 10000 |
| CAMK2G | CAMK2G | 79 | 10000 |
| CAMK4 | CAMK4 | 98 | 10000 |
| CAMKK1 | CAMKK1 | 84 | 10000 |
| CAMKK2 | CAMKK2 | 80 | 10000 |
| CASK | CASK | 83 | 10000 |
| CDC2L1 | CDK11B | 74 | 10000 |
| CDC2L2 | CDC2L2 | 87 | 10000 |
| CDC2L5 | CDK13 | 100 | 10000 |
| CDK11 | CDK19 | 71 | 10000 |
| CDK2 | CDK2 | 81 | 10000 |
| CDK3 | CDK3 | 87 | 10000 |
| CDK4 | CDK4 | 100 | 10000 |
| CDK4-cyclinD1 | CDK4 | 100 | 10000 |
| CDK4-cyclinD3 | CDK4 | 95 | 10000 |
| CDK5 | CDK5 | 71 | 10000 |
| CDK7 | CDK7 | 94 | 10000 |
| CDK8 | CDK8 | 78 | 10000 |
| CDK9 | CDK9 | 74 | 10000 |
| CDKL1 | CDKL1 | 72 | 10000 |
| CDKL2 | CDKL2 | 75 | 10000 |
| CDKL3 | CDKL3 | 75 | 10000 |
| CDKL5 | CDKL5 | 97 | 10000 |
| CHEK1 | CHEK1 | 79 | 10000 |
| CHEK2 | CHEK2 | 72 | 10000 |
| CIT | CIT | 73 | 10000 |
| CLK1 | CLK1 | 90 | 10000 |
| CLK2 | CLK2 | 72 | 10000 |
| CLK3 | CLK3 | 97 | 10000 |
| CLK4 | CLK4 | 76 | 10000 |
| CSF1R | CSF1R | 36 | 10000 |
| CSF1R-autoinhibited | CSF1R | 90 | 10000 |
| CSK | CSK | 85 | 10000 |
| CSNK1A1 | CSNK1A1 | 62 | 10000 |
| CSNK1A1L | CSNK1A1L | 78 | 10000 |
| CSNK1D | CSNK1D | 54 | 10000 |
| CSNK1E | CSNK1E | 82 | 10000 |
| CSNK1G1 | CSNK1G1 | 86 | 10000 |
| CSNK1G2 | CSNK1G2 | 81 | 10000 |
| CSNK1G3 | CSNK1G3 | 87 | 10000 |

TABLE 2-continued

Compound 3 engagement levels in the KinomeScan ®.

| DiscoveRX Gene Symbol | Entrez Gene Symbol | Percent Control | Compound Concentration (nM) |
|---|---|---|---|
| CSNK2A1 | CSNK2A1 | 93 | 10000 |
| CSNK2A2 | CSNK2A2 | 87 | 10000 |
| CTK | MATK | 98 | 10000 |
| DAPK1 | DAPK1 | 72 | 10000 |
| DAPK2 | DAPK2 | 60 | 10000 |
| DAPK3 | DAPK3 | 62 | 10000 |
| DCAMKL1 | DCLK1 | 91 | 10000 |
| DCAMKL2 | DCLK2 | 87 | 10000 |
| DCAMKL3 | DCLK3 | 81 | 10000 |
| DDR1 | DDR1 | 89 | 10000 |
| DDR2 | DDR2 | 100 | 10000 |
| DLK | MAP3K12 | 90 | 10000 |
| DMPK | DMPK | 99 | 10000 |
| DMPK2 | CDC42BPG | 91 | 10000 |
| DRAK1 | STK17A | 95 | 10000 |
| DRAK2 | STK17B | 100 | 10000 |
| DYRK1A | DYRK1A | 100 | 10000 |
| DYRK1B | DYRK1B | 69 | 10000 |
| DYRK2 | DYRK2 | 100 | 10000 |
| EGFR | EGFR | 90 | 10000 |
| EGFR(E746-A750del) | EGFR | 67 | 10000 |
| EGFR(G719C) | EGFR | 34 | 10000 |
| EGFR(G719S) | EGFR | 48 | 10000 |
| EGFR(L747-E749del, A750P) | EGFR | 95 | 10000 |
| EGFR(L747-S752del, P753S) | EGFR | 99 | 10000 |
| EGFR(L747-T751del, Sins) | EGFR | 52 | 10000 |
| EGFR(L858R) | EGFR | 79 | 10000 |
| EGFR(L858R, T790M) | EGFR | 100 | 10000 |
| EGFR(L861Q) | EGFR | 38 | 10000 |
| EGFR(S752-I759del) | EGFR | 47 | 10000 |
| EGFR(T790M) | EGFR | 100 | 10000 |
| EIF2AK1 | EIF2AK1 | 73 | 10000 |
| EPHA1 | EPHA1 | 54 | 10000 |
| EPHA2 | EPHA2 | 91 | 10000 |
| EPHA3 | EPHA3 | 99 | 10000 |
| EPHA4 | EPHA4 | 87 | 10000 |
| EPHA5 | EPHA5 | 65 | 10000 |
| EPHA6 | EPHA6 | 83 | 10000 |
| EPHA7 | EPHA7 | 71 | 10000 |
| EPHA8 | EPHA8 | 64 | 10000 |
| EPHB1 | EPHB1 | 48 | 10000 |
| EPHB2 | EPHB2 | 53 | 10000 |
| EPHB3 | EPHB3 | 70 | 10000 |
| EPHB4 | EPHB4 | 61 | 10000 |
| EPHB6 | EPHB6 | 45 | 10000 |
| ERBB2 | ERBB2 | 98 | 10000 |
| ERBB3 | ERBB3 | 100 | 10000 |
| ERBB4 | ERBB4 | 57 | 10000 |
| ERK1 | MAPK3 | 88 | 10000 |
| ERK2 | MAPK1 | 60 | 10000 |
| ERK3 | MAPK6 | 89 | 10000 |
| ERK4 | MAPK4 | 84 | 10000 |
| ERK5 | MAPK7 | 80 | 10000 |
| ERK8 | MAPK15 | 86 | 10000 |
| ERN1 | ERN1 | 93 | 10000 |
| FAK | PTK2 | 0.55 | 10000 |
| FER | FER | 74 | 10000 |
| FES | FES | 81 | 10000 |
| FGFR1 | FGFR1 | 75 | 10000 |
| FGFR2 | FGFR2 | 80 | 10000 |
| FGFR3 | FGFR3 | 92 | 10000 |
| FGFR3(G697C) | FGFR3 | 78 | 10000 |
| FGFR4 | FGFR4 | 90 | 10000 |
| FGR | FGR | 77 | 10000 |
| FLT1 | FLT1 | 87 | 10000 |
| FLT3 | FLT3 | 100 | 10000 |
| FLT3(D835H) | FLT3 | 67 | 10000 |
| FLT3(D835V) | FLT3 | 57 | 10000 |
| FLT3(D835Y) | FLT3 | 76 | 10000 |
| FLT3(ITD) | FLT3 | 83 | 10000 |
| FLT3(ITD, D835V) | FLT3 | 100 | 10000 |
| FLT3(ITD, F691L) | FLT3 | 100 | 10000 |
| FLT3(K663Q) | FLT3 | 96 | 10000 |
| FLT3(N841I) | FLT3 | 98 | 10000 |
| FLT3(R834Q) | FLT3 | 100 | 10000 |
| FLT3-autoinhibited | FLT3 | 100 | 10000 |

TABLE 2-continued

Compound 3 engagement levels in the KinomeScan ®.

| DiscoveRX Gene Symbol | Entrez Gene Symbol | Percent Control | Compound Concentration (nM) |
|---|---|---|---|
| FLT4 | FLT4 | 92 | 10000 |
| FRK | FRK | 37 | 10000 |
| FYN | FYN | 73 | 10000 |
| GAK | GAK | 4.2 | 10000 |
| GCN2(Kin.Dom.2, S808G) | EIF2AK4 | 88 | 10000 |
| GRK1 | GRK1 | 86 | 10000 |
| GRK2 | ADRBK1 | 100 | 10000 |
| GRK3 | ADRBK2 | 100 | 10000 |
| GRK4 | GRK4 | 72 | 10000 |
| GRK7 | GRK7 | 97 | 10000 |
| GSK3A | GSK3A | 82 | 10000 |
| GSK3B | GSK3B | 95 | 10000 |
| HASPIN | GSG2 | 96 | 10000 |
| HCK | HCK | 69 | 10000 |
| HIPK1 | HIPK1 | 83 | 10000 |
| HIPK2 | HIPK2 | 100 | 10000 |
| HIPK3 | HIPK3 | 100 | 10000 |
| HIPK4 | HIPK4 | 82 | 10000 |
| HPK1 | MAP4K1 | 68 | 10000 |
| HUNK | HUNK | 95 | 10000 |
| ICK | ICK | 100 | 10000 |
| IGF1R | IGF1R | 86 | 10000 |
| IKK-alpha | CHUK | 100 | 10000 |
| IKK-beta | IKBKB | 100 | 10000 |
| IKK-epsilon | IKBKE | 78 | 10000 |
| INSR | INSR | 83 | 10000 |
| INSRR | INSRR | 84 | 10000 |
| IRAK1 | IRAK1 | 100 | 10000 |
| IRAK3 | IRAK3 | 80 | 10000 |
| IRAK4 | IRAK4 | 100 | 10000 |
| ITK | ITK | 87 | 10000 |
| JAK1(JH1domain-catalytic) | JAK1 | 85 | 10000 |
| JAK1(JH2domain-pseudokinase) | JAK1 | 85 | 10000 |
| JAK2(JH1domain-catalytic) | JAK2 | 100 | 10000 |
| JAK3(JH1domain-catalytic) | JAK3 | 83 | 10000 |
| JNK1 | MAPK8 | 100 | 10000 |
| JNK2 | MAPK9 | 100 | 10000 |
| JNK3 | MAPK10 | 100 | 10000 |
| KIT | KIT | 54 | 10000 |
| KIT(A829P) | KIT | 47 | 10000 |
| KIT(D816H) | KIT | 22 | 10000 |
| KIT(D816V) | KIT | 11 | 10000 |
| KIT(L576P) | KIT | 47 | 10000 |
| KIT(V559D) | KIT | 56 | 10000 |
| KIT(V559D, T670I) | KIT | 86 | 10000 |
| KIT(V5S9D, V654A) | SGT | 108 | 10000 |
| KIT-autoinhibited | KIT | 100 | 10000 |
| LATS1 | LATS1 | 77 | 10000 |
| LATS2 | LATS2 | 100 | 10000 |
| LCK | LCK | 45 | 10000 |
| LIMK1 | LIMK1 | 96 | 10000 |
| LIMK2 | LIMK2 | 91 | 10000 |
| LKB1 | STK11 | 44 | 10000 |
| LOK | STK10 | 84 | 10000 |
| LRRK2 | LRRK2 | 98 | 10000 |
| LRRK2(G2019S) | LRRK2 | 100 | 10000 |
| LTK | LTK | 81 | 10000 |
| LYN | LYN | 69 | 10000 |
| LZK | MAP3K13 | 100 | 10000 |
| MAK | MAK | 71 | 10000 |
| MAP3K1 | MAP3K1 | 100 | 10000 |
| MAP3K15 | MAP3K15 | 90 | 10000 |
| MAP3K2 | MAP3K2 | 100 | 10000 |
| MAP3K3 | MAP3K3 | 100 | 10000 |
| MAP3K4 | MAP3K4 | 73 | 10000 |
| MAP4K2 | MAP4K2 | 100 | 10000 |
| MAP4K3 | MAP4K3 | 100 | 10000 |
| MAP4K4 | MAP4K4 | 79 | 10000 |
| MAP4K5 | MAP4K5 | 82 | 10000 |
| MAPKAPK2 | MAPKAPK2 | 100 | 10000 |
| MAPKAPX5 | MAPKAPK5 | 100 | 10000 |
| MARK1 | MARK1 | 87 | 10000 |
| MARK2 | MARK2 | 100 | 10000 |
| MARK3 | MARK3 | 96 | 10000 |
| MARK4 | MARK4 | 83 | 10000 |
| MAST1 | MAST1 | 84 | 10000 |

TABLE 2-continued

Compound 3 engagement levels in the KinomeScan®.

| DiscoveRX Gene Symbol | Entrez Gene Symbol | Percent Control | Compound Concentration (nM) |
|---|---|---|---|
| MEK1 | MAP2K1 | 100 | 10000 |
| MEK2 | MAP2K2 | 100 | 10000 |
| MEK3 | MAP2K3 | 92 | 10000 |
| MEK4 | MAP2K4 | 100 | 10000 |
| MEK5 | MAP2K5 | 22 | 10000 |
| MEK6 | MAP2K6 | 100 | 10000 |
| MELK | MELK | 99 | 10000 |
| MERTK | MERTK | 93 | 10000 |
| MET | MET | 92 | 10000 |
| MET(M1250T) | MET | 82 | 10000 |
| MET(Y1235D) | MET | 90 | 10000 |
| MINK | MINK1 | 100 | 10000 |
| MKK7 | MAP2K7 | 100 | 10000 |
| MKNK1 | MKNK1 | 100 | 10000 |
| MKNK2 | MKNK2 | 80 | 10000 |
| MLCK | MYLK3 | 94 | 10000 |
| MLK1 | MAP3K9 | 94 | 10000 |
| MLK2 | MAP3K10 | 96 | 10000 |
| MLK3 | MAP3K11 | 73 | 10000 |
| MRCKA | CDC42BPA | 98 | 10000 |
| MRCKB | CDC42BPB | 100 | 10000 |
| MST1 | STK4 | 89 | 10000 |
| MST1R | MST1R | 90 | 10000 |
| MST2 | STK3 | 100 | 10000 |
| MST3 | STK24 | 89 | 10000 |
| MST4 | MST4 | 100 | 10000 |
| MTOR | MTOR | 85 | 10000 |
| MUSK | MUSK | 92 | 10000 |
| MYLK | MYLK | 53 | 10000 |
| MYLK2 | MYLK2 | 84 | 10000 |
| MYLK4 | MYLK4 | 77 | 10000 |
| MYO3A | MYO3A | 79 | 10000 |
| MYO3B | MYO3B | 74 | 10000 |
| NDR1 | STK38 | 97 | 10000 |
| NDR2 | STK38L | 86 | 10000 |
| NEK1 | NEK1 | 78 | 10000 |
| NEK10 | NEK10 | 100 | 10000 |
| NEK11 | NEK11 | 100 | 10000 |
| NEK2 | NEK2 | 84 | 10000 |
| NEK3 | NEK3 | 88 | 10000 |
| NEK4 | NEK4 | 100 | 10000 |
| NEK5 | NEK5 | 97 | 10000 |
| NEK6 | NEK6 | 78 | 10000 |
| NEK7 | NEK7 | 63 | 10000 |
| NEK9 | NEK9 | 84 | 10000 |
| NIK | MAP3K14 | 85 | 10000 |
| NIM1 | MGC42105 | 100 | 10000 |
| NLK | NLK | 59 | 10000 |
| OSR1 | OXSR1 | 100 | 10000 |
| p38-alpha | MAPK14 | 75 | 10000 |
| p38-beta | MAPK11 | 55 | 10000 |
| p38-delta | MAPK13 | 82 | 10000 |
| p38-gamma | MAPK12 | 67 | 10000 |
| PAK1 | PAK1 | 64 | 10000 |
| PAK2 | PAK2 | 72 | 10000 |
| PAK3 | PAK3 | 78 | 10000 |
| PAK4 | PAK4 | 65 | 10000 |
| PAK6 | PAK6 | 97 | 10000 |
| PAK7 | PAK7 | 97 | 10000 |
| PCTK1 | CDK16 | 100 | 10000 |
| PCTK2 | CDK17 | 76 | 10000 |
| PCTK3 | CDK18 | 90 | 10000 |
| PDGFRA | PDGFRA | 100 | 10000 |
| RDGFRB | PDGFRB | 50 | 10000 |
| PDPK1 | PDPK1 | 76 | 10000 |
| PFCDPK1(P. falciparum) | CDPK1 | 100 | 10000 |
| PFPK5(P. falciparum) | MAL13P1.279 | 100 | 10000 |
| PFTAIRE2 | CDK15 | 86 | 10000 |
| PFTK1 | CDK14 | 90 | 10000 |
| PHKG1 | PHKG1 | 78 | 10000 |
| PHKG2 | PHKG2 | 69 | 10000 |
| PIK3C2B | PIK3C2B | 86 | 10000 |
| PIK3C2G | PIK3C2G | 69 | 10000 |
| PIK3CA | PIK3CA | 100 | 10000 |
| PIK3CA(C420R) | PIK3CA | 90 | 10000 |
| PIK3CA(E542K) | PIK3CA | 100 | 10000 |

TABLE 2-continued

Compound 3 engagement levels in the KinomeScan®.

| DiscoveRX Gene Symbol | Entrez Gene Symbol | Percent Control | Compound Concentration (nM) |
|---|---|---|---|
| PIK3CA(E545A) | PIK3CA | 84 | 10000 |
| PIK3CA(E545K) | PIK3CA | 90 | 10000 |
| PIK3CA(H1047L) | PIK3CA | 66 | 10000 |
| PIK3CA(H1047Y) | PIK3CA | 91 | 10000 |
| PIK3CA(I800L) | PIK3CA | 100 | 10000 |
| PIK3CA(M1043I) | PIK3CA | 87 | 10000 |
| PIK3CA(Q546K) | PIK3CA | 100 | 10000 |
| PIK3CB | PIK3CB | 97 | 10000 |
| PIK3CD | PIK3CD | 98 | 10000 |
| PIK3CG | PIK3CG | 93 | 10000 |
| PIK4CB | PI4KB | 85 | 10000 |
| PIKFYVE | PIKFYVE | 98 | 10000 |
| PIM1 | PIM1 | 70 | 10000 |
| PIM2 | PIM2 | 92 | 10000 |
| PIM3 | PIM3 | 70 | 10000 |
| PIP5K1A | PIP5K1A | 100 | 10000 |
| PIP5K1C | PIP5K1C | 99 | 10000 |
| PIP5K2B | PIP4K2B | 76 | 10000 |
| PIP5K2C | PIP4K2C | 86 | 10000 |
| PKAC-alpha | PRKACA | 72 | 10000 |
| PKAC-beta | PPKACB | 82 | 10000 |
| PKMYT1 | PKMYT1 | 90 | 10000 |
| PKN1 | PKN1 | 69 | 10000 |
| PKN2 | PKN2 | 100 | 10000 |
| PKNB(*M. tuberculosis*) | pknB | 91 | 10000 |
| PLK1 | PLK1 | 100 | 10000 |
| PLK2 | PLK2 | 100 | 10000 |
| PLK3 | PLK3 | 52 | 10000 |
| PLK4 | PLK4 | 81 | 10000 |
| PRKCD | PRKCD | 86 | 10000 |
| PRKCE | PRKCE | 100 | 10000 |
| PRKCH | PRKCH | 89 | 10000 |
| PRKCI | PRKCI | 73 | 10000 |
| PRKCQ | PRKCQ | 89 | 10000 |
| PRKD1 | PRKD1 | 78 | 10000 |
| PRKD2 | PRKD2 | 72 | 10000 |
| PRKD3 | PRKD3 | 75 | 10000 |
| PRKG1 | PRKG1 | 93 | 10000 |
| PRKG2 | PRKG2 | 73 | 10000 |
| PRKR | EIF2AK2 | 100 | 10000 |
| PRKX | PRKX | 96 | 10000 |
| PRP4 | PRPF4B | 100 | 10000 |
| PYK2 | PTK2B | 41 | 10000 |
| QSK | KIAA0999 | 100 | 10000 |
| RAF1 | RAF1 | 85 | 10000 |
| RET | RET | 99 | 10000 |
| RET(M918T) | RET | 87 | 10000 |
| RET(V804L) | RET | 95 | 10000 |
| RET(V804M) | RET | 100 | 10000 |
| RIOK1 | RIOK1 | 62 | 10000 |
| RIOK2 | RIOK2 | 82 | 10000 |
| RIOK3 | RIOK3 | 79 | 10000 |
| RIPK1 | RIPK1 | 100 | 10000 |
| RIPK2 | RIPK2 | 88 | 10000 |
| PIPK4 | RIPK4 | 100 | 10000 |
| RIPK5 | DSTYK | 100 | 10000 |
| ROCK1 | ROCK1 | 100 | 10000 |
| ROCK2 | ROCK2 | 100 | 10000 |
| ROS1 | ROS1 | 74 | 10000 |
| RPS6KA4(Kin.Dom.1-N-terminal) | RPS6KA4 | 100 | 10000 |
| RPS6KA4(Kin.Dom.2-C-terminal) | RPS6KA4 | 100 | 10000 |
| RPS6KA5(Kin.Dom.1-N-terminal) | RPS6KA5 | 70 | 10000 |
| RPS6KA5(Kin.Dom.2-C-terminal) | RPS6KA5 | 72 | 10000 |
| RSK1(Kin.Dom.1-N-terminal) | RPS6KA1 | 78 | 10000 |
| RSK1(Kin.Dom.2-C-terminal) | RPS6KA1 | 81 | 10000 |
| RSK2(Kin.Dom.1-N-terminal) | RPS6KA3 | 99 | 10000 |
| RSK2(Kin.Dom.2-C-terminal) | RPS6KA3 | 100 | 10000 |
| RSK3(Kin.Dom.1-N-terminal) | RPS6KA2 | 83 | 10000 |
| RSK3(Kin.Dom.2-C-terminal) | RPS6KA2 | 84 | 10000 |
| RSK4(Kin.Dom.1-N-terminal) | RPS6KA6 | 100 | 10000 |
| RSK4(Kin.Dom.2-C-terminal) | RPS6KA6 | 69 | 10000 |
| S6K1 | RPS6KB1 | 100 | 10000 |
| SBK1 | SBK1 | 100 | 10000 |
| SGK | SGK1 | 100 | 10000 |
| SgK110 | SgK110 | 86 | 10000 |
| SGK2 | SGK2 | 99 | 10000 |

TABLE 2-continued

Compound 3 engagement levels in the KinomeScan®.

| DiscoveRX Gene Symbol | Entrez Gene Symbol | Percent Control | Compound Concentration (nM) |
|---|---|---|---|
| SGK3 | SGK3 | 100 | 10000 |
| SIK | SIK1 | 69 | 10000 |
| SIK2 | SIK2 | 86 | 10000 |
| SLK | SLK | 70 | 10000 |
| SNARK | NUAK2 | 100 | 10000 |
| SNRK | SNRK | 94 | 10000 |
| SRC | SRC | 63 | 10000 |
| SRMS | SRMS | 78 | 10000 |
| SRPK1 | SRPK1 | 100 | 10000 |
| SRPK2 | SRPK2 | 87 | 10000 |
| SRPK3 | SRPK3 | 75 | 10000 |
| STK16 | STK16 | 81 | 10000 |
| STK33 | STK33 | 84 | 10000 |
| STK35 | STK35 | 89 | 10000 |
| STK36 | STK36 | 61 | 10000 |
| STK39 | STK39 | 100 | 10000 |
| SYK | SYK | 77 | 10000 |
| TAK1 | MAP3K7 | 95 | 10000 |
| TAOK1 | TAOK1 | 100 | 10000 |
| TAOK2 | TAOK2 | 95 | 10000 |
| TAOK3 | TAOK3 | 100 | 10000 |
| TBK1 | TBK1 | 71 | 10000 |
| TEC | TEC | 69 | 10000 |
| TESK1 | TESK1 | 81 | 10000 |
| TGFBR1 | TGFBR1 | 88 | 10000 |
| TGFBR2 | TGFBR2 | 96 | 10000 |
| TIE1 | TIE1 | 80 | 10000 |
| TIE2 | TIK | 83 | 10000 |
| TLK1 | TLK1 | 90 | 10000 |
| TLK2 | TLK2 | 100 | 10000 |
| TNIK | TNIK | 94 | 10000 |
| TNK1 | TNK1 | 53 | 10000 |
| TNK2 | TNK2 | 20 | 10000 |
| TNNI3K | TNNI3K | 79 | 10000 |
| TRKA | NTRK1 | 100 | 10000 |
| TRKB | NTRK2 | 100 | 10000 |
| TRKC | NTRK3 | 100 | 10000 |
| TRPM6 | TRPM6 | 100 | 10000 |
| TSSK1B | TSSK1B | 74 | 10000 |
| TSSK3 | TSSK3 | 98 | 10000 |
| TTK | TTK | 51 | 10000 |
| TXK | TXK | 73 | 10000 |
| TYK2(JH1domain-catalytic) | TYK2 | 84 | 10000 |
| TYK2(JH2domain-pseudokinase) | TYK2 | 100 | 10000 |
| TYRO3 | TYRO3 | 92 | 10000 |
| ULK1 | ULK1 | 100 | 10000 |
| ULK2 | ULK2 | 100 | 10000 |
| ULK3 | ULK3 | 95 | 10000 |
| VEGFR2 | KDR | 100 | 10000 |
| VPS34 | PIK3C3 | 100 | 10000 |
| VRK2 | VRK2 | 91 | 10000 |
| WEE1 | WEE1 | 88 | 10000 |
| WEE2 | WEE2 | 65 | 10000 |
| WNK1 | WNK1 | 100 | 10000 |
| WNK2 | WNK2 | 74 | 10000 |
| WNK3 | WNK3 | 100 | 10000 |
| WNK4 | WNK4 | 100 | 10000 |
| YANK1 | STK32A | 77 | 10000 |
| YANK2 | STK32B | 85 | 10000 |
| YANK3 | STK32C | 68 | 10000 |
| YES | YES1 | 72 | 10000 |
| YSK1 | STK25 | 79 | 10000 |
| YSK4 | MAPSK19 | 100 | 10000 |
| ZAK | ZAK | 92 | 10000 |
| ZAP70 | ZAP70 | 100 | 10000 |

Example 60: KINOMEscan® of Compound 5

Selectivity profiling of compound 5 among a panel of kinases was performed with KINOMEscan® as set forth below. The KINOMEscan® screening platform employs an active site-directed competition binding assay to quantitatively measure interactions between a test compound, e.g., compound 5, and more than 450 kinases and disease-relevant mutant variants.

Screening of compound 5 was conducted at a concentration of 10 µM by Eurofins DiscoverX. Activity is measured as the ability of compound 5 to displace the kinase from a solid support relative to a negative control (i.e., DMSO). The output is % control. Compounds that do not engage the kinase are reported as 100% signal relative to control, while compounds that completely engage the kinase and displace it from the support are reported as 0% signal relative to the control. Accordingly, low numbers signify more potent kinase binding of compound 5.

As shown in FIG. 2, for compound 5, 16 non-mutant kinases out of 403 non-mutant kinases displayed <35% relative to control. Specifically, compound 5 successfully engaged FAK, cyclin G-associated kinase (GAK), DCAMKL1 (DCLK1), DCAMKL2 (DCLK2), ERK5, INSRR, LRRK2, MTOR, PLK1, PLK3, PLK4, PRKD3, RPS6KA4 (kinase domain 2—C-terminal), RSK3 (kinase domain 2—C-terminal), STK33, TNK1, and TTK. The raw data presented in Table 3 shows the specific engagement levels for each kinase examined in the KINOMEscan®. Specifically, as shown in Table 3, FAK, DCAMKL1 (DCLK1), DCAMKL2 (DCLK2), ERK5, GAK, INSRR, LRRK2, MTOR, PLK1, PLK3, PLK4, PRKD3, RPS6KA4 (kinase domain 2—C-terminal), RSK3 (kinase domain 2—C-terminal), STK33, TNK1, and TTK displayed 0.1%, 7.9%, 3%, 30%, 31%, 22%, 32%, 31%, 0.7%, 20%, 19%, 34%, 30%, 31%, 10%, 10%, and 6.9% relative to a control, respectively. Table 4 lists the biochemical $IC_{50}$ values (Invitrogen™) which were obtained for off-targets that displayed <10% relative to control.

The selectivity score (S-Score) refers to the number of non-mutant kinases that display a % control below a specific number, divided by the number of non-mutant kinases that were examined. As shown in FIG. 2, compound 5 had an S-Score (35) of 0.042, an S(10) of 0.012 and an S(1) of 0.005, which illustrates the selective nature of compound 5 for FAK amongst all the kinases examined.

TABLE 3

Compound 5 engagement levels in the KinomeScan ®.

| DiscoveRx Gene Symbol | Entrez Gene Symbol | Percent Control | Compound Concentration (nM) |
| --- | --- | --- | --- |
| ABL1(E255K)-phosphorylated | ABL1 | 100 | 10000 |
| ABL1(F317I)-nonphosphorylated | ABL1 | 48 | 10000 |
| ABL1(F317I)-phosphorylated | ABL1 | 26 | 10000 |
| ABL1(F317L)-nonphosphorylated | ABL1 | 54 | 10000 |
| ABL1(F317L)-phosphorylated | ABL1 | 39 | 10000 |
| ABL1(H396P)-nonphosphorylated | ABL1 | 100 | 10000 |
| ABL1(H396P)-phosphorylated | ABL1 | 100 | 10000 |
| ABL1(M351T)-phosphorylated | ABL1 | 95 | 10000 |
| ABL1(Q252H)-nonphosphorylated | ABL1 | 93 | 10000 |
| ABL1(Q252H)-phosphorylated | ABL1 | 100 | 10000 |
| ABL1(T315I)-nonphosphorylated | ABL1 | 100 | 10000 |
| ABL1(T315I)-phosphorylated | ABL1 | 98 | 10000 |
| ABL1(Y253F)-phosphorylated | ABL1 | 100 | 10000 |
| ABL1-nonphosphorylated | ABL1 | 77 | 10000 |
| ABL1-phosphorylated | ABL1 | 79 | 10000 |
| ABL2 | ABL2 | 95 | 10000 |
| ACVR1 | ACVR1 | 93 | 10000 |
| ACVR1B | ACVR1B | 95 | 10000 |
| ACVR2A | ACVR2A | 97 | 10000 |
| ACVR2B | ACVR2B | 100 | 10000 |
| ACVRL1 | ACVRL1 | 99 | 10000 |
| ADCK3 | CABC1 | 88 | 10000 |
| ADCK4 | ADCK4 | 73 | 10000 |
| AKT1 | AKT1 | 100 | 10000 |
| AKT2 | AKT2 | 100 | 10000 |
| AKT3 | AKT3 | 100 | 10000 |
| ALK | ALK | 99 | 10000 |
| ALK(C1156Y) | ALK | 89 | 10000 |
| ALK(L1196M) | ALK | 79 | 10000 |
| AMPK-alpha1 | PRKAA1 | 91 | 10000 |
| AMPK-alpha2 | PRKAA2 | 100 | 10000 |
| ANKK1 | ANKK1 | 92 | 10000 |
| ARK5 | NUAK1 | 94 | 10000 |
| ASK1 | MAP3K5 | 88 | 10000 |
| ASK2 | MAP3K6 | 100 | 10000 |
| AURKA | AURKA | 78 | 10000 |
| AURKB | AURKB | 99 | 10000 |
| AURKC | AURKC | 100 | 10000 |
| AXL | AXL | 97 | 10000 |
| BIKE | BMP2K | 100 | 10000 |
| BLK | BLK | 95 | 10000 |
| BMPR1A | BMPR1A | 97 | 10000 |
| BMPR1B | BMPR1B | 94 | 10000 |
| BMPR2 | BMPR2 | 100 | 10000 |
| BMX | BMX | 90 | 10000 |
| BRAF | BRAF | 95 | 10000 |

TABLE 3-continued

Compound 5 engagement levels in the KinomeScan®.

| DiscoveRx Gene Symbol | Entrez Gene Symbol | Percent Control | Compound Concentration (nM) |
|---|---|---|---|
| BRAF(V600E) | BRAF | 97 | 10000 |
| BRK | PTK6 | 100 | 10000 |
| BRSK1 | BRSK1 | 100 | 10000 |
| BRSK2 | BRSK2 | 91 | 10000 |
| BTK | BTK | 100 | 10000 |
| BUB1 | BUB1 | 100 | 10000 |
| CAMK1 | CAMK1 | 92 | 10000 |
| CAMK1B | PNCK | 92 | 10000 |
| CAMK1D | CAMK1D | 86 | 10000 |
| CAMK1G | CAMK1G | 95 | 10000 |
| CAMK2A | CAMK2A | 100 | 10000 |
| CAMK2B | CAMK2B | 93 | 10000 |
| CAMK2D | CAMK2D | 92 | 10000 |
| CAMK2G | CAMK2G | 97 | 10000 |
| CAMK4 | CAMK4 | 100 | 10000 |
| CAMKK1 | CAMKK1 | 100 | 10000 |
| CAMKK2 | CAMKK2 | 88 | 10000 |
| CASK | CASK | 100 | 10000 |
| CDC2L1 | CDK11B | 100 | 10000 |
| CDC2L2 | CDC2L2 | 95 | 10000 |
| CDC2L5 | CDK13 | 100 | 10000 |
| CDK11 | CDK19 | 90 | 10000 |
| CDK2 | CDK2 | 100 | 10000 |
| CDK3 | CDK3 | 100 | 10000 |
| CDK4 | CDK4 | 100 | 10000 |
| CDK4-cyclinD1 | CDK4 | 90 | 10000 |
| CDK4-cyclinD3 | CDK4 | 100 | 10000 |
| CDK5 | CDK5 | 98 | 10000 |
| CDK7 | CDK7 | 100 | 10000 |
| CDK8 | CDK8 | 100 | 10000 |
| CDK9 | CDK9 | 98 | 10000 |
| CDKL1 | CDKL1 | 80 | 10000 |
| CDKL2 | CDKL2 | 95 | 10000 |
| CDKL3 | CDKL3 | 100 | 10000 |
| CDKL5 | CDKL5 | 100 | 10000 |
| CHEK1 | CHEK1 | 59 | 10000 |
| CHEK2 | CHEK2 | 100 | 10000 |
| CIT | CIT | 98 | 10000 |
| CLK1 | CLK1 | 100 | 10000 |
| CLK2 | CLK2 | 100 | 10000 |
| CLK3 | CLK3 | 97 | 10000 |
| CLK4 | CLK4 | 85 | 10000 |
| CSF1R | CSF1R | 80 | 10000 |
| CSF1R-autoinhibited | CSF1R | 100 | 10000 |
| CSK | CSK | 100 | 10000 |
| CSNK1A1 | CSNK1A1 | 97 | 10000 |
| CSNK1A1L | CSNK1A1L | 100 | 10000 |
| CSNK1D | CSNK1D | 87 | 10000 |
| CSNK1E | CSNK1E | 100 | 10000 |
| CSNK1G1 | CSNK1G1 | 97 | 10000 |
| CSNK1G2 | CSNK1G2 | 80 | 10000 |
| CSNK1G3 | CSNK1G3 | 100 | 10000 |
| CSNK2A1 | CSNK2A1 | 95 | 10000 |
| CSNK2A2 | CSNK2A2 | 93 | 10000 |
| CTK | MATK | 96 | 10000 |
| DAPK1 | DAPK1 | 84 | 10000 |
| DAPK2 | DAPK2 | 83 | 10000 |
| DAPK3 | DAPK3 | 97 | 10000 |
| DCAMKL1 | DCLK1 | 7.9 | 10000 |
| DCAMKL2 | DCLK2 | 3 | 10000 |
| DCAMKL3 | DCLK3 | 86 | 10000 |
| DDR1 | DDR1 | 100 | 10000 |
| DDR2 | DDR2 | 100 | 10000 |
| DLK | MAP3K12 | 86 | 10000 |
| DMPK | DMPK | 100 | 10000 |
| DMPK2 | CDC42BPG | 93 | 10000 |
| DRAK1 | STK17A | 100 | 10000 |
| DRAK2 | STK17B | 100 | 10000 |
| DYRK1A | DYRK1A | 87 | 10000 |
| DYRK1B | DYRK1B | 87 | 10000 |
| DYRK2 | DYRK2 | 100 | 10000 |
| EGFR | EGFR | 100 | 10000 |
| EGFR(E746-A750del) | EGFR | 79 | 10000 |
| EGFR(G719C) | EGFR | 100 | 10000 |
| EGFR(G719S) | EGFR | 100 | 10000 |
| EGFR(L747-E749del, A750P) | EGFR | 97 | 10000 |

TABLE 3-continued

Compound 5 engagement levels in the KinomeScan ®.

| DiscoveRx Gene Symbol | Entrez Gene Symbol | Percent Control | Compound Concentration (nM) |
|---|---|---|---|
| EGFR(L747-S752del, P753S) | EGFR | 91 | 10000 |
| EGFR(L747-T751del, Sins) | EGFR | 100 | 10000 |
| EGFR(L858R) | EGFR | 100 | 10000 |
| EGFR(L858R, T790M) | EGFR | 80 | 10000 |
| EGFR(L861Q) | EGFR | 100 | 10000 |
| EGFR(S752-I759del) | EGFR | 100 | 10000 |
| EGFR(T790M) | EGFR | 93 | 10000 |
| EIF2AK1 | EIF2AK1 | 100 | 10000 |
| EPHA1 | EPHA1 | 100 | 10000 |
| EPHA2 | EPHA2 | 91 | 10000 |
| EPHA3 | EPHA3 | 100 | 10000 |
| EPHA4 | EPHA4 | 68 | 10000 |
| EPHA5 | EPHA5 | 95 | 10000 |
| EPHA6 | EPHA6 | 86 | 10000 |
| EPHA7 | EPHA7 | 97 | 10000 |
| EPHA8 | EPHA8 | 100 | 10000 |
| EPHB1 | EPHB1 | 93 | 10000 |
| EPHB2 | EPHB2 | 99 | 10000 |
| EPHB3 | EPHB3 | 100 | 10000 |
| EPHB4 | EPHB4 | 100 | 10000 |
| EPHB6 | EPHB6 | 100 | 10000 |
| ERBB2 | ERBB2 | 100 | 10000 |
| ERBB3 | ERBB3 | 100 | 10000 |
| ERBB4 | ERBB4 | 100 | 10000 |
| ERK1 | MAPK3 | 92 | 10000 |
| ERK2 | MAPK1 | 98 | 10000 |
| ERK3 | MAPK6 | 100 | 10000 |
| ERK4 | MAPK4 | 100 | 10000 |
| ERK5 | MAPK7 | 30 | 10000 |
| ERK8 | MAPK15 | 100 | 10000 |
| ERN1 | ERN1 | 88 | 10000 |
| FAK | PTK2 | 0.1 | 10000 |
| FER | FER | 57 | 10000 |
| FES | FES | 97 | 10000 |
| FGFR1 | FGFR1 | 90 | 10000 |
| FGFR2 | FGFR2 | 100 | 10000 |
| FGFR3 | FGFR3 | 98 | 10000 |
| FGFR3(G697C) | FGFR3 | 100 | 10000 |
| FGFR4 | FGFR4 | 88 | 10000 |
| FGR | FGR | 100 | 10000 |
| FLT1 | FLT1 | 100 | 10000 |
| FLT3 | FLT3 | 99 | 10000 |
| FLT3(D835H) | FLT3 | 100 | 10000 |
| FLT3(D835V) | FLT3 | 97 | 10000 |
| FLT3(D835Y) | FLT3 | 91 | 10000 |
| FLT3(ITD) | FLT3 | 100 | 10000 |
| FLT3(ITD, D835V) | FLT3 | 100 | 10000 |
| FLT3(ITD, F691L) | FLT3 | 93 | 10000 |
| FLT3(K663Q) | FLT3 | 96 | 10000 |
| FLT3(N841I) | FLT3 | 83 | 10000 |
| FLT3(R834Q) | FLT3 | 81 | 10000 |
| FLT3-autoinhibited | FLT3 | 99 | 10000 |
| FLT4 | FLT4 | 100 | 10000 |
| FRK | FRK | 99 | 10000 |
| FYN | FYN | 93 | 10000 |
| GAK | GAK | 31 | 10000 |
| GCN2(Kin.Dom.2, S808G) | EIF2AK4 | 94 | 10000 |
| GRK1 | GRK1 | 81 | 10000 |
| GRK2 | ADRBK1 | 100 | 10000 |
| GRK3 | ADRBK2 | 81 | 10000 |
| GRK4 | GRK4 | 97 | 10000 |
| GRK7 | GRK7 | 100 | 10000 |
| GSK3A | GSK3A | 100 | 10000 |
| GSK3B | GSK3B | 99 | 10000 |
| HASPIN | GSG2 | 89 | 10000 |
| HCK | HCK | 95 | 10000 |
| HIPK1 | HIPK1 | 94 | 10000 |
| HIPK2 | HIPK2 | 100 | 10000 |
| HIPK3 | HIPK3 | 100 | 10000 |
| HIPK4 | HIPK4 | 100 | 10000 |
| HPK1 | MAP4K1 | 100 | 10000 |
| HUNK | HUNK | 97 | 10000 |
| ICK | ICK | 100 | 10000 |
| IGF1R | IGF1R | 40 | 10000 |
| IKK-alpha | CHUK | 100 | 10000 |
| IKK-beta | IKBKB | 96 | 10000 |

TABLE 3-continued

Compound 5 engagement levels in the KinomeScan ®.

| DiscoveRx Gene Symbol | Entrez Gene Symbol | Percent Control | Compound Concentration (nM) |
|---|---|---|---|
| IKK-epsilon | IKBKE | 100 | 10000 |
| INSR | INSR | 40 | 10000 |
| INSRR | INSRR | 22 | 10000 |
| IRAK1 | IRAK1 | 100 | 10000 |
| IRAK3 | IRAK3 | 99 | 10000 |
| IRAK4 | IRAK4 | 88 | 10000 |
| ITK | ITK | 99 | 10000 |
| JAK1(JH1domain-catalytic) | JAK1 | 100 | 10000 |
| JAK1(JH2domain-pseudokinase) | JAK1 | 89 | 10000 |
| JAK2(JH1domain-catalytic) | JAK2 | 99 | 10000 |
| JAK3(JH1domain-catalytic) | JAK3 | 100 | 10000 |
| JNK1 | MAPK8 | 100 | 10000 |
| JNK2 | MAPK9 | 98 | 10000 |
| JNK3 | MAPK10 | 97 | 10000 |
| KIT | KIT | 100 | 10000 |
| KIT(A829P) | KIT | 100 | 10000 |
| KIT(D816H) | KIT | 100 | 10000 |
| KIT(D816V) | KIT | 100 | 10000 |
| KIT(L576P) | KIT | 100 | 10000 |
| KIT(V559D) | KIT | 100 | 10000 |
| KIT(V559D, T670I) | KIT | 95 | 10000 |
| KIT(V559D, V654A) | KIT | 100 | 10000 |
| KIT-autoinhibited | KIT | 100 | 10000 |
| LATS1 | LATS1 | 50 | 10000 |
| LATS2 | LATS2 | 98 | 10000 |
| LCK | LCK | 100 | 10000 |
| LIMK1 | LIMK1 | 95 | 10000 |
| LIMK2 | LIMK2 | 98 | 10000 |
| LKB1 | STK11 | 100 | 10000 |
| LOK | STK10 | 99 | 10000 |
| LRRK2 | LRRK2 | 32 | 10000 |
| LRRK2(G2019S) | LRRK2 | 21 | 10000 |
| LTK | LTK | 97 | 10000 |
| LYN | LYN | 100 | 10000 |
| LZK | MAP3K13 | 100 | 10000 |
| MAK | MAK | 100 | 10000 |
| MAP3K1 | MAP3K1 | 100 | 10000 |
| MAP3K15 | MAP3K15 | 84 | 10000 |
| MAP3K2 | MAP3K2 | 100 | 10000 |
| MAP3K3 | MAP3K3 | 100 | 10000 |
| MAP3K4 | MAP3K4 | 100 | 10000 |
| MAP4K2 | MAP4K2 | 94 | 10000 |
| MAP4K3 | MAP4K3 | 100 | 10000 |
| MAP4K4 | MAP4K4 | 100 | 10000 |
| MAP4K5 | MAP4K5 | 91 | 10000 |
| MAPKAPK2 | MAPKAPK2 | 100 | 10000 |
| MAPKAPK5 | MAPKAPK5 | 93 | 10000 |
| MARK1 | MARK1 | 89 | 10000 |
| MARK2 | MARK2 | 100 | 10000 |
| MARK3 | MARK3 | 81 | 10000 |
| MARK4 | MARK4 | 87 | 10000 |
| MAST1 | MAST1 | 100 | 10000 |
| MEK1 | MAP2K1 | 95 | 10000 |
| MEK2 | MAP2K2 | 99 | 10000 |
| MEK3 | MAP2K3 | 100 | 10000 |
| MEK4 | MAP2K4 | 100 | 10000 |
| MEK5 | MAP2K5 | 100 | 10000 |
| MEK6 | MAP2K6 | 98 | 10000 |
| MELK | MELK | 88 | 10000 |
| MERTK | MERTK | 100 | 10000 |
| MET | MET | 97 | 10000 |
| MET(M1250T) | MET | 100 | 10000 |
| MET(Y1235D) | MET | 98 | 10000 |
| MINK | MINK1 | 100 | 10000 |
| MKK7 | MAP2K7 | 100 | 10000 |
| MKNK1 | MKNK1 | 96 | 10000 |
| MKNK2 | MKNK2 | 90 | 10000 |
| MLCK | MYLK3 | 100 | 10000 |
| MLK1 | MAP3K9 | 41 | 10000 |
| MLK2 | MAP3K10 | 76 | 10000 |
| MLK3 | MAP3K11 | 100 | 10000 |
| MRCKA | CDC42BPA | 84 | 10000 |
| MRCKB | CDC42BPB | 100 | 10000 |
| MST1 | STK4 | 100 | 10000 |
| MST1R | MST1R | 100 | 10000 |
| MST2 | STK3 | 100 | 10000 |

TABLE 3-continued

Compound 5 engagement levels in the KinomeScan®.

| DiscoveRx Gene Symbol | Entrez Gene Symbol | Percent Control | Compound Concentration (nM) |
|---|---|---|---|
| MST3 | STK24 | 90 | 10000 |
| MST4 | MST4 | 100 | 10000 |
| MTOR | MTOR | 31 | 10000 |
| MUSK | MUSK | 100 | 10000 |
| MYLK | MYLK | 36 | 10000 |
| MYLK2 | MYLK2 | 97 | 10000 |
| MYLK4 | MYLK4 | 100 | 10000 |
| MYO3A | MYO3A | 100 | 10000 |
| MYO3B | MYO3B | 100 | 10000 |
| NDR1 | STK38 | 98 | 10000 |
| NDR2 | STK38L | 64 | 10000 |
| NEK1 | NEK1 | 97 | 10000 |
| NEK10 | NEK10 | 94 | 10000 |
| NEK11 | NEK11 | 100 | 10000 |
| NEK2 | NEK2 | 100 | 10000 |
| NEK3 | NEK3 | 100 | 10000 |
| NEK4 | NEK4 | 100 | 10000 |
| NEK5 | NEK5 | 100 | 10000 |
| NEK6 | NEK6 | 90 | 10000 |
| NEK7 | NEK7 | 100 | 10000 |
| NEK9 | NEK9 | 100 | 10000 |
| NIK | MAP3K14 | 93 | 10000 |
| NIM1 | MGC42105 | 100 | 10000 |
| NLK | NLK | 93 | 10000 |
| OSR1 | OXSR1 | 100 | 10000 |
| p38-alpha | MAPK14 | 93 | 10000 |
| p38-beta | MAPK11 | 95 | 10000 |
| p38-delta | MAPK13 | 100 | 10000 |
| p38-gamma | MAPK12 | 95 | 10000 |
| PAK1 | PAK1 | 92 | 10000 |
| PAK2 | PAK2 | 89 | 10000 |
| PAK3 | PAK3 | 92 | 10000 |
| PAK4 | PAK4 | 100 | 10000 |
| PAK6 | PAK6 | 100 | 10000 |
| PAK7 | PAK7 | 88 | 10000 |
| PCTK1 | CDK16 | 100 | 10000 |
| PCTK2 | CDK17 | 100 | 10000 |
| PCTK3 | CDK18 | 98 | 10000 |
| PDGFRA | PDGFRA | 88 | 10000 |
| PDGFRB | PDGFRB | 100 | 10000 |
| PDPK1 | PDPK1 | 96 | 10000 |
| PFCDPK1(P. falciparum) | CDPK1 | 99 | 10000 |
| PFPK5(P. falciparum) | MAL13P1.279 | 97 | 10000 |
| PFTAIRE2 | CDK15 | 100 | 10000 |
| PFTK1 | CDK14 | 100 | 10000 |
| PHKG1 | PHKG1 | 84 | 10000 |
| PHKG2 | PHKG2 | 38 | 10000 |
| PIK3C2B | PIK3C2B | 100 | 10000 |
| PIK3C2G | PIK3C2G | 100 | 10000 |
| PIK3CA | PIK3CA | 100 | 10000 |
| PIK3CA(C420R) | PIK3CA | 100 | 10000 |
| PIK3CA(E542K) | PIK3CA | 93 | 10000 |
| PIK3CA(E545A) | PIK3CA | 100 | 10000 |
| PIK3CA(E545K) | PIK3CA | 100 | 10000 |
| PIK3CA(H1047L) | PIK3CA | 80 | 10000 |
| PIK3CA(H1047Y) | PIK3CA | 100 | 10000 |
| PIK3CA(I800L) | PIK3CA | 70 | 10000 |
| PIK3CA(M1043I) | PIK3CA | 100 | 10000 |
| PIK3CA(Q546K) | PIK3CA | 94 | 10000 |
| PIK3CB | PIK3CB | 87 | 10000 |
| PIK3CD | PIK3CD | 92 | 10000 |
| PIK3CG | PIK3CG | 88 | 10000 |
| PIK4CB | PI4KB | 100 | 10000 |
| PIKFYVE | PIKFYVE | 60 | 10000 |
| PIM1 | PIM1 | 97 | 10000 |
| PIM2 | PIM2 | 100 | 10000 |
| PIM3 | PIM3 | 100 | 10000 |
| PIP5K1A | PIP5K1A | 100 | 10000 |
| PIP5K1C | PIP5K1C | 95 | 10000 |
| PIP5K2B | PIP4K2B | 39 | 10000 |
| PIP5K2C | PIP4K2C | 75 | 10000 |
| PKAC-alpha | PRKACA | 100 | 10000 |
| PKAC-beta | PRKACB | 100 | 10000 |
| PKMYT1 | PKMYT1 | 95 | 10000 |
| PKN1 | PKN1 | 100 | 10000 |
| PKN2 | PKN2 | 100 | 10000 |

TABLE 3-continued

Compound 5 engagement levels in the KinomeScan®.

| DiscoveRx Gene Symbol | Entrez Gene Symbol | Percent Control | Compound Concentration (nM) |
|---|---|---|---|
| PKNB(*M. tuberculosis*) | PKNB | 98 | 10000 |
| PLK1 | PLK1 | 0.7 | 10000 |
| PLK2 | PLK2 | 62 | 10000 |
| PLK3 | PLK3 | 20 | 10000 |
| PLK4 | PLK4 | 19 | 10000 |
| PRKCD | PRKCD | 94 | 10000 |
| PRKCE | PRKCE | 100 | 10000 |
| PRKCH | PRKCH | 94 | 10000 |
| PRKCI | PRKCI | 97 | 10000 |
| PRKCQ | PRKCQ | 88 | 10000 |
| PRKD1 | PRKD1 | 43 | 10000 |
| PRKD2 | PRKD2 | 46 | 10000 |
| PRKD3 | PRKD3 | 34 | 10000 |
| PRKG1 | PRKG1 | 100 | 10000 |
| PRKG2 | PRKG2 | 100 | 10000 |
| PRKR | EIF2AK2 | 65 | 10000 |
| PRKX | PRKX | 99 | 10000 |
| PRP4 | PRPF4B | 100 | 10000 |
| PYK2 | PTK2B | 85 | 10000 |
| QSK | KIAA0999 | 94 | 10000 |
| RAF1 | RAFI | 95 | 10000 |
| RET | RET | 100 | 10000 |
| RET(M918T) | RET | 100 | 10000 |
| RET(V804L) | RET | 93 | 10000 |
| RET(V804M) | RET | 73 | 10000 |
| RIOK1 | RIOK1 | 100 | 10000 |
| RIOK2 | RIOK2 | 100 | 10000 |
| RIOK3 | RIOK3 | 99 | 10000 |
| RIPK1 | RIPK1 | 96 | 10000 |
| RIPK2 | RIPK2 | 95 | 10000 |
| RIPK4 | RIPK4 | 100 | 10000 |
| RIPK5 | DSTYK | 60 | 10000 |
| ROCK1 | ROCK1 | 100 | 10000 |
| ROCK2 | ROCK2 | 100 | 10000 |
| ROS1 | ROS1 | 75 | 10000 |
| RPS6KA4(Kin.Dom.1-N-terminal) | RPS6KA4 | 100 | 10000 |
| RPS6KA4(Kin.Dom.2-C-terminal) | RPS6KA4 | 30 | 10000 |
| RPS6KA5(Kin.Dom.1-N-terminal) | RPS6KA5 | 91 | 10000 |
| RPS6KA5(Kin.Dom.2-C-terminal) | RPS6KA5 | 63 | 10000 |
| RSK1(Kin.Dom.1-N-terminal) | RPS6KA1 | 83 | 10000 |
| RSK1(Kin.Dom.2-C-terminal) | RPS6KA1 | 55 | 10000 |
| RSK2(Kin.Dom.1-N-terminal) | RPS6KA3 | 97 | 10000 |
| RSK2(Kin.Dom.2-C-terminal) | RPS6KA3 | 99 | 10000 |
| RSK3(Kin.Dom.1-N-terminal) | RPS6KA2 | 100 | 10000 |
| RSK3(Kin.Dom.2-C-terminal) | RPS6KA2 | 31 | 10000 |
| RSK4(Kin.Dom.1-N-terminal) | RPS6KA6 | 91 | 10000 |
| RSK4(Kin.Dom.2-C-terminal) | RPS6KA6 | 67 | 10000 |
| S6K1 | RPS6KB1 | 100 | 10000 |
| SBK1 | SBK1 | 98 | 10000 |
| SGK | SGK1 | 100 | 10000 |
| SgK110 | SgK110 | 92 | 10000 |
| SGK2 | SGK2 | 98 | 10000 |
| SGK3 | SGK3 | 100 | 10000 |
| SIK | SIK1 | 100 | 10000 |
| SIK2 | SIK2 | 99 | 10000 |
| SLK | SLK | 100 | 10000 |
| SNARK | NUAK2 | 91 | 10000 |
| SNRK | SNRK | 100 | 10000 |
| SRC | SRC | 100 | 10000 |
| SRMS | SRMS | 97 | 10000 |
| SRPK1 | SRPK1 | 100 | 10000 |
| SRPK2 | SRPK2 | 89 | 10000 |
| SRPK3 | SRPK3 | 100 | 10000 |
| STK16 | STK16 | 100 | 10000 |
| STK33 | STK33 | 10 | 10000 |
| STK35 | STK35 | 100 | 10000 |
| STK36 | STK36 | 100 | 10000 |
| STK39 | STK39 | 77 | 10000 |
| SYK | SYK | 89 | 10000 |
| TAK1 | MAP3K7 | 100 | 10000 |
| TAOK1 | TAOK1 | 80 | 10000 |
| TAOK2 | TAOK2 | 93 | 10000 |
| TAOK3 | TAOK3 | 77 | 10000 |
| TBK1 | TBK1 | 88 | 10000 |
| TEC | TEC | 100 | 10000 |
| TESK1 | TESK1 | 100 | 10000 |

TABLE 3-continued

Compound 5 engagement levels in the KinomeScan®.

| DiscoveRx Gene Symbol | Entrez Gene Symbol | Percent Control | Compound Concentration (nM) |
|---|---|---|---|
| TGFBR1 | TGFBR1 | 100 | 10000 |
| TGFBR2 | TGFBR2 | 98 | 10000 |
| TIE1 | TIE1 | 96 | 10000 |
| TIE2 | TEK | 100 | 10000 |
| TLK1 | TLK1 | 81 | 10000 |
| TLK2 | TLK2 | 100 | 10000 |
| TNIK | TNIK | 99 | 10000 |
| TNK1 | TNK1 | 10 | 10000 |
| TNK2 | TNK2 | 87 | 10000 |
| TNNI3K | TNNI3K | 88 | 10000 |
| TRKA | NTRK1 | 100 | 10000 |
| TRKB | NTRK2 | 100 | 10000 |
| TRKC | NTRK3 | 100 | 10000 |
| TRPM6 | TRPM6 | 92 | 10000 |
| TSSK1B | TSSK1B | 68 | 10000 |
| TSSK3 | TSSK3 | 98 | 10000 |
| TTK | TTK | 6.9 | 10000 |
| TXK | TXK | 99 | 10000 |
| TYK2(JH1domain-catalytic) | TYK2 | 97 | 10000 |
| TYK2(JH2domain-pseudokinase) | TYK2 | 100 | 10000 |
| TYRO3 | TYRO3 | 88 | 10000 |
| ULK1 | ULK1 | 98 | 10000 |
| ULK2 | ULK2 | 81 | 10000 |
| ULK3 | ULK3 | 97 | 10000 |
| VEGFR2 | KDR | 95 | 10000 |
| VPS34 | PIK3C3 | 89 | 10000 |
| VRK2 | VRK2 | 97 | 10000 |
| WEE1 | WEE1 | 98 | 10000 |
| WEE2 | WEE2 | 100 | 10000 |
| WNK1 | WNK1 | 89 | 10000 |
| WNK2 | WNK2 | 100 | 10000 |
| WNK3 | WNK3 | 97 | 10000 |
| WNK4 | WNK4 | 100 | 10000 |
| YANK1 | STK32A | 100 | 10000 |
| YANK2 | STK32B | 100 | 10000 |
| YANK3 | STK32C | 98 | 10000 |
| YES | YES1 | 97 | 10000 |
| YSK1 | STK25 | 100 | 10000 |
| YSK4 | MAP3K19 | 93 | 10000 |
| ZAK | ZAK | 100 | 10000 |
| ZAP70 | ZAP70 | 100 | 10000 |

TABLE 4

Biochemical $IC_{50}$ values of off-targets for compound 5 displaying ≤10% control in KinomeScan®.

| Kinase | Biochemical $IC_{50}$ (nM) | Fold-Selectivity |
|---|---|---|
| FAK | 20.2 ± 1.9 | — |
| DCLK1 | 6500 | 321 |
| DCLK2 | 3120 | 154 |
| PLK1 | 8280 | 410 |
| STK33 | 2130 | 105 |
| TNK1 | 3170 | 157 |
| TTK | 3610 | 178 |

Example 61: Antiproliferative Effects of Inventive Compounds

For 2D-adherent monolayer experiments, MDA-MB-231 cells were plated in 384-well format and allowed to adhere overnight. Cells were treated with indicated molecules from compound stock plates using a JANUS® Workstation pin tool for 120 hrs. To measure cell viability, Cell Titer-Glo® was added to wells for 15 minutes at room temperature and luminescence was measured on an EnVision™ 2104 Multilabel Plate Reader.

For ultra-low adherent 3D-spheroid suspensions, MDA-MB-231 cells were plated in 384-well format in media containing 10% Matrigel® and allowed to form spheroids overnight. Cells were treated with indicated molecules from compound stock plates using a JANUS® Workstation pin tool for 120 hours. To measure cell viability, 3D Cell Titer-Glo® was added to wells for 15 minutes at room temperature and luminescence was measured on an EnVision™ 2104 Multilabel Plate Reader.

Inventive compound treatment (0.00063-20 μM) led to antiproliferative effects in MDA-MB-231 cells cultured as 2D-adherent monolayers or as ultra-low adherent 3D-spheroid suspensions (Table 5). These data indicate that FAK inhibition leads to antiproliferative effects in 2D and 3D cultures.

TABLE 5

Antiproliferative effects upon treatment with inventive compounds.

| Compound # | 2D $IC_{50}$ (μM) | 3D $IC_{50}$ (μM) |
|---|---|---|
| 3 | >10 | 6.8 |
| 5 | 7.6 | 3.6 |
| 12 | >10 | 2.5 |
| 14 | >10 | 2.3 |
| 16 | >10 | 6.1 |
| 132 | >10 | 0.93 |
| 198 | >10 | >10 |
| 197 | >10 | 5.9 |

TABLE 5-continued

Antiproliferative effects upon treatment with inventive compounds.

| Compound # | 2D IC$_{50}$ (µM) | 3D IC$_{50}$ (µM) |
|---|---|---|
| 21 | >10 | >10 |
| 18 | >10 | 7.7 |
| 22 | >10 | >10 |
| 159 | >10 | >10 |
| 28 | >10 | >10 |
| 23 | >10 | >10 |
| 19 | 8.9 | 3.7 |
| 20 | >10 | >10 |

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A compound having a structure represented by formula I:

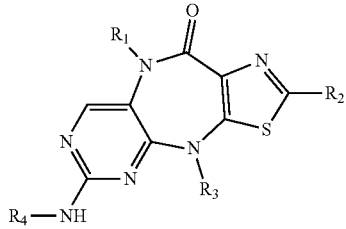
(I)

wherein:
R$_1$ is hydrogen, optionally substituted alkyl, optionally substituted carbocyclyl, or optionally substituted heterocyclyl;
R$_2$ is hydrogen, optionally substituted alkyl, optionally substituted carbocyclyl, or optionally substituted heterocyclyl;
R$_3$ is hydrogen, optionally substituted alkyl, optionally substituted carbocyclyl, or optionally substituted heterocyclyl;
R$_4$ is optionally substituted pyrazolyl, optionally substituted pyridinyl, optionally substituted benzopiperidinyl,

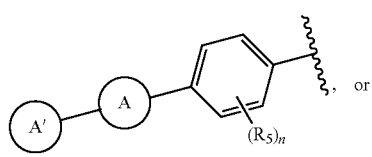, or

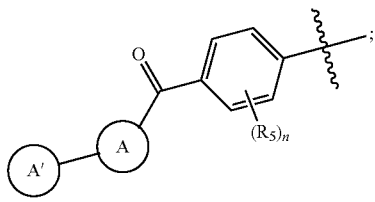;

wherein each R$_5$ is independently H, OH, CN, alkyl, alkoxy, halo, haloalkyl, haloalkoxy, amino, acyl, or amide;
n is 0, 1, or 2;

is an optionally substituted amide or an optionally substituted heterocycle;

is absent if

is an optionally substituted amide, and if

is optionally substituted heterocycle,

is absent, optionally substituted piperidinyl or optionally substituted piperazinyl;
or a pharmaceutically acceptable salt or stereoisomer thereof.

2. The compound of claim 1, wherein R$_4$ is optionally substituted pyrazolyl and the compound has a structure represented by formula (Ia):

(Ia)

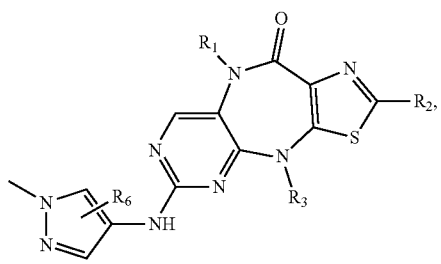

wherein
R$_6$ is H, alkyl or alkoxy;
or a pharmaceutically acceptable salt or stereoisomer thereof.

3. The compound of claim 1, wherein R$_4$ is optionally substituted pyridinyl and the compound has a structure represented by formula (Ib):

(Ib)

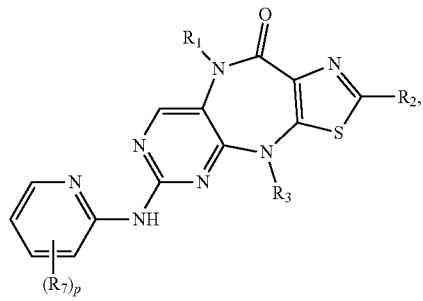

wherein
each R$_7$ is independently alkyl, alkoxy, or optionally substituted heterocyclyl; and
p is 0, 1, or 2;
or a pharmaceutically acceptable salt or stereoisomer thereof.

4. The compound of claim 1, wherein R$_4$ is optionally substituted benzopiperidinyl and the compound has a structure represented by formula (Ic):

(Ic)

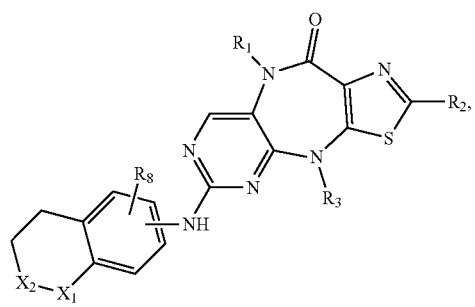

wherein
R$_8$ is H, alkyl or alkoxy;
X$_1$ represents NH or CH$_2$;
X$_2$ represents C=O or NMe;
provided that when X$_1$ represents NH, X$_2$ represents C=O and when X$_1$ represents CH$_2$, X$_2$ represents NMe;
or a pharmaceutically acceptable salt or stereoisomer thereof.

5. The compound of claim 1, wherein R$_4$ is

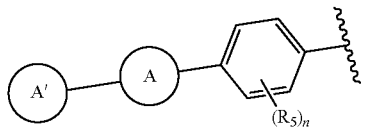

and the compound has a structure represented by formula (Id):

(Id)

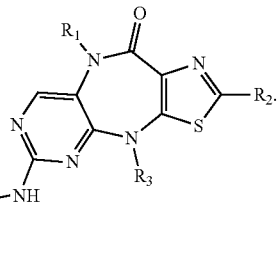

6. The compound of claim 5, wherein

is an amide and

is absent and the compound has a structure represented by formula (Id1):

(Id1)

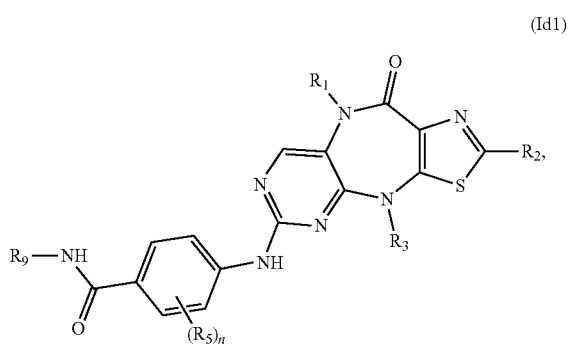

wherein
R$_9$ is C$_1$-C$_6$ alkyl;
or a pharmaceutically acceptable salt or stereoisomer thereof.

7. The compound of claim 5, wherein

is an optionally substituted heterocycle and

is absent and the compound has a structure represented by formula (Id2):

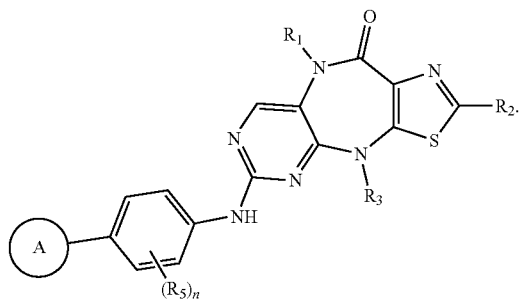

(Id2)

8. The compound of claim 7, wherein

is piperidinyl, and the compound has a structure represented by formula (Id2a):

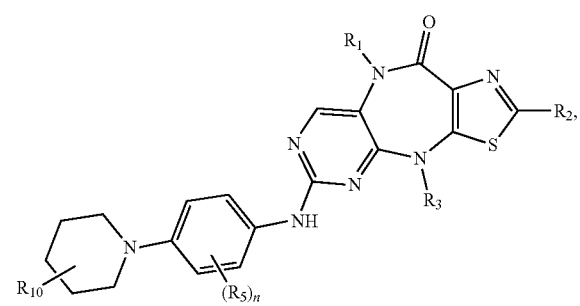

(Id2a)

$R_{10}$ is H, OH, $C_1$-$C_6$ alkyl, $C_1$-$C_6$ alkoxy, or halo; or wherein

is piperazinyl and the compound has a structure represented by formula (Id2b):

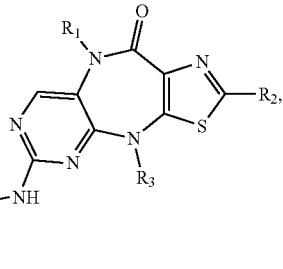

(Id2b)

$R_{11}$ is H, $SO_2Me$ or optionally substituted $C_1$-$C_4$ alkyl; and $R_{12}$ is H or $C_1$-$C_6$ alkyl; or wherein

is piperidinyl and the compound has a structure represented by formula (Id2c):

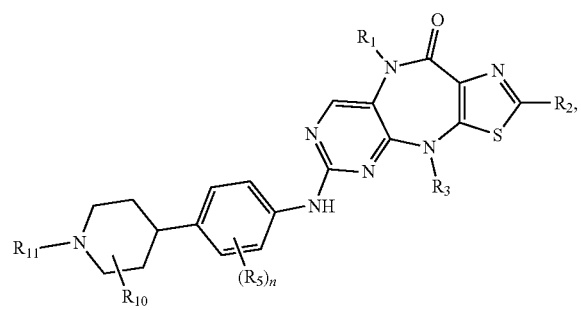

(Id2c)

$R_{10}$ is H, OH, $C_1$-$C_6$ alkyl, $C_1$-$C_6$ alkoxy, or halo; and
$R_{11}$ is H, $SO_2Me$ or optionally substituted $C_1$-$C_4$ alkyl;
or a pharmaceutically acceptable salt or stereoisomer thereof.

9. The compound of claim 5, wherein

is an optionally substituted heterocycle and

is piperazinyl and the compound has a structure represented by formula (Id3):

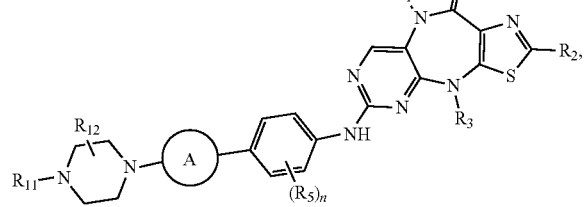
(Id3)

$R_{11}$ is H, SO$_2$Me, or optionally substituted $C_1$-$C_4$ alkyl; and $R_{12}$ is H or $C_1$-$C_6$ alkyl;

or a pharmaceutically acceptable salt or stereoisomer thereof.

10. The compound of claim 9, wherein

is piperidinyl and

is piperazinyl and the compound has a structure represented by formula (Id3a):

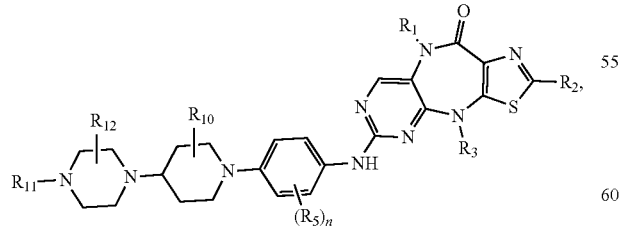
(Id3a)

$R_{10}$ is H, $C_1$-$C_6$ alkyl, $C_1$-$C_6$ alkoxy, or halo;

$R_{11}$ is H, SO$_2$Me, or optionally substituted $C_1$-$C_4$ alkyl; and $R_{12}$ is H or $C_1$-$C_6$ alkyl; or wherein

is piperazinyl and

is piperidinyl and the compound has a structure represented by formula (Id3b):

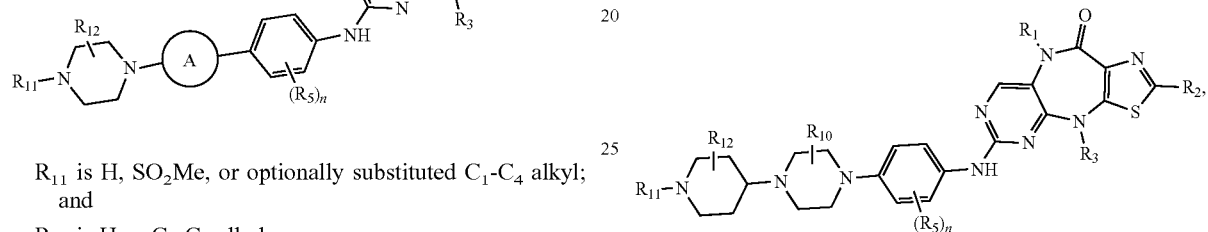
(Id3b)

$R_{10}$ is H, $C_1$-$C_6$ alkyl, $C_1$-$C_6$ alkoxy, or halo;
$R_{11}$ is H, SO$_2$Me, or optionally substituted $C_1$-$C_4$ alkyl; and
$R_{12}$ is H or $C_1$-$C_6$ alkyl;

or a pharmaceutically acceptable salt or stereoisomer thereof.

11. The compound of claim 1, wherein $R_4$ is

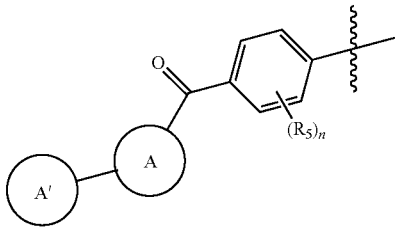

and the compound has a structure represented by formula (Ie):

(Ie)

12. The compound of claim 11, wherein

is piperidinyl and

is piperazinyl and the compound has a structure represented by formula (Ie1):

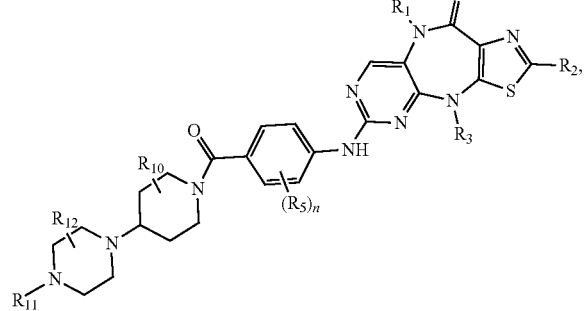

(Ie1)

$R_{10}$ is H, $C_1$-$C_6$ alkyl, $C_1$-$C_6$ alkoxy, or halo;
$R_{11}$ is H, $SO_2Me$, or optionally substituted $C_1$-$C_4$ alkyl; and
$R_{12}$ is H or $C_1$-$C_6$ alkyl;
or a pharmaceutically acceptable salt or stereoisomer thereof.

13. The compound of claim 9, wherein

is an optionally heterocycle substituted with 0-4 substituents, independently
selected from Me, OH,

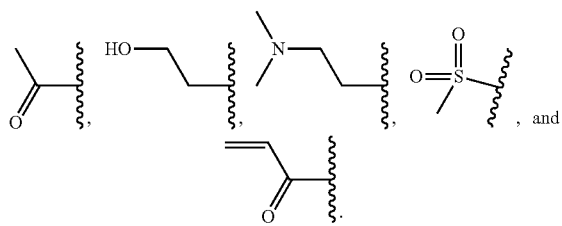

, and

14. The compound of claim 5, where $R_5$ is OMe.
15. The compound of claim 1, wherein $R_3$ is H, methyl, ethyl, i-Pr, n-Pr, or $CH_2CF_3$.
16. The compound of claim 1, wherein $R_2$ is H, methyl, ethyl, i-Pr, $CH_2CF_3$, or Ph.
17. The compound of claim 1, wherein $R_1$ is H, methyl, ethyl, i-Pr, n-Pr, or $CH_2CF_3$.
18. The compound of claim 1, wherein $R_2$ and $R_3$ are methyl.
19. The compound of claim 1, wherein $R_1$ and $R_3$ are methyl.
20. The compound of claim 1, wherein $R_1$ is H and $R_2$ and $R_3$ are methyl.
21. The compound of claim 1, wherein $R_1$, $R_2$, and $R_3$ are methyl.
22. The compound of claim 1, which is selected from the group consisting of:

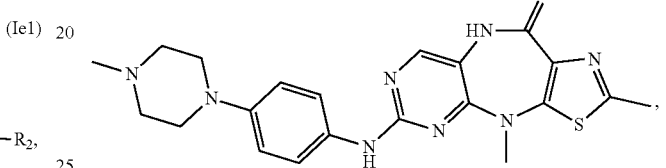

(1)

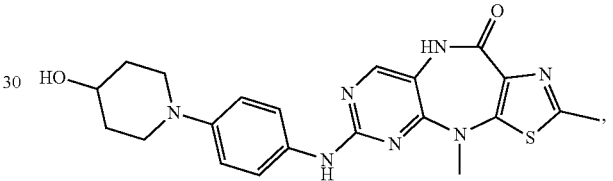

(2)

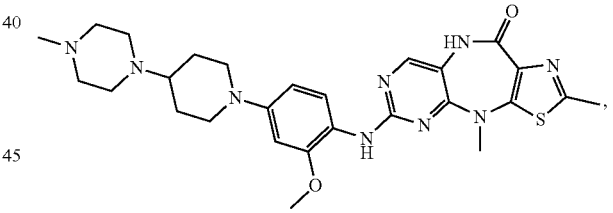

(3)

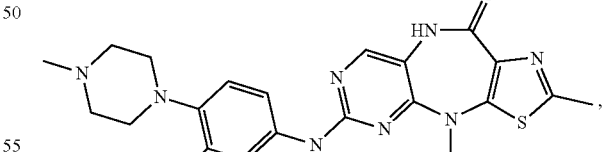

(4)

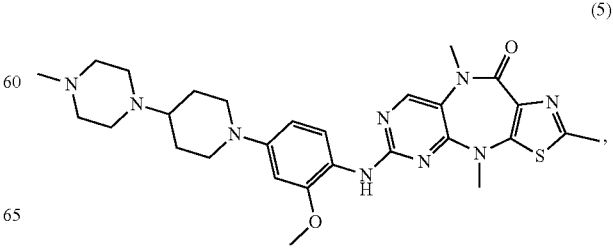

(5)

-continued
(6)
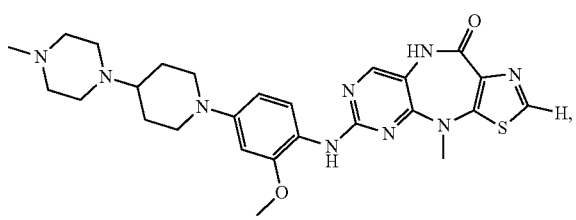
(7)
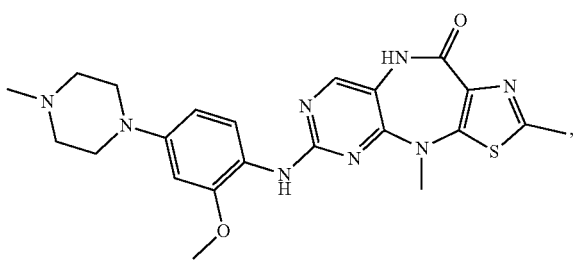
(8)
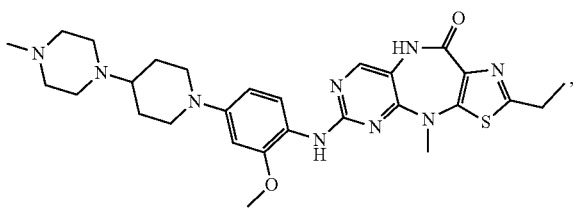
(9)
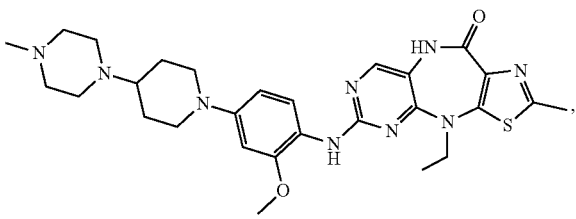
(10)
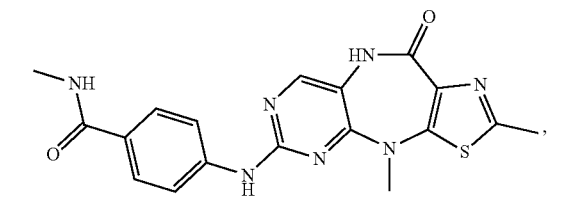
(11)
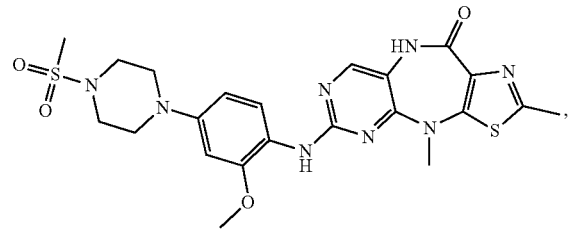
-continued
(12)
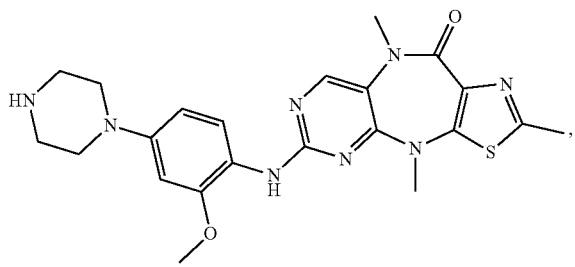
(13)
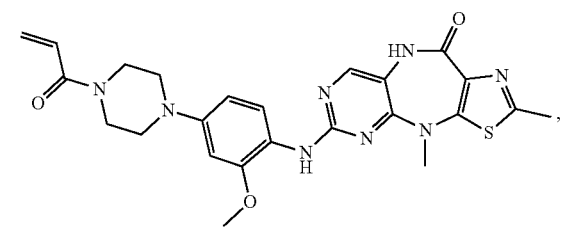
(14)
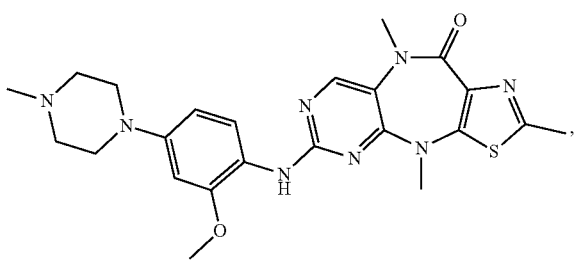
(15)
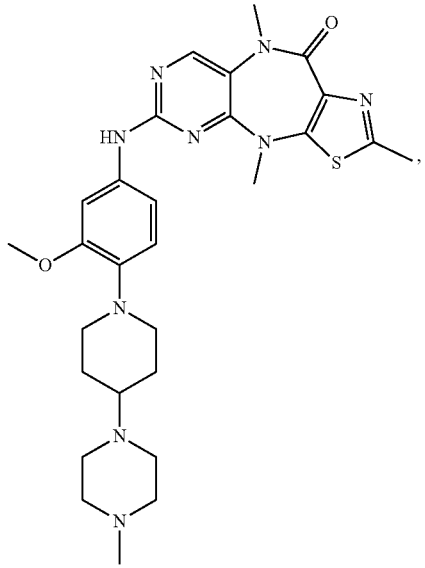

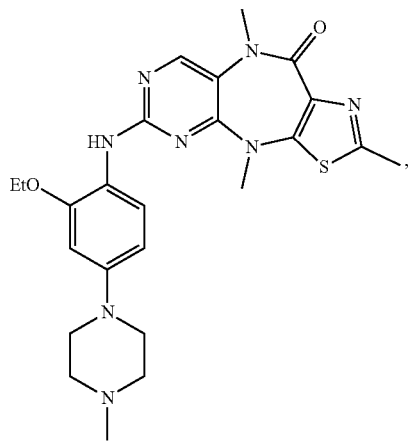
(16)
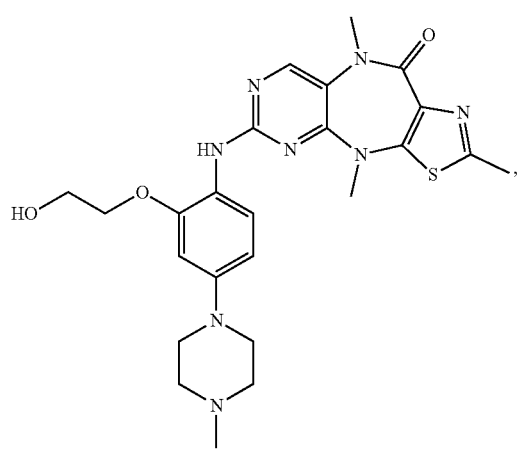
(17)
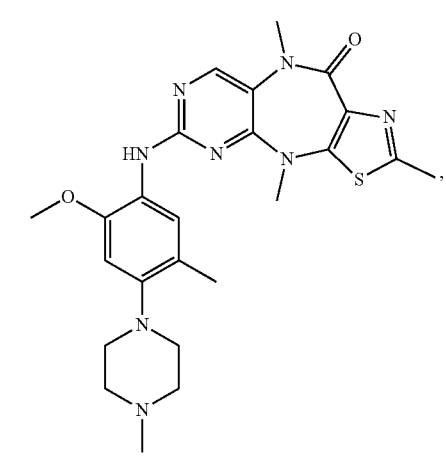
(18)
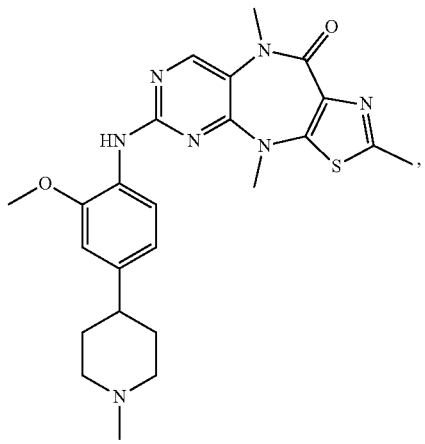
(19)
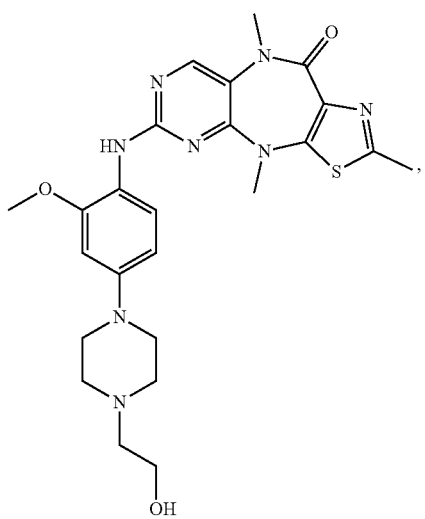
(20)
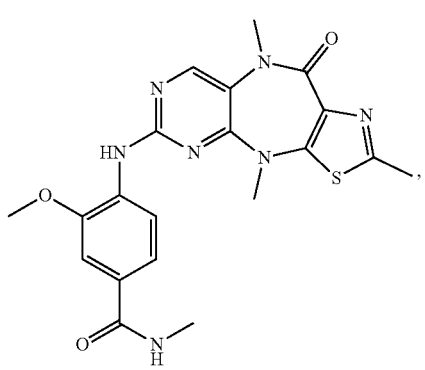
(21)
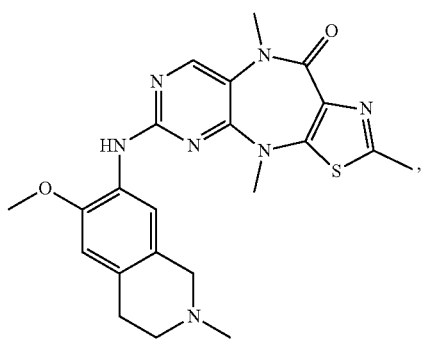
(22)

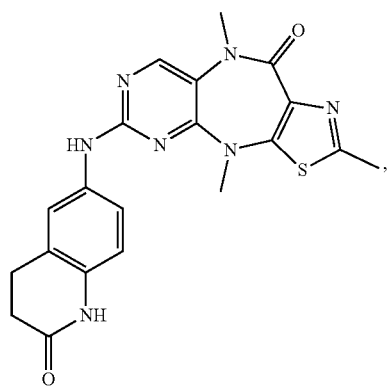
(23)
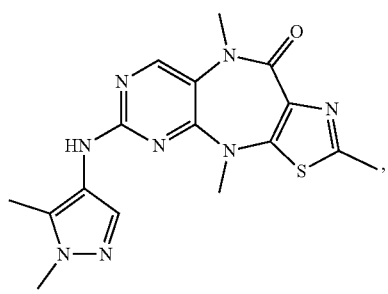
(27)
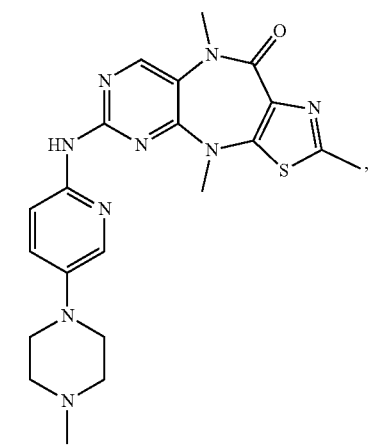
(24)
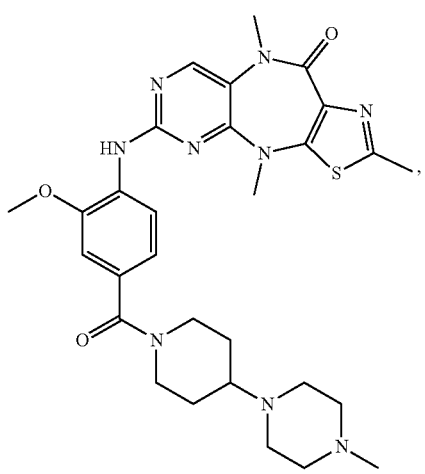
(28)
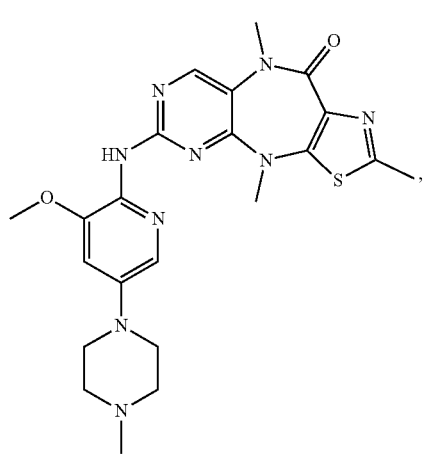
(25)
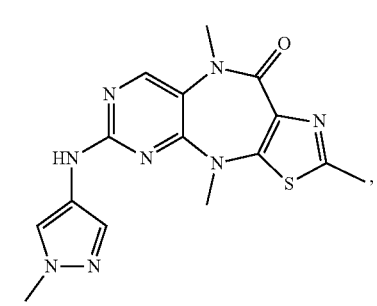
(26)
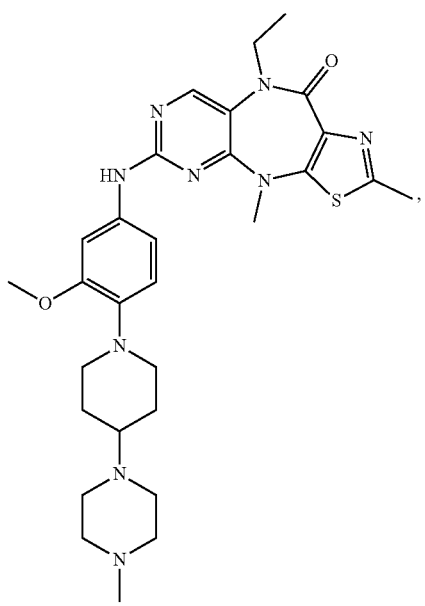
(29)

(30)
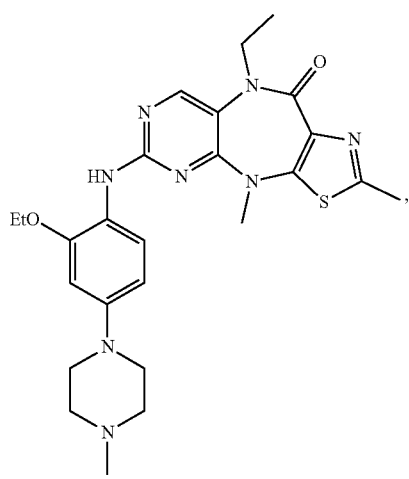
(31)
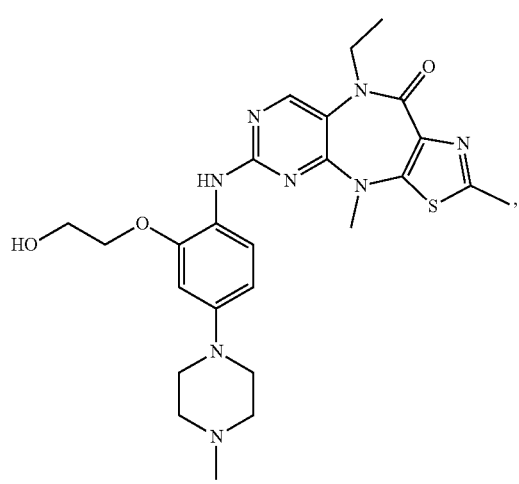
(32)
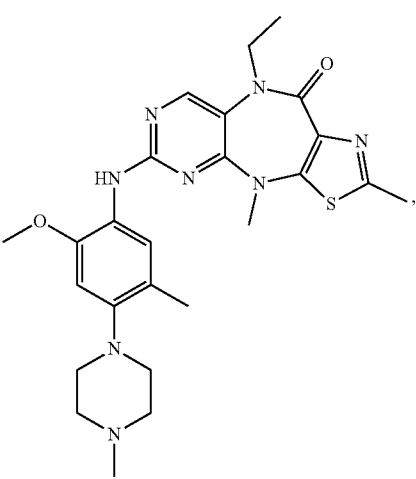
(33)
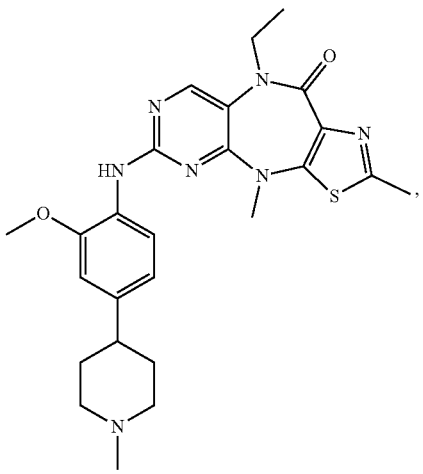
(34)
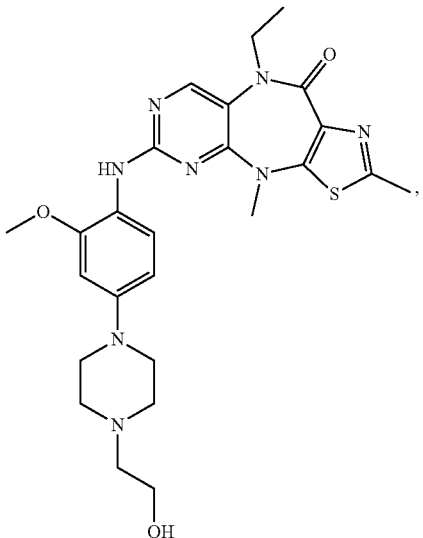
(35)
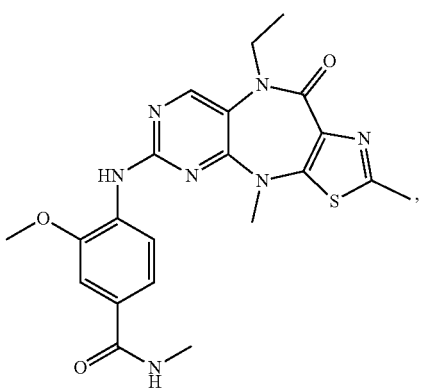

-continued
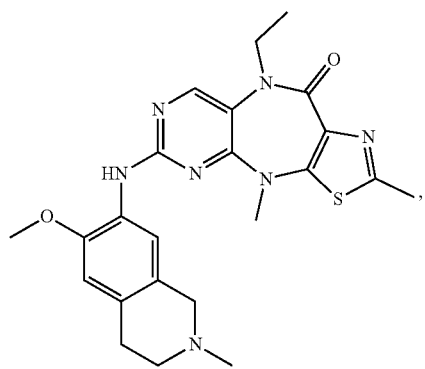
(36)
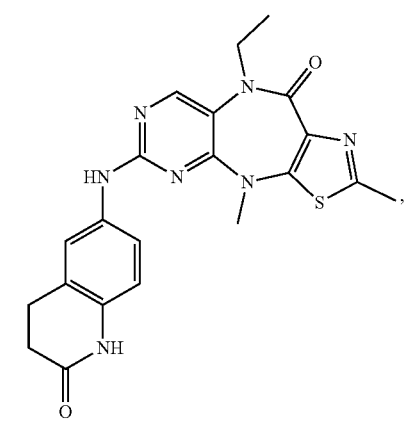
(37)
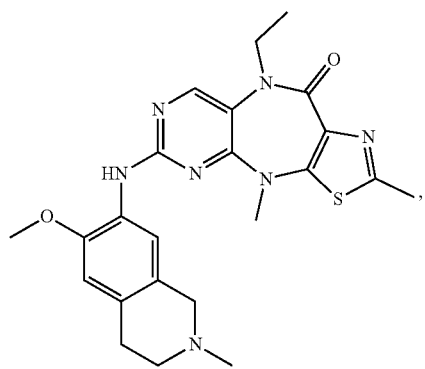
(38)
-continued
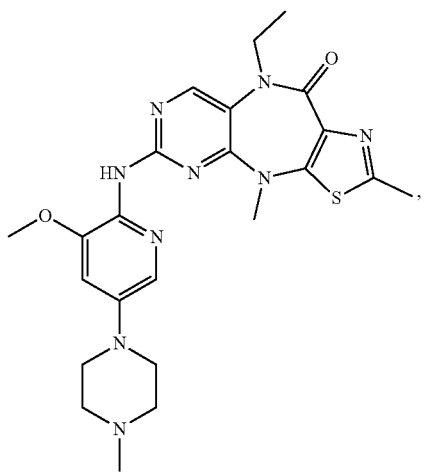
(39)
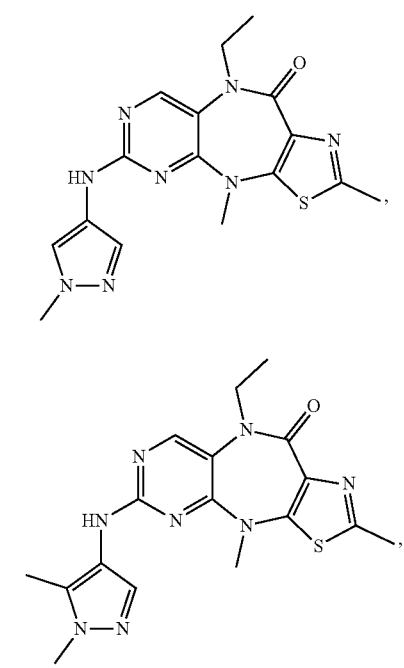
(40)
(41)
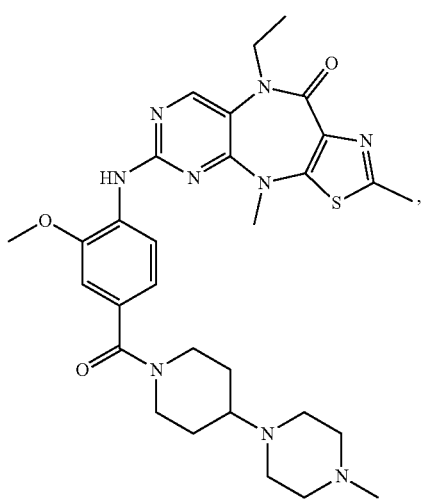
(42)

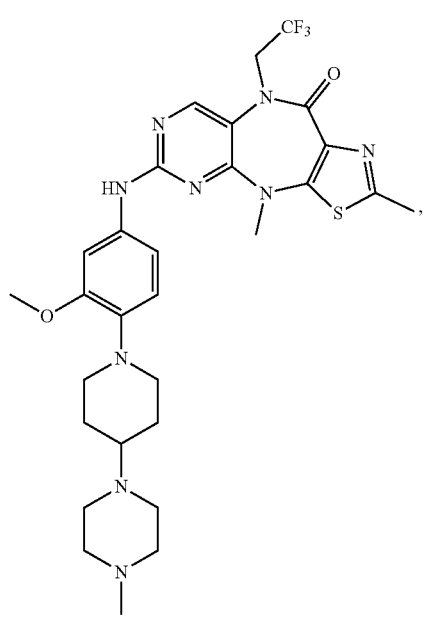
(43)
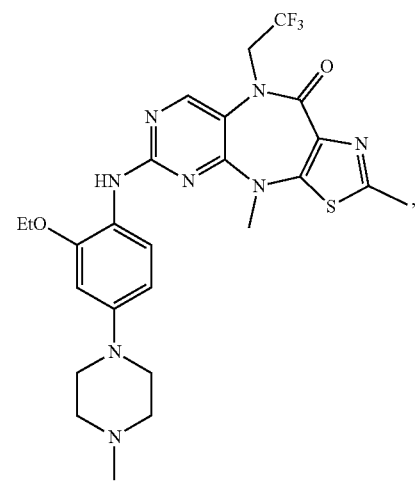
(44)
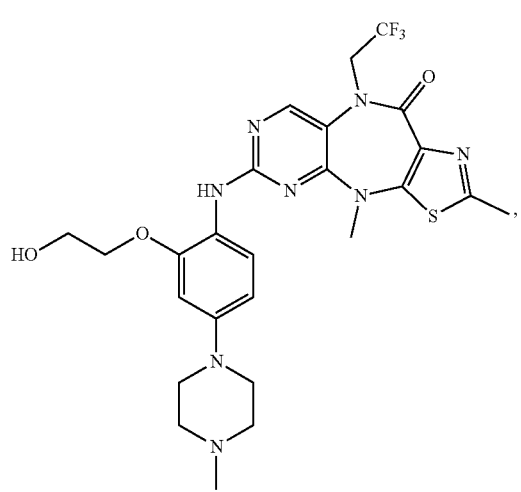
(45)
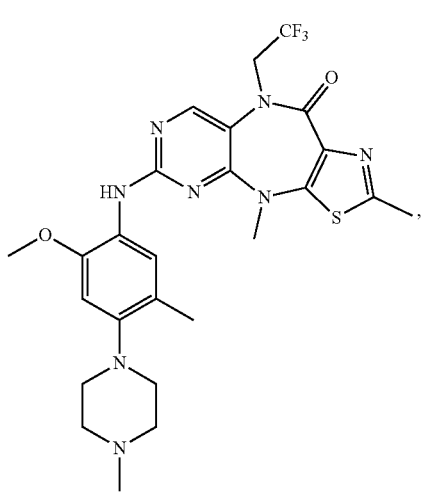
(46)
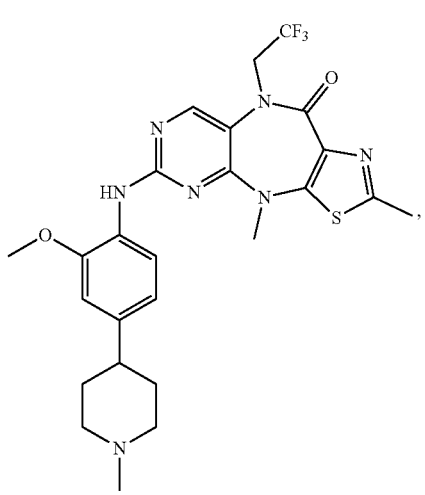
(47)
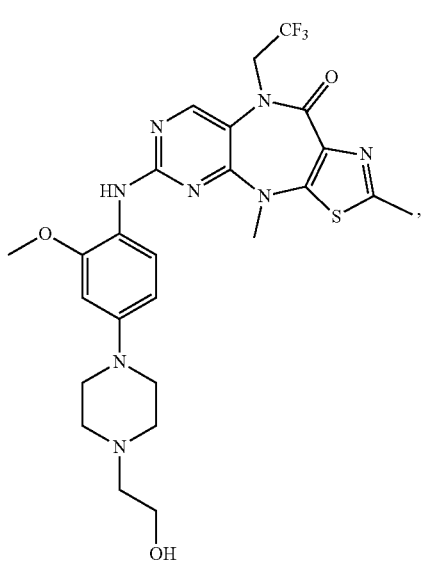
(48)

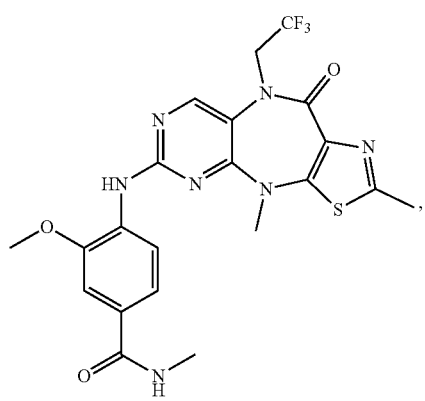
(49)
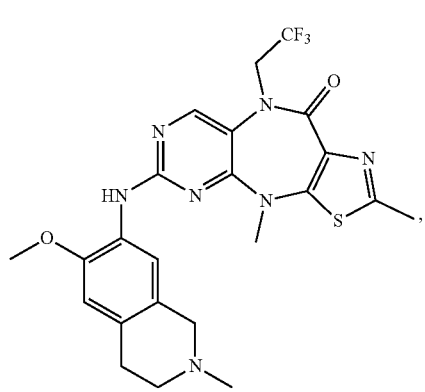
(50)
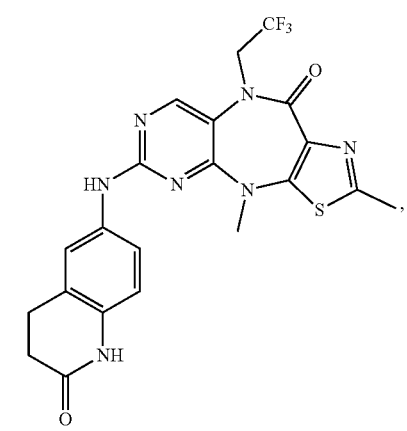
(51)
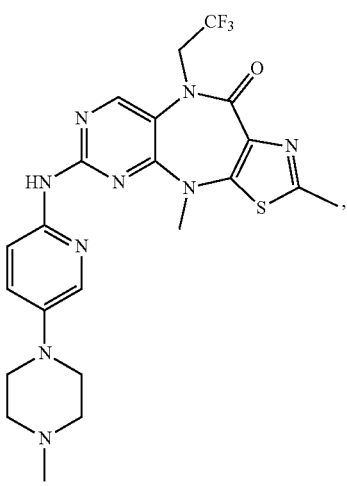
(52)
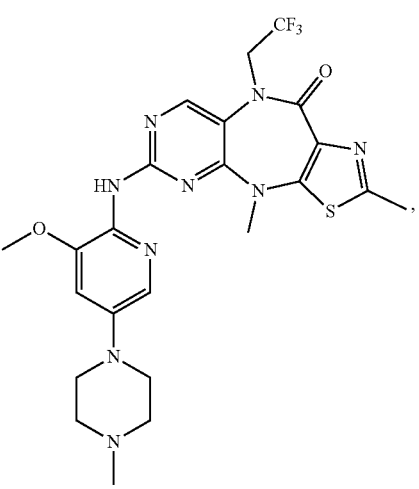
(56)
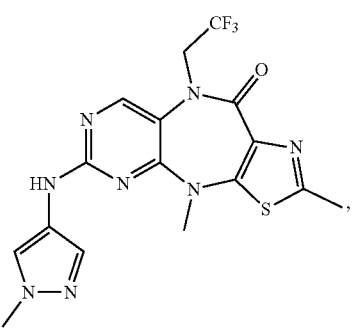
(57)
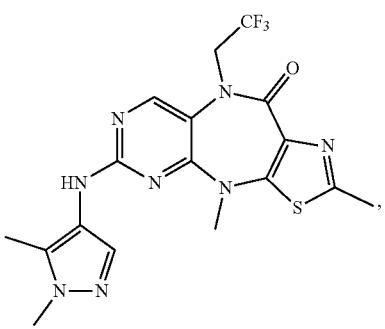
(58)

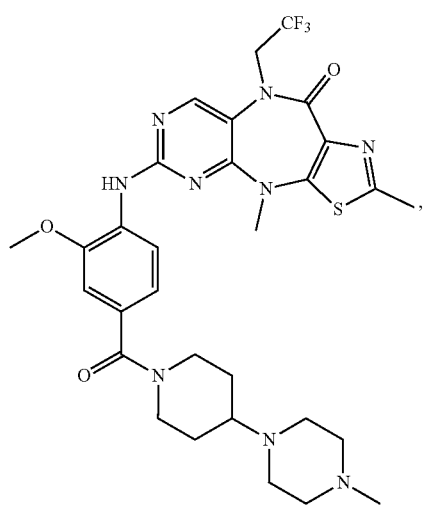
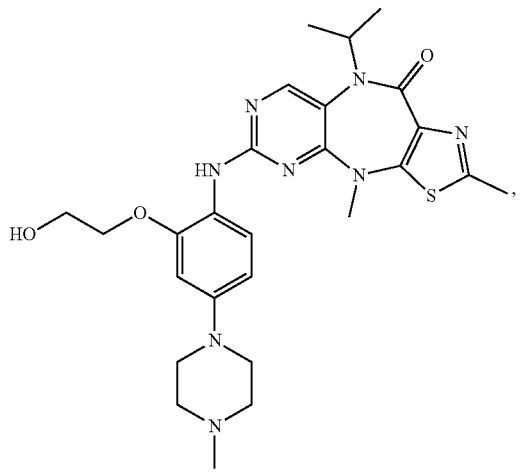

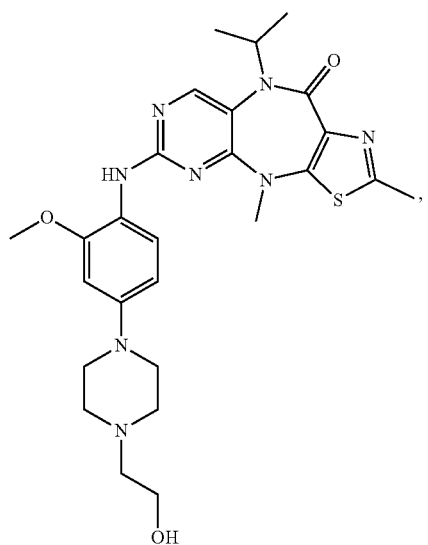
(65)
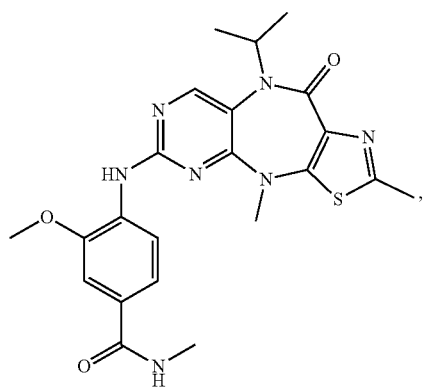
(66)
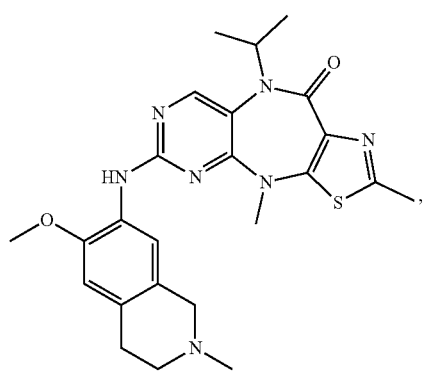
(67)
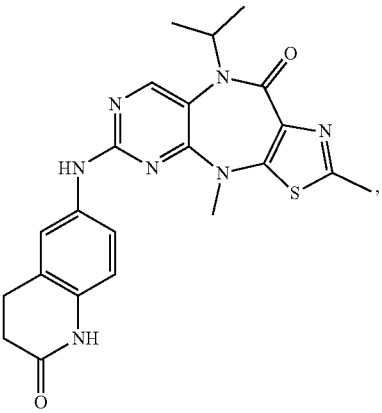
(68)
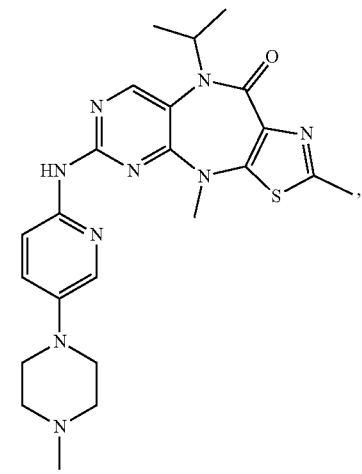
(69)
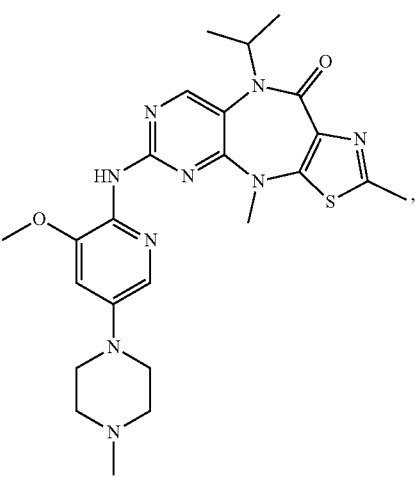
(70)

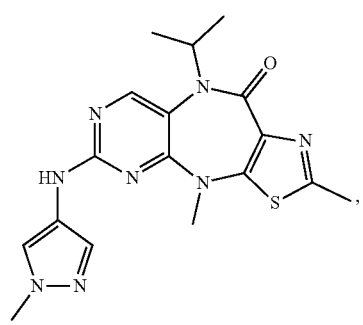
(71)
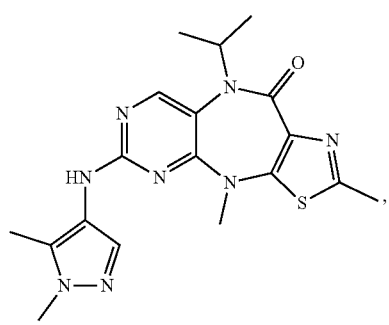
(72)
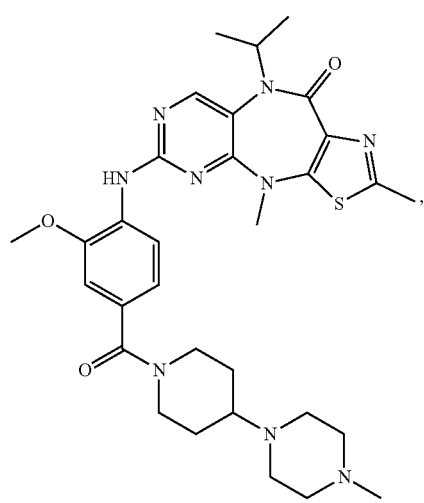
(73)
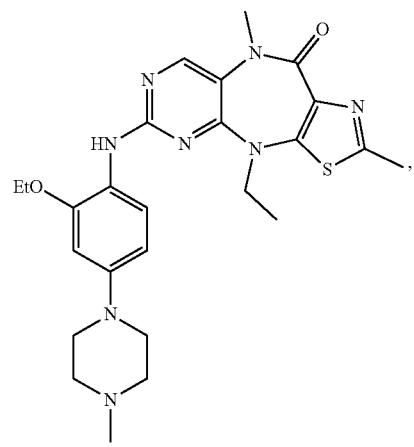
(74)
(75)
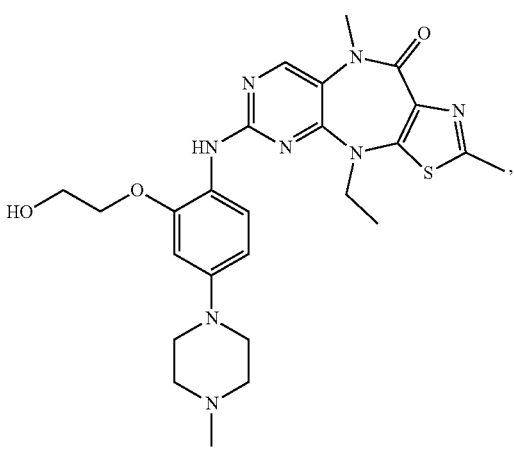
(76)

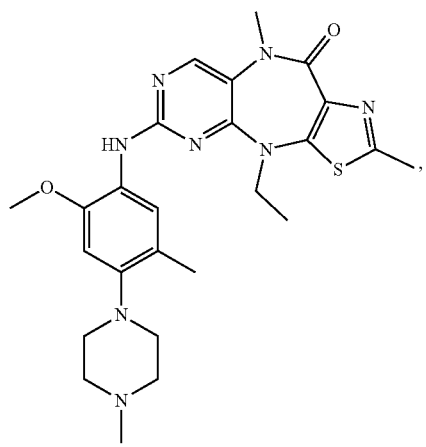
(77)
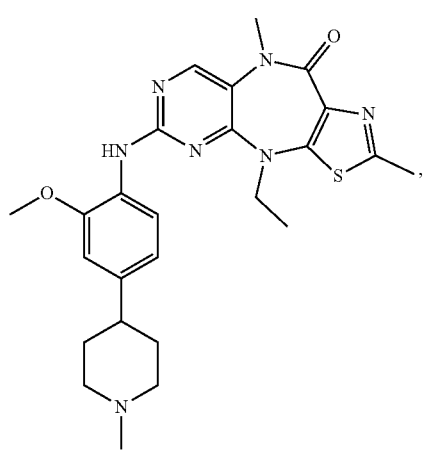
(78)
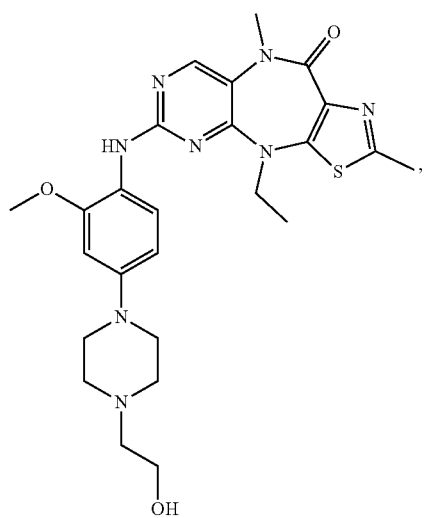
(79)
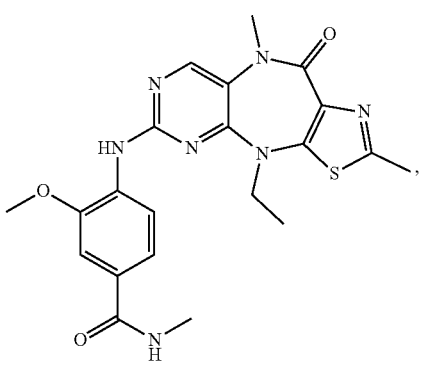
(80)
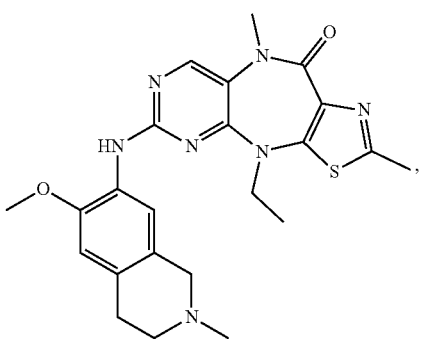
(81)
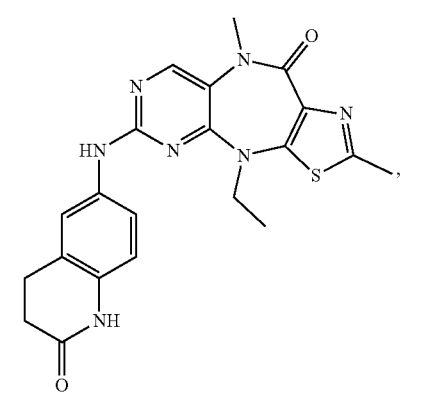
(82)
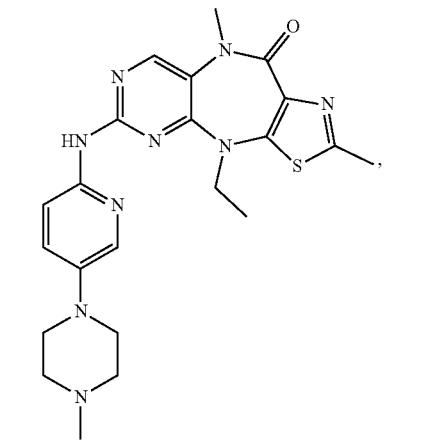
(83)

205
-continued
(84)
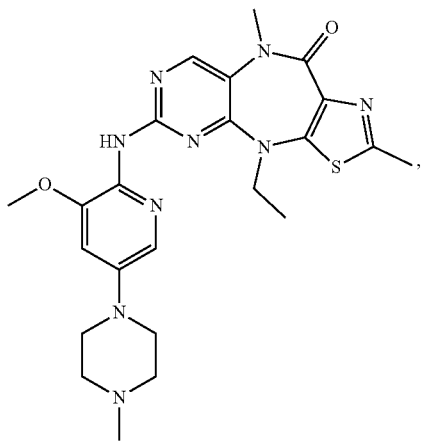
(85)
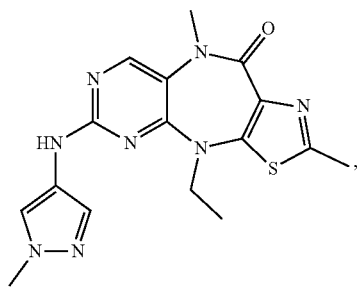
(86)
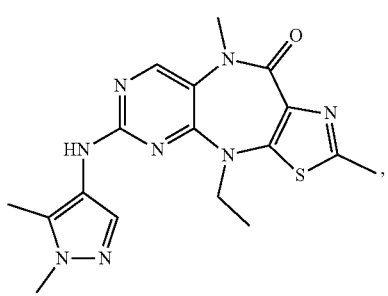
(87)
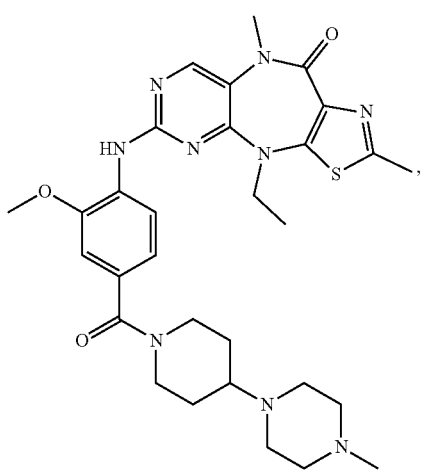
206
-continued
(88)
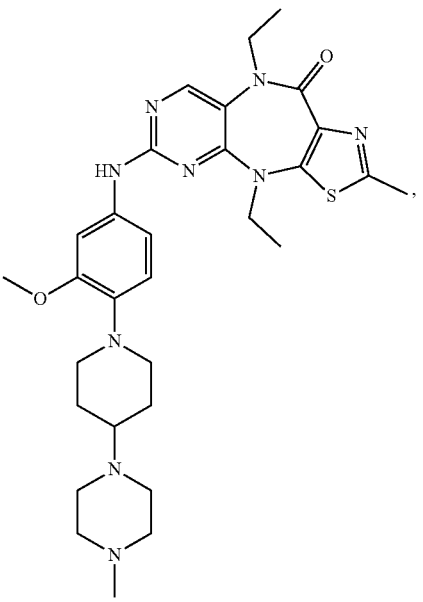
(89)
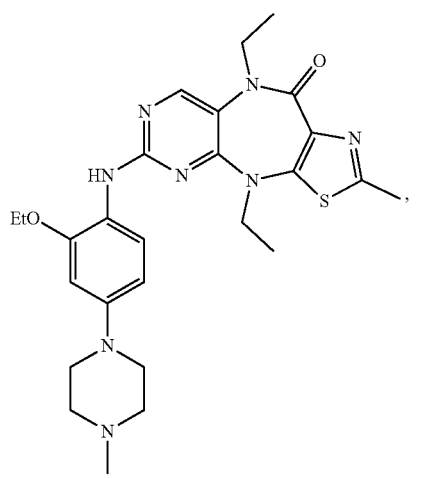
(90)
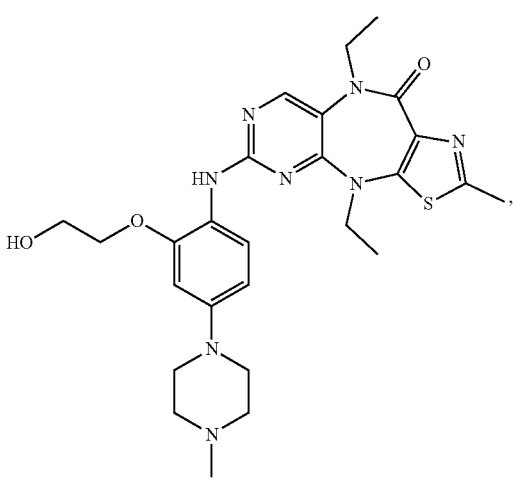

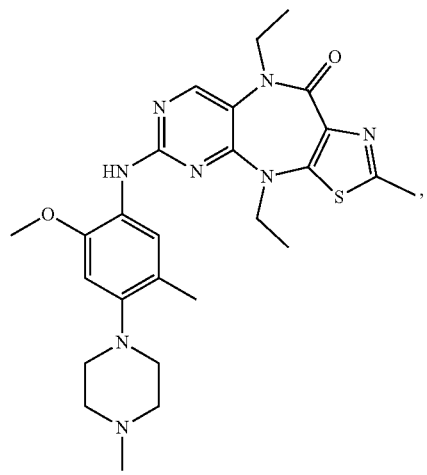
(91)
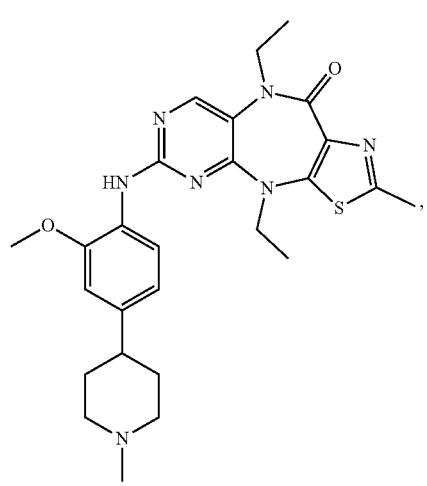
(92)
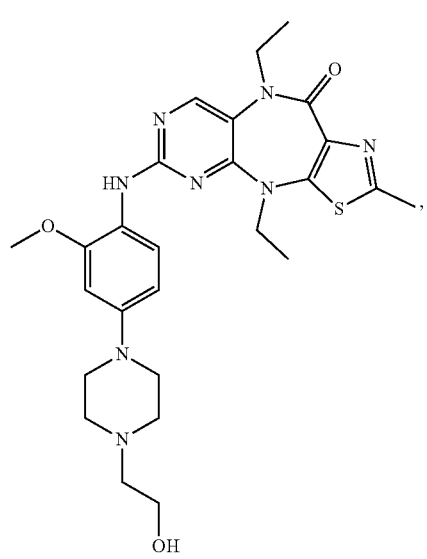
(93)
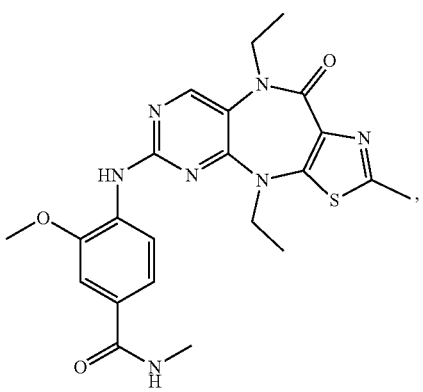
(94)
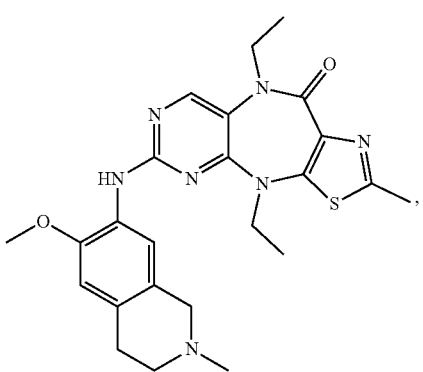
(95)
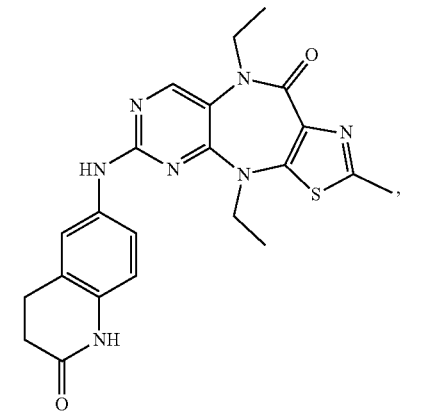
(96)
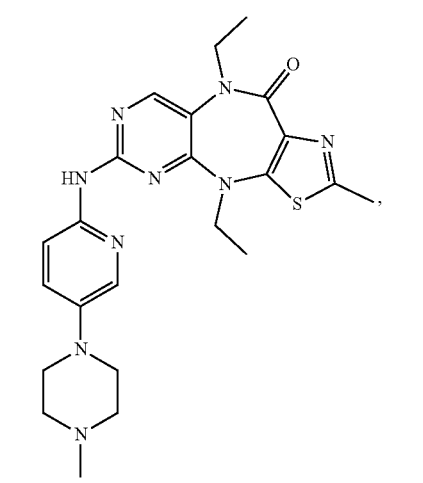
(97)

(98)
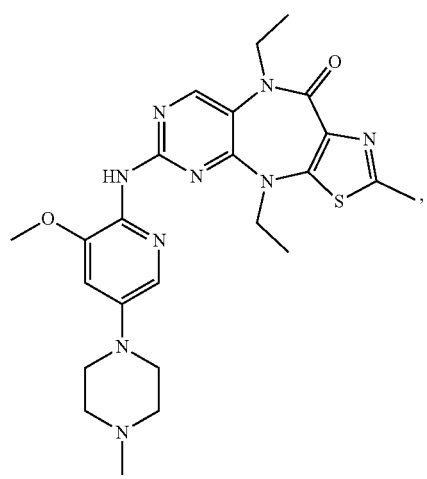
(99)
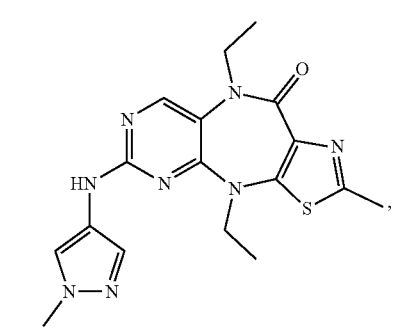
(100)
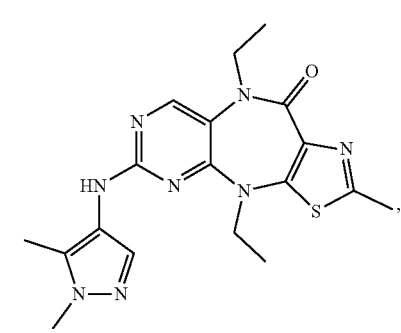
(101)
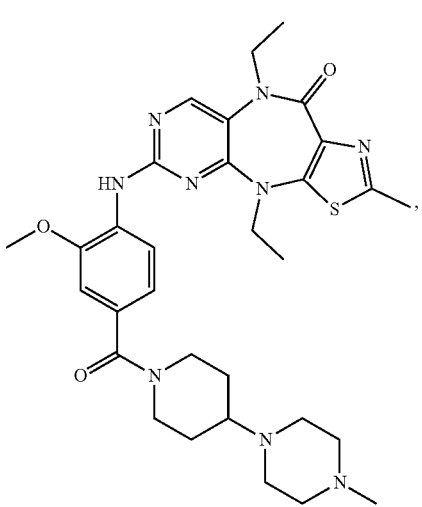
(102)
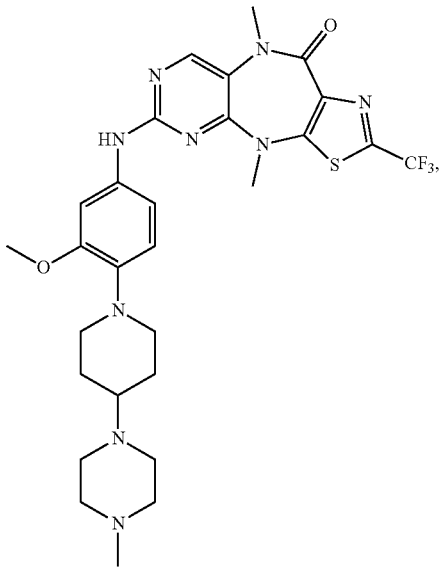
(103)
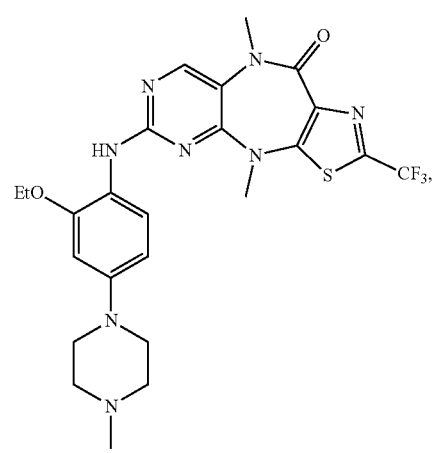
(104)
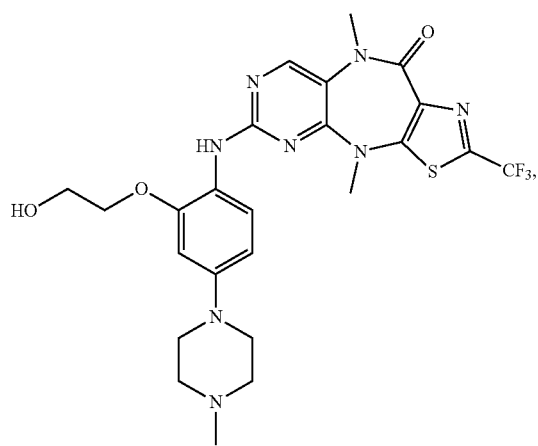

-continued
(105)
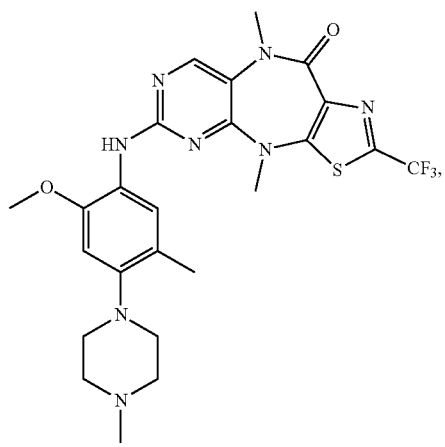
(106)
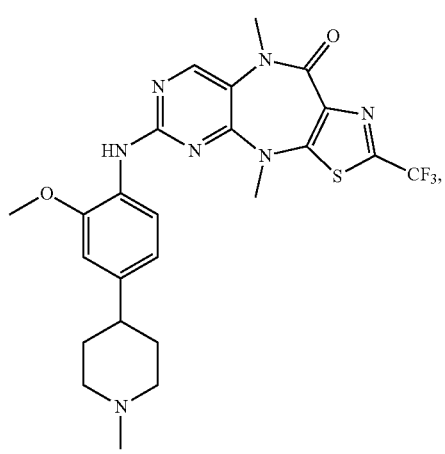
(107)
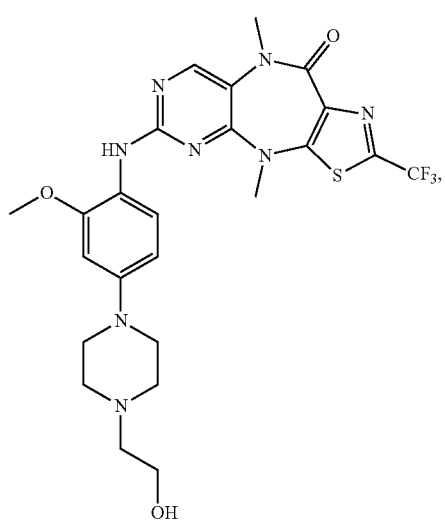
-continued
(108)
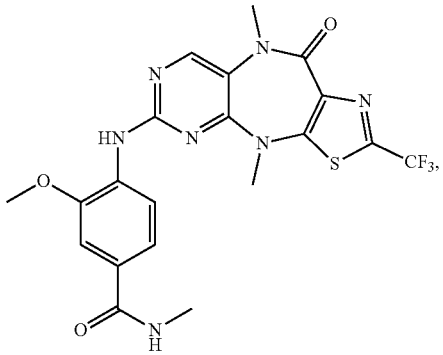
(109)
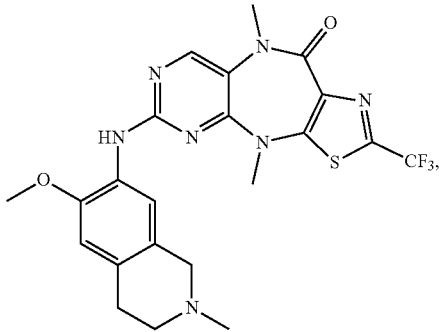
(110)
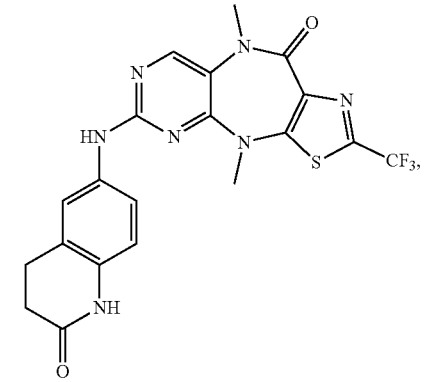
(111)
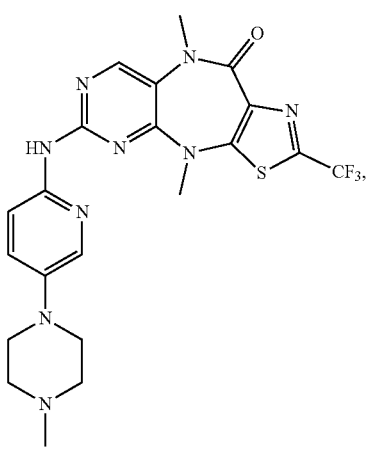

-continued
(112)
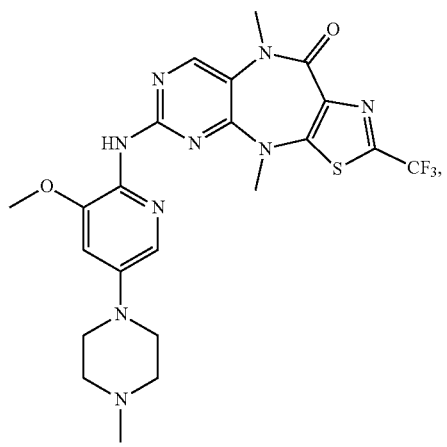
(113)
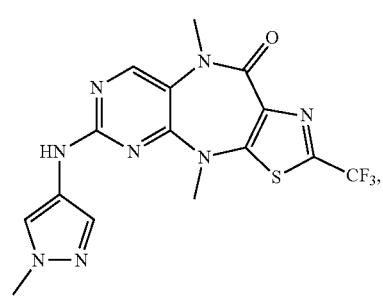
(114)
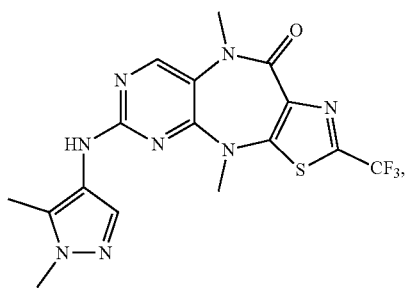
(115)
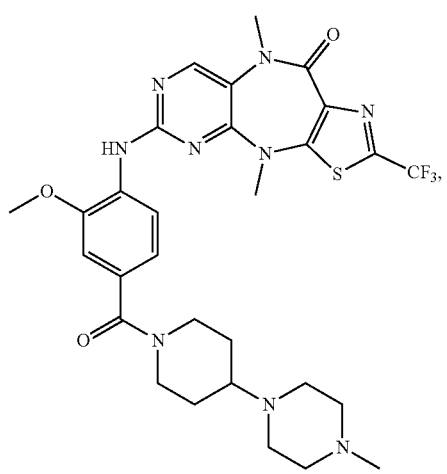
-continued
(116)
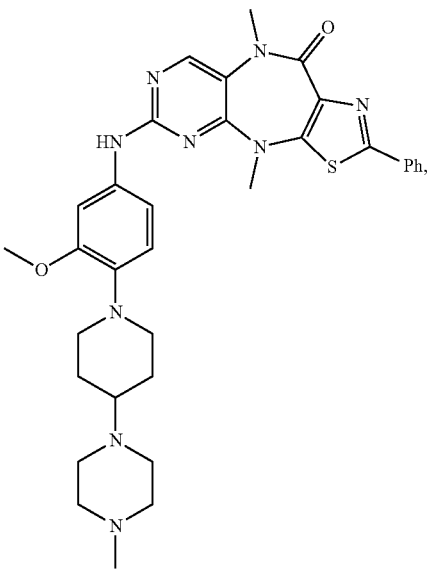
(117)
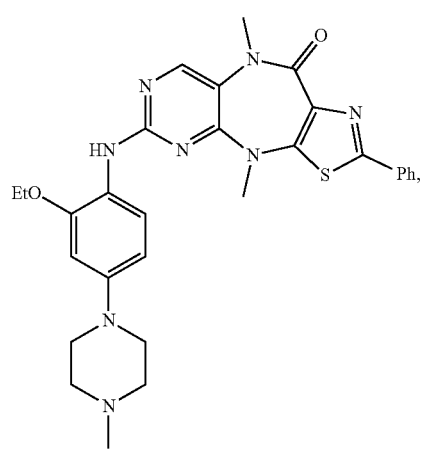
(118)
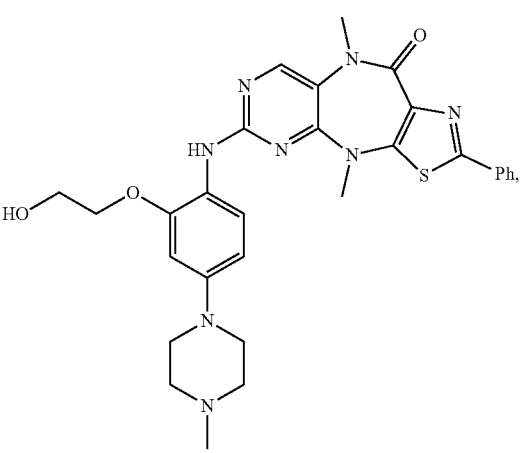

(119)
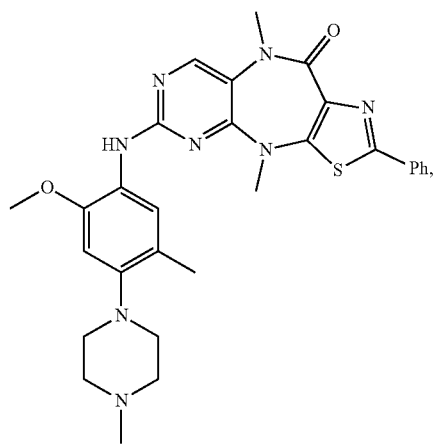
(120)
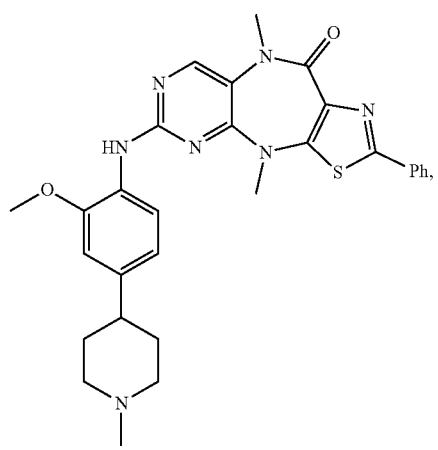
(121)
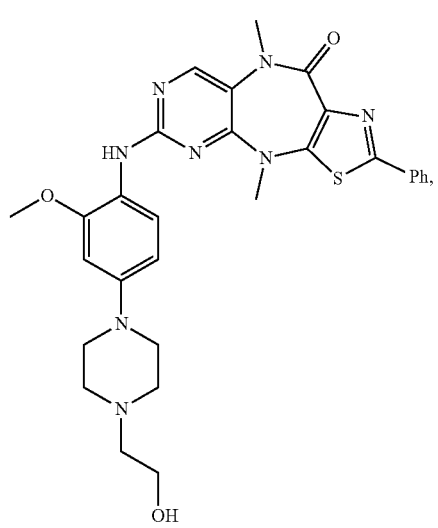
(122)
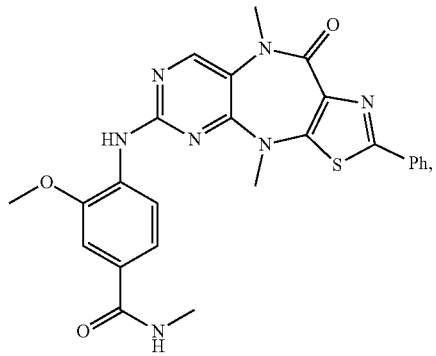
(123)
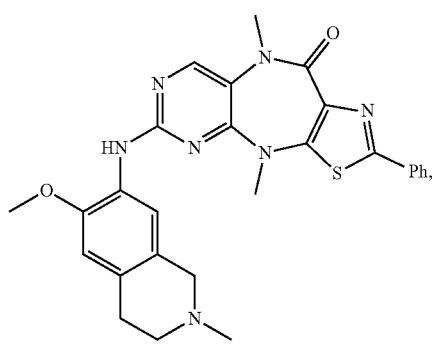
(124)
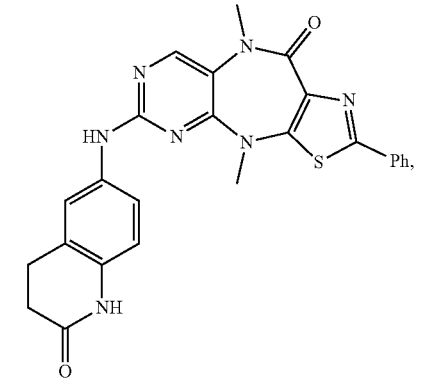
(125)
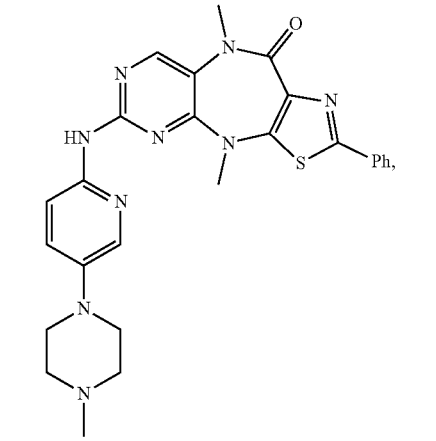

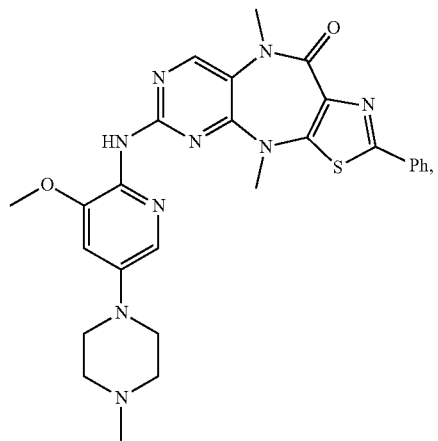
(126)
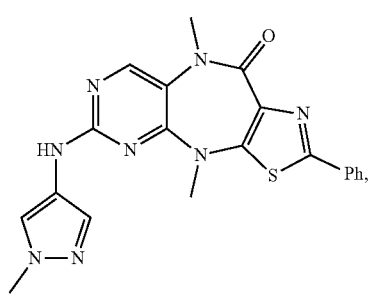
(127)
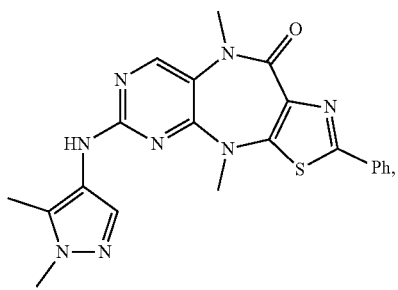
(128)
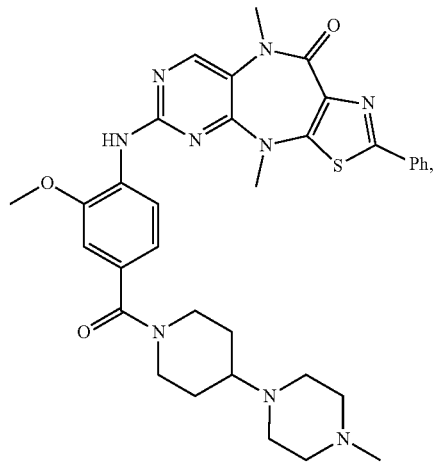
(129)
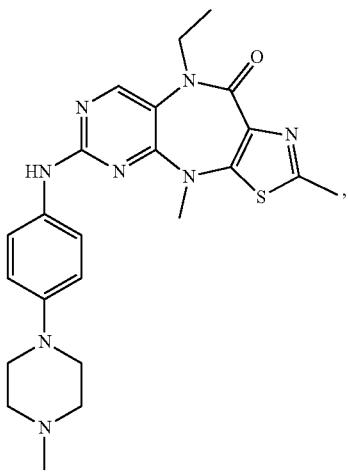
(130)
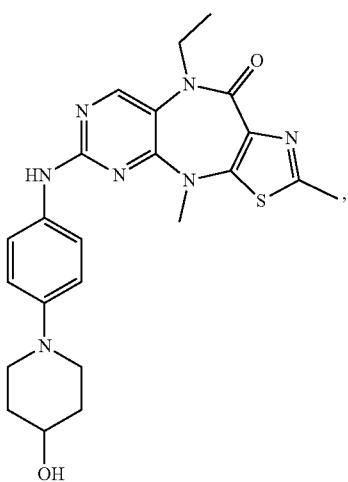
(131)
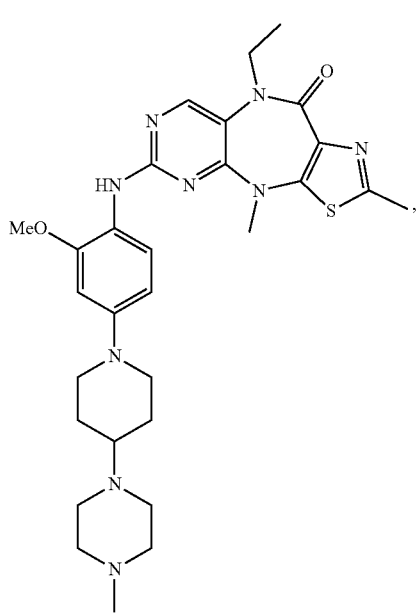
(132)

(133)
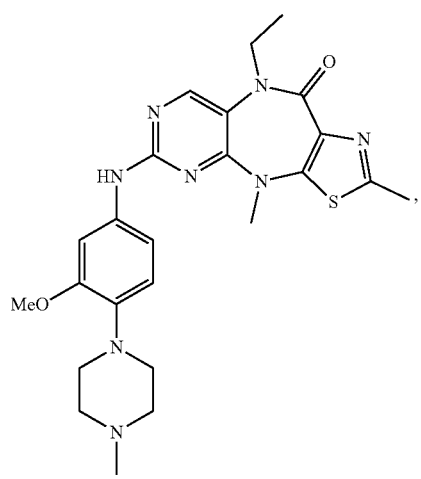
(136)
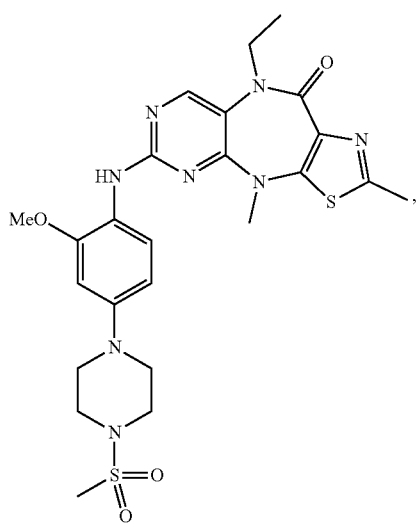
(134)
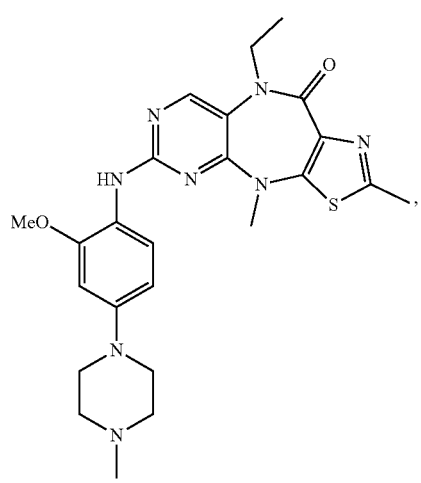
(137)
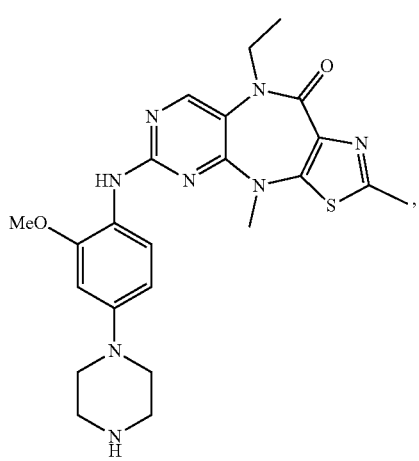
(135)
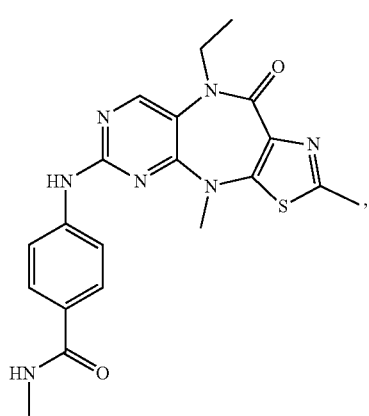
(138)
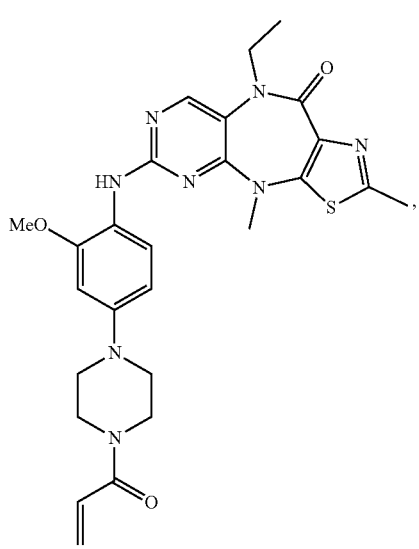

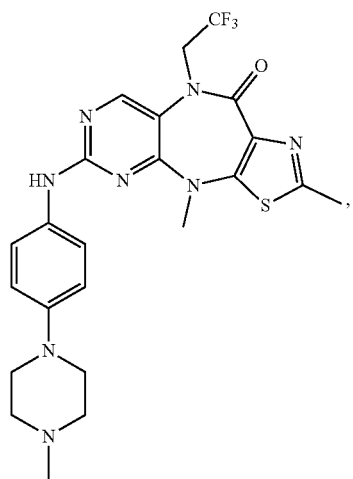 (139)
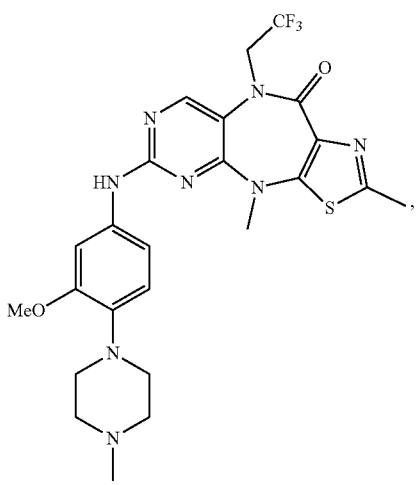 (142)
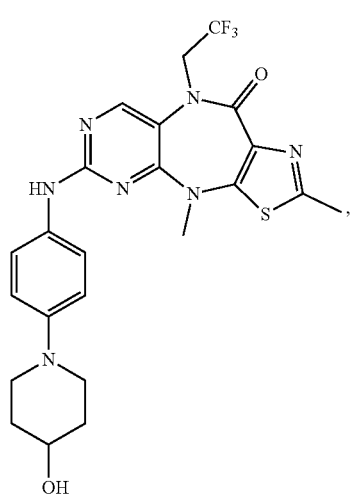 (140)
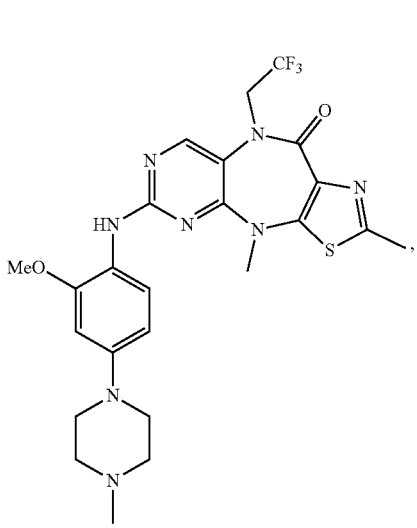 (143)
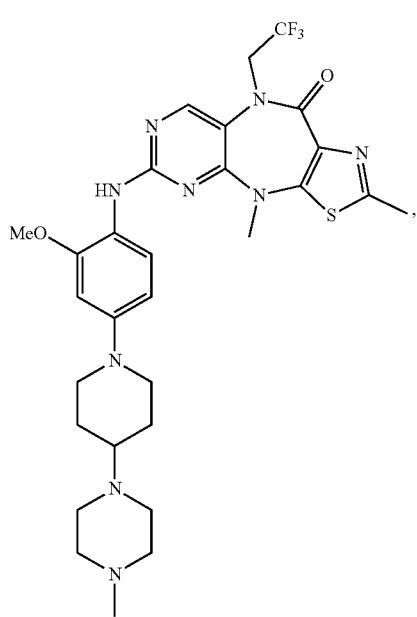 (141)
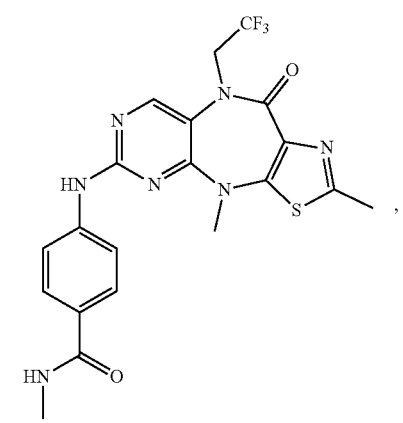 (144)

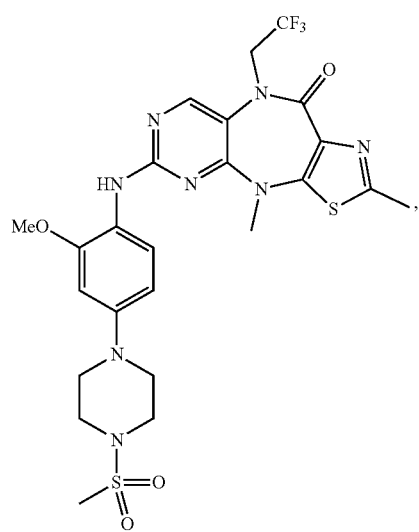
(145)
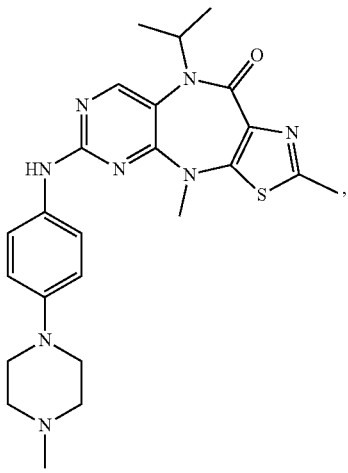
(148)
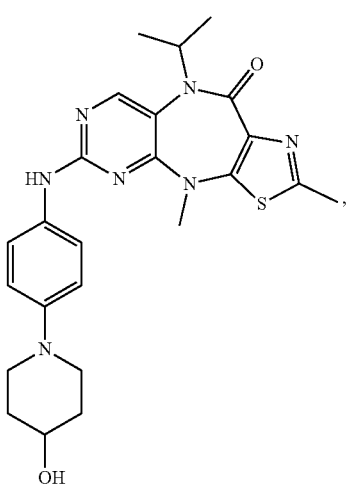
(149)
(146)
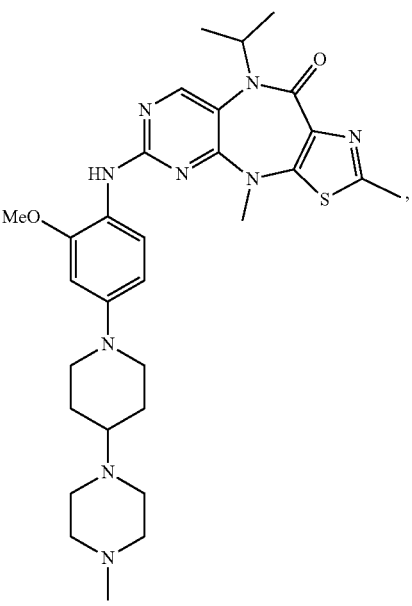
(150)
(147)

-continued
(151)
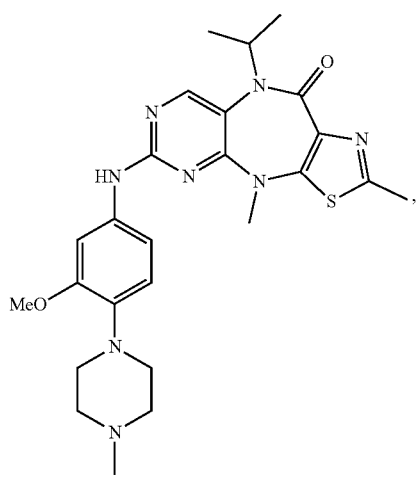
(152)
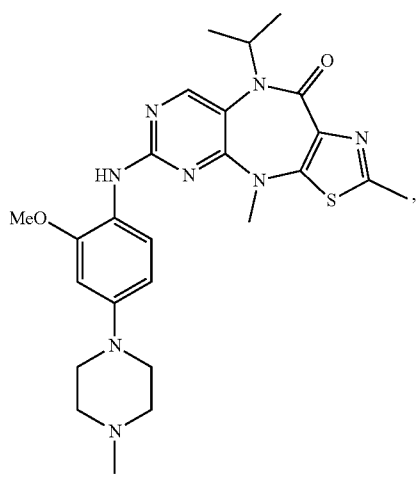
(153)
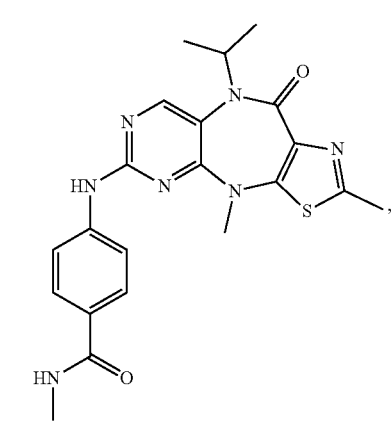
-continued
(154)
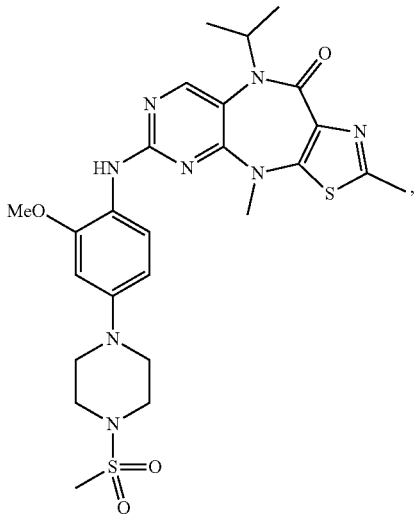
(155)
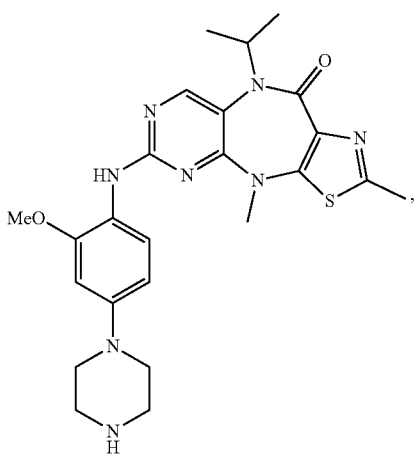
(156)
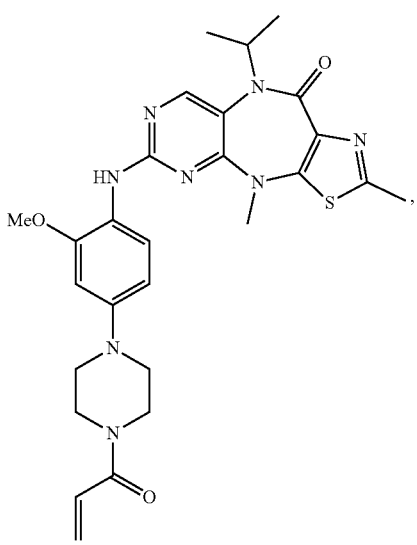

227
-continued
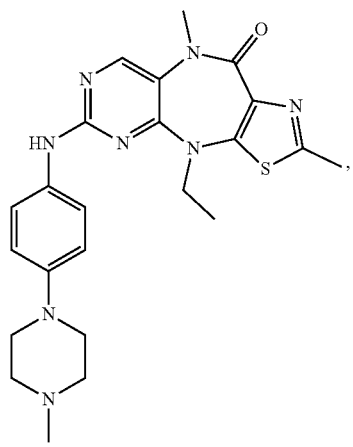
(157)
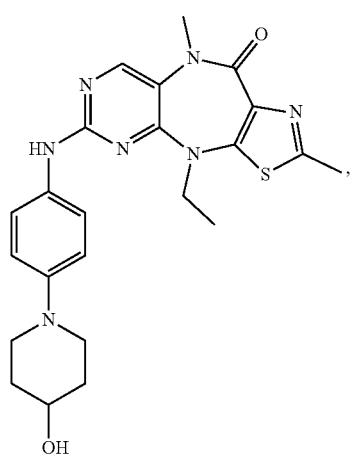
(158)
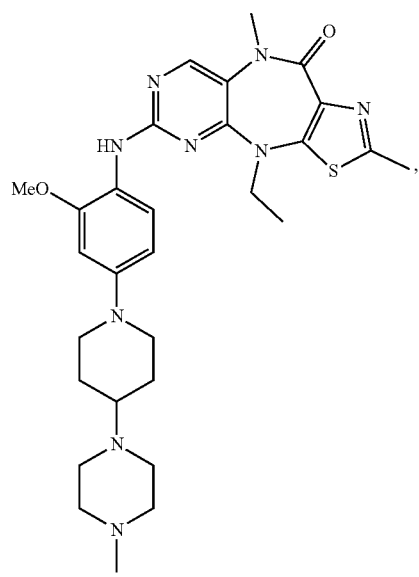
(159)
228
-continued
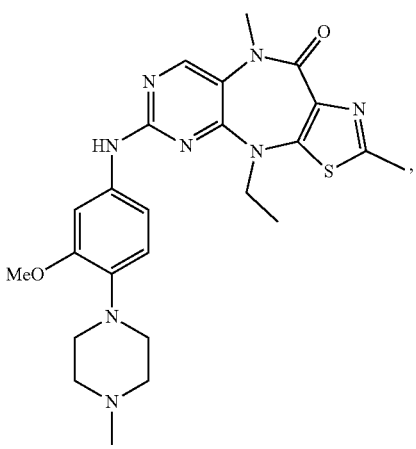
(160)
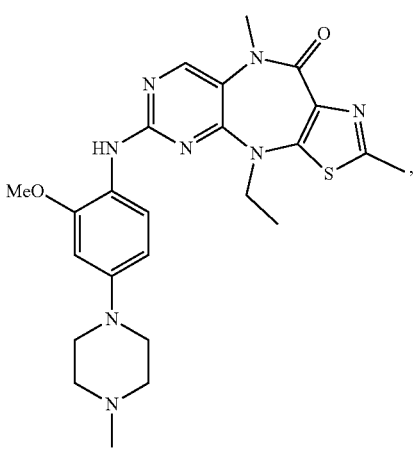
(161)
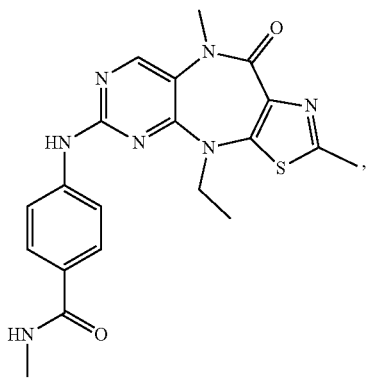
(162)

-continued
(163)
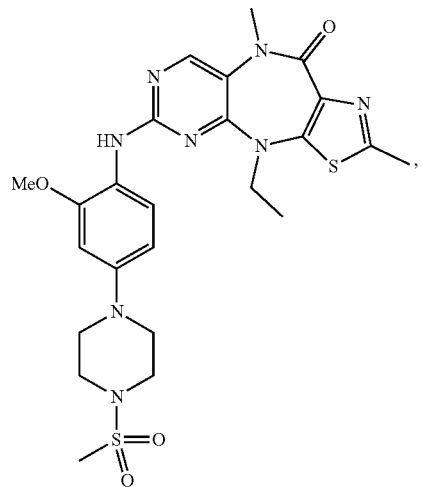
(164)
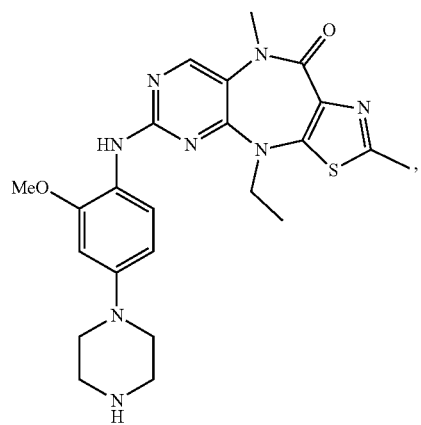
(165)
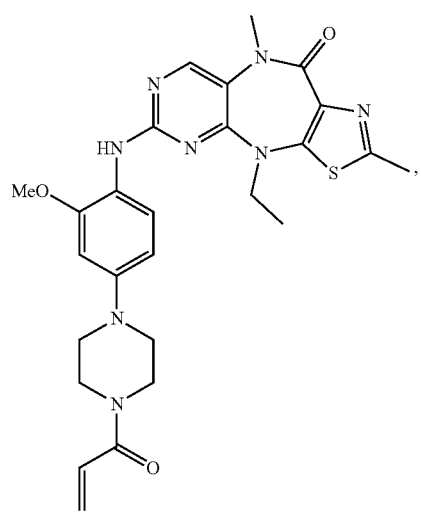
-continued
(166)
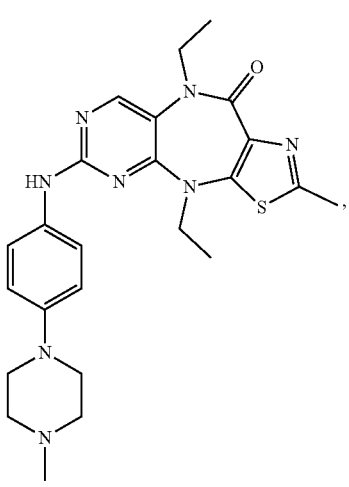
(167)
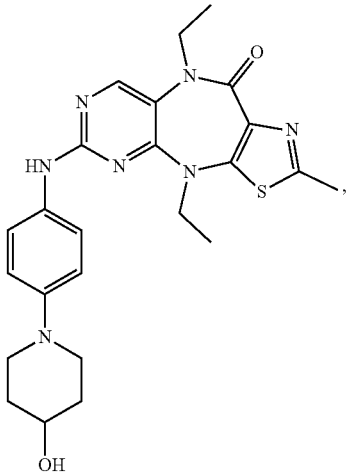
(168)
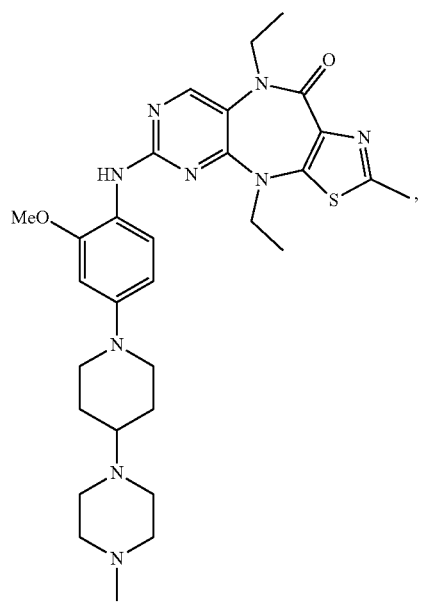

(169) 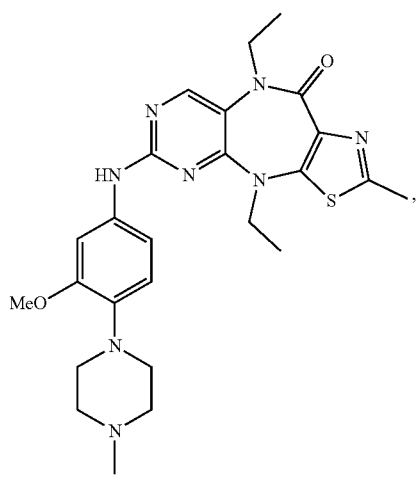
(170) 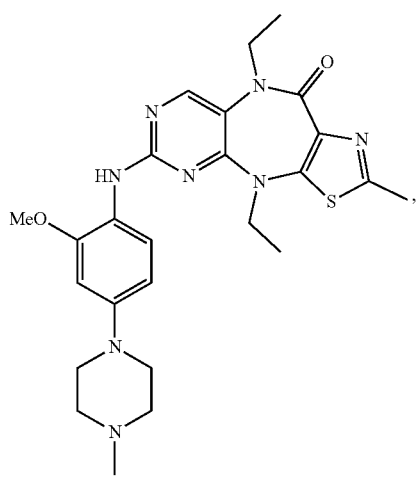
(171) 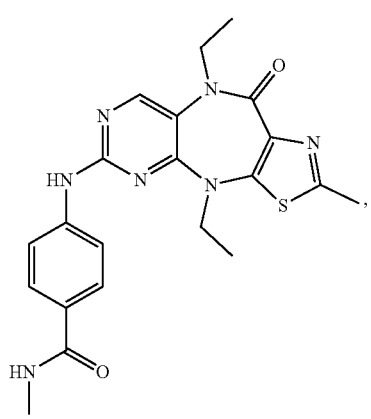
(172) 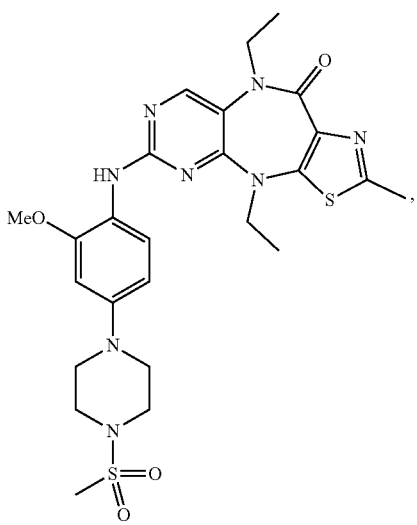
(173) 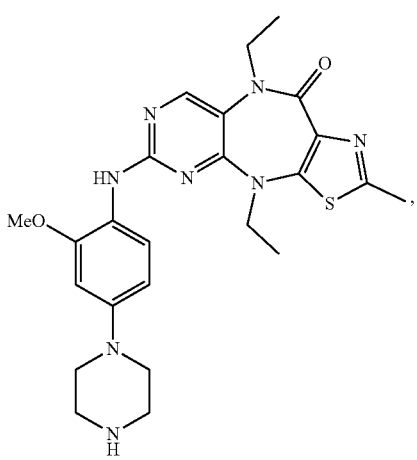
(174) 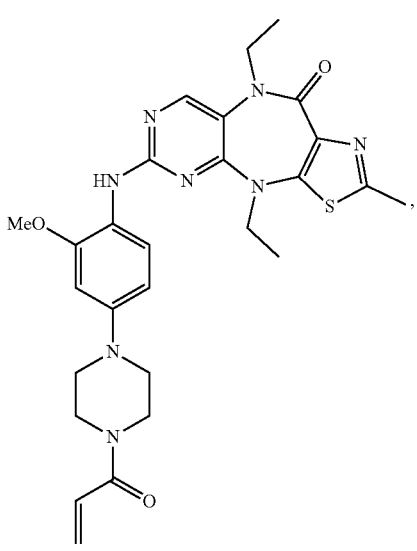

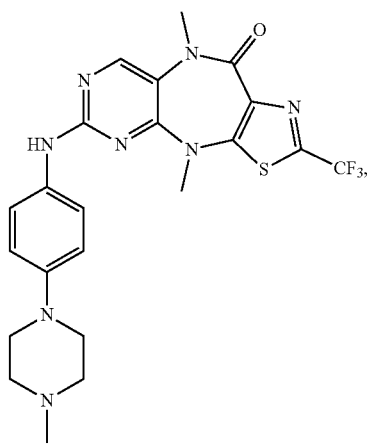
(175)
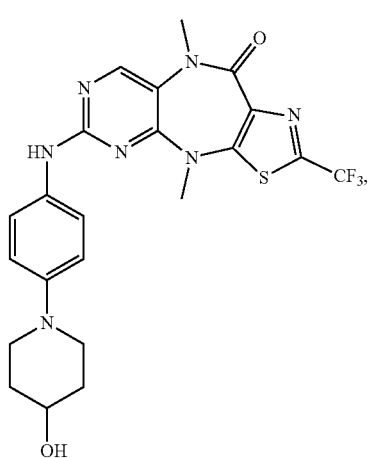
(176)
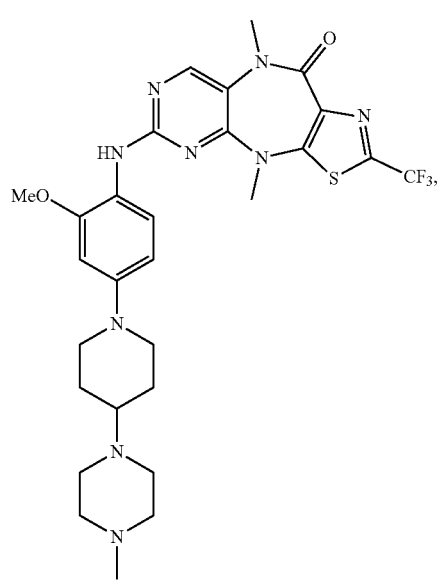
(177)
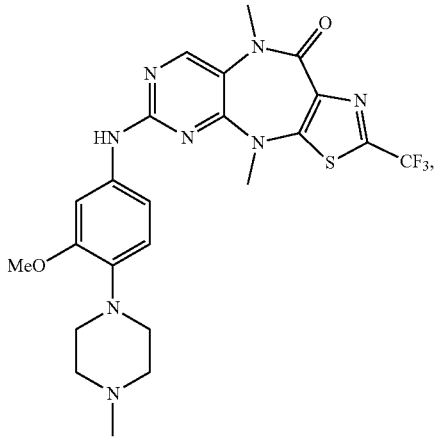
(178)
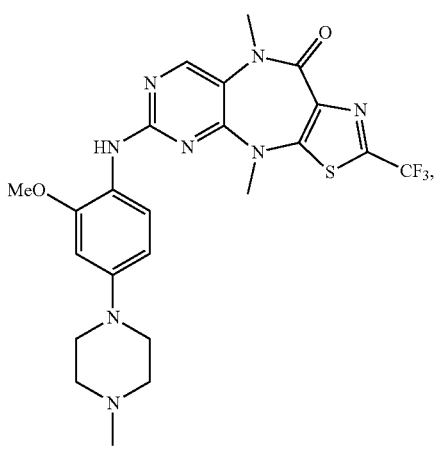
(179)
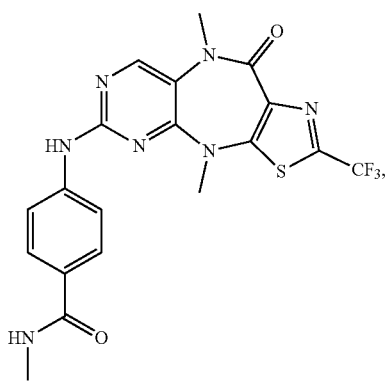
(180)

235
-continued
(181)
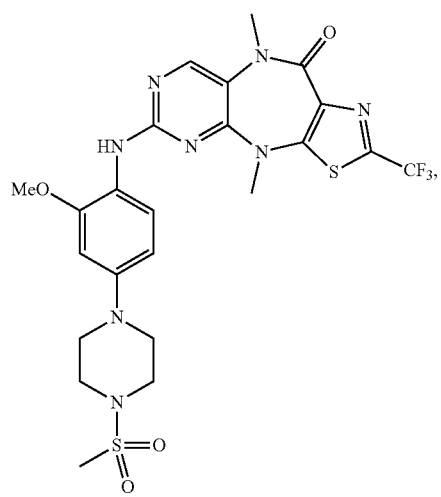
(182)
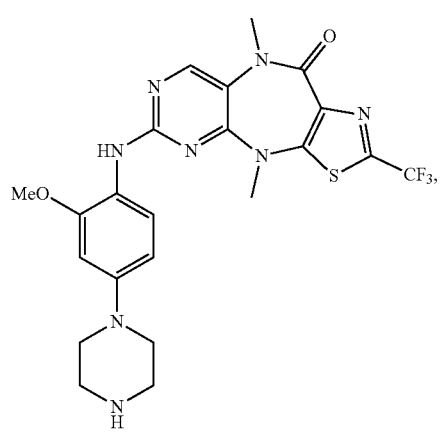
(183)
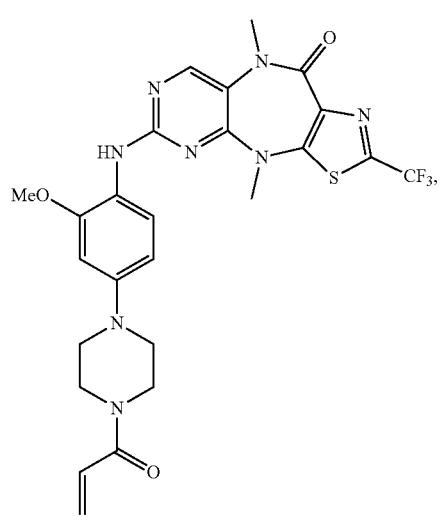
236
-continued
(184)
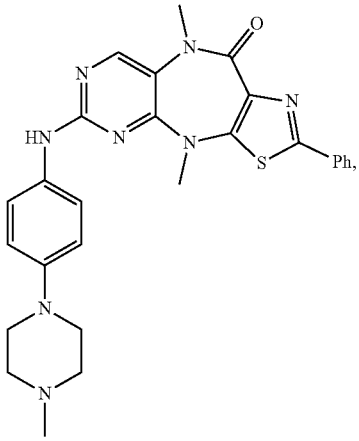
(185)
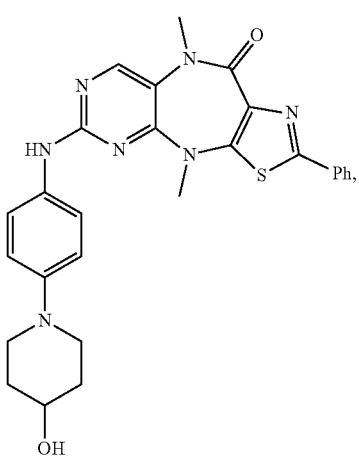
(186)
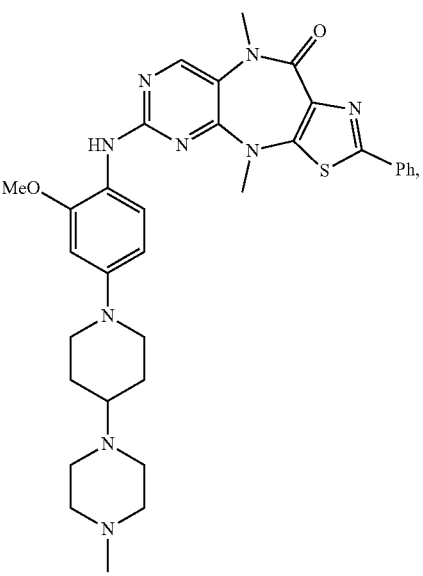

-continued
(187)
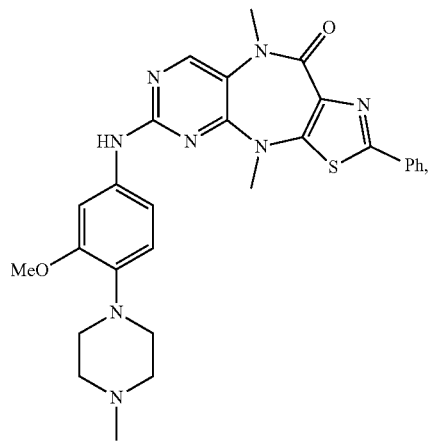
(188)
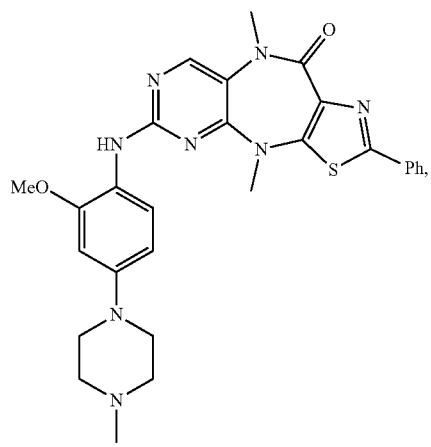
(189)
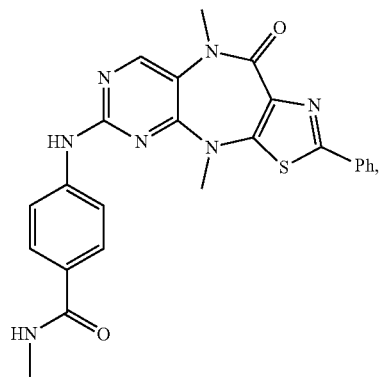
-continued
(190)
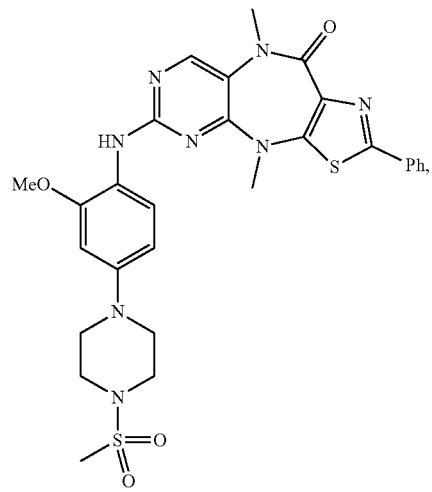
(191)
(192)
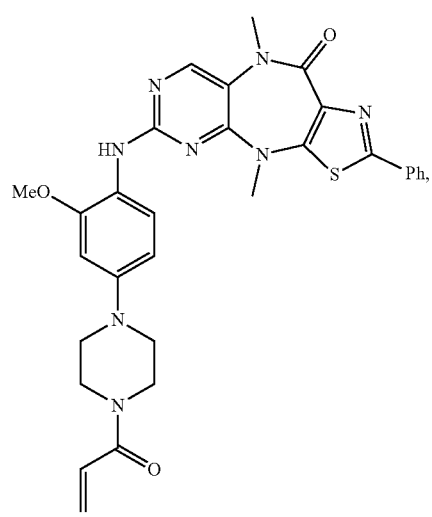

-continued
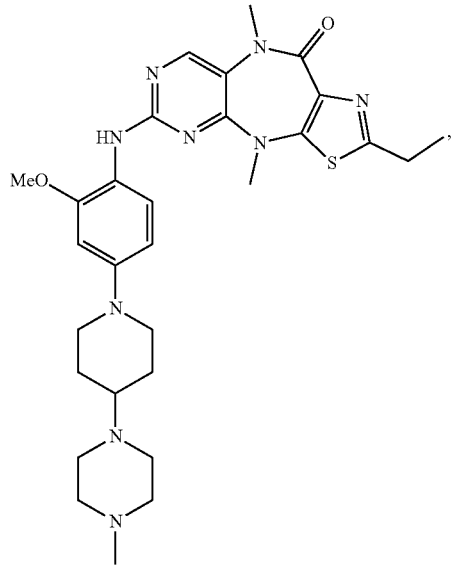
(193)
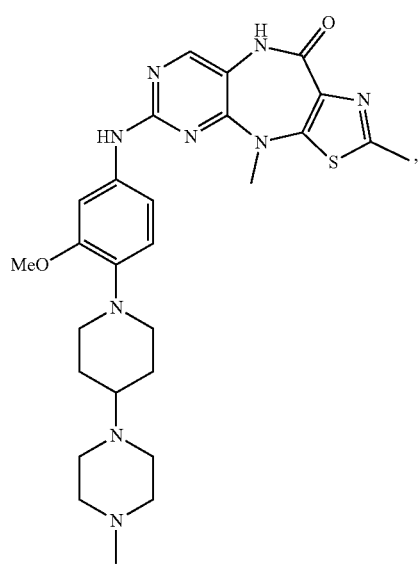
(194)
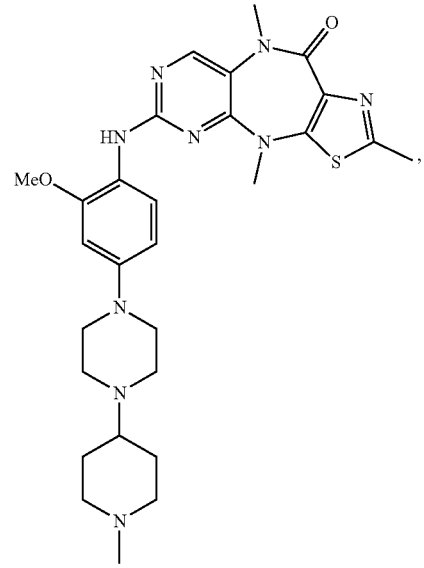
(195)
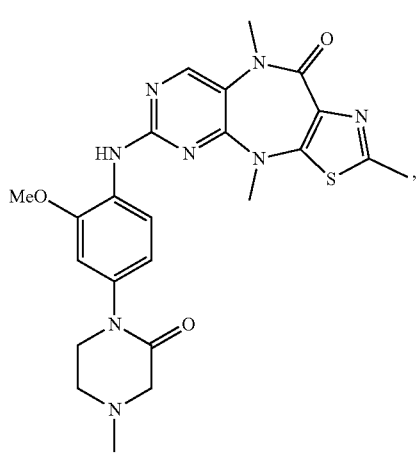
(196)
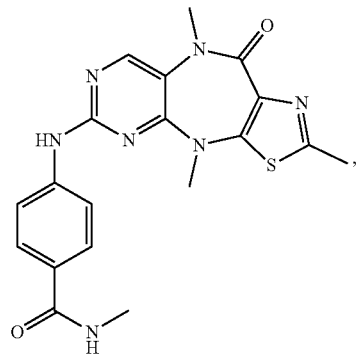
(197)

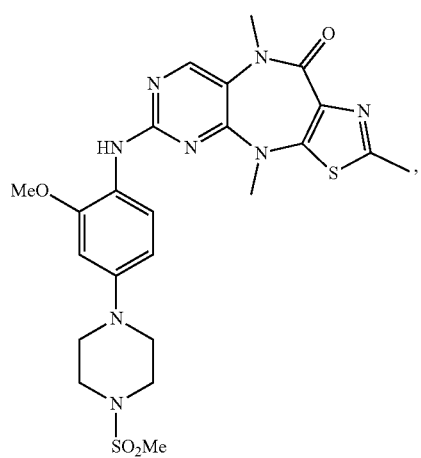
(198)
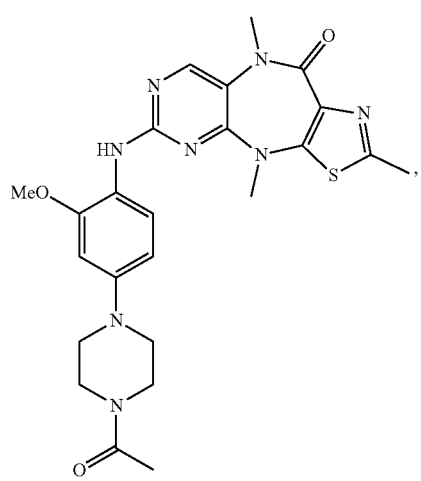
(199)
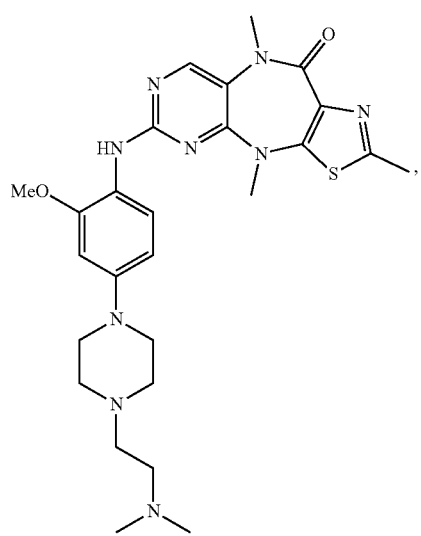
(200)
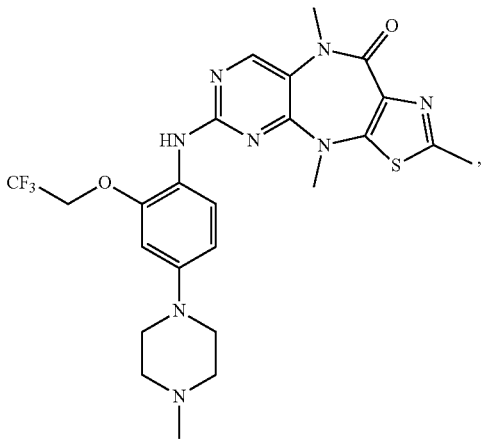
(201)
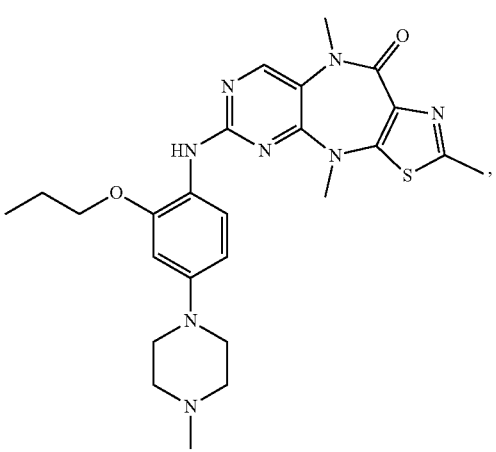
(202)

(203)

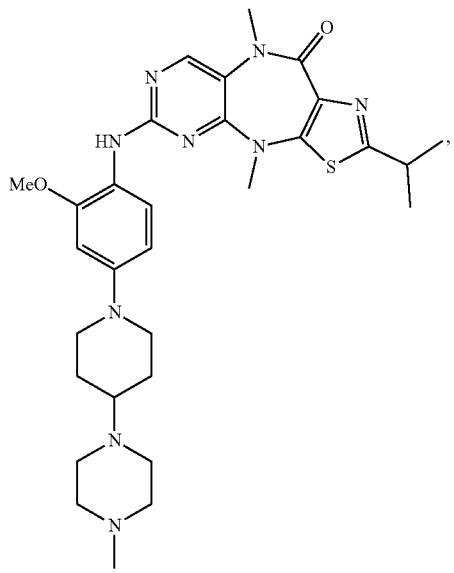

(204)

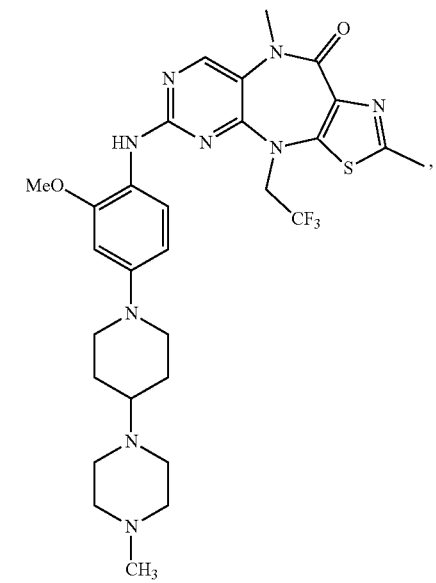

(205)

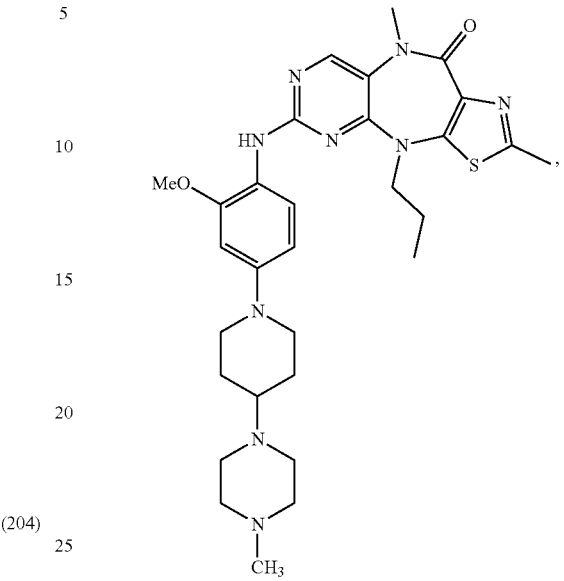

or a pharmaceutically acceptable salt or stereoisomer thereof.

23. A pharmaceutical composition comprising the compound of claim 1, or a pharmaceutically acceptable salt or stereoisomer thereof, and a pharmaceutically acceptable carrier.

24. A method of treating a cancer that is mediated by aberrant FAK activity, comprising administering to a subject in need thereof a therapeutically effective amount of the compound of claim 1, or a pharmaceutically acceptable salt or stereoisomer thereof.

25. The method of claim 24, wherein the cancer is pancreatic, ovarian or lung cancer.

26. The method of claim 24, further comprising co-administering an additional therapeutic agent to the subject.

* * * * *